United States Patent
Bin et al.

(10) Patent No.: US 9,126,892 B2
(45) Date of Patent: *Sep. 8, 2015

(54) BLUE FLUORESCENCE COMPOUND AND ORGANIC ELECTROLUMINESCENCE DEVICE USING THE SAME

(75) Inventors: Jong-Kwan Bin, Paju-si (KR); Soon-Wook Cha, Goyang-si (KR); Seung-Jae Lee, Goyang-si (KR); Jung-Keun Kim, Seoul (KR); Chun-Gun Park, Seoul (KR)

(73) Assignee: LG DISPLAY CO., LTD., Seoul (KR)

( * ) Notice: Subject to any disclaimer, the term of this patent is extended or adjusted under 35 U.S.C. 154(b) by 468 days.

This patent is subject to a terminal disclaimer.

(21) Appl. No.: 12/858,372

(22) Filed: Aug. 17, 2010

(65) Prior Publication Data

US 2011/0156011 A1    Jun. 30, 2011

(30) Foreign Application Priority Data

Dec. 29, 2009  (KR) .................. 10-2009-0132606

(51) Int. Cl.
| | |
|---|---|
| *H01L 51/54* | (2006.01) |
| *C07C 211/61* | (2006.01) |
| *C07C 255/58* | (2006.01) |
| *C07F 7/10* | (2006.01) |
| *C07C 217/92* | (2006.01) |
| *C07F 7/08* | (2006.01) |
| *C09K 11/06* | (2006.01) |
| *H01L 51/00* | (2006.01) |
| *H01L 51/50* | (2006.01) |
| *H05B 33/14* | (2006.01) |

(52) U.S. Cl.
CPC ............. *C07C 211/61* (2013.01); *C07C 217/92* (2013.01); *C07C 255/58* (2013.01); *C07F 7/0818* (2013.01); *C09K 11/06* (2013.01); *H01L 51/006* (2013.01); *H01L 51/5012* (2013.01); *H05B 33/14* (2013.01); *C07C 2103/50* (2013.01); *C09K 2211/1007* (2013.01); *C09K 2211/1011* (2013.01); *C09K 2211/1014* (2013.01)

(58) Field of Classification Search
CPC   C07C 2103/50; C07C 211/61; C07C 217/92; C07C 255/58; C07F 7/0818; C09K 11/06; C09K 2211/1007; C09K 2211/1011; C09K 2211/1014; H01L 51/006; H01L 51/5012; H05B 33/14
See application file for complete search history.

(56) References Cited

U.S. PATENT DOCUMENTS

| | | | |
|---|---|---|---|
| 8,835,020 B2 * | 9/2014 | Lee et al. ................ | 428/690 |
| 2003/0118866 A1 * | 6/2003 | Oh et al. ................. | 428/690 |
| 2004/0137270 A1 * | 7/2004 | Seo et al. ................ | 428/690 |

(Continued)

FOREIGN PATENT DOCUMENTS

| | | |
|---|---|---|
| CN | 1535089 A | 10/2004 |
| CN | 1784376 A | 6/2006 |

(Continued)

OTHER PUBLICATIONS

Journal of Organic Chemistry, (2009), 74(21), pp. 8472-8475.*

Primary Examiner — Dawn Garrett
(74) Attorney, Agent, or Firm — Birch, Stewart, Kolasch & Birch, LLP

(57) ABSTRACT

The present invention relates to a blue fluorescence compound which enables to achieve high brightness, a long lifetime and high efficiency; and an organic electroluminescence device thereof.

4 Claims, 1 Drawing Sheet

(56) References Cited

U.S. PATENT DOCUMENTS

2007/0009758 A1* 1/2007 Funahashi .................... 428/690
2008/0185971 A1* 8/2008 Kinoshita .................. 315/169.3
2010/0052526 A1* 3/2010 Je et al. ........................ 313/504
2010/0141124 A1* 6/2010 Lee et al. ..................... 313/504
2011/0006669 A1* 1/2011 Lee et al. ..................... 313/504

FOREIGN PATENT DOCUMENTS

KR 2007-0053753 A 7/2007
KR 10-2007-0115588 A 12/2007

\* cited by examiner

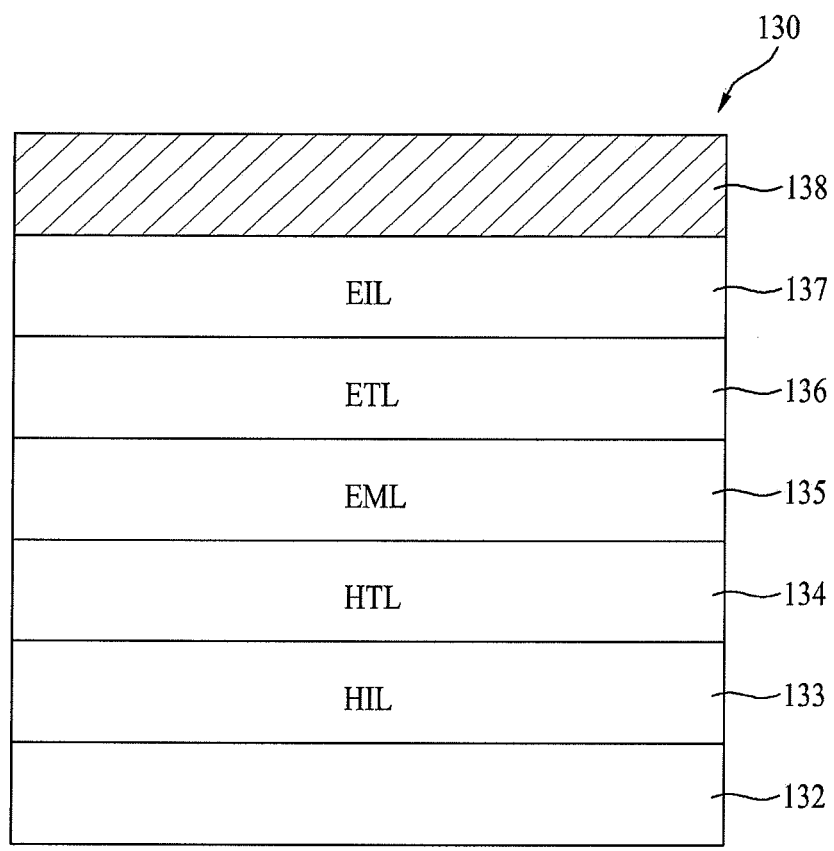

BLUE FLUORESCENCE COMPOUND AND ORGANIC ELECTROLUMINESCENCE DEVICE USING THE SAME

CROSS REFERENCE TO RELATED APPLICATION

This application claims the benefit of the Korean Patent Application No. 10-2009-0132606, filed on Dec. 29, 2009, which is hereby incorporated by reference as if fully set forth herein.

BACKGROUND OF THE DISCLOSURE

1. Field of the Disclosure

The present invention relates to a blue fluorescence compound and an organic electroluminescence device thereof, and more particularly, to a blue fluorescence compound which enables to achieve high brightness, a long lifetime and high efficiency; and an organic electroluminescence device using the same.

2. Discussion of the Related Art

Being a core technology in the times of information and communication, an image display device which displays different information in pictures is developing in a direction of being thinner, lighter, and high performance while being portable.

As various forms of demands on the display devices increases along with recent development of an information oriented society, active researches on flat display devices, such as LCD (Liquid Crystalline Display), PDP (Plasma Display Panel), ELD (Electro Luminescent Display), FED (Field Emission Display) and so on are underway.

Of the flat display devices, the organic electroluminescence device emits a light as an electron and a hole which form a pair upon injection of charge into an organic electroluminescence layer formed between an electron injection electrode (a cathode) and a hole injection electrode (an anode) annihilate.

The organic electroluminescence device, not only can be formed on a flexible transparent substrate, such as plastic, but also can be driven by a voltage lower than the plasma display panel or an inorganic electroluminescence device, has comparatively low power consumption and an excellent color feeling.

The organic electroluminescence layer can emit a light of red, green, or blue color depending on an organic compound included to the electroluminescence layer. As the organic compounds, 2,2-(diaryl)vinylphosphine compound, a compound in which an aryl group is substituted at an end of a diphenylanthracene structure, and so on are known.

However, since known organic compounds including above compounds have no adequate lifetimes, light emission efficiency, and brightness, and has poor blue color purity, making production of a clean blue color difficult, production of full color display of natural color is difficult.

SUMMARY OF THE DISCLOSURE

Accordingly, the present invention is directed to a blue fluorescence compound, and an organic electroluminescence device using the same.

An object of the present invention is to provide a blue fluorescence compound which enables to achieve high brightness, a long lifetime and high efficiency; and an organic electroluminescence device thereof.

Additional advantages, objects, and features of the disclosure will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, a blue fluorescence compound consisting of the following chemical formula 1.

[Chemical Formula 1]

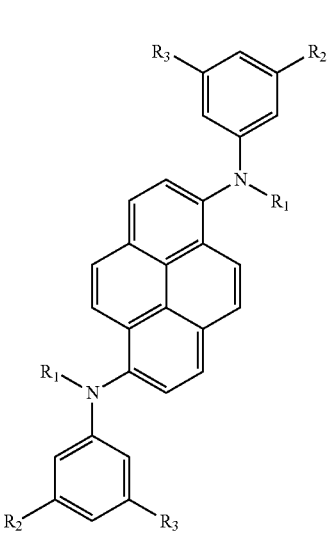

where, $R_1$, $R_2$, and $R_3$ may or may not be identical substances, and each of the $R_1$, $R_2$, and $R_3$ is one of substances selected from an aromatic group, a heterocyclic group, an aliphatic group and hydrogen, independently.

The organic electroluminescence device of a blue fluorescence compound of the present invention, having an electroluminescence layer between a cathode and an anode, the electroluminescence layer includes a dopant substance and a host substance, wherein the dopant substance has the chemical formula 1.

Each of the $R_1$, $R_2$, and $R_3$ is one of substances selected from biphenyl, naphthyl, phenanthrene, terphenyl, pyridine), quinoline, deuterium, and a substituent thereof, independently.

The aromatic group is an aromatic compound having alkyl, alkoxy, halogen, cyano, or silyl group.

The alkyl group is one selected from methyl, ethyl, propyl, i-prophy, and t-butyl, the alkoxy group is one selected from methoxy, ethoxy, and buthoxy, the halogen group is one selected from fluorine and chorine, and the silyl group is trimethylsilyl.

The organic electroluminescence device further includes a hole injection layer and a hole transport layer formed between the anode and the electroluminescence layer in succession, and an electron transport layer and an electron injection layer formed between the electroluminescence layer and the cathode in succession.

Thus, the organic electroluminescence device of a blue fluorescence compound of the present invention permits to drive at a low voltage, and to improve color purity, a lifetime, and light emission efficiency.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the disclosure and are incorporated in and constitute a part of this application, illustrate embodiment(s) of the disclosure and together with the description serve to explain the principle of the disclosure. In the drawings:

FIG. 1 illustrates a diagram of an organic electroluminescence device in accordance with a preferred embodiment of the present invention.

DESCRIPTION OF SPECIFIC EMBODIMENTS

Reference will now be made in detail to the specific embodiments of the present invention, examples of which are illustrated in the accompanying drawings. Wherever possible, the same reference numbers will be used throughout the drawings to refer to the same or like parts.

The blue fluorescence compound of the present invention has the following chemical formula 1.

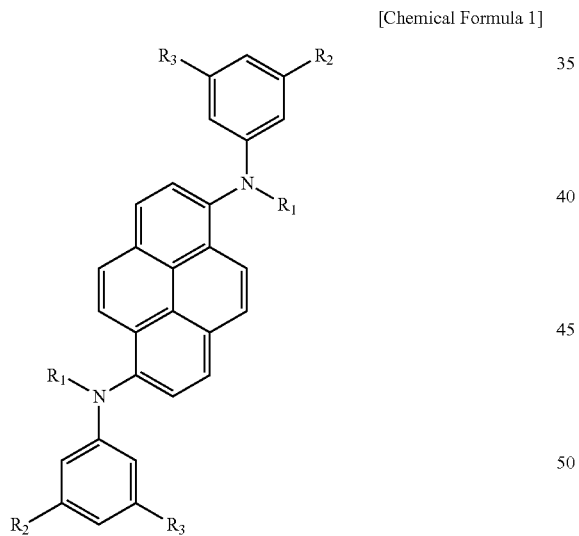

[Chemical Formula 1]

Where, each of R1, R2, and R3 is one of substances selected from an aromatic group, a heterocyclic group, an aliphatic group and hydrogen which is substituted or not substituted, independently. The R1, R2, and R3 may or may not be identical substances.

In detail, each of the R1, R2, and R3 may be one of substances selected from the aromatic group including phenyl, biphenyl, naphthyl, phenanthrene, terphenyl, pyridine, quinoline, deuterium, and a substituent thereof.

Or, each of the R1, R2, and R3 may be one of substances selected from aromatic compound having alkyl, alkoxy, halogen, cyano, and silyl groups.

The alkyl group is one selected from methyl, ethyl, propyl, isopropyl, and t-butyl, and the alkoxy group is one selected from methoxy, ethoxy, and buthoxy. The halogen group is one selected from fluorine and chorine, and the silyl group may be trimethylsilyl.

In detail, the compounds of the chemical formula 1 may be compounds having the following chemical formulae BD-1 to BD-360. However, the compounds of the chemical formula 1 are not limited to those.

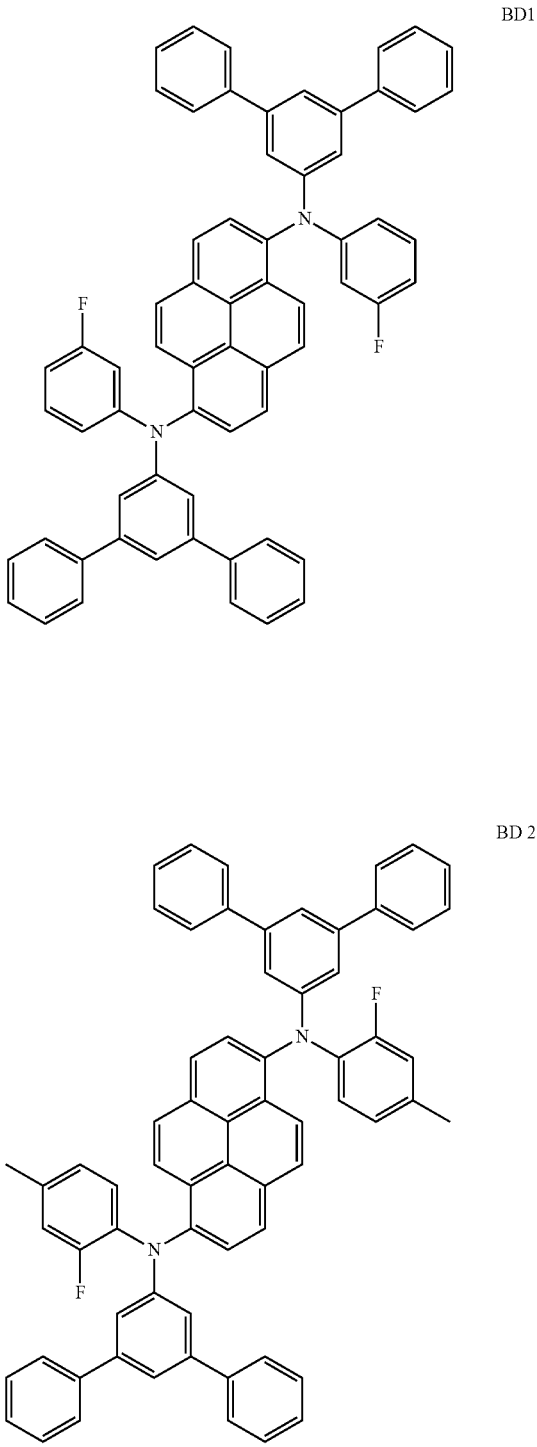

BD3
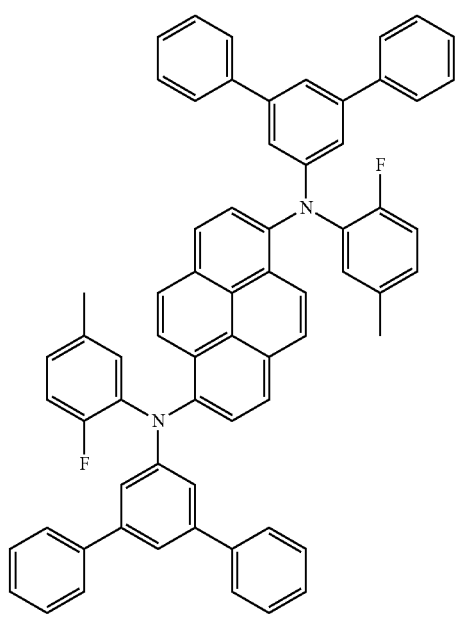
BD5
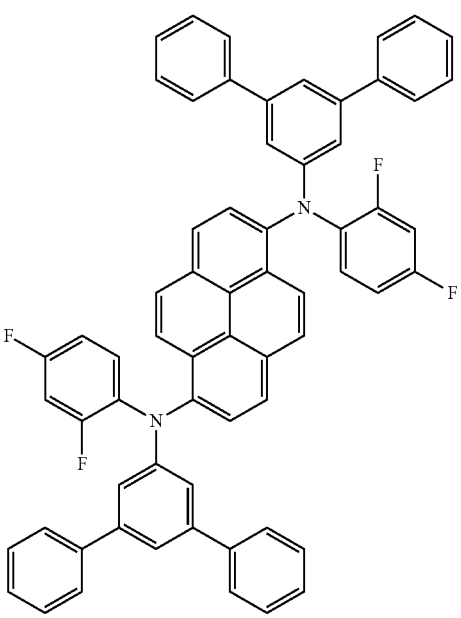
BD4
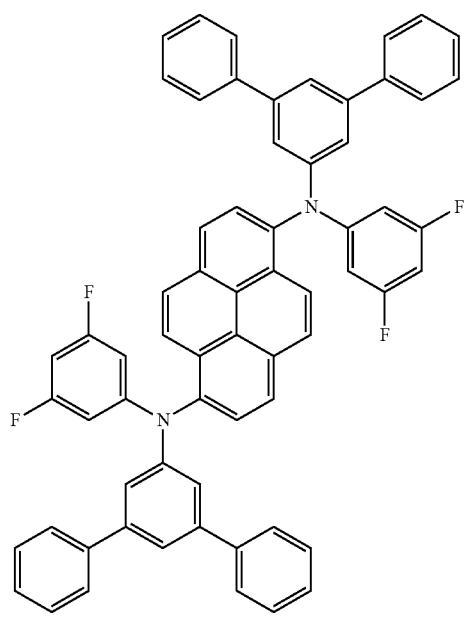
BD6
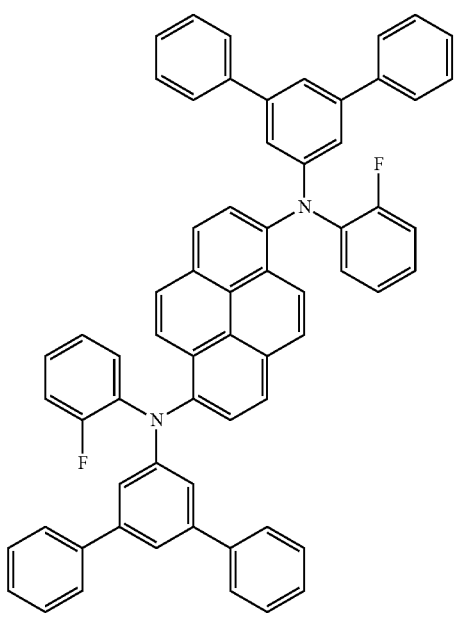

BD7
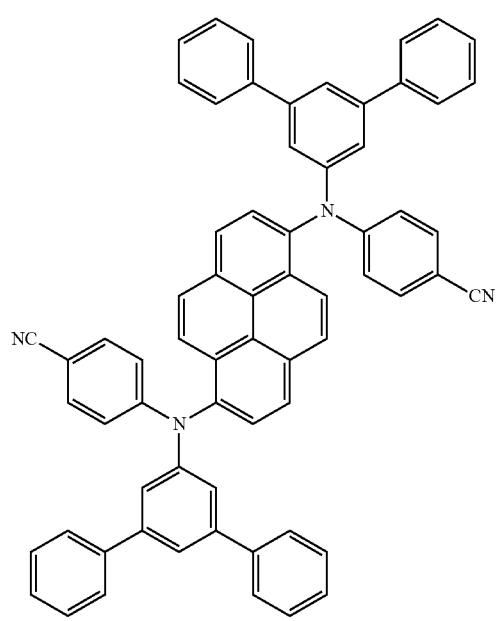
BD9
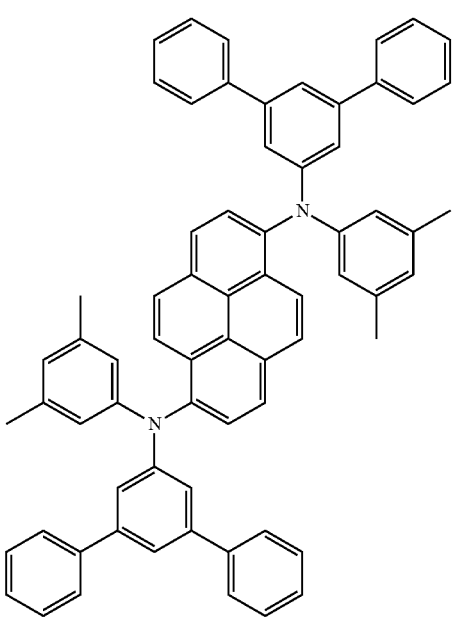
BD 8
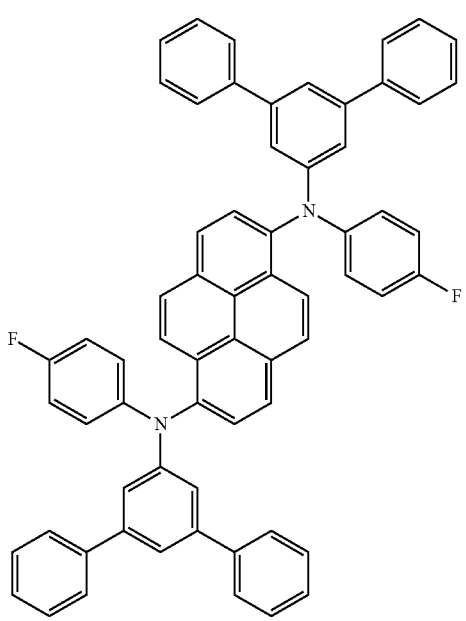
BD 10
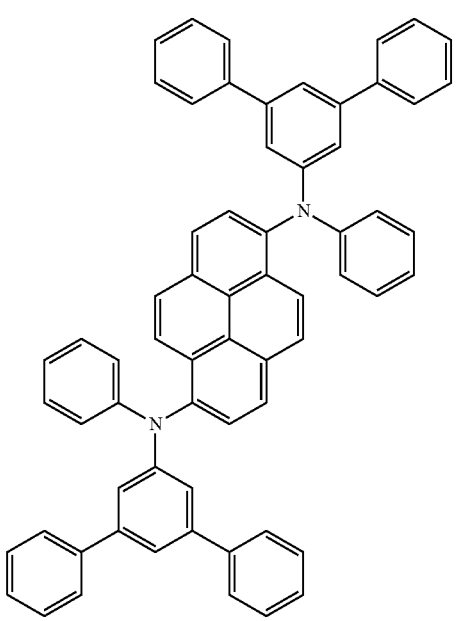

BD 11
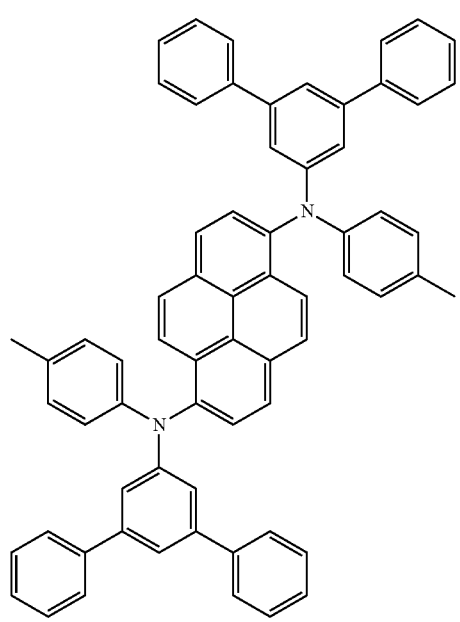
BD 13
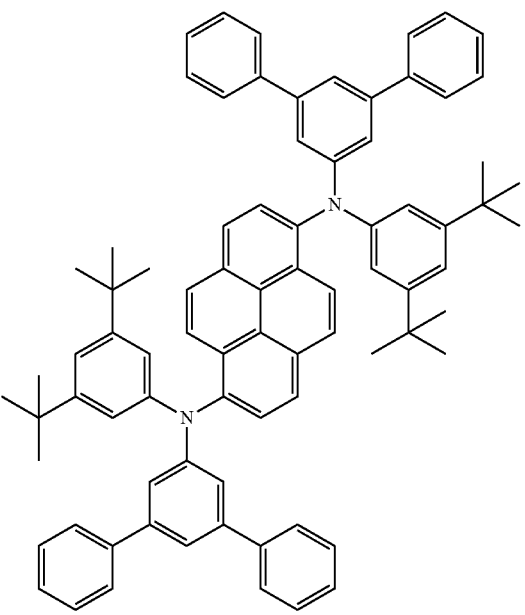
BD 12
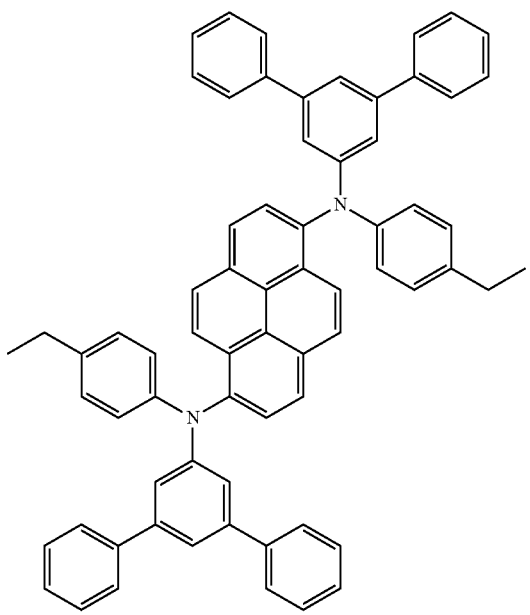
BD 14
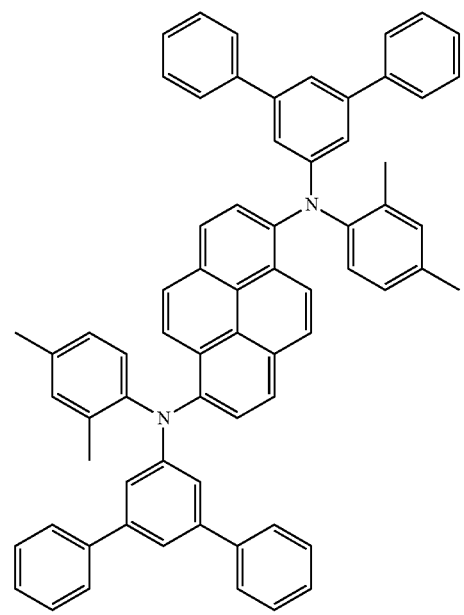

BD 15
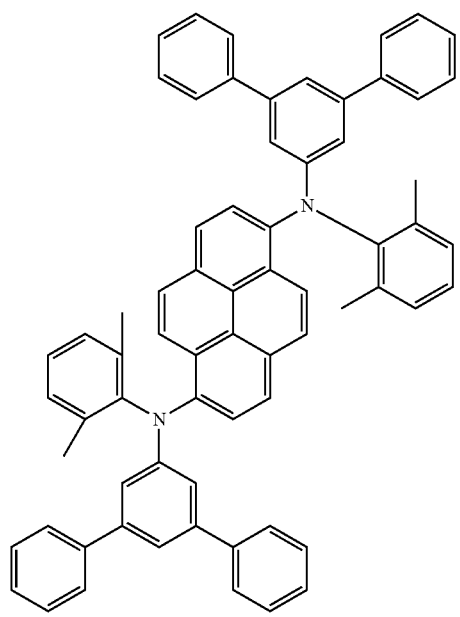
BD 17
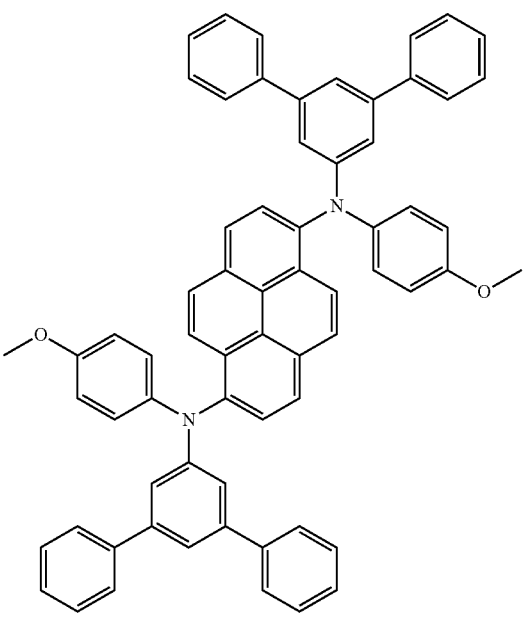
BD 16
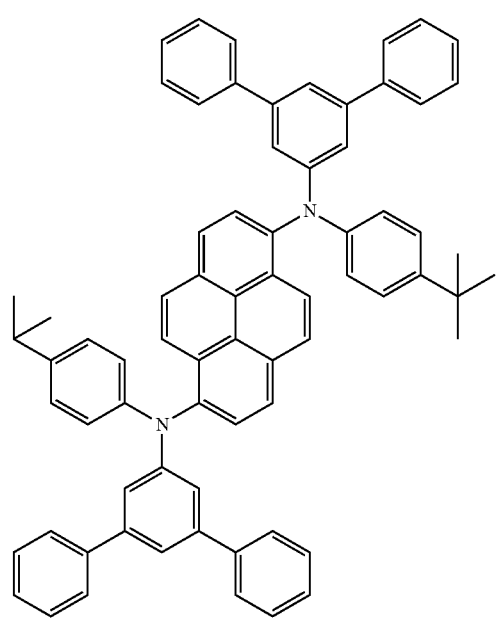
BD 18
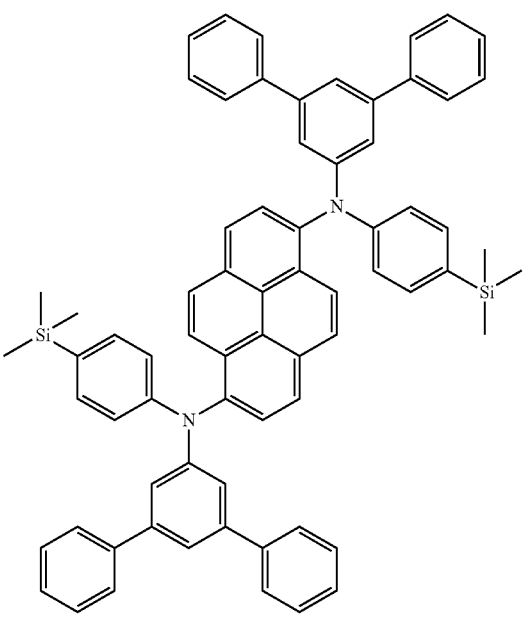

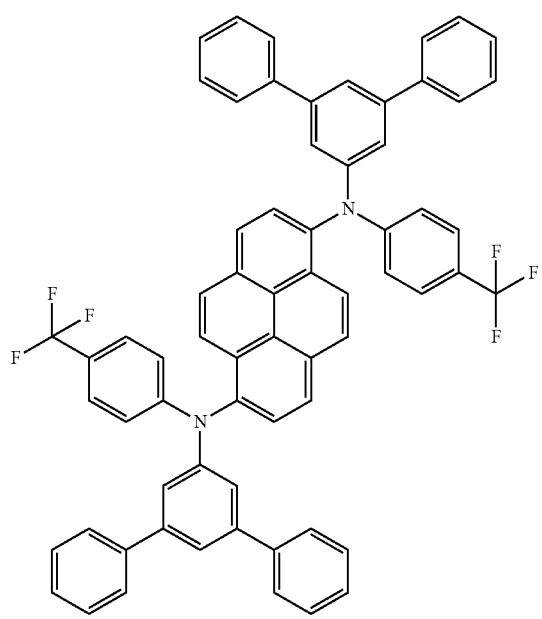
BD 19
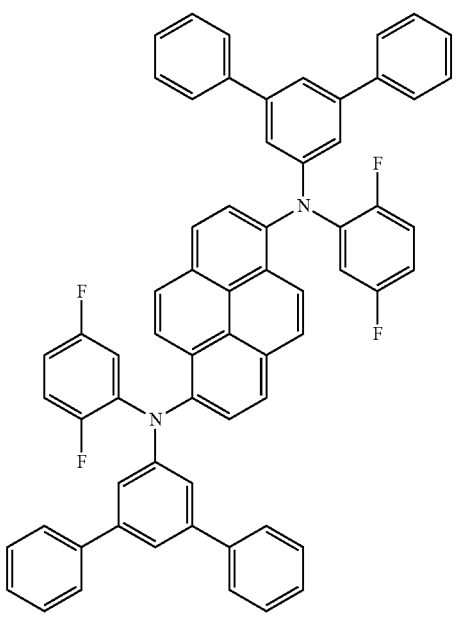
BD 21
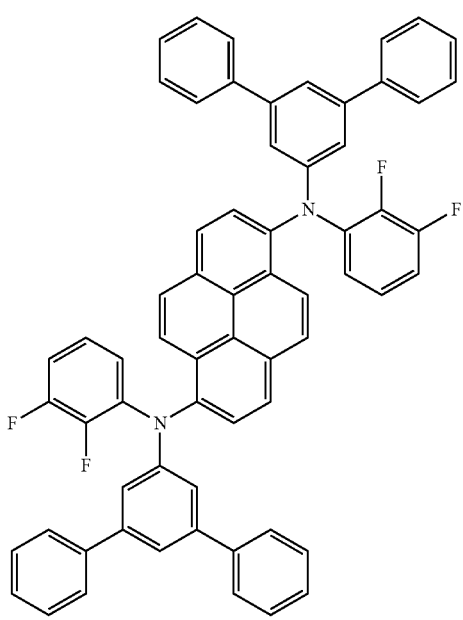
BD 20
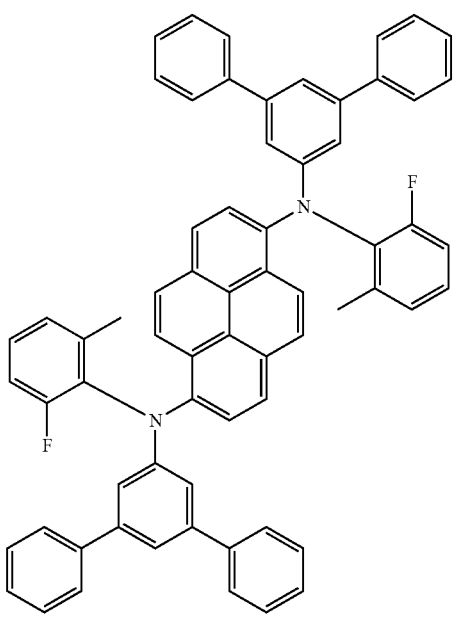
BD 22

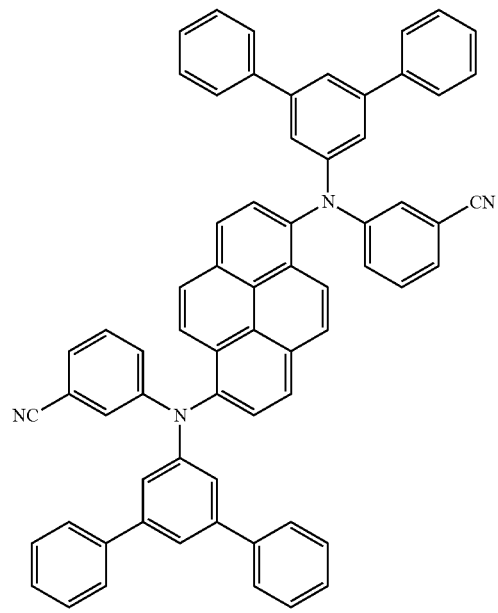
BD 23
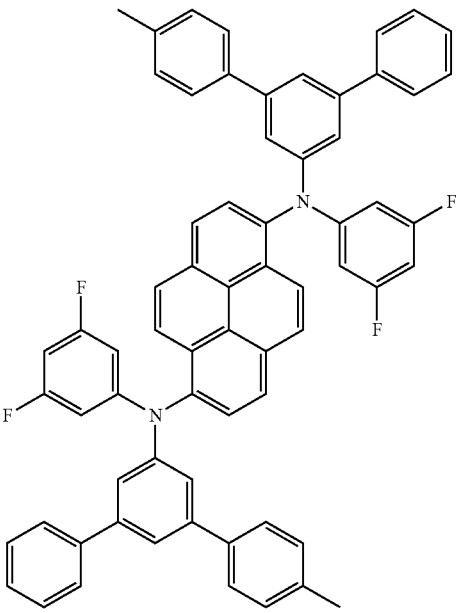
BD 25
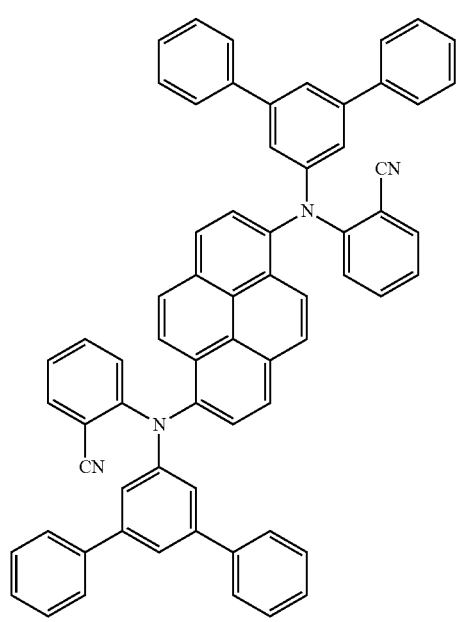
BD 24
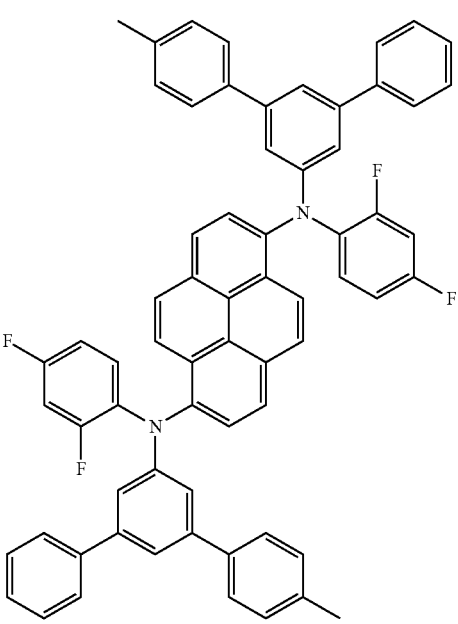
BD 26

BD 27
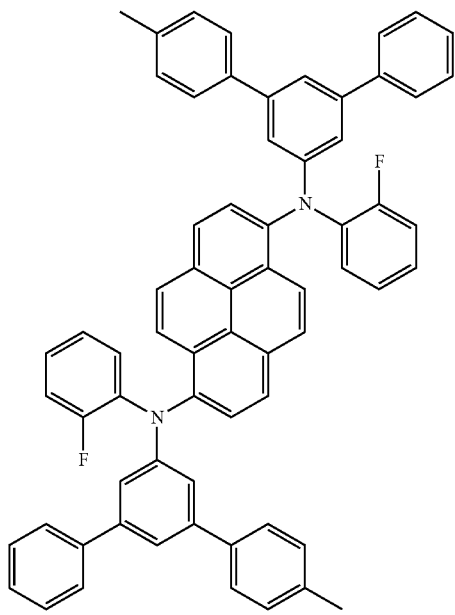
BD 28
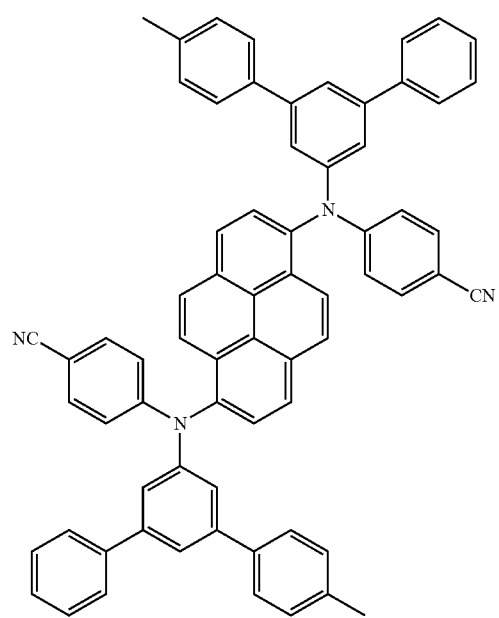
BD 29
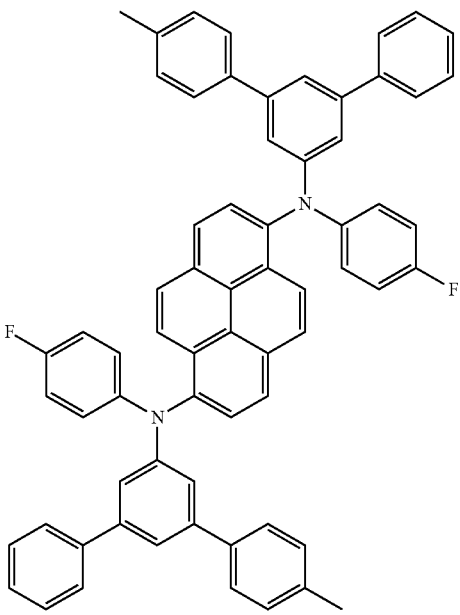
BD 30
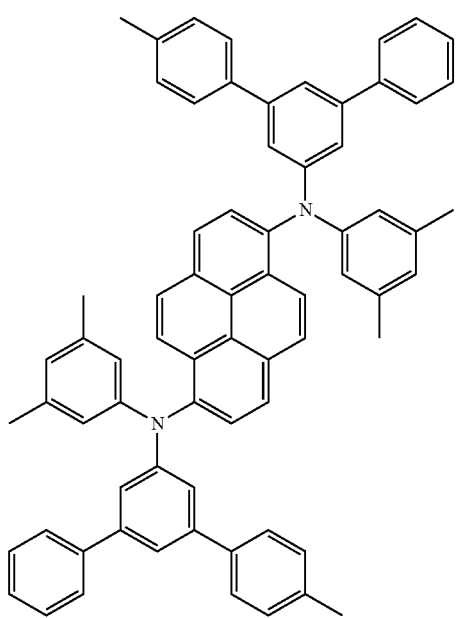

BD 31
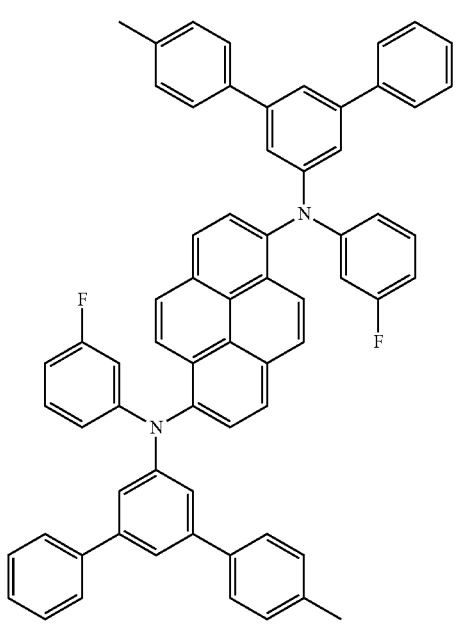
BD 32
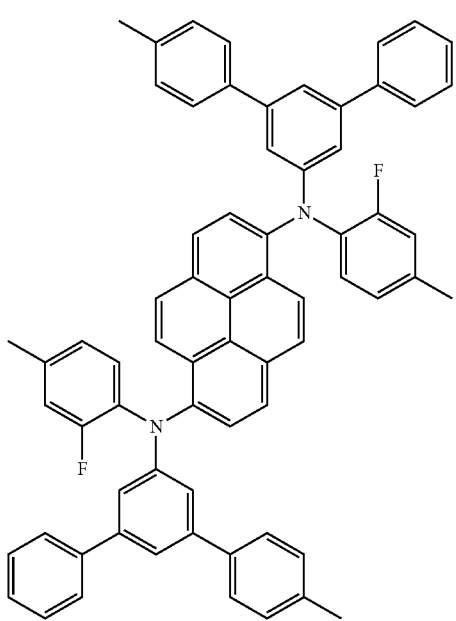
BD 33
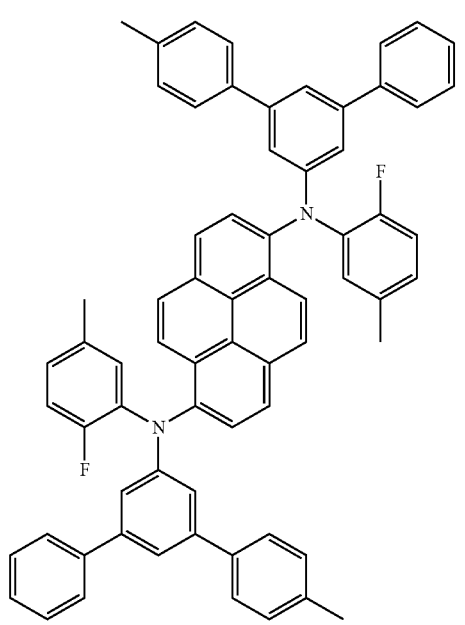
BD 34
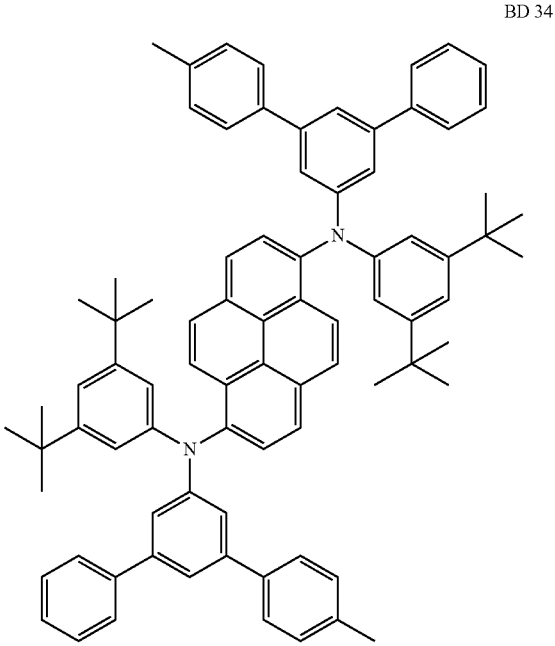

BD 35
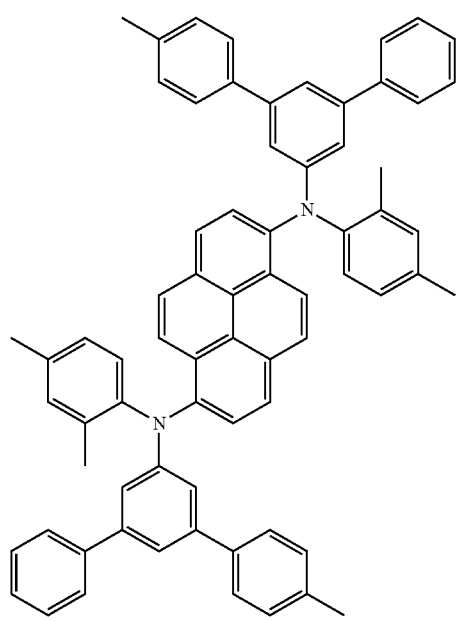
BD 36
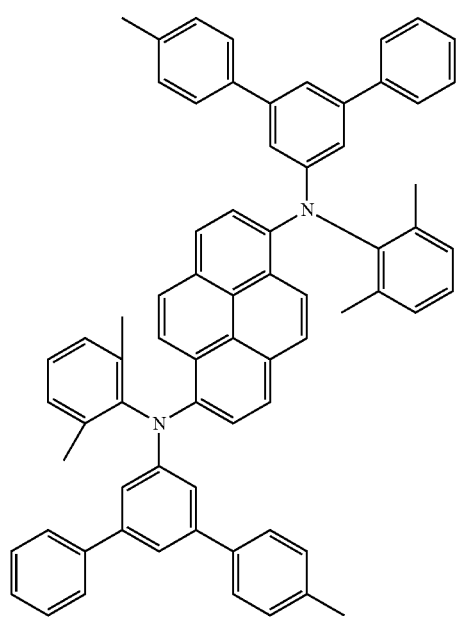
BD 37
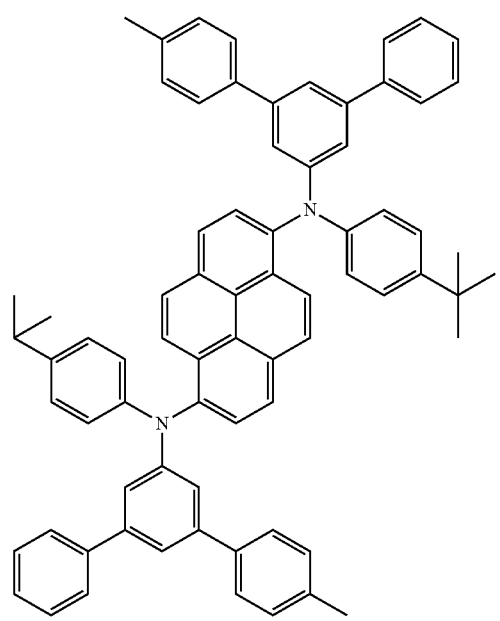
BD 38
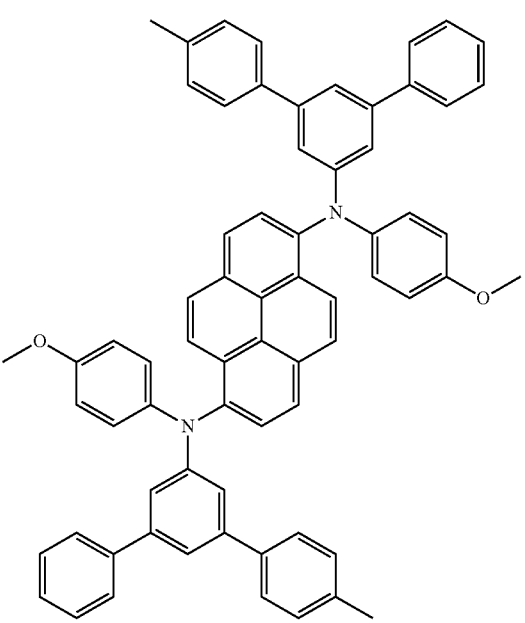

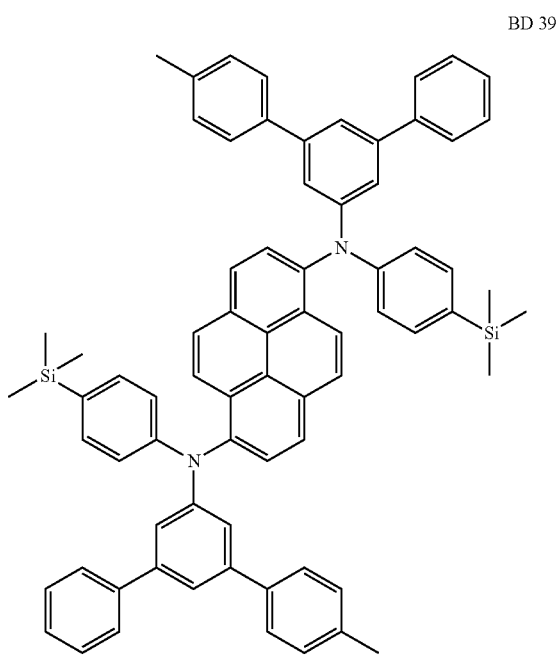
BD 39
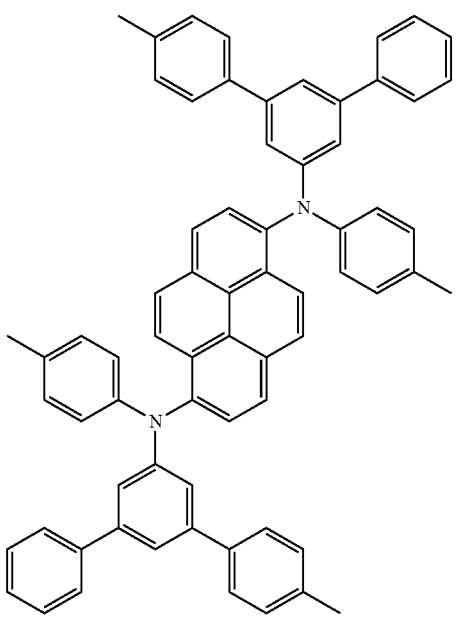
BD 41
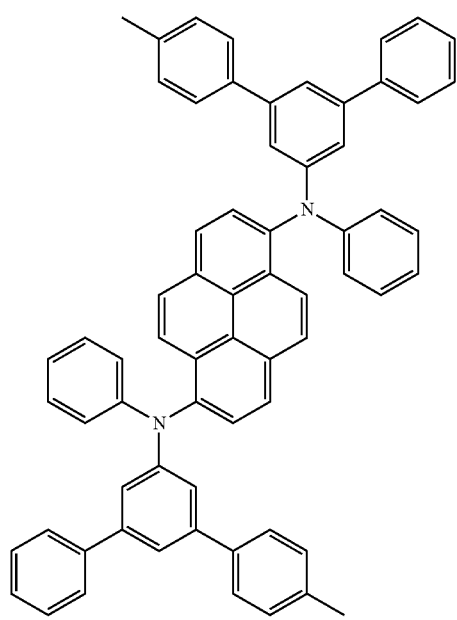
BD 40
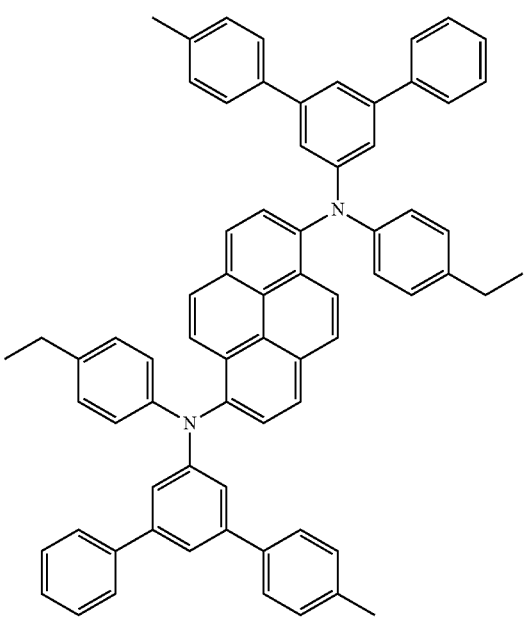
BD 42

BD 43
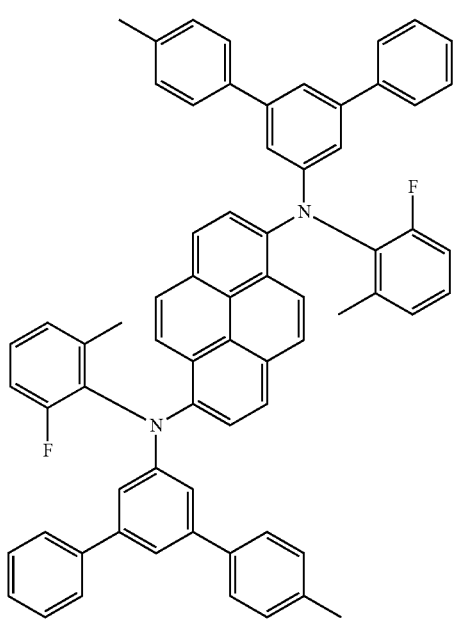
BD 44
BD 45
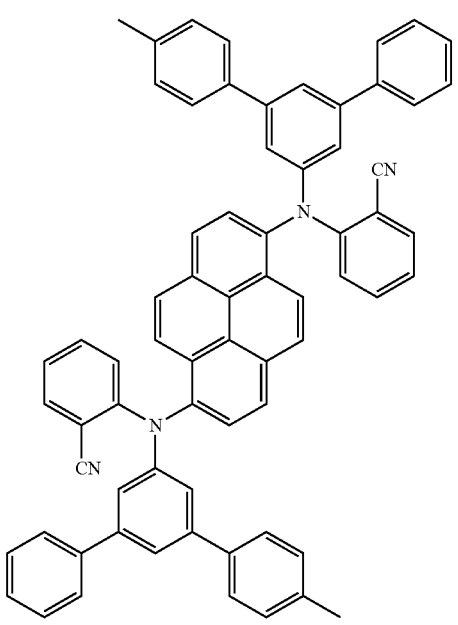
BD 46

-continued

BD 47

BD 48

BD 49

BD 50

BD 51
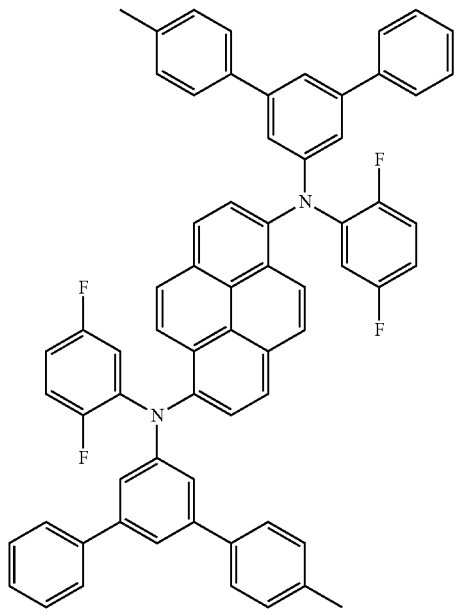
BD 52
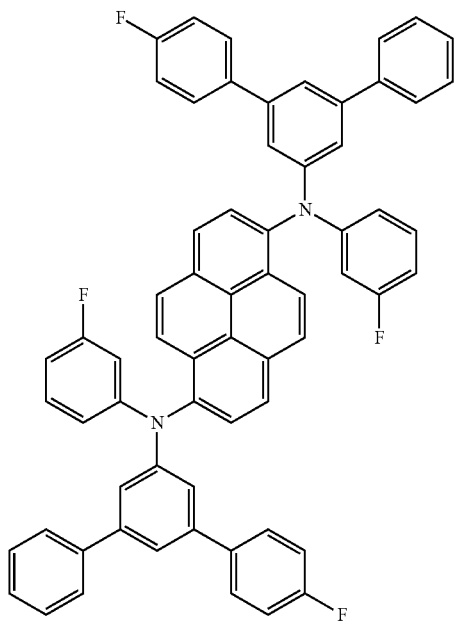
BD 53
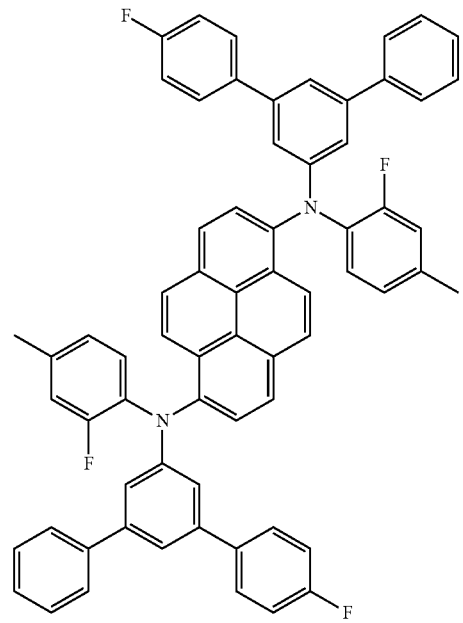
BD 54
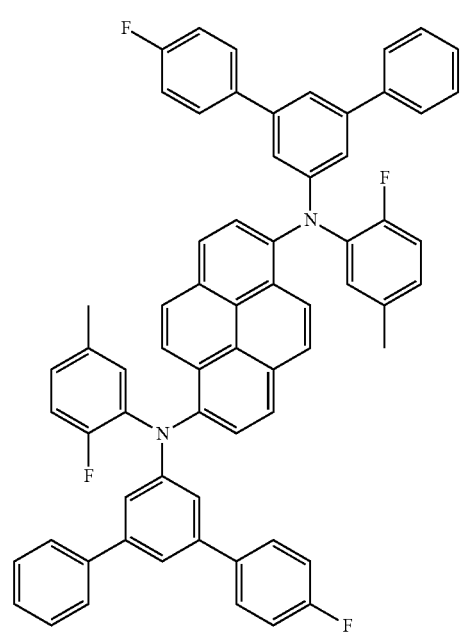

-continued
BD 55
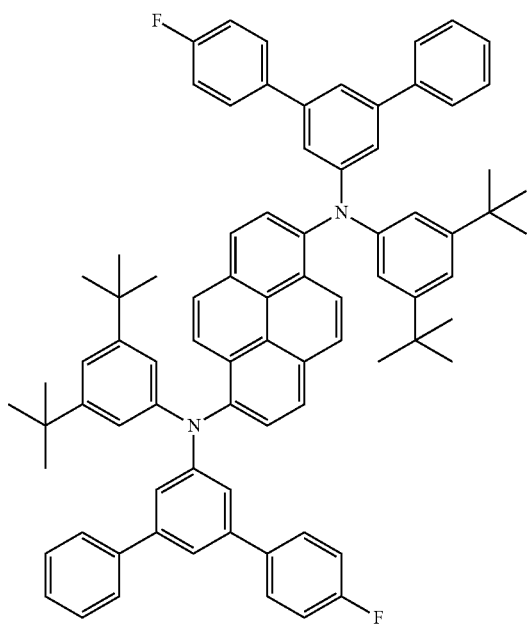
BD 57
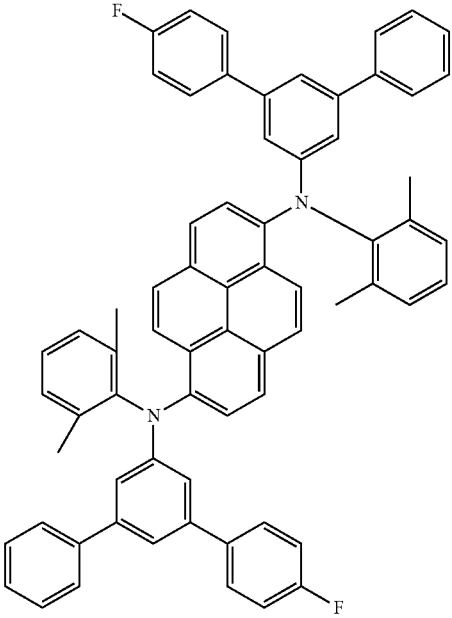
BD 56
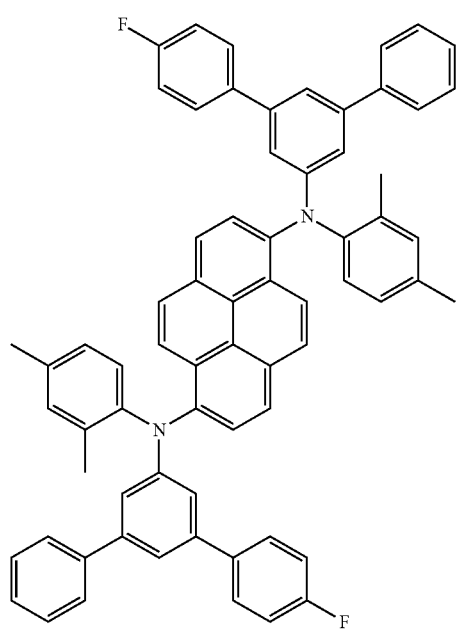
BD 58
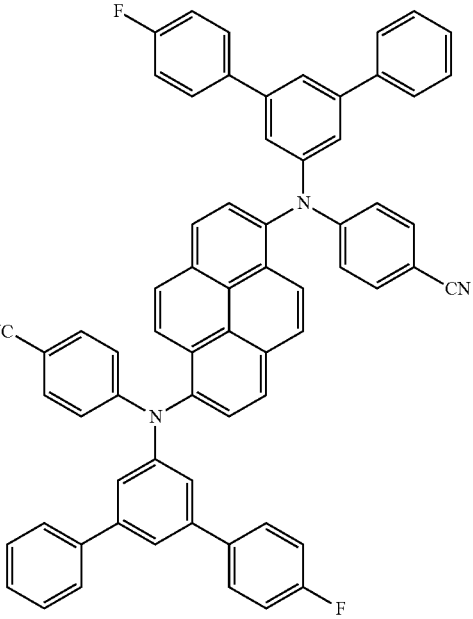

-continued
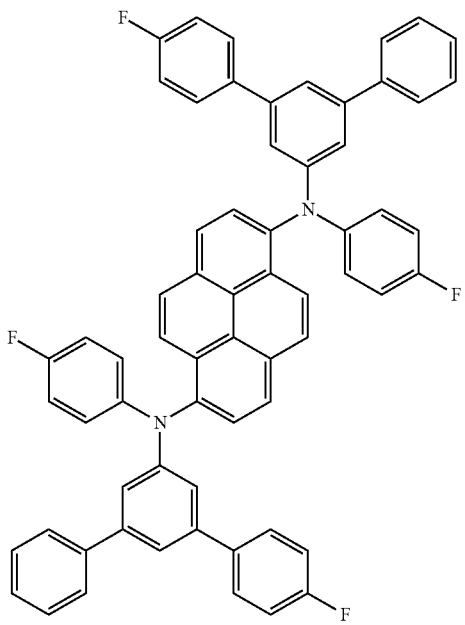
BD 59
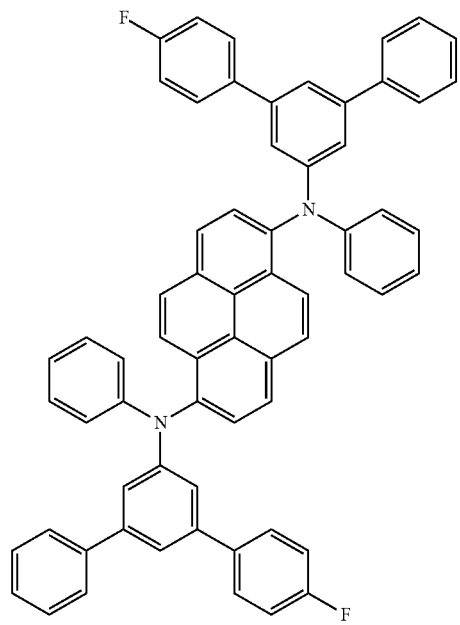
BD 61
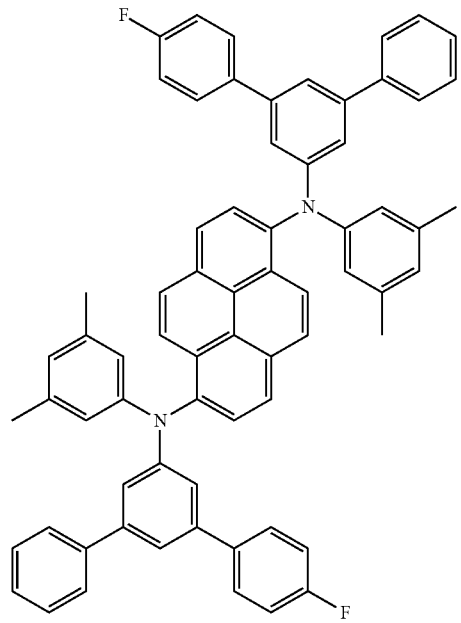
BD 60
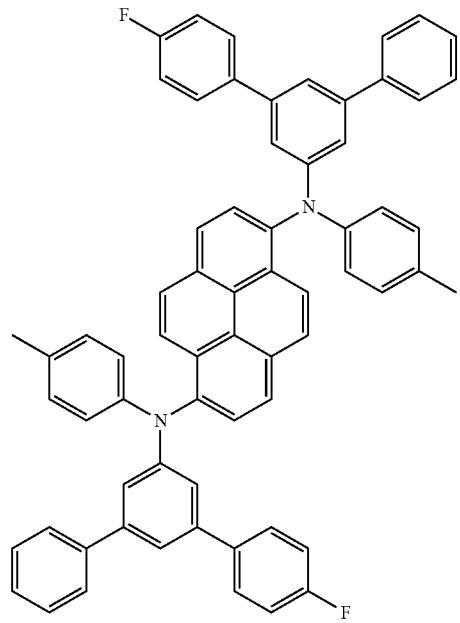
BD 62

BD 63
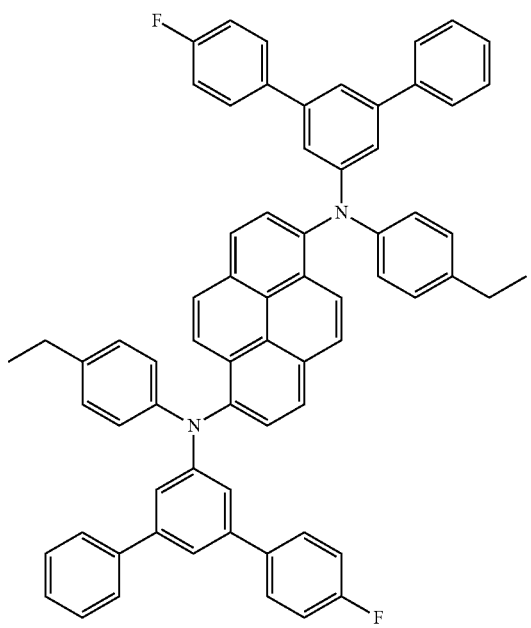
BD 64
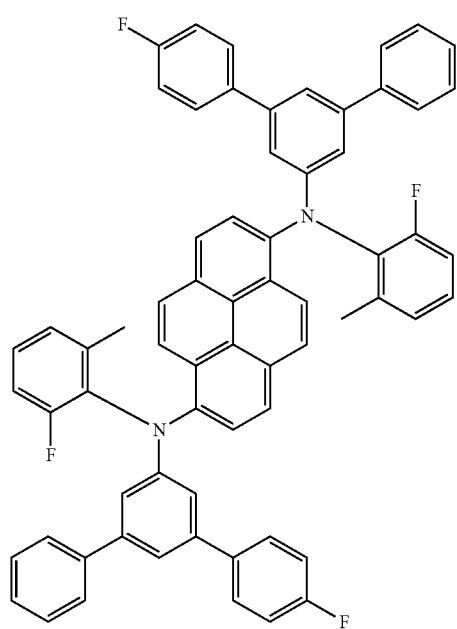
BD 65
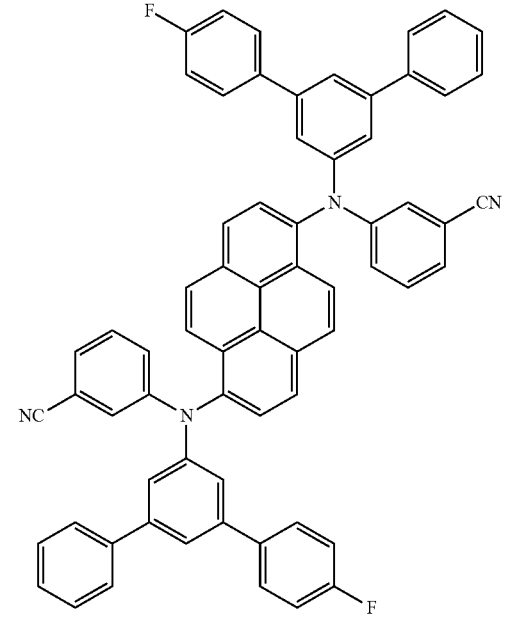
BD 66
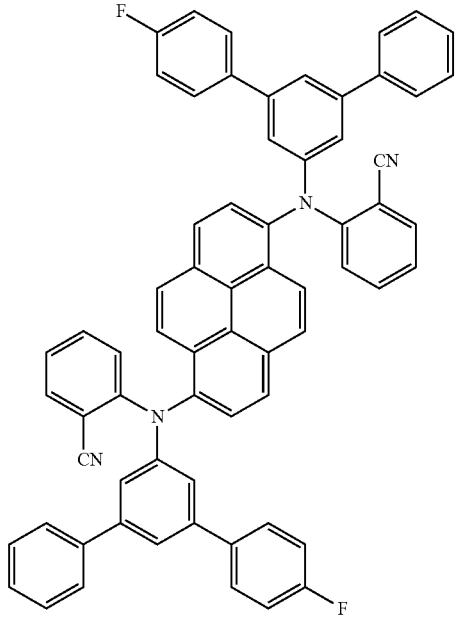

BD 67
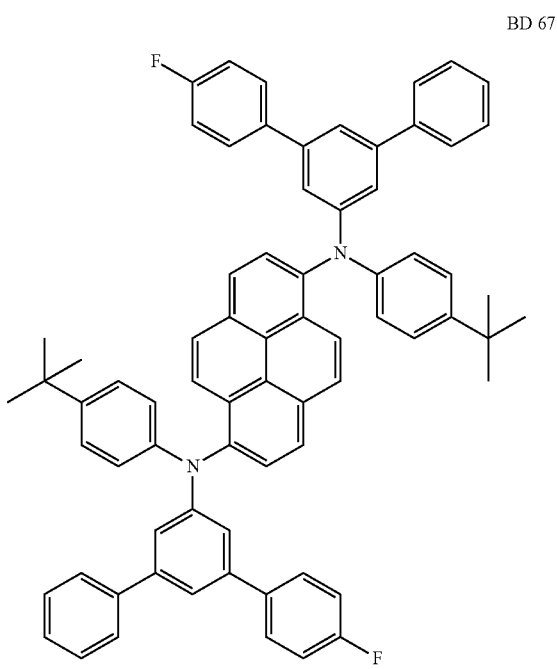
BD 69
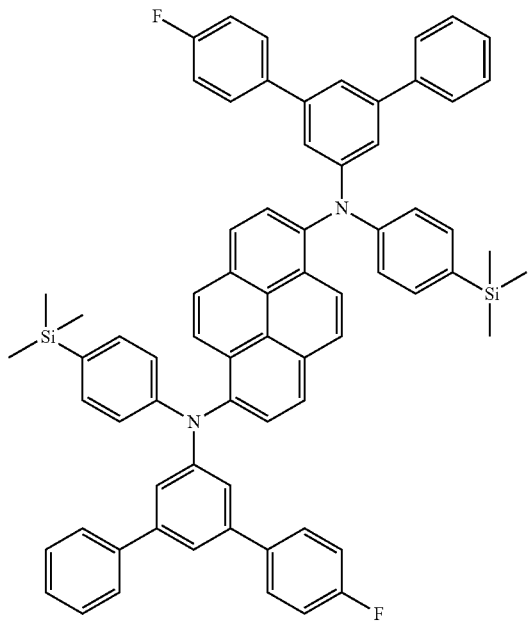
BD 68
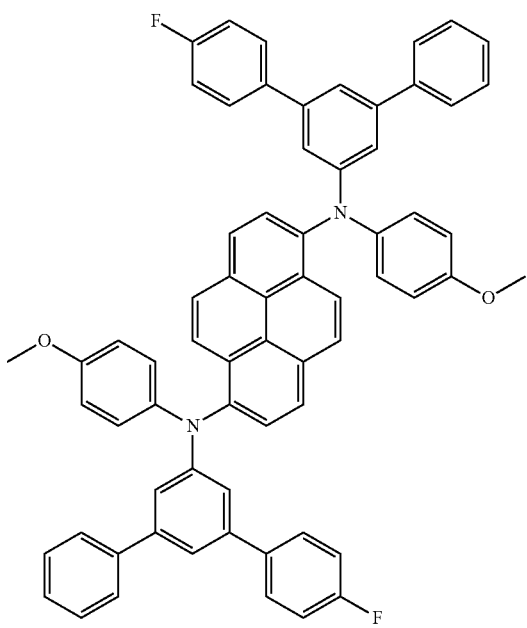
BD 70
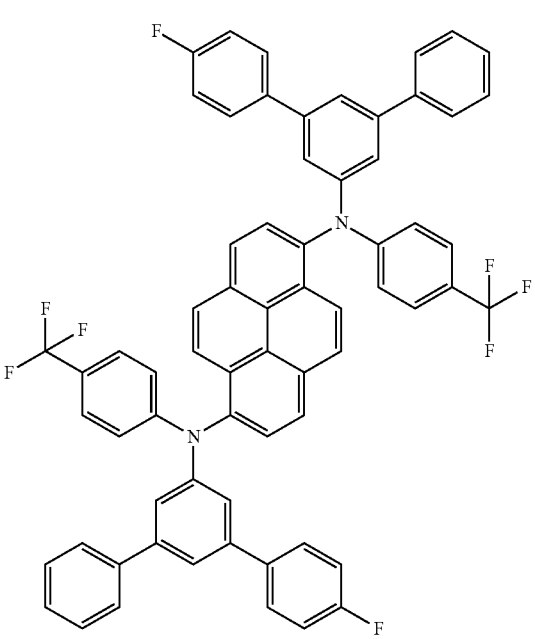

BD 71
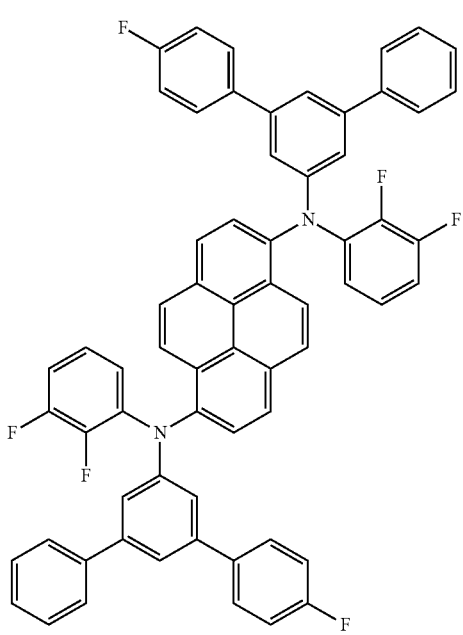
BD 72
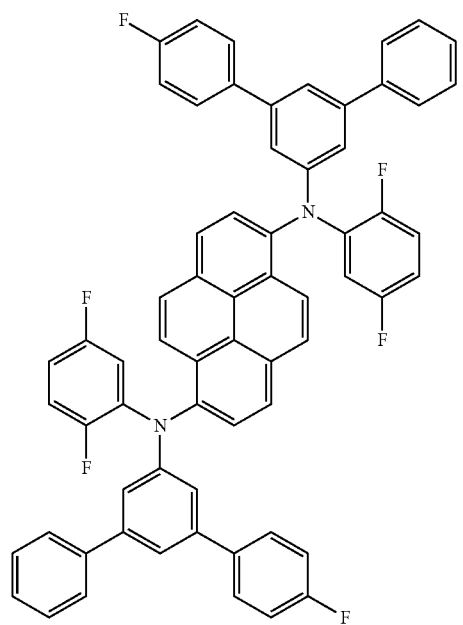
BD 73
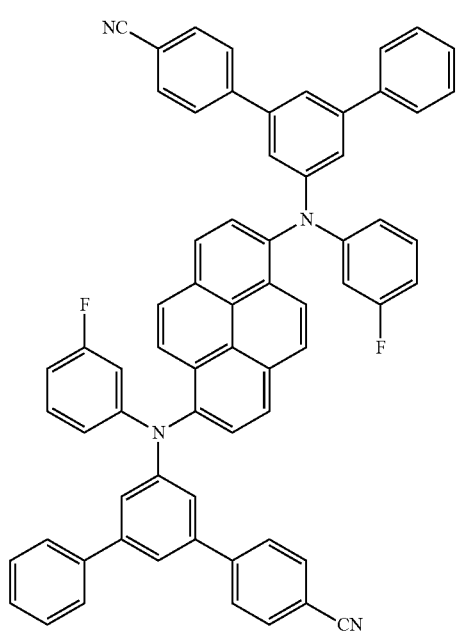
BD 74

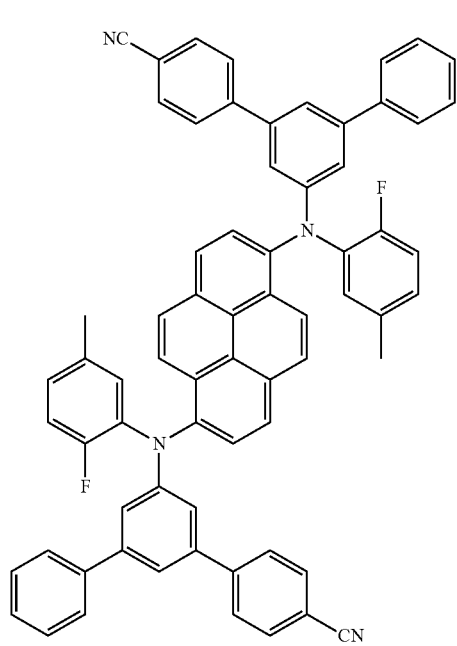
BD 75
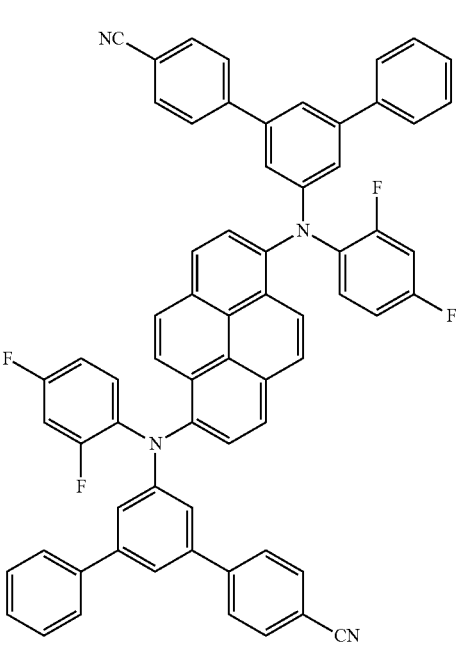
BD 77
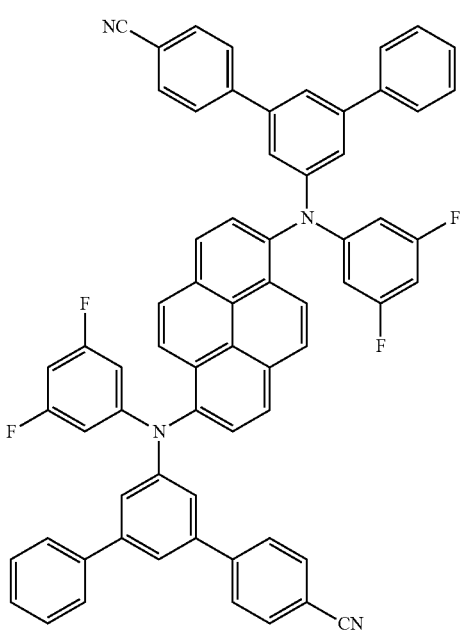
BD 76
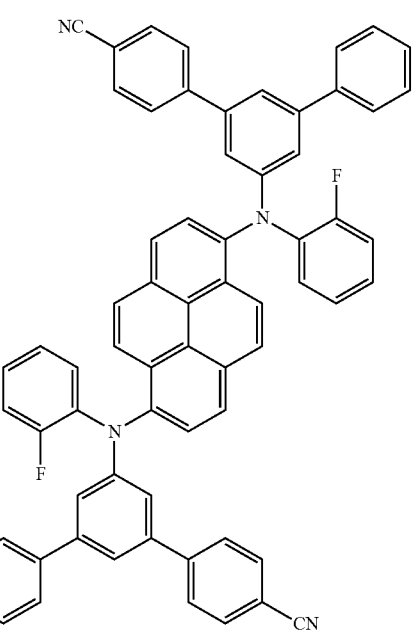
BD 78

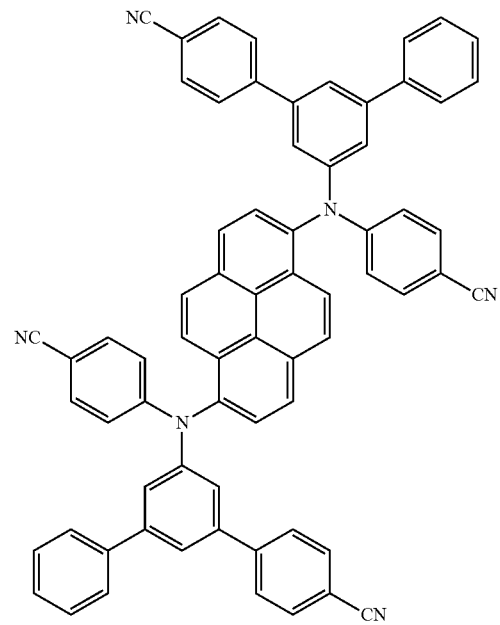
BD 79
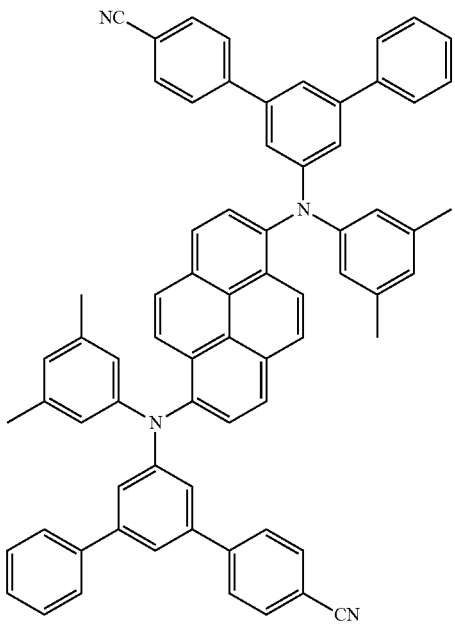
BD 81
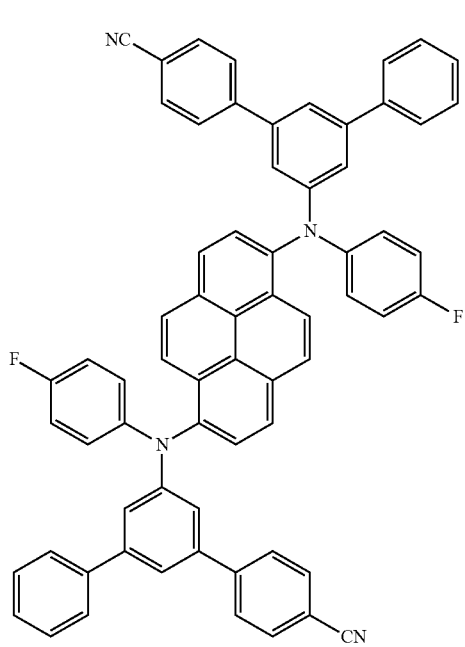
BD 80
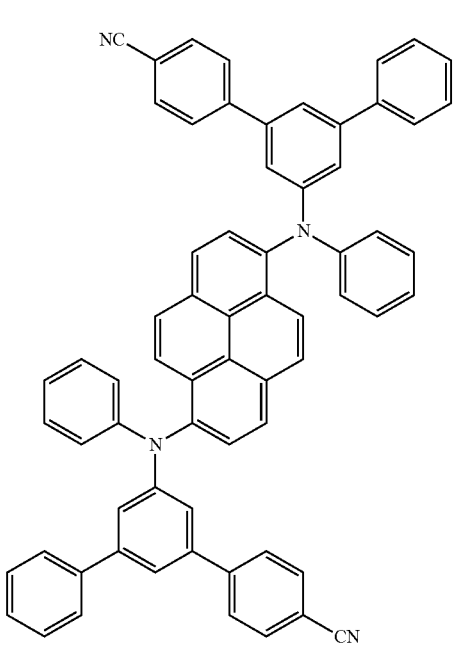
BD 82

45
-continued
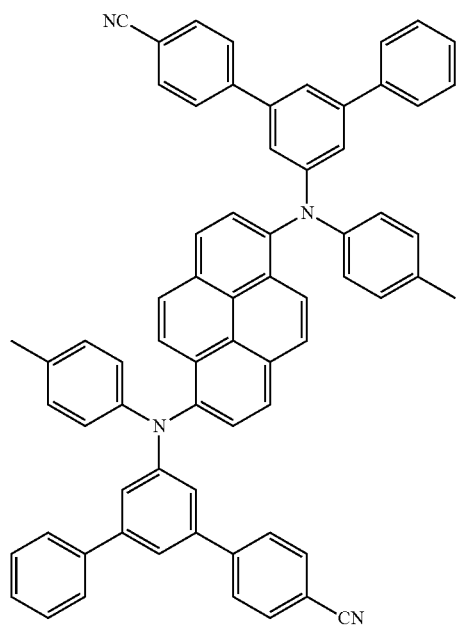
BD 83
BD 84
46
-continued
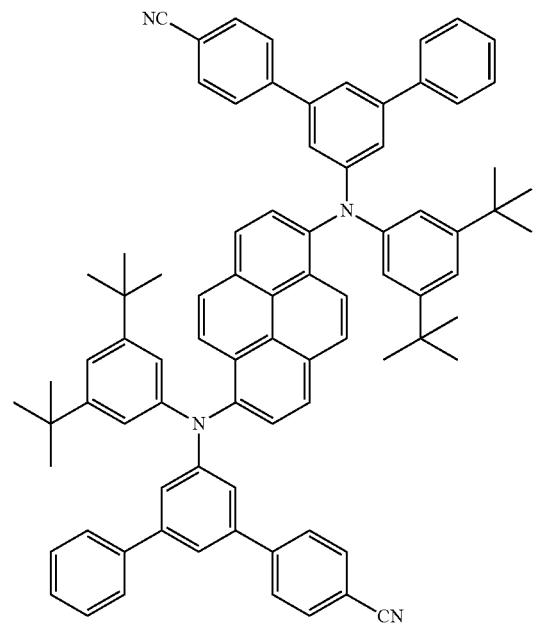
BD 85
BD 86

BD 87
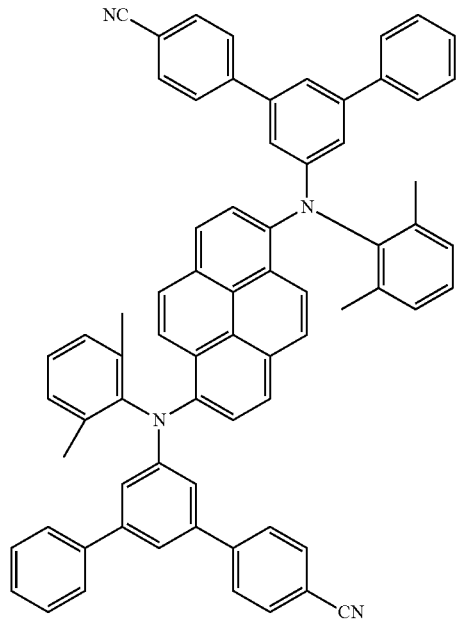
BD 89
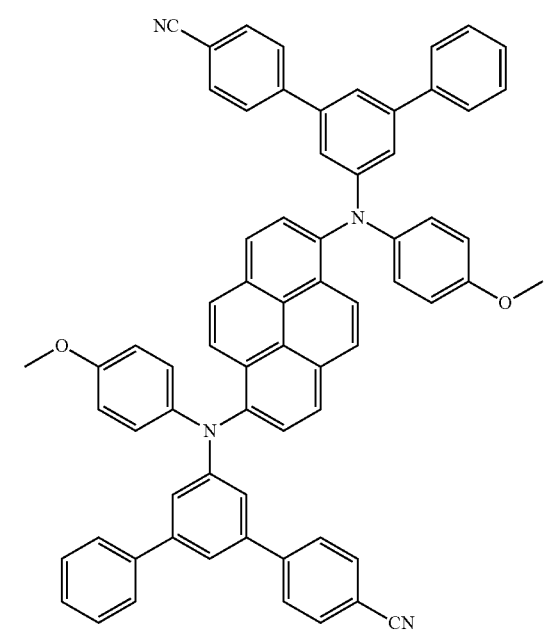
BD 88
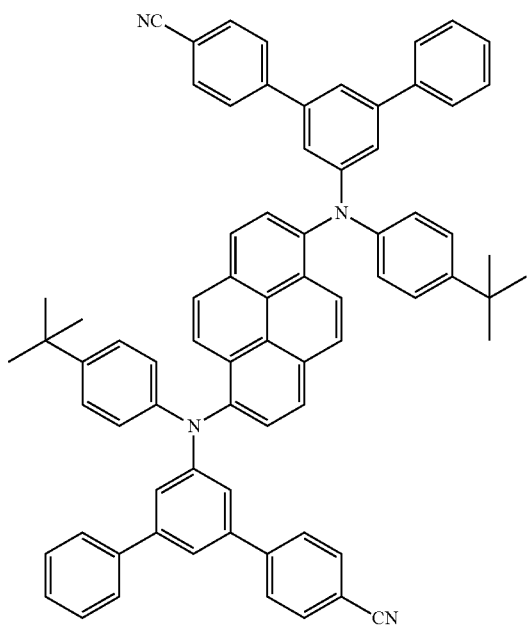
BD 90
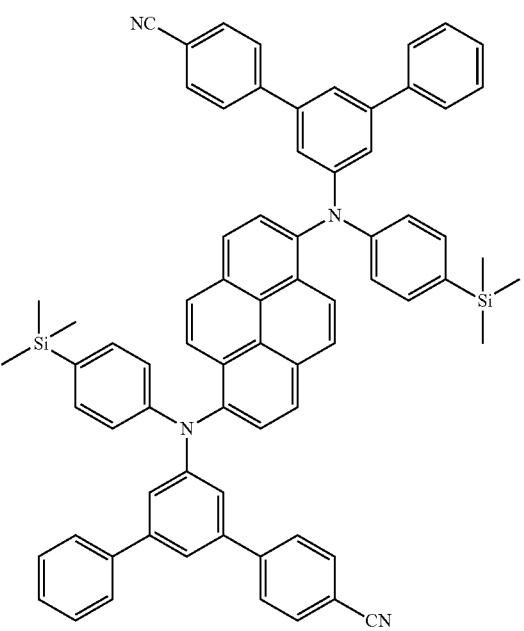

BD 91
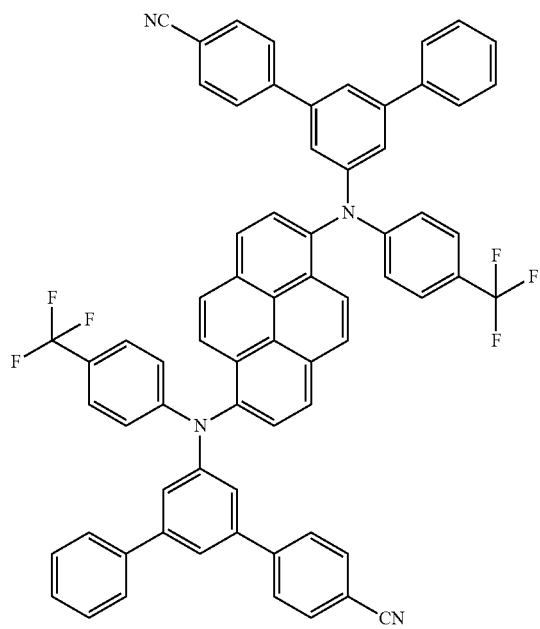
BD 93
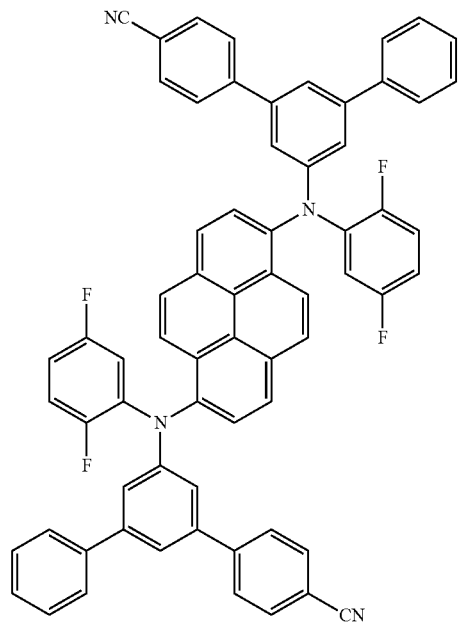
BD 92
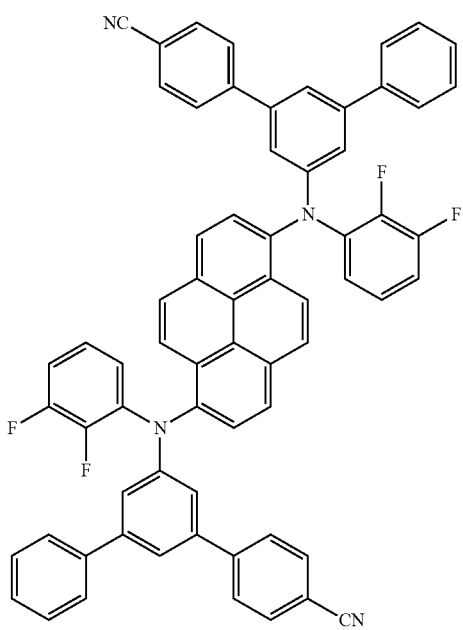
BD 94
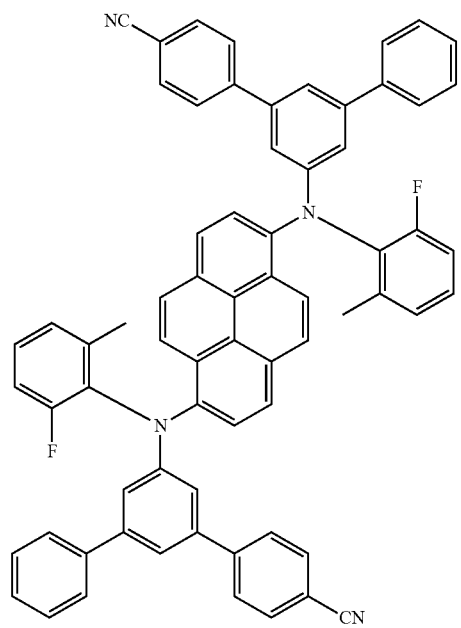

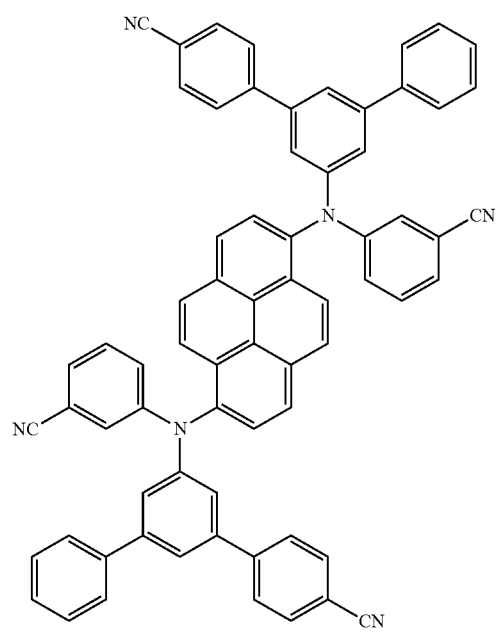
BD 95
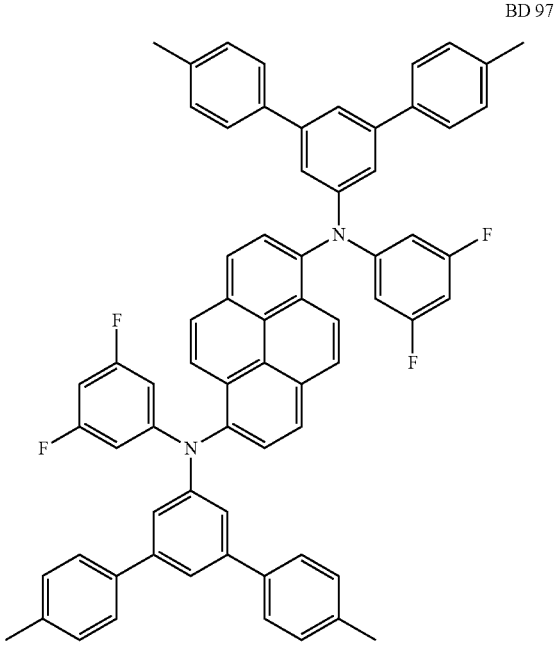
BD 97
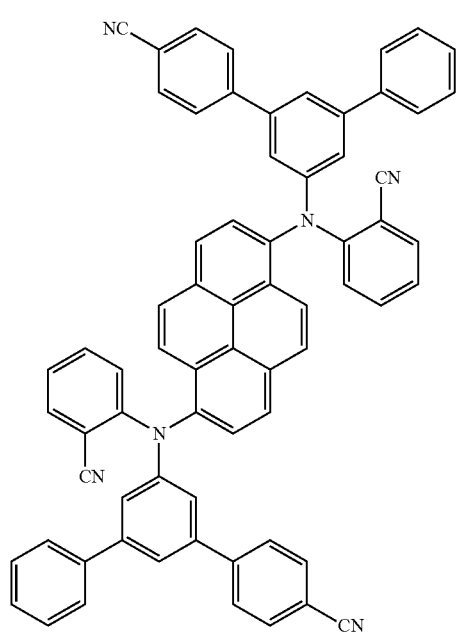
BD 96
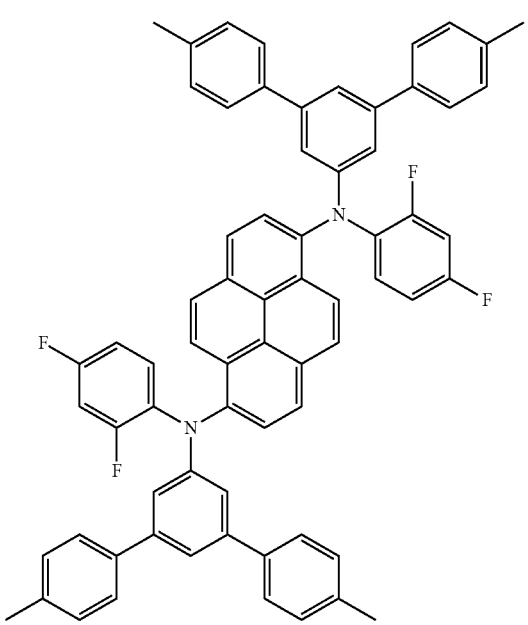
BD 98

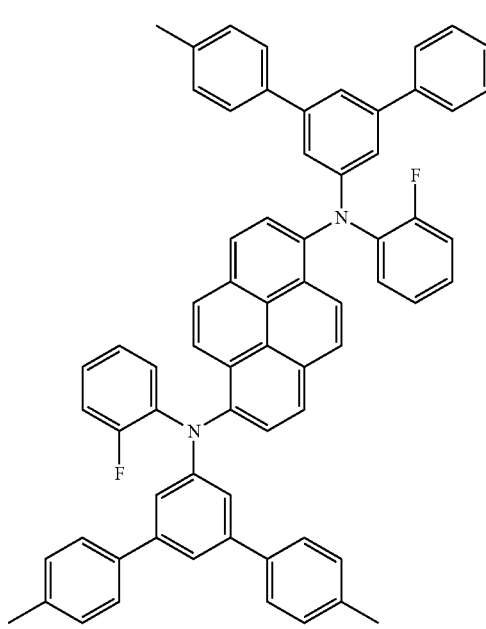
BD 99
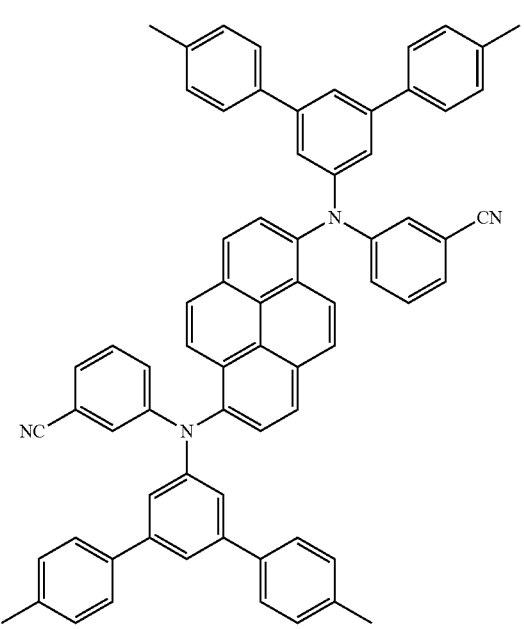
BD 101
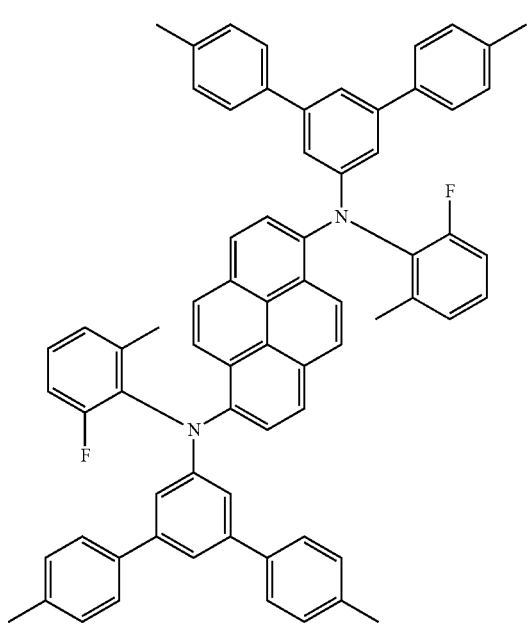
BD 100
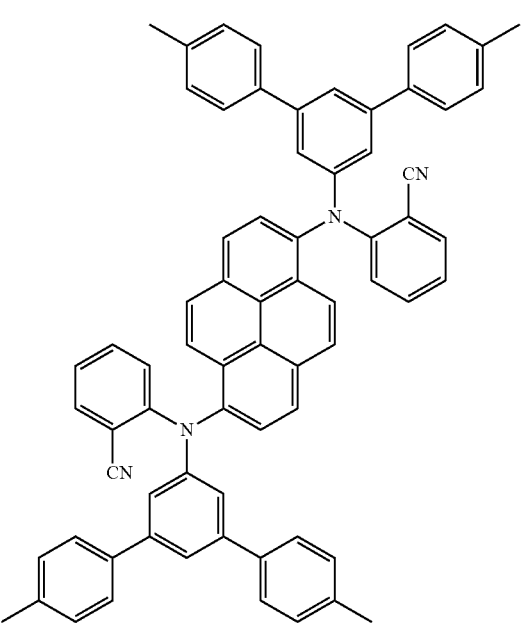
BD 102

BD 103
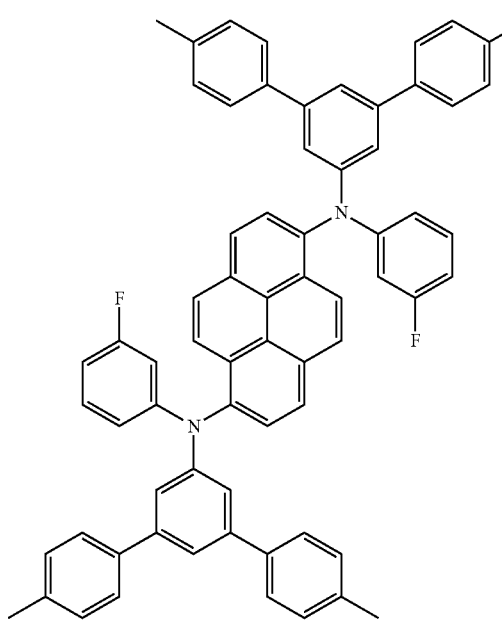
BD 104
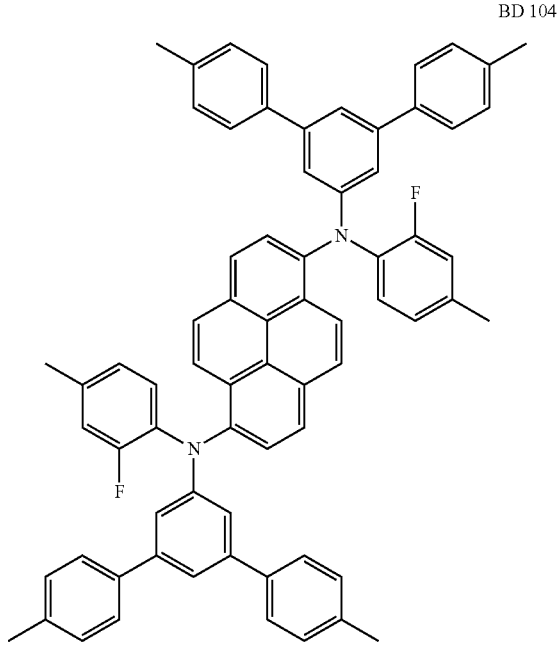
BD 105
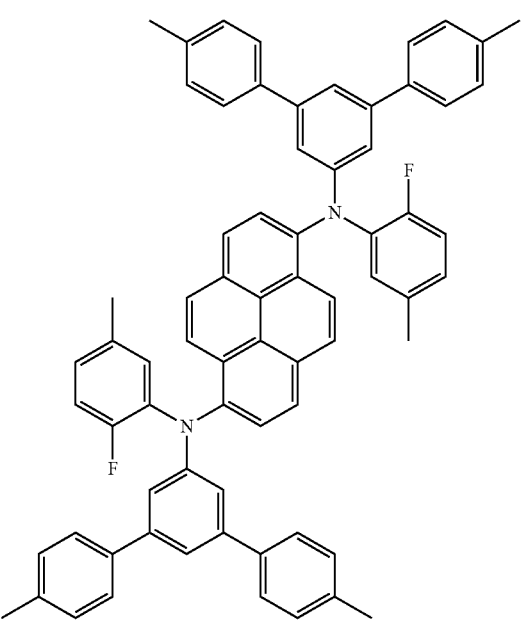
BD 106
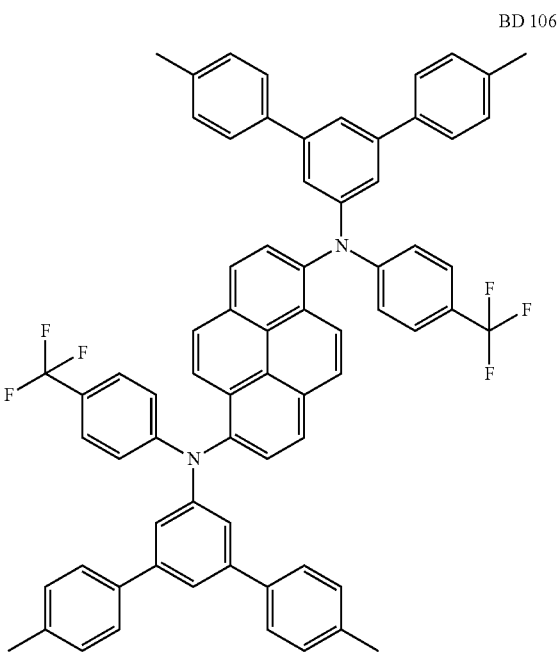

BD 107
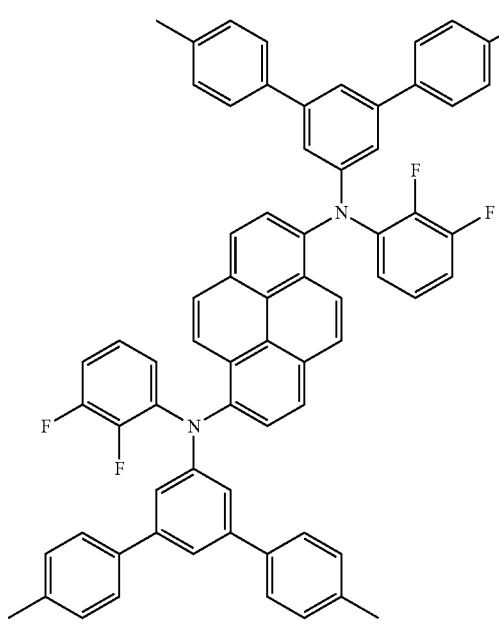
BD 109
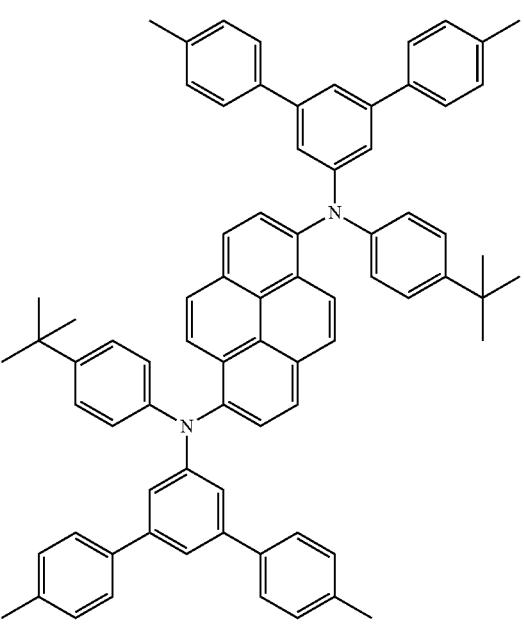
BD 108
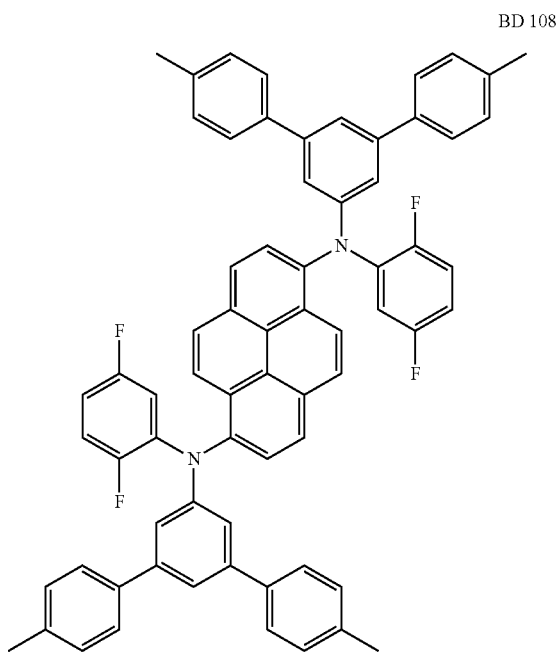
BD 110

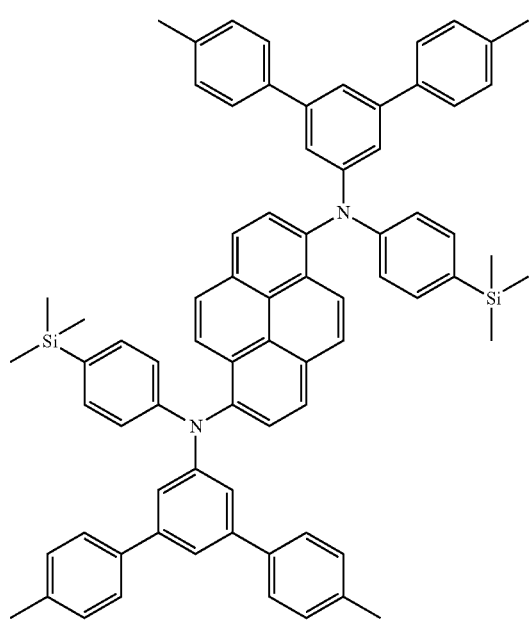
BD 111
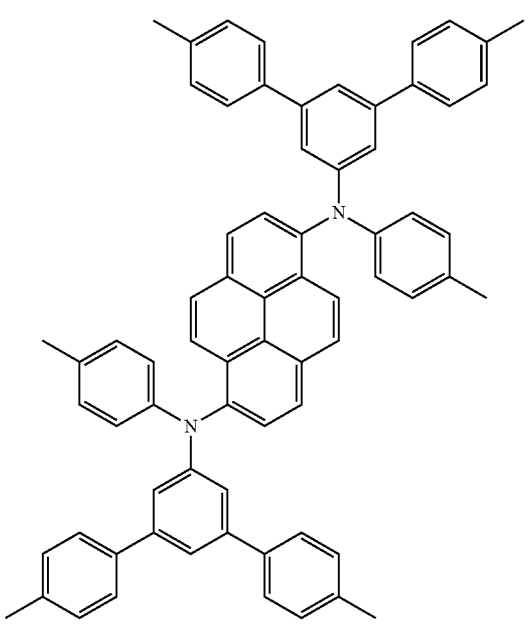
BD 113
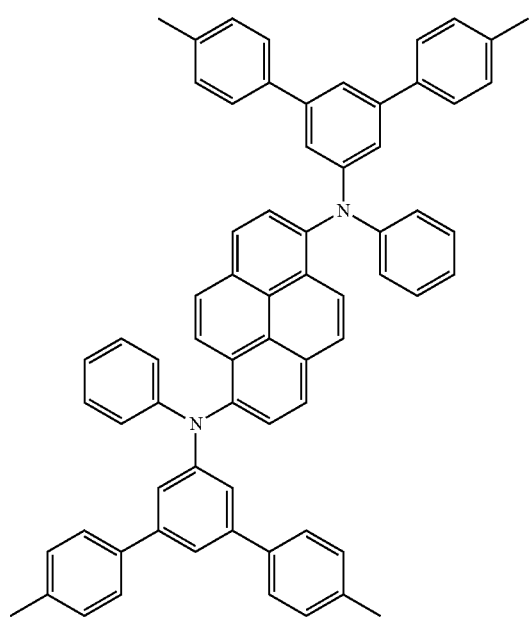
BD 112
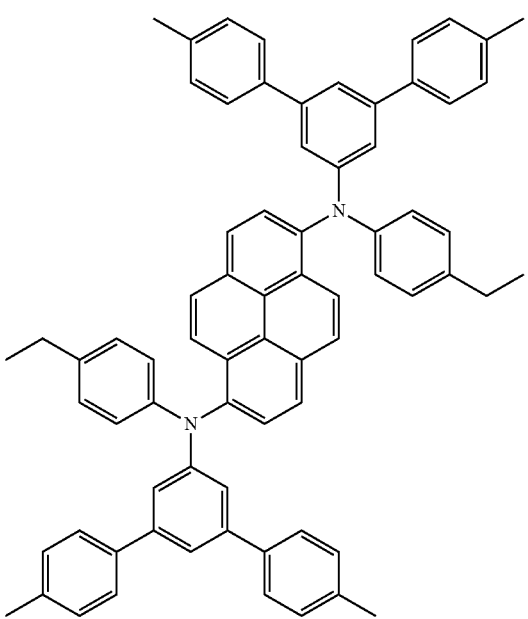
BD 114

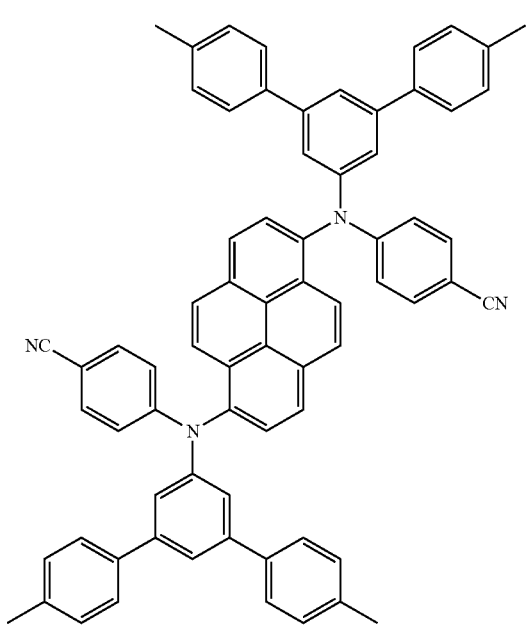
BD 115
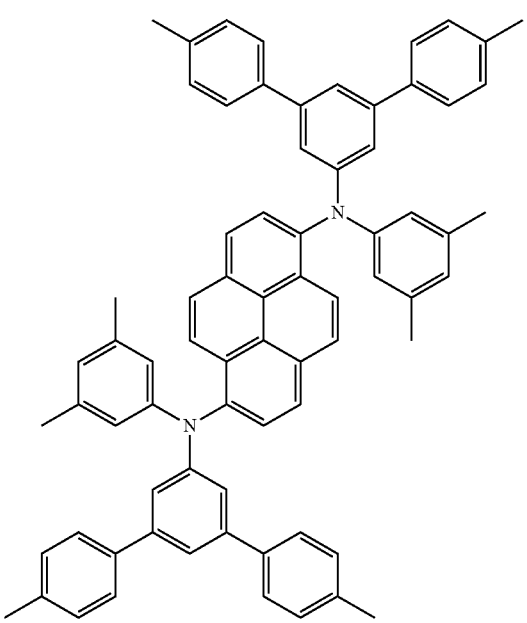
BD 117
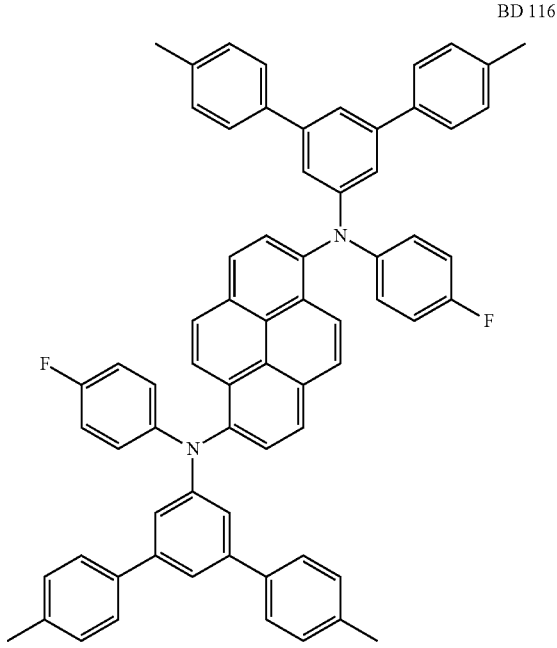
BD 116
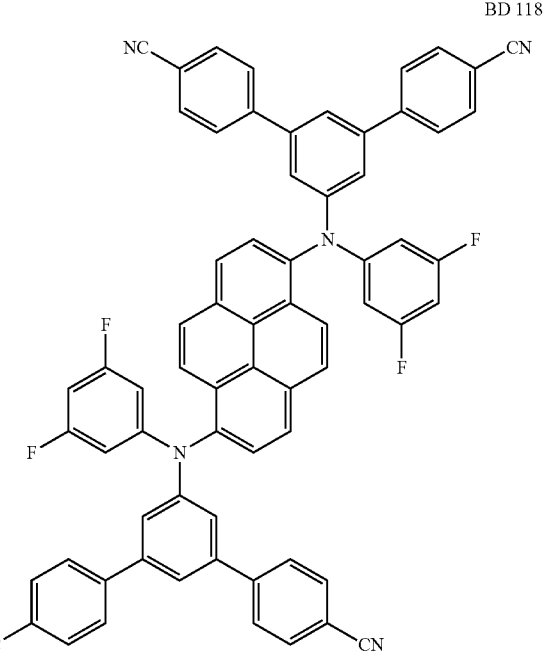
BD 118

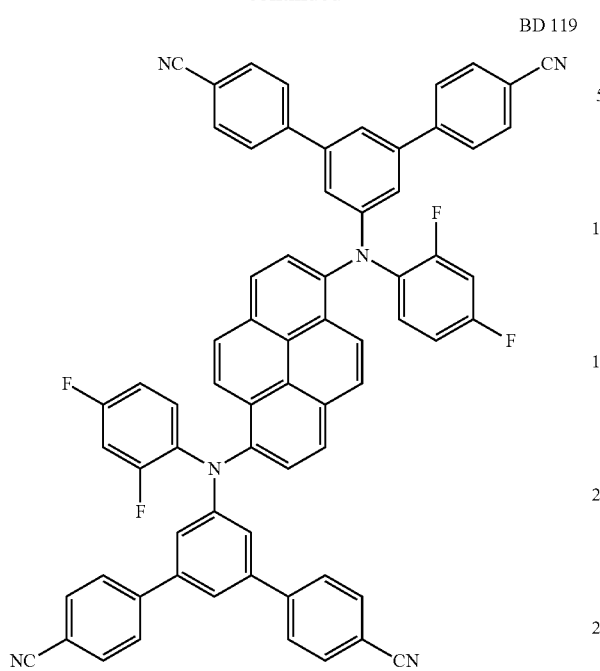
BD 119
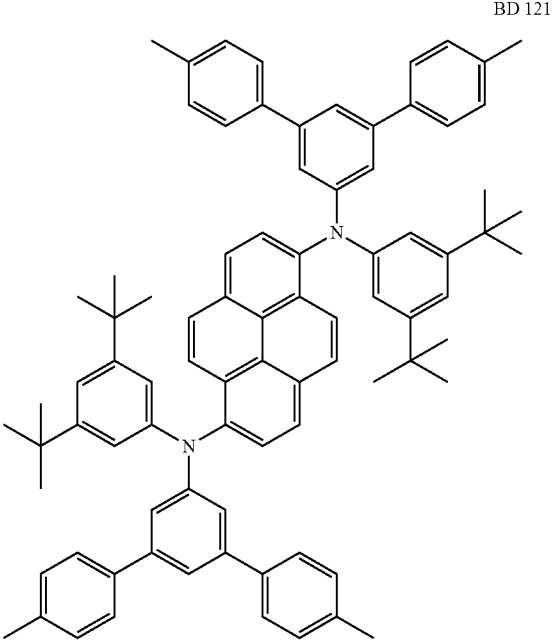
BD 121
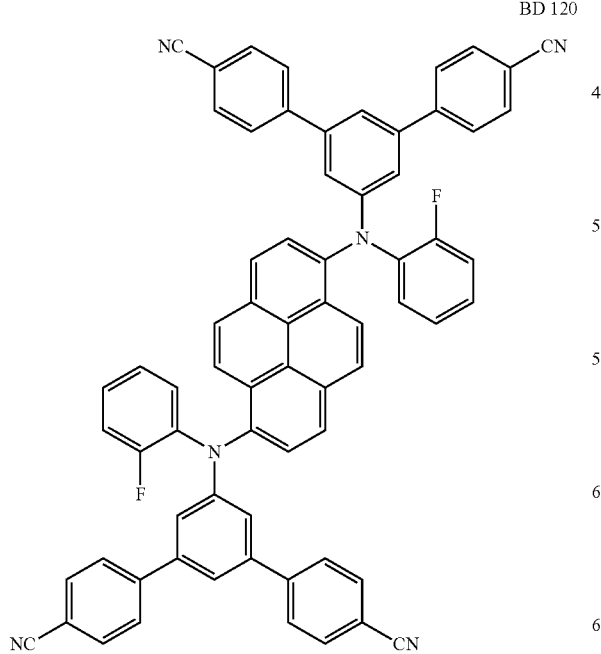
BD 120
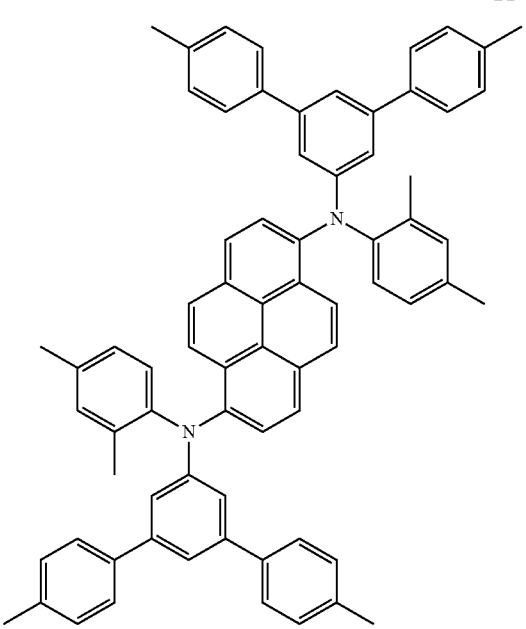
BD 122

BD 123
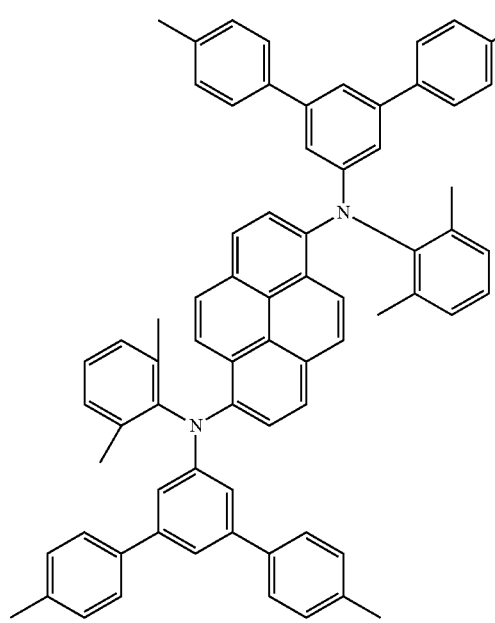
BD 125
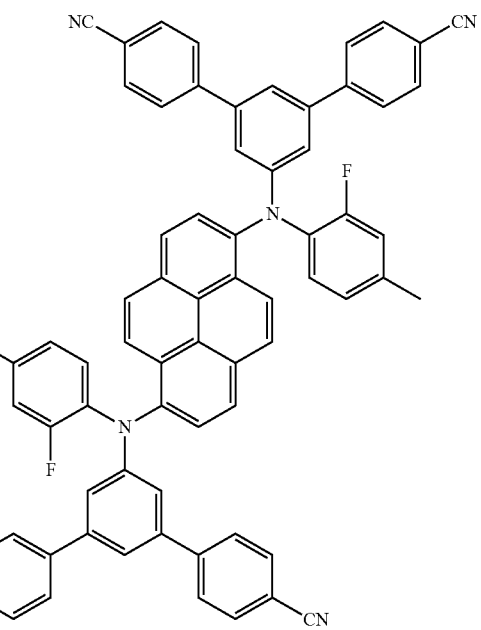
BD 124
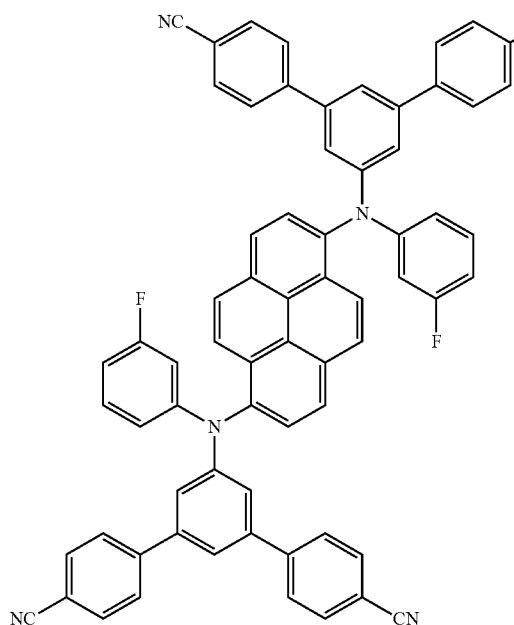
BD 126
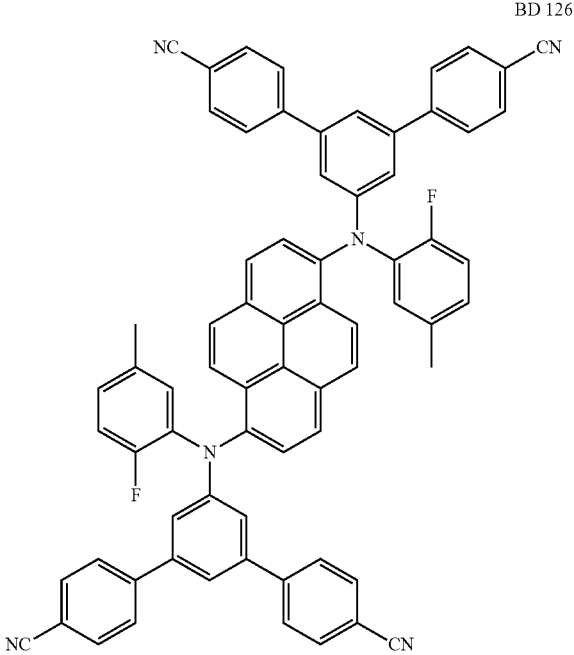

BD 127
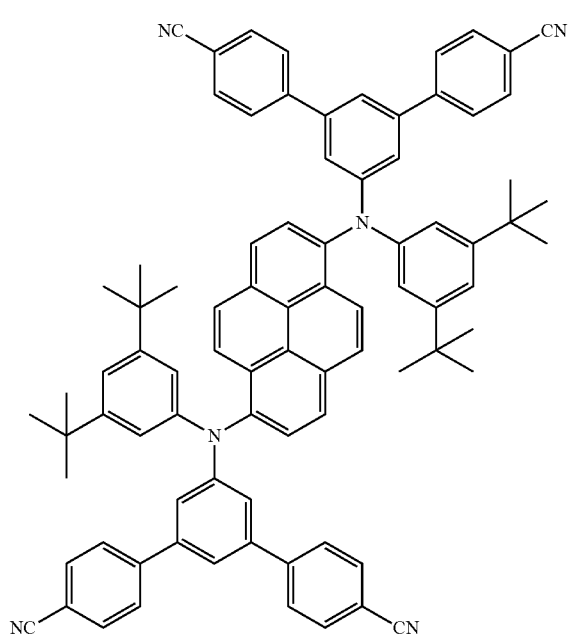
BD 129
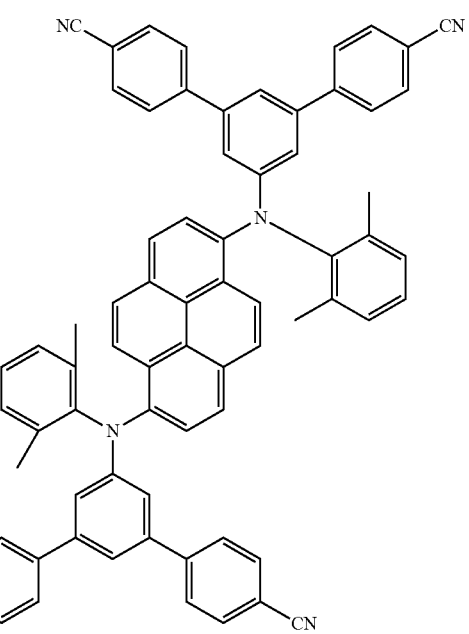
BD 128
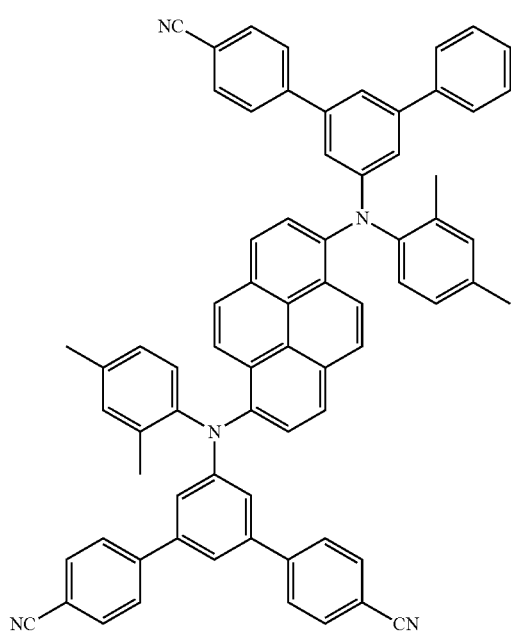
BD 130
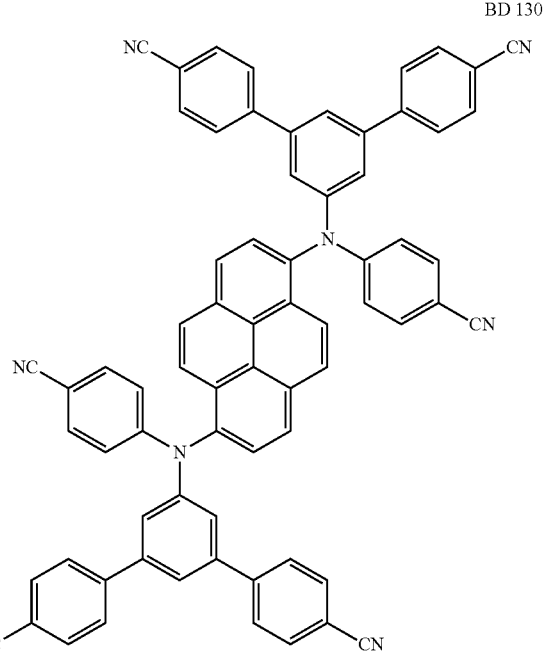

-continued
BD 131
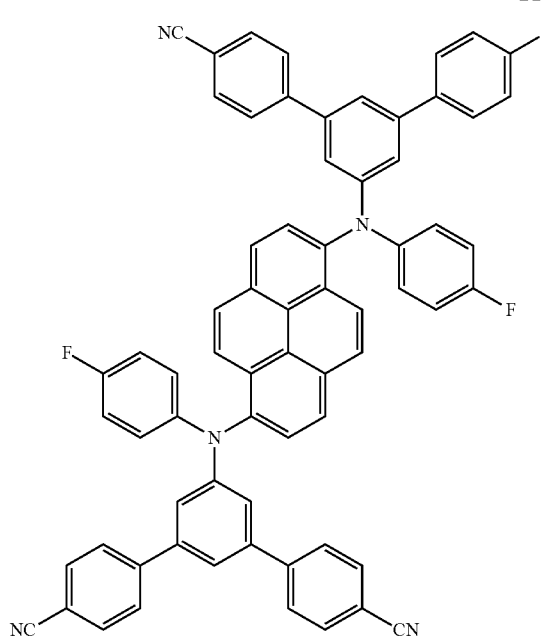
BD 133
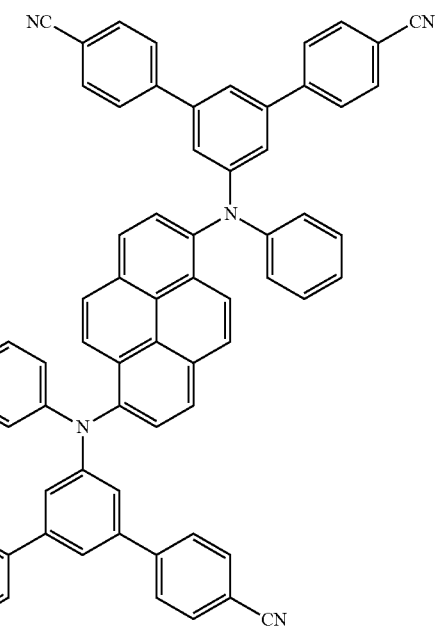
BD 132
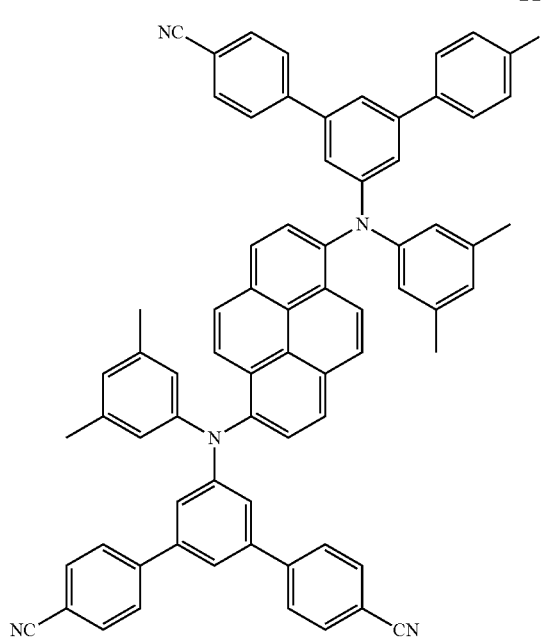
BD 134
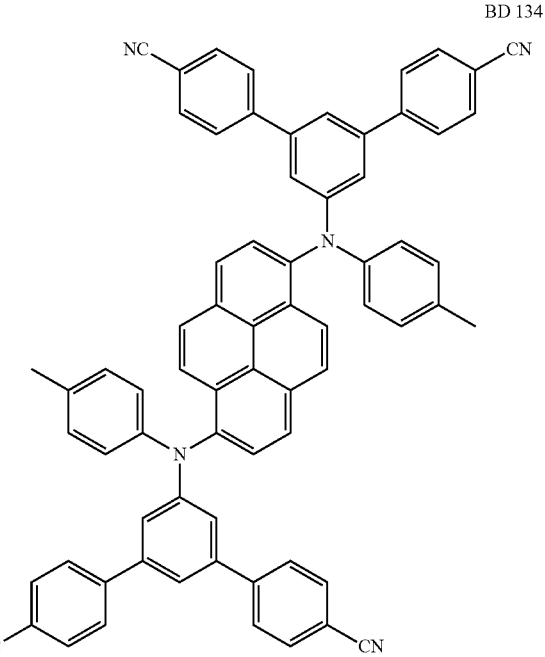

BD 135
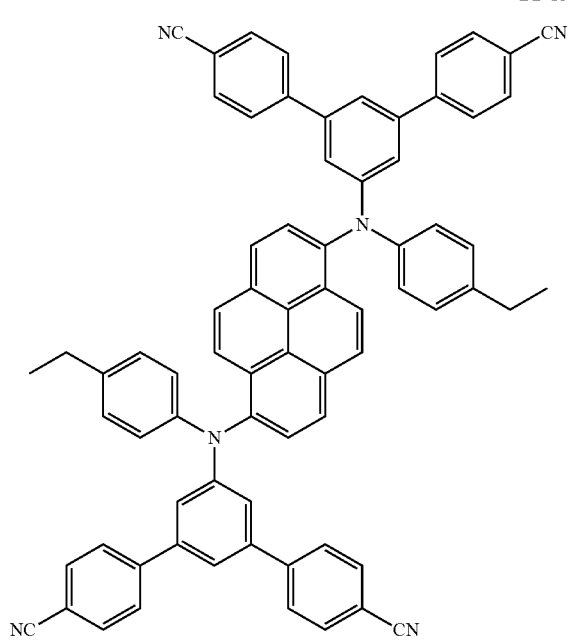
BD 137
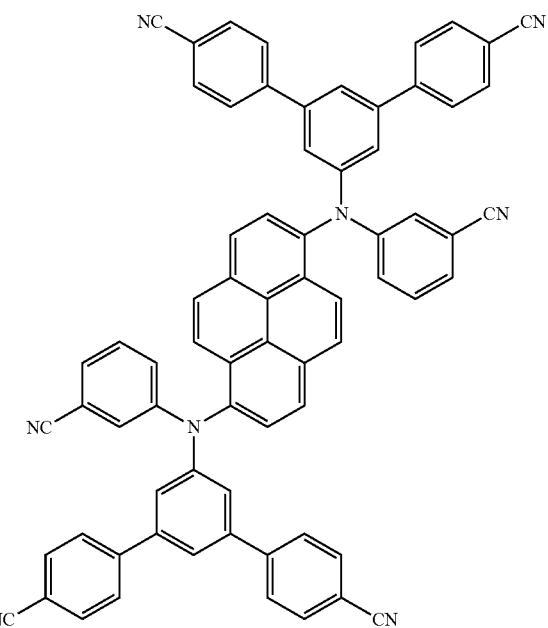
BD 136
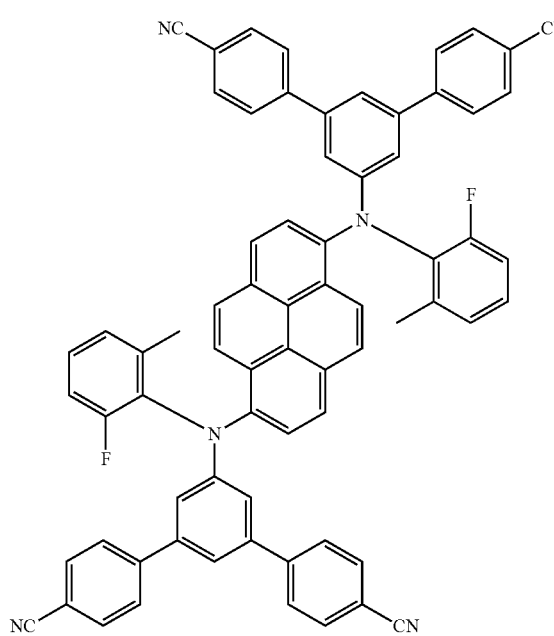
BD 138
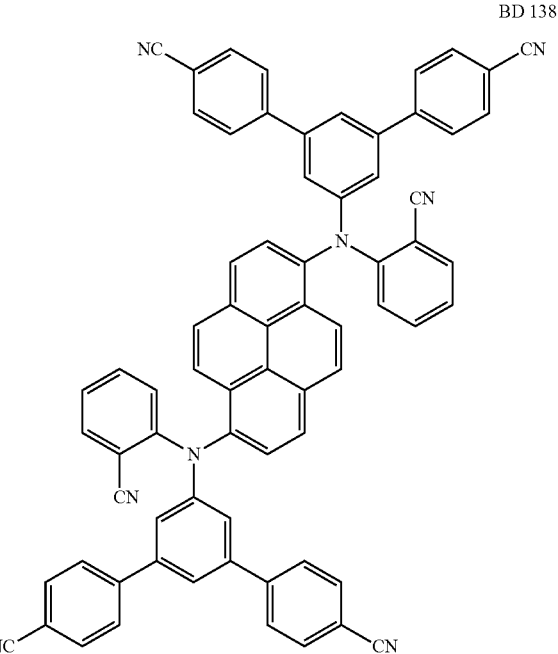

-continued

BD139

BD140

BD141

BD142

-continued
BD 143
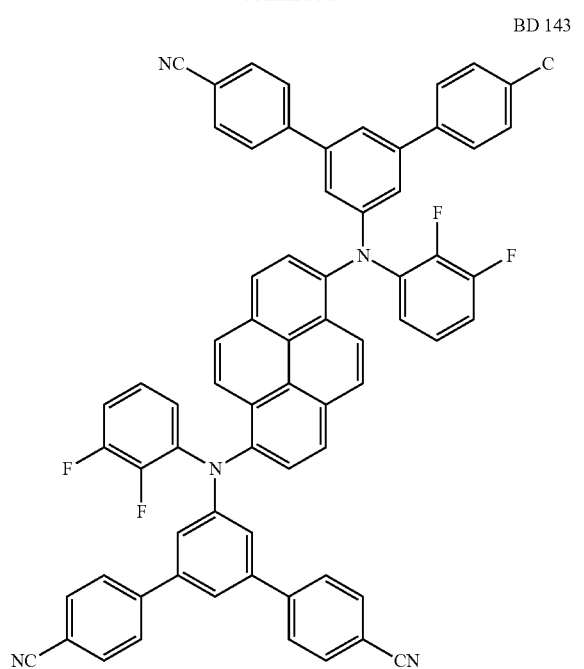
BD 144
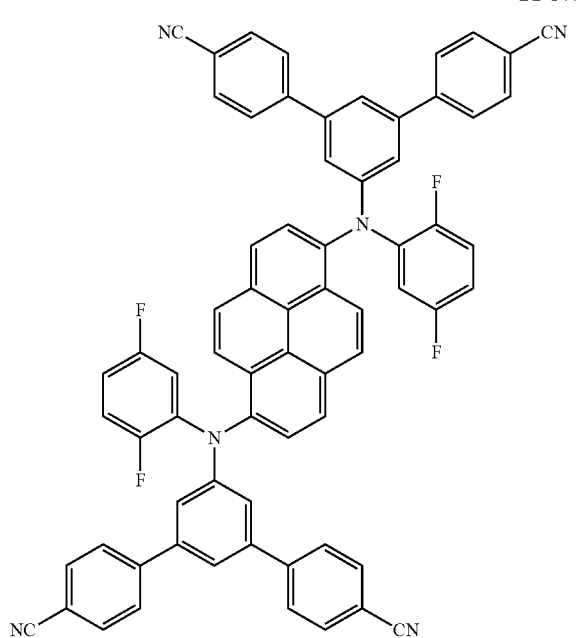
-continued
BD 145
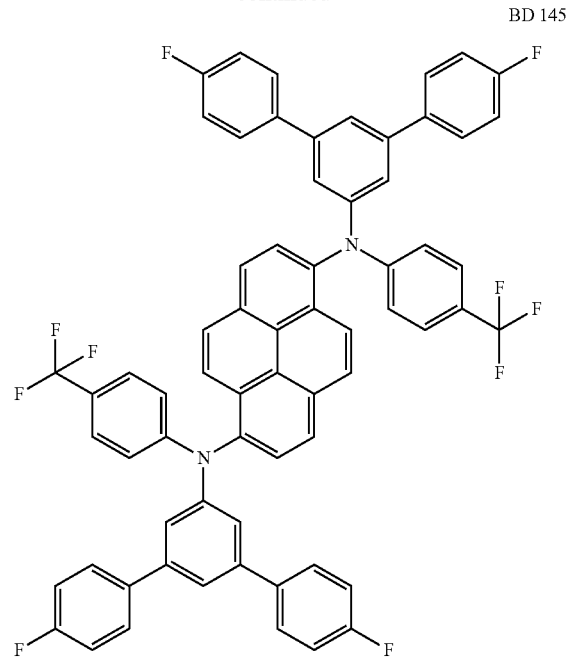
BD 146
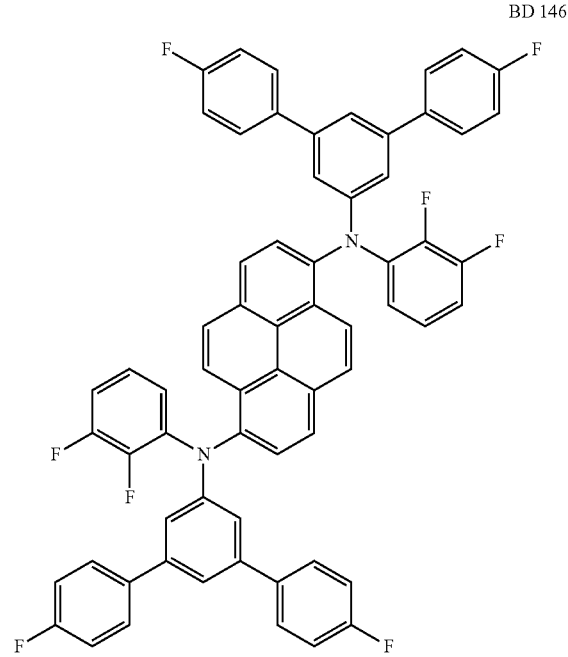

BD 147
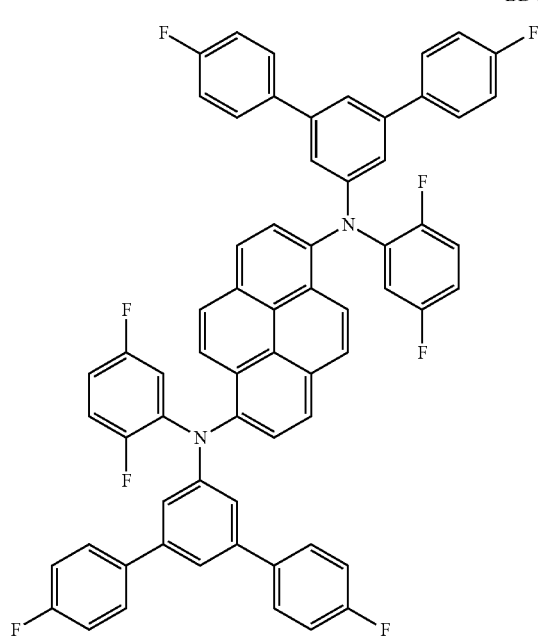
BD 149
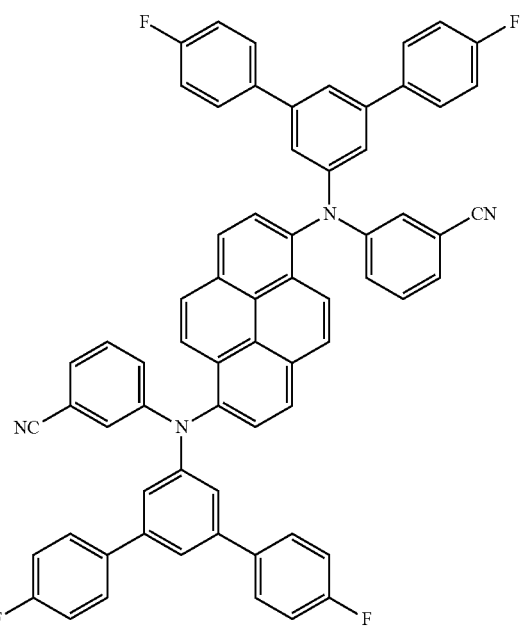
BD 148
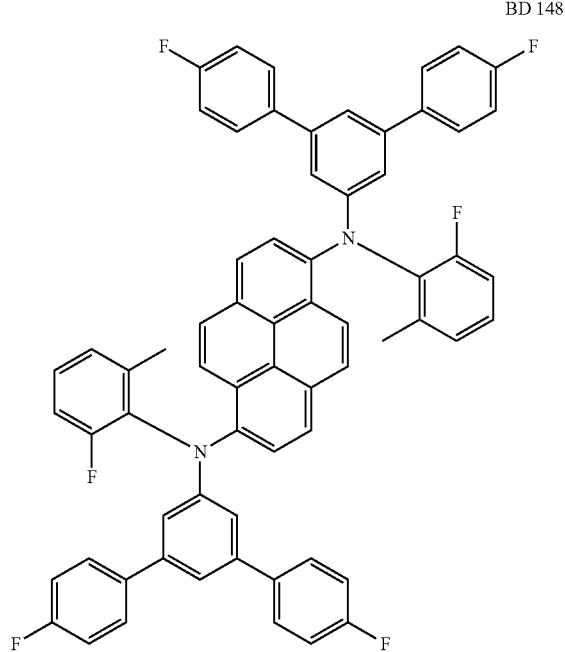
BD 150
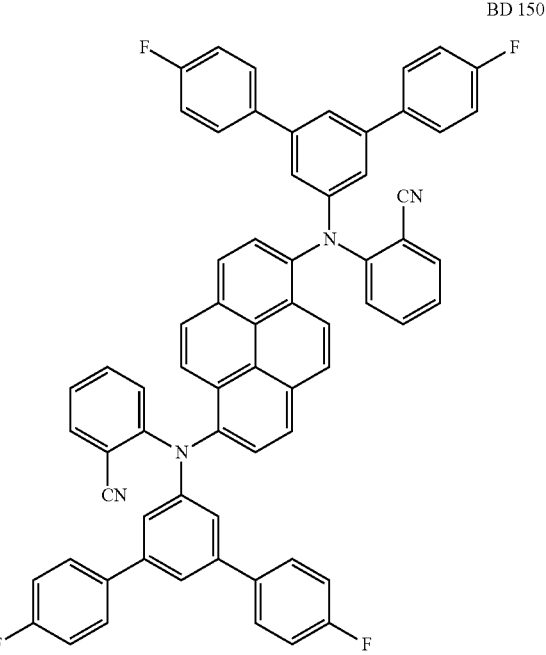

BD 151
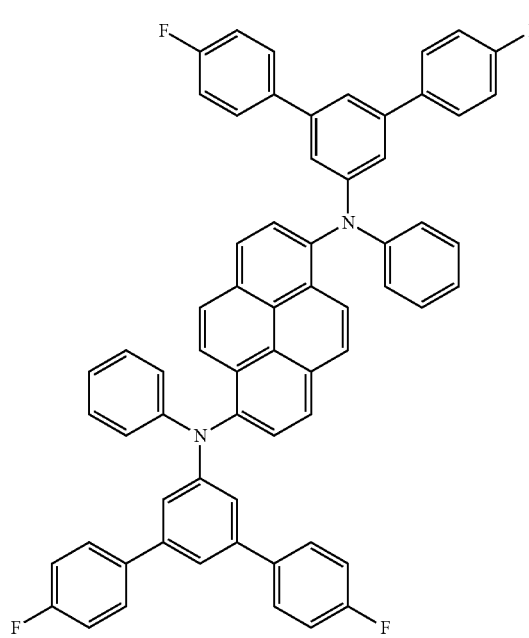
BD 152
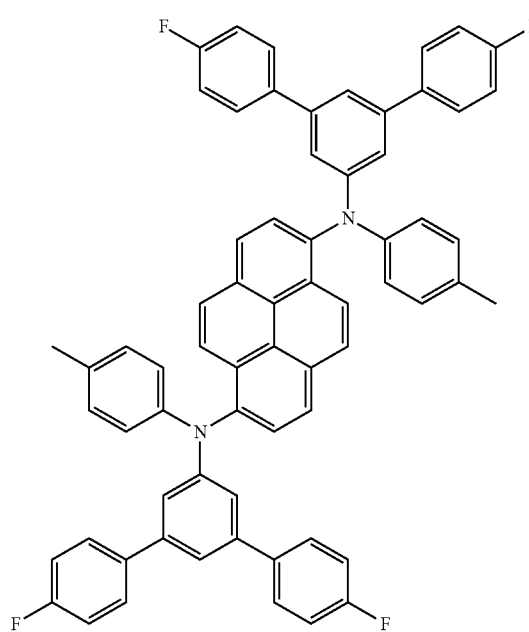
BD 153
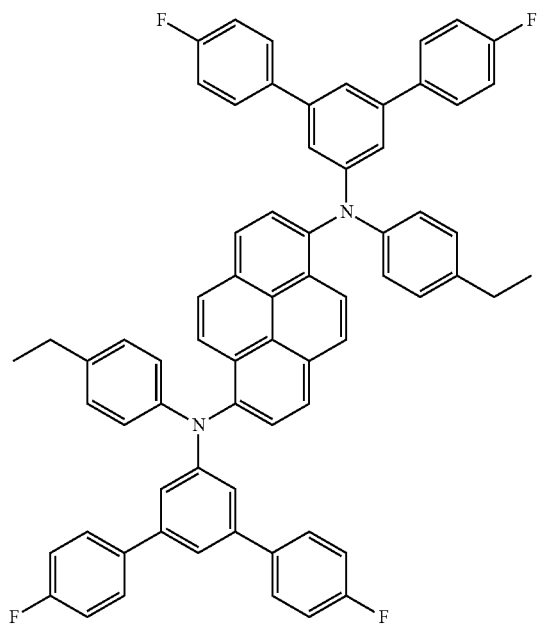
BD 154
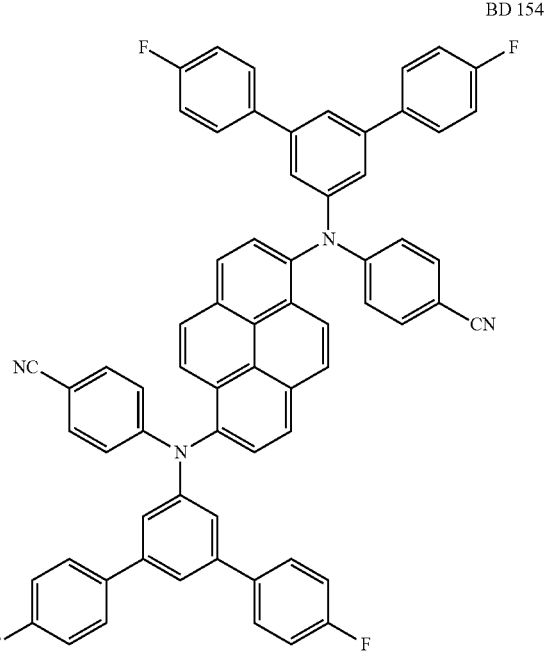

BD 155
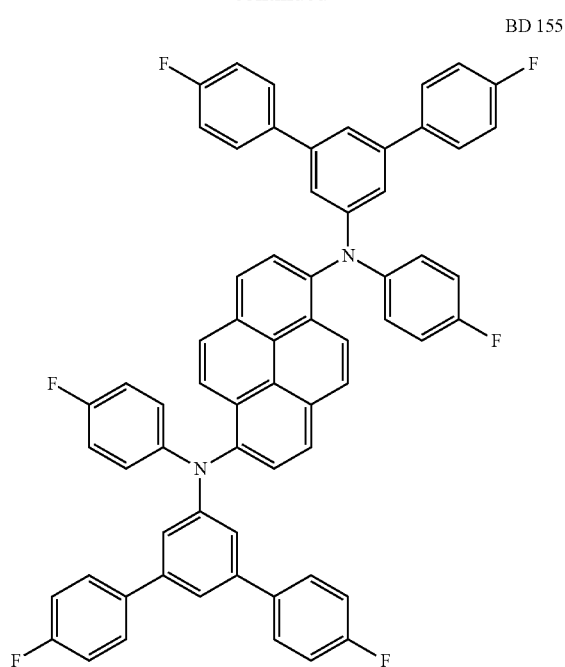
BD 157
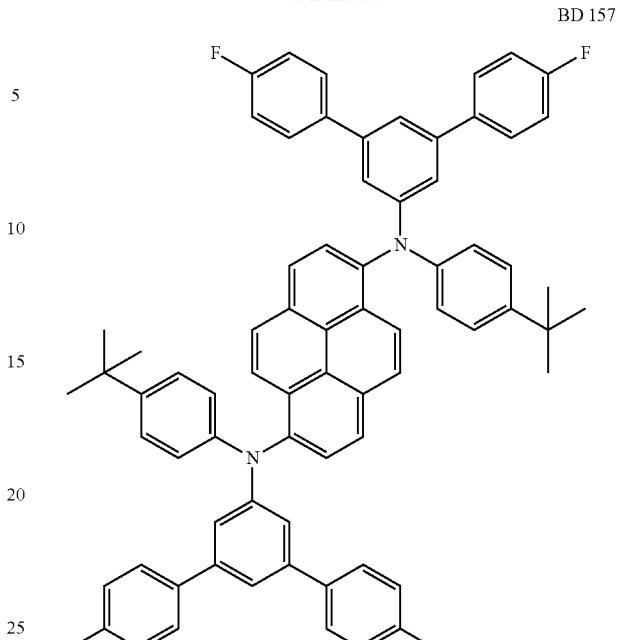
BD 156
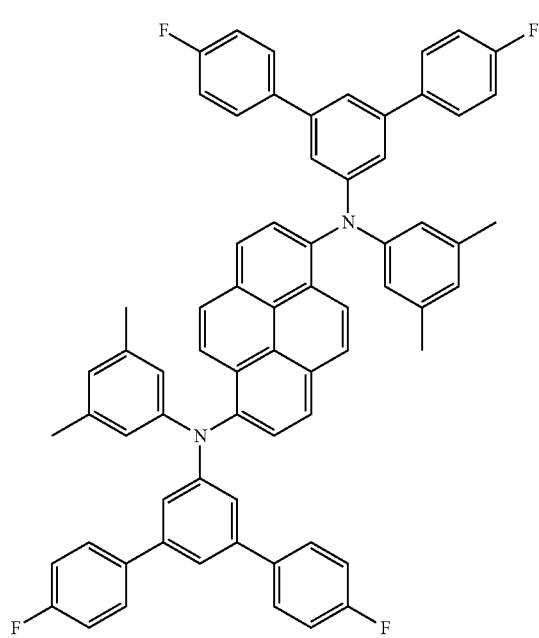
BD 158
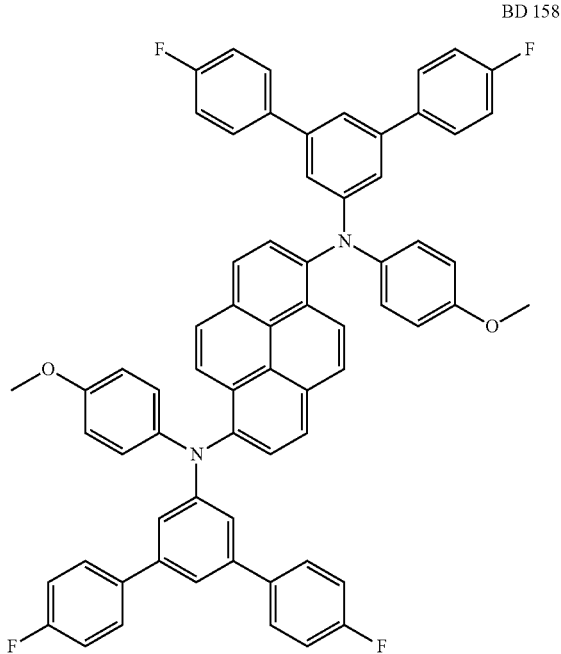

BD 159
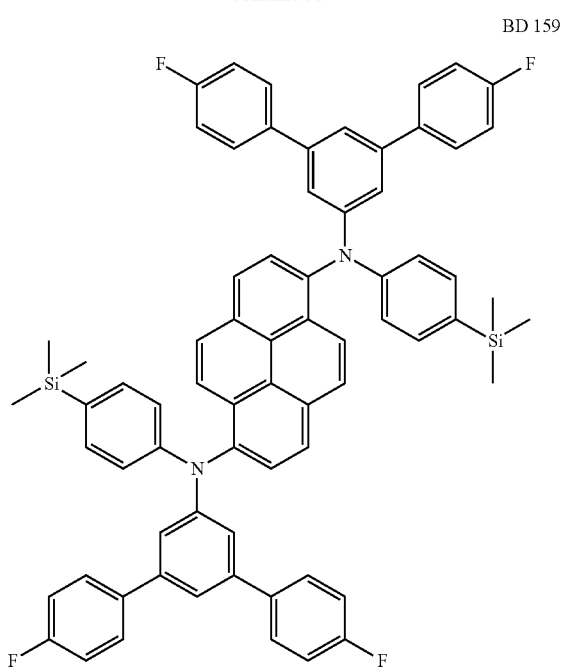
BD 161
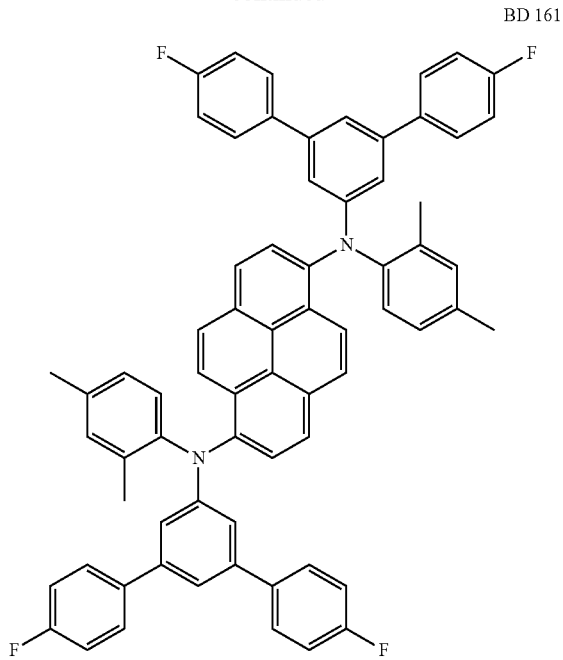
BD 160
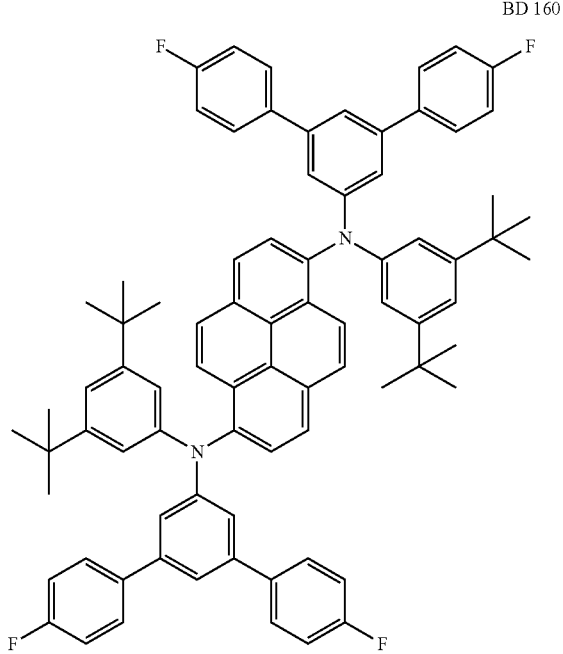
BD 162
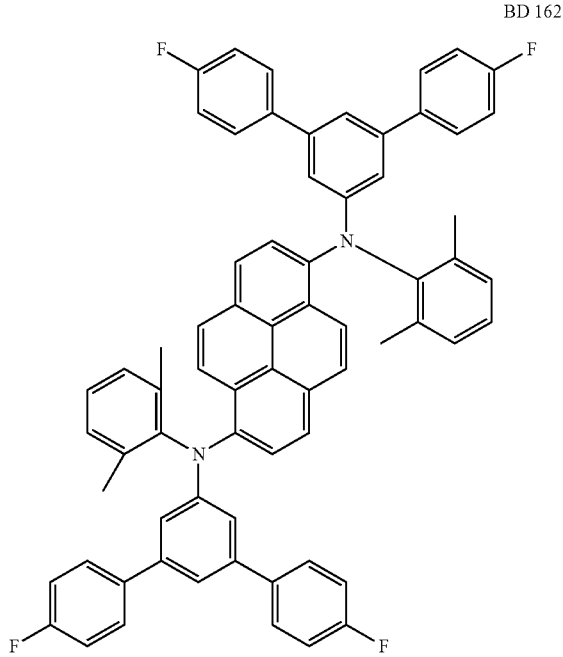

BD 163
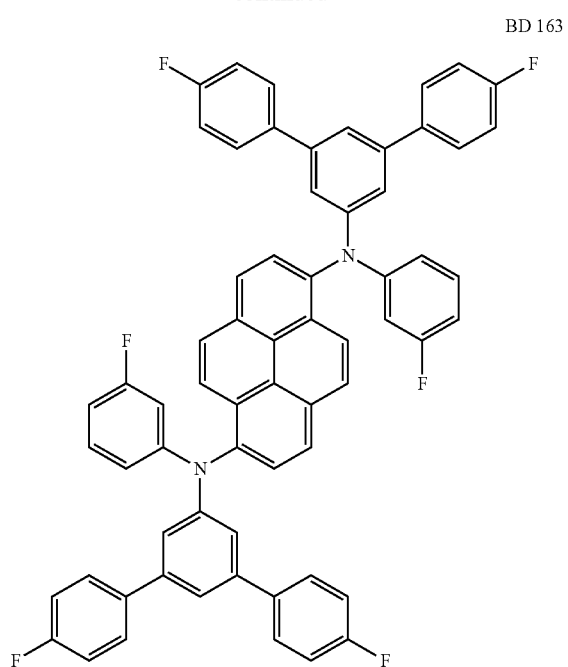
BD 165
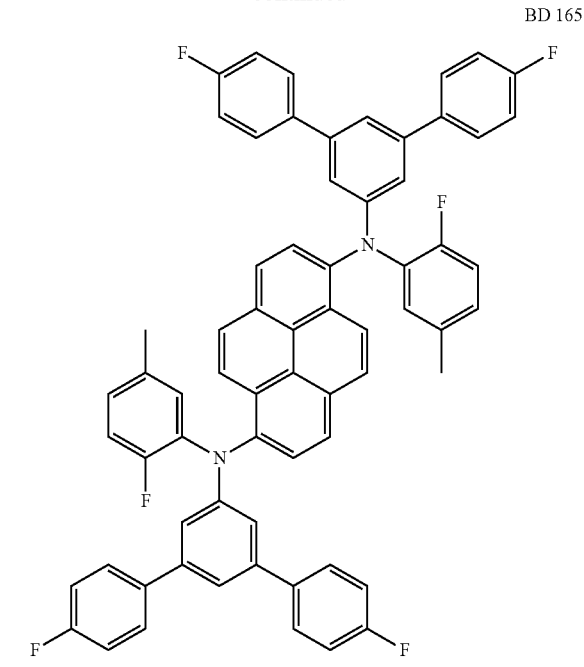
BD 164
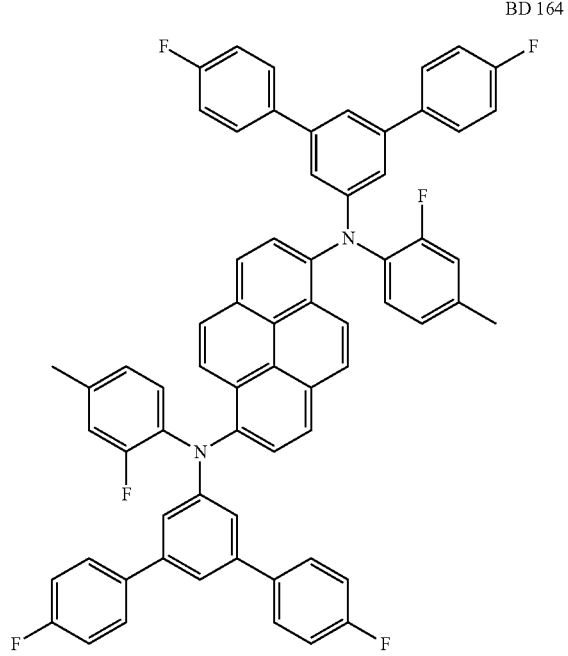
BD 166
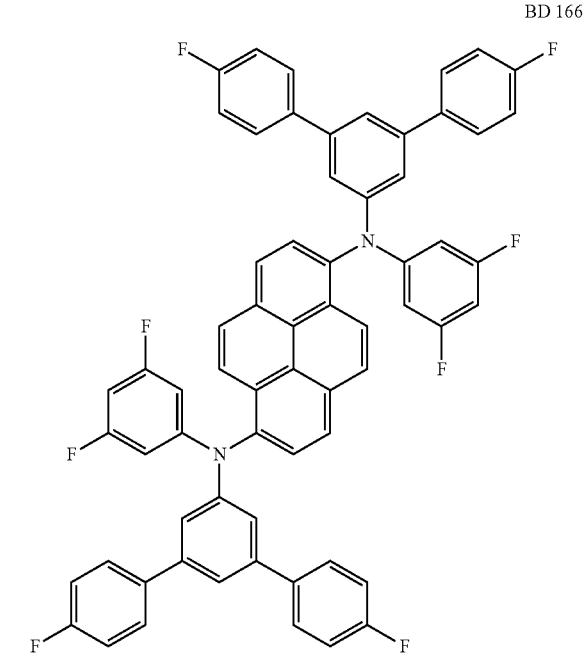

BD 167
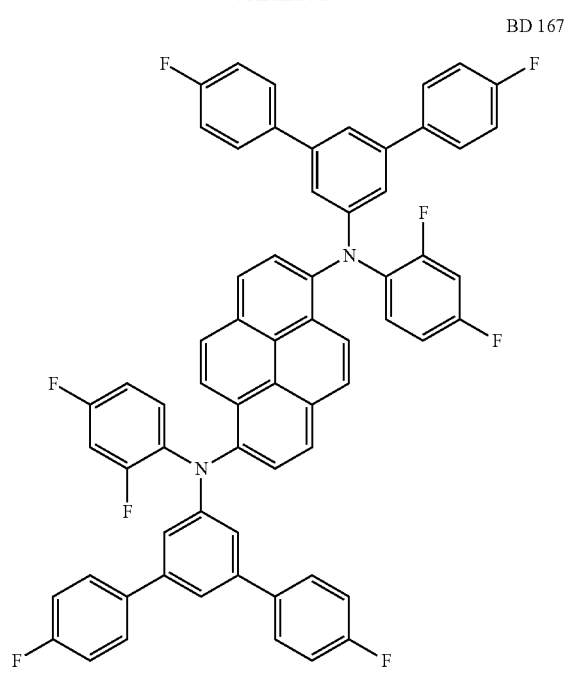
BD 169
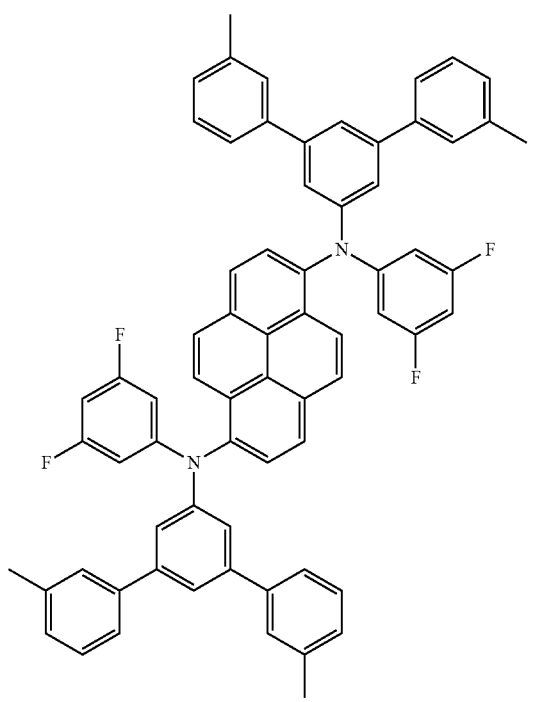
BD 168
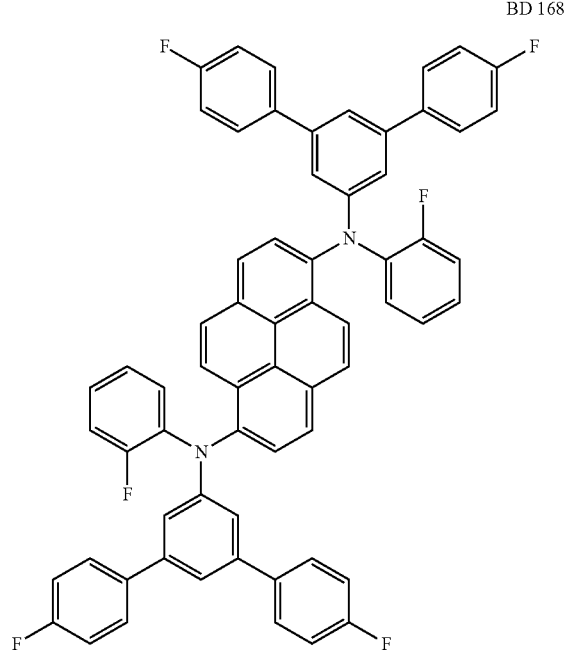
BD 170
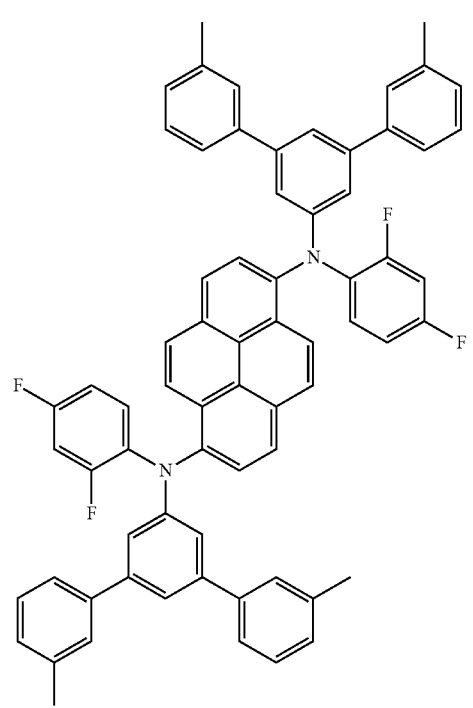

-continued
BD 171
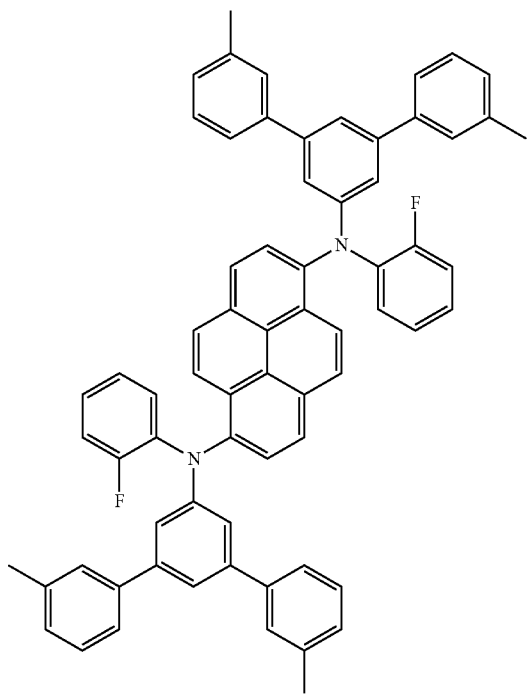
BD 173
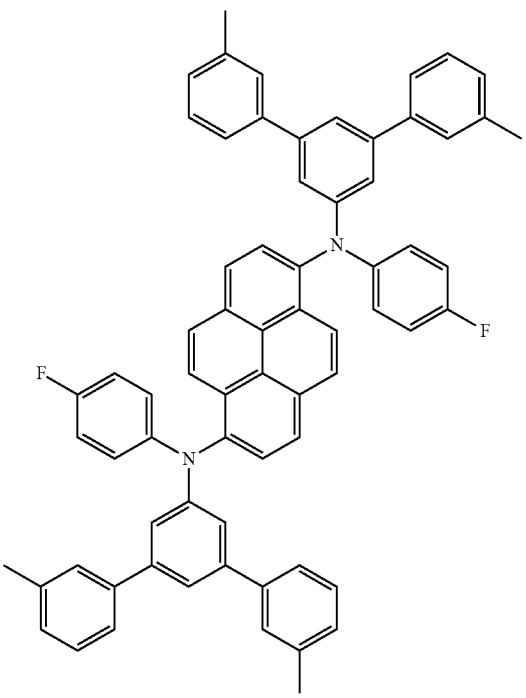
BD 172
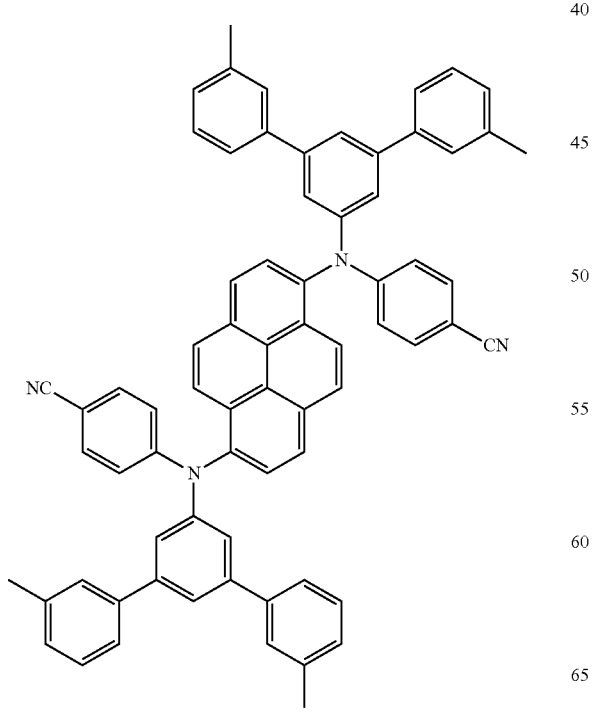
BD 174
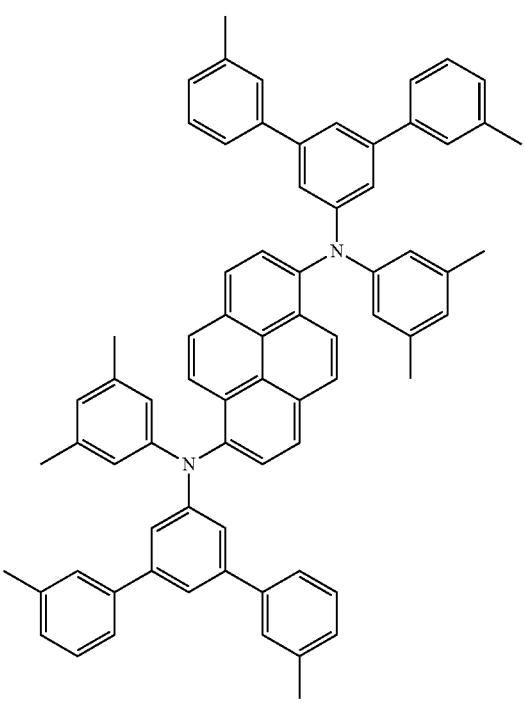

BD 175
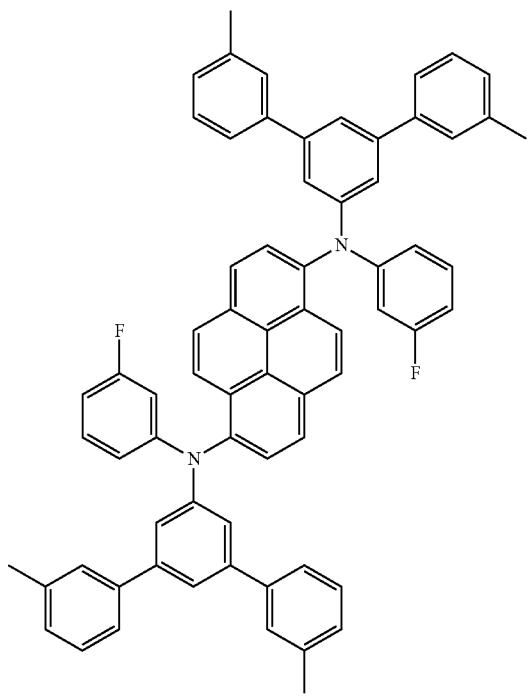
BD 177
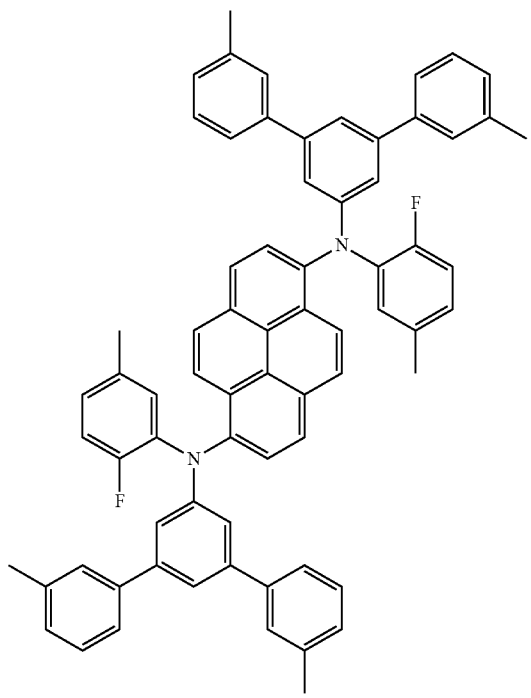
BD 176
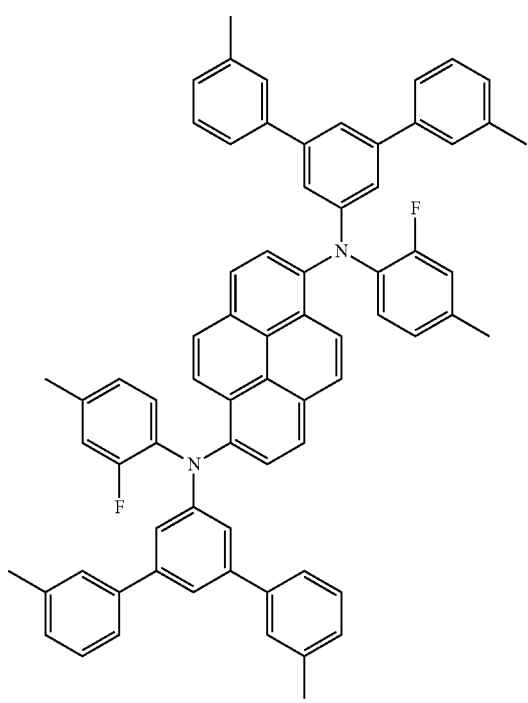
BD 178
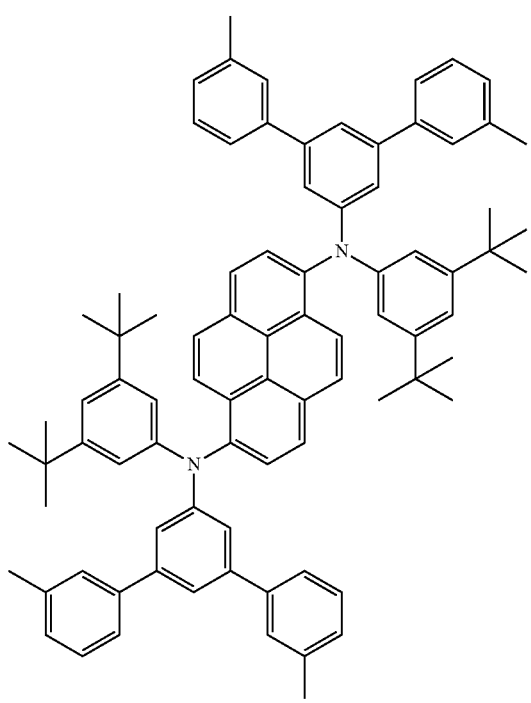

BD 179
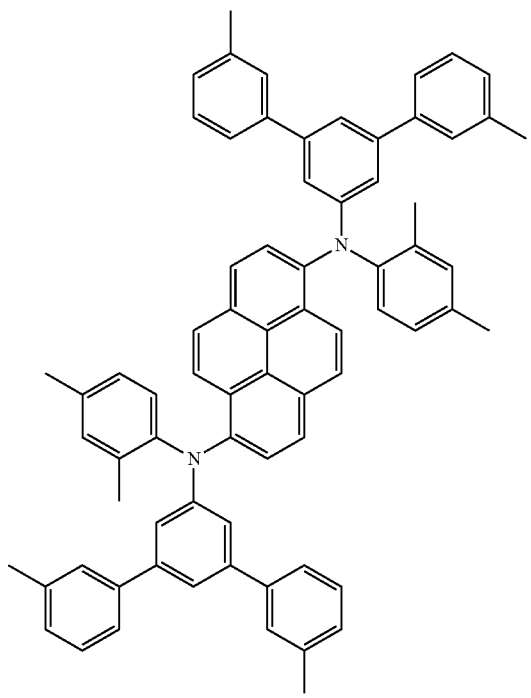
BD 181
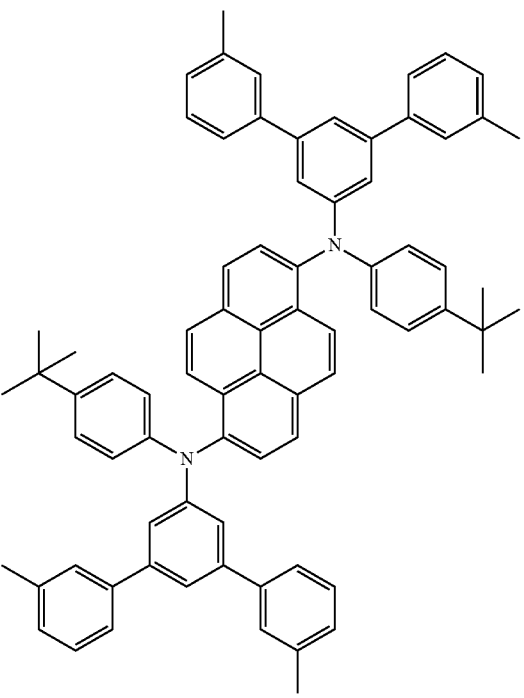
BD 180
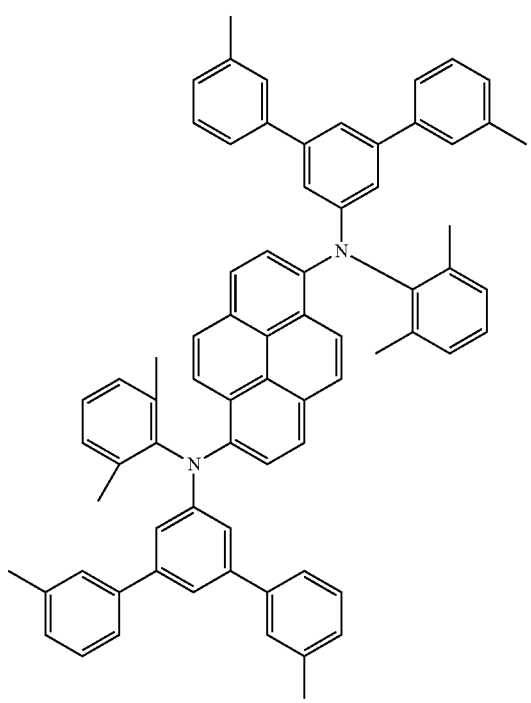
BD 182
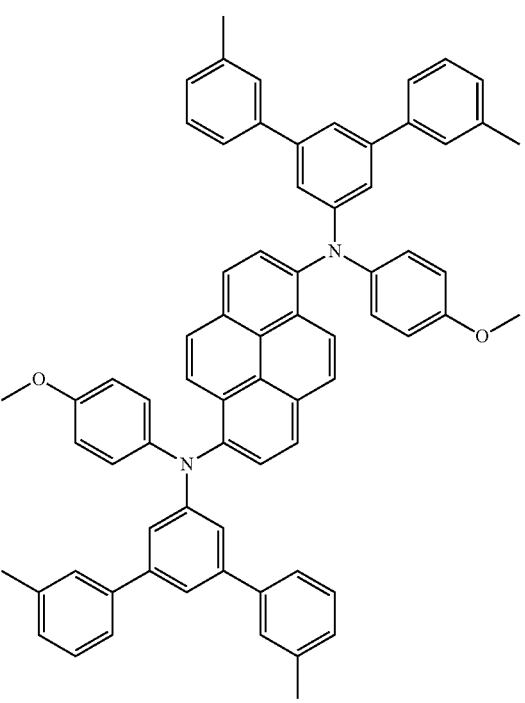

BD 183
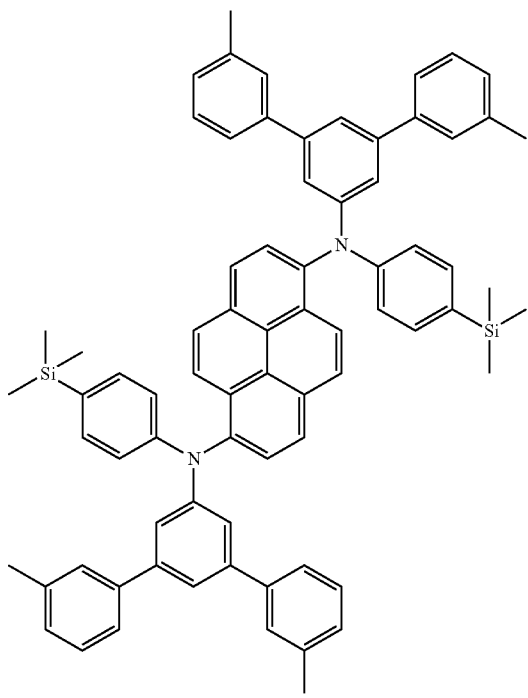
BD 184
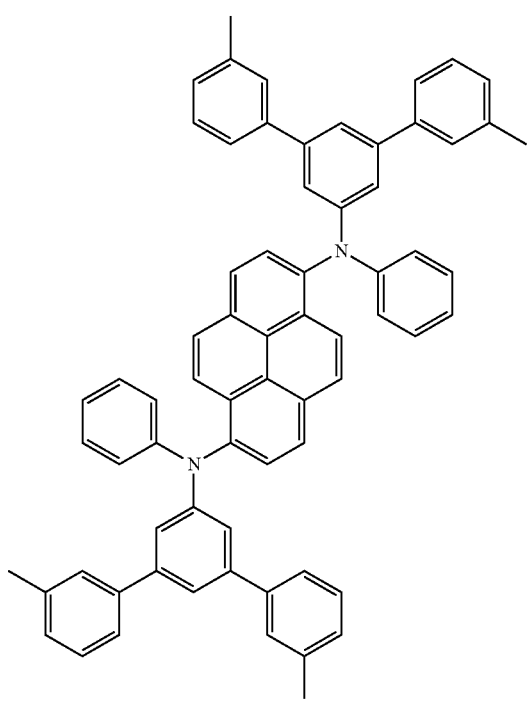
BD 185
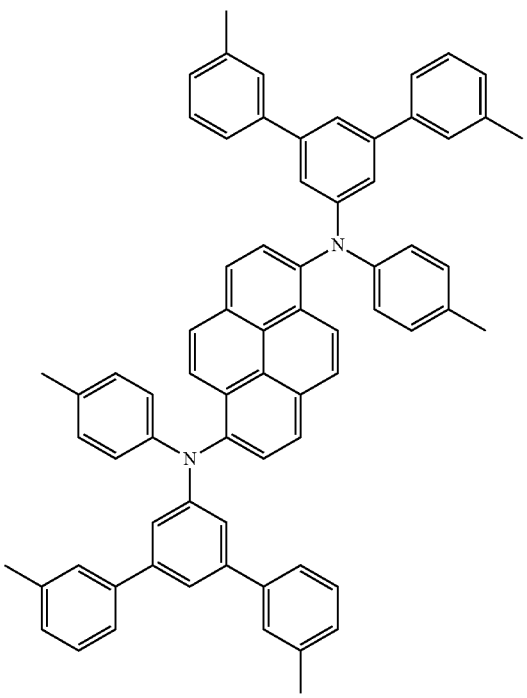
BD 186
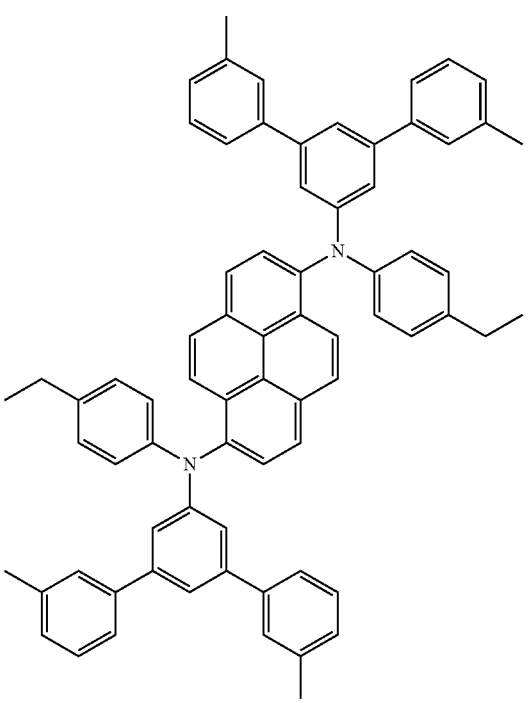

BD 187
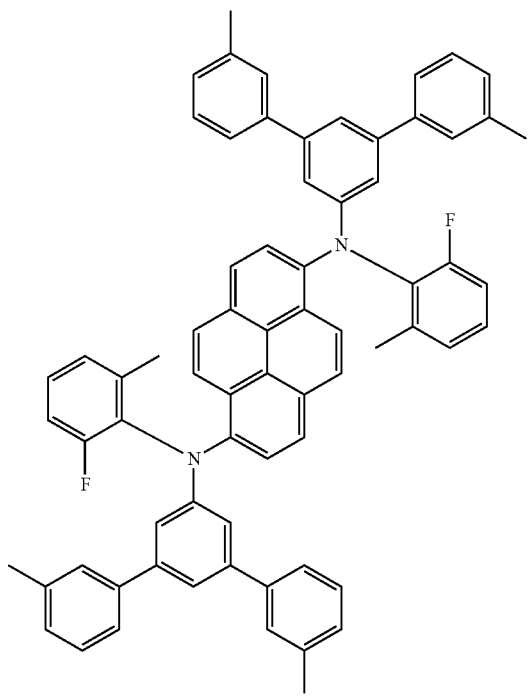
BD 189
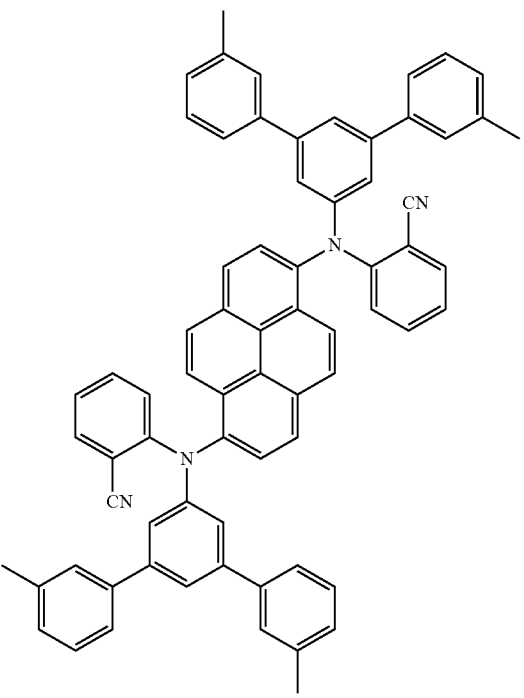
BD 188
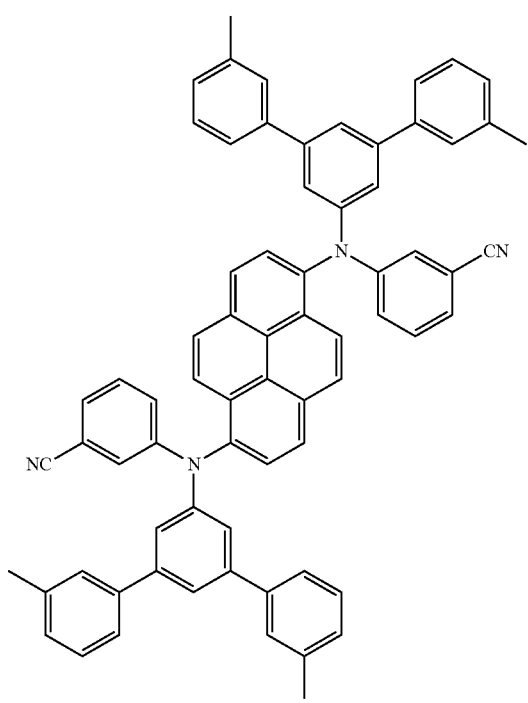
BD 190
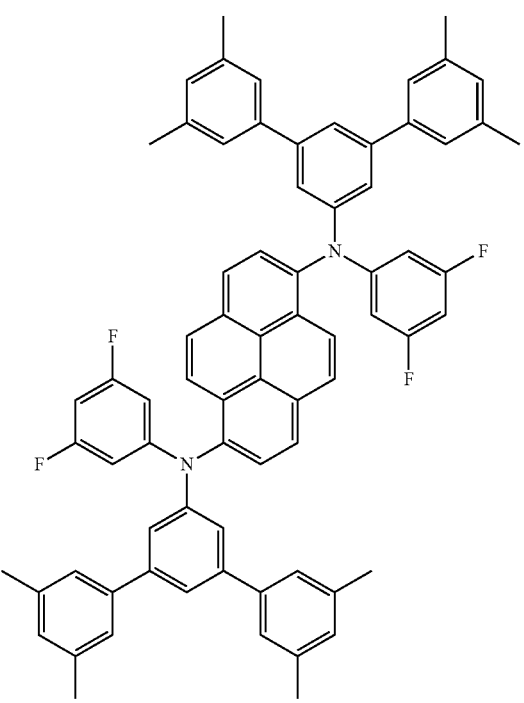

BD 191
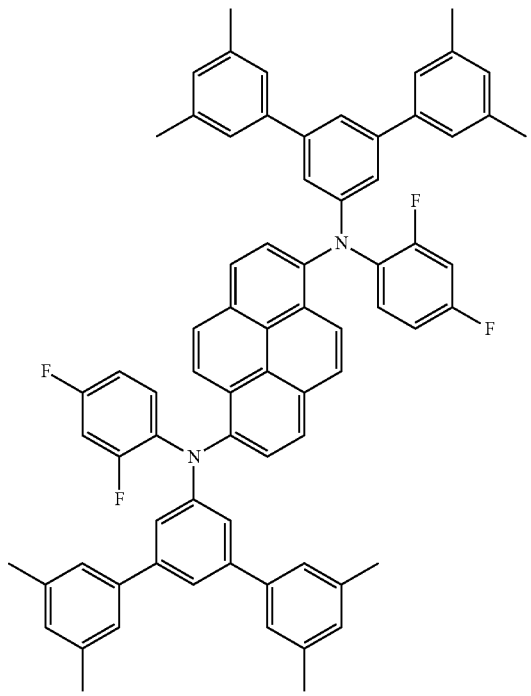
BD 193
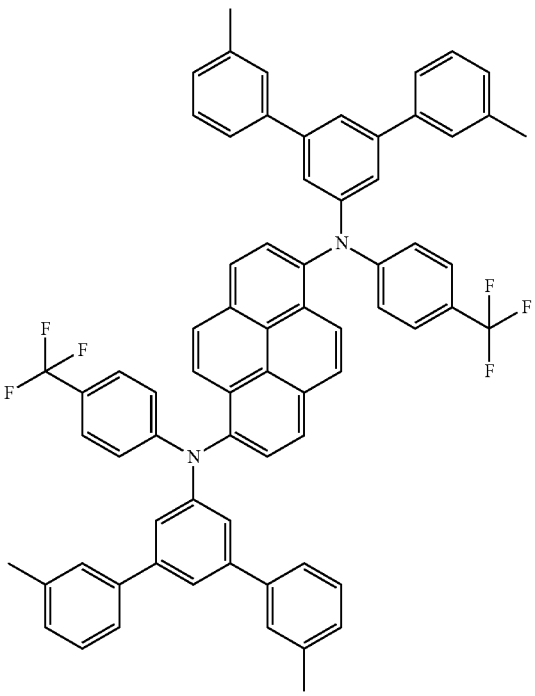
BD 192
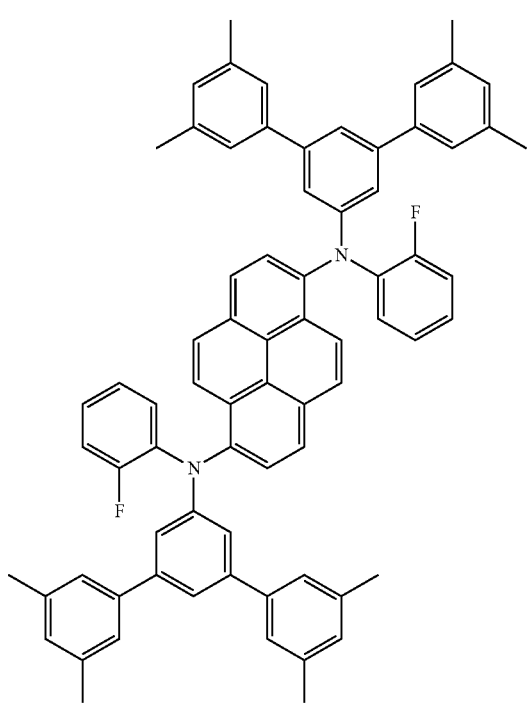
BD 194
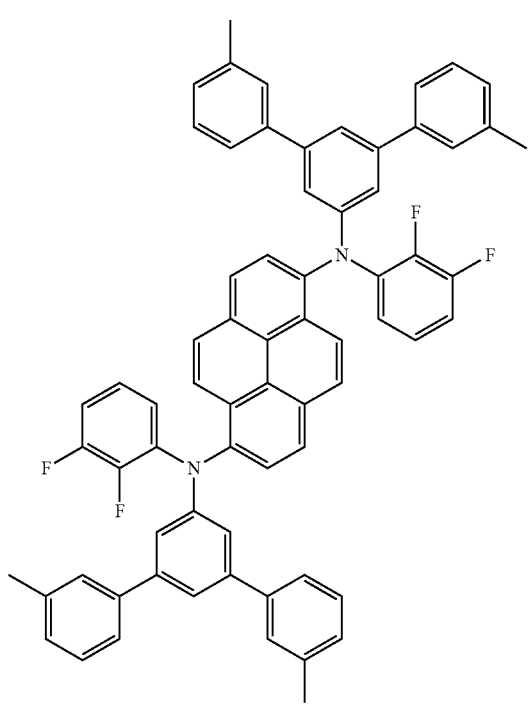

BD 195
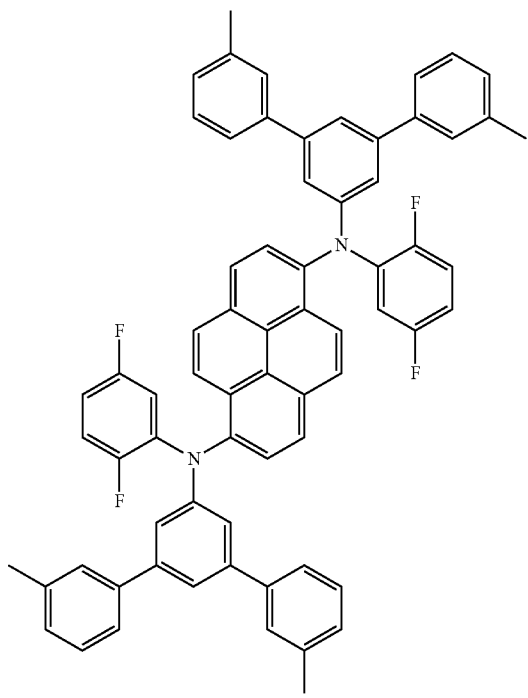
BD 197
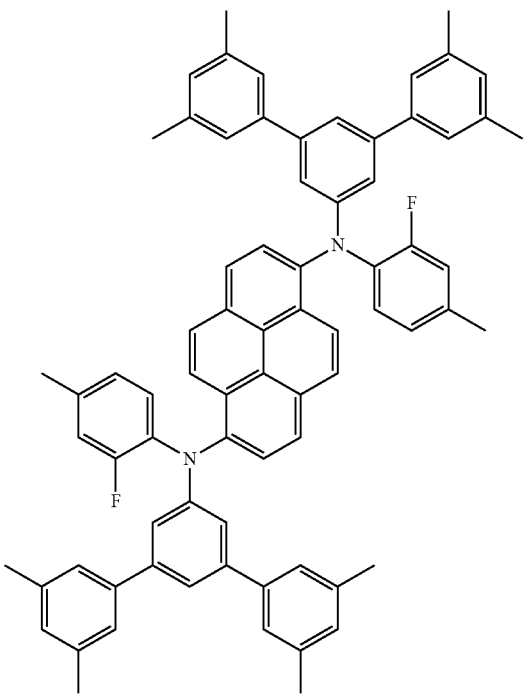
BD 196
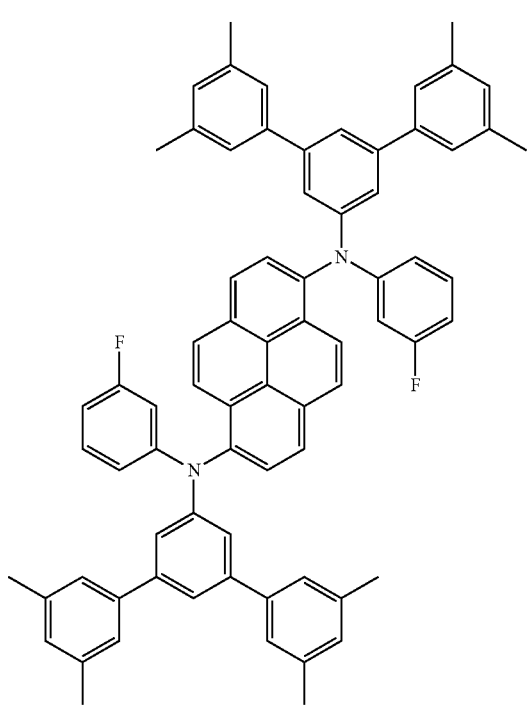
BD 198
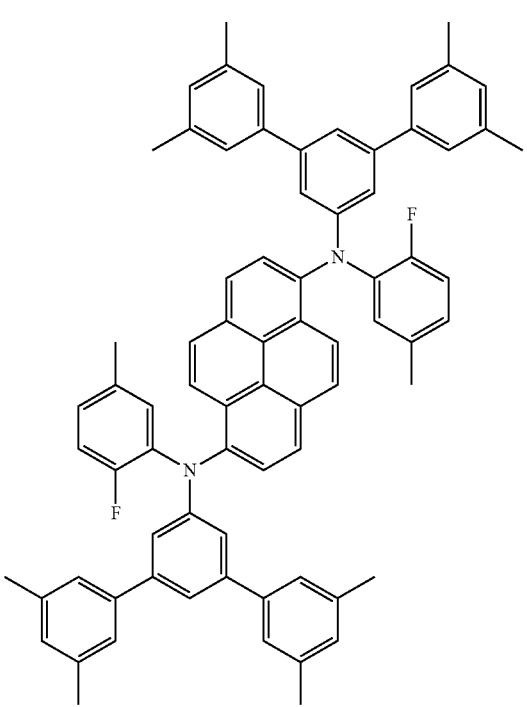

BD 199
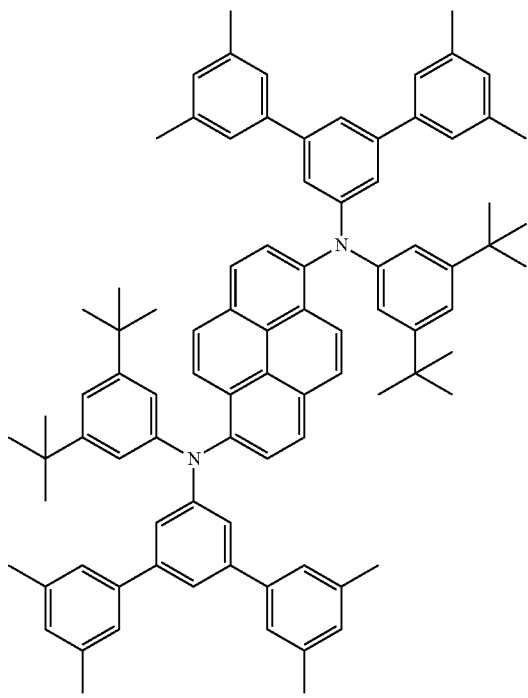
BD 201
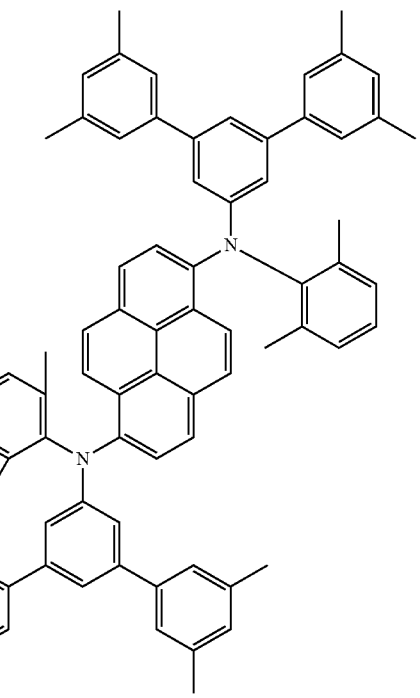
BD 200
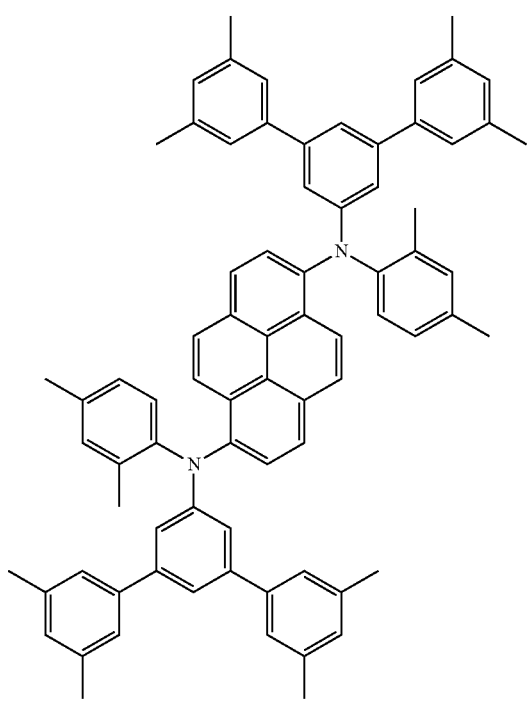
BD 202
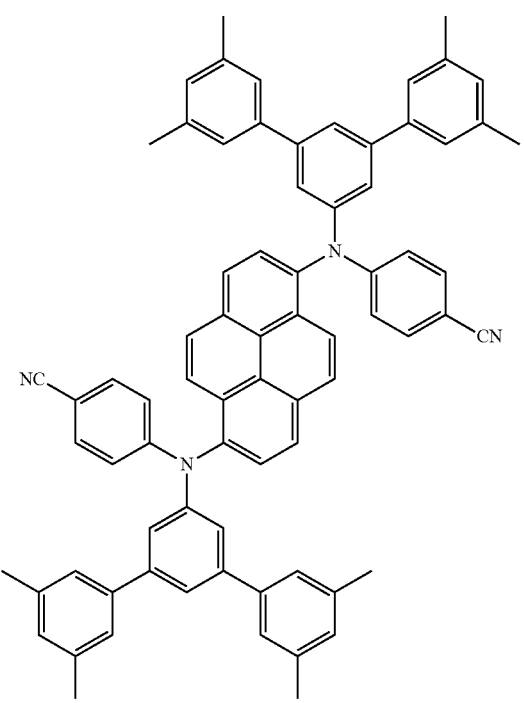

BD 203
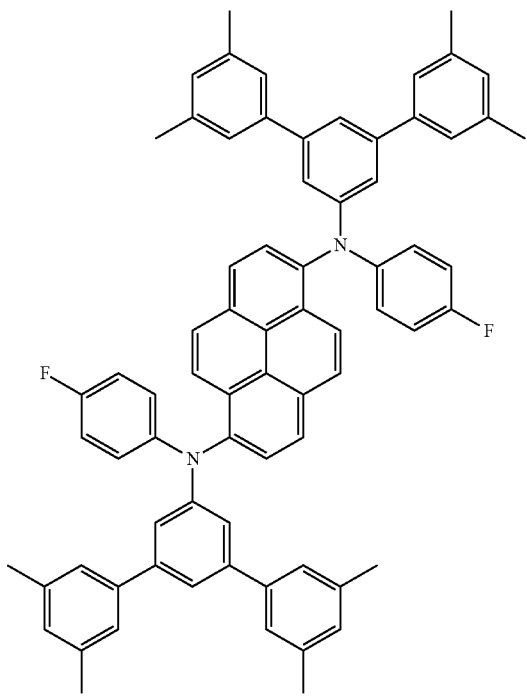
BD 205
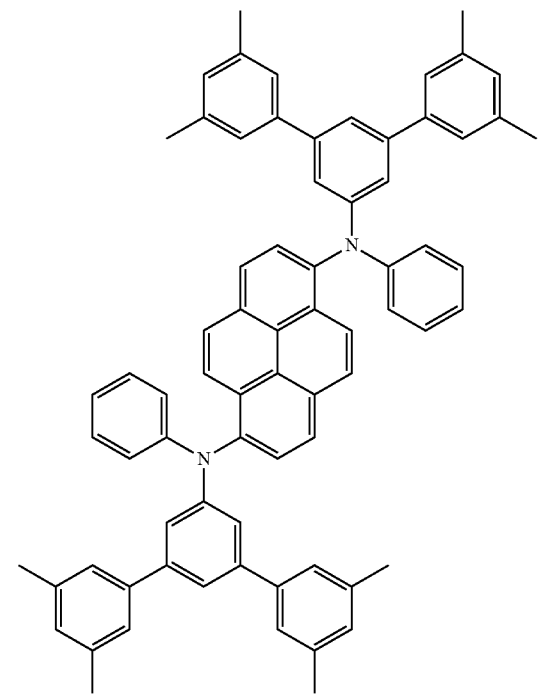
BD 204
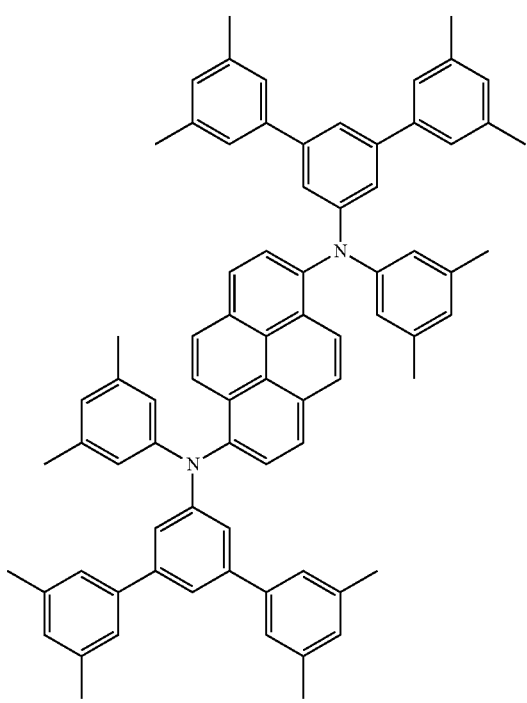
BD 206
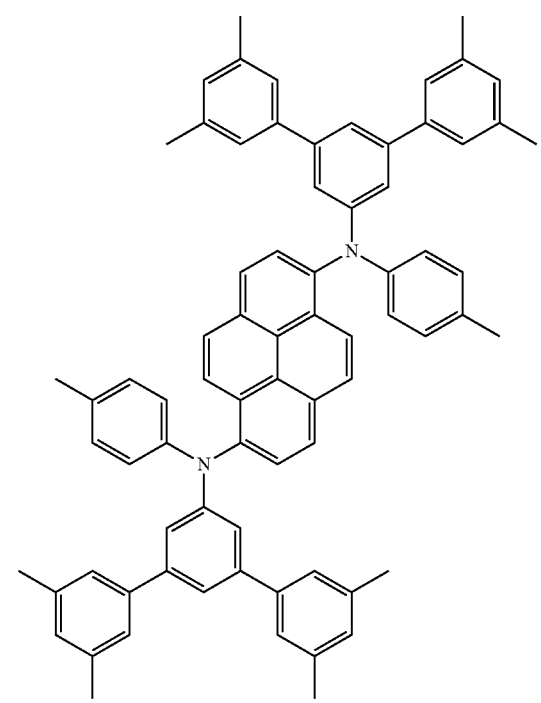

BD 207

BD 208

BD 209

BD 210

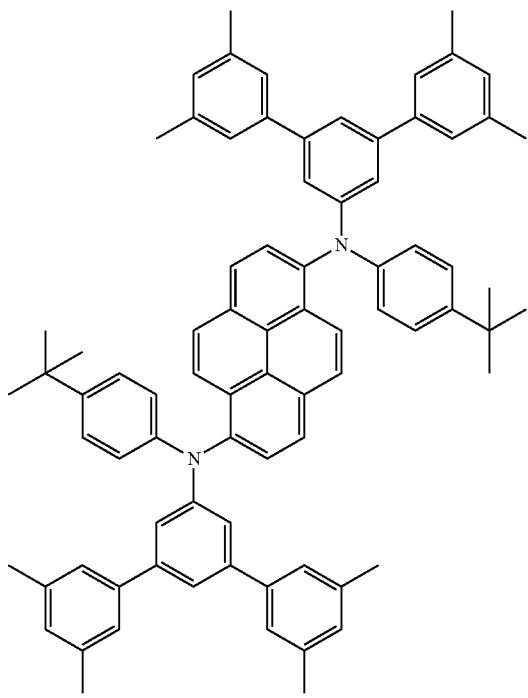
BD 211
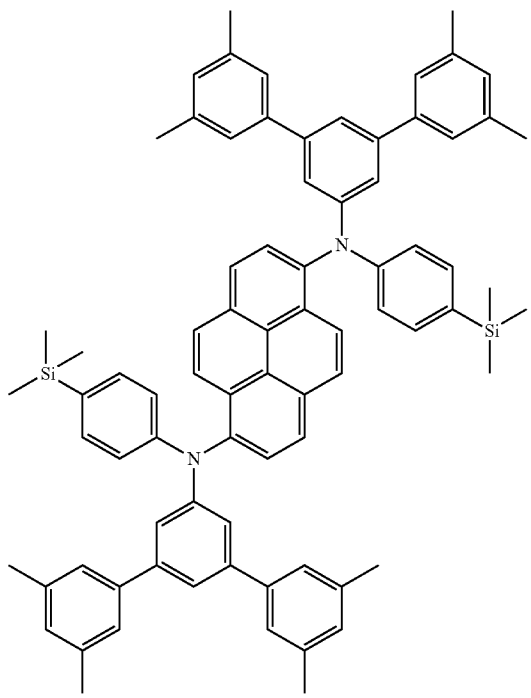
BD 213
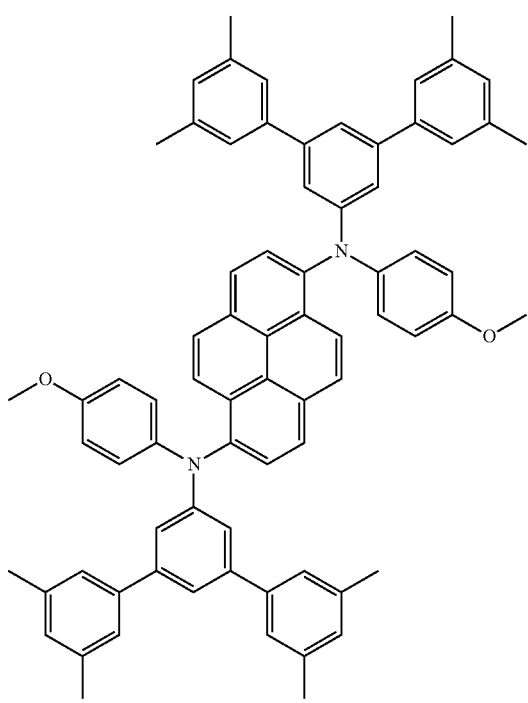
BD 212
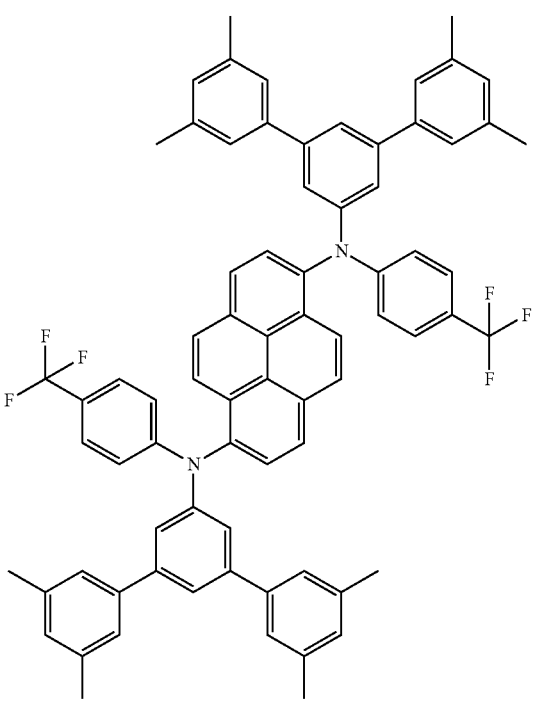
BD 214

BD 215
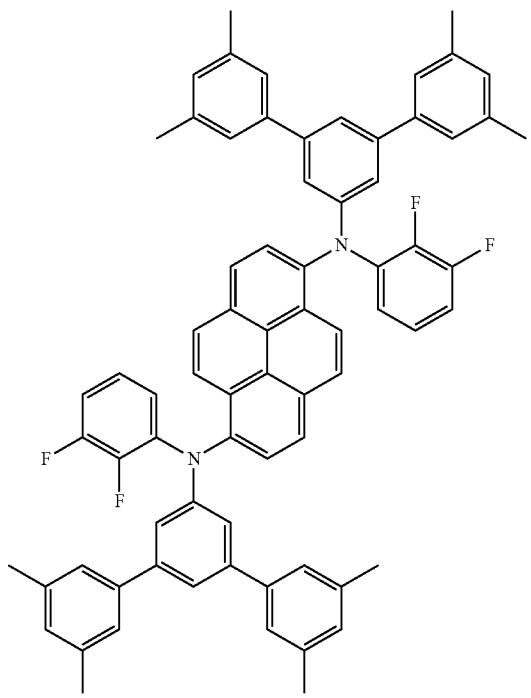
BD 216
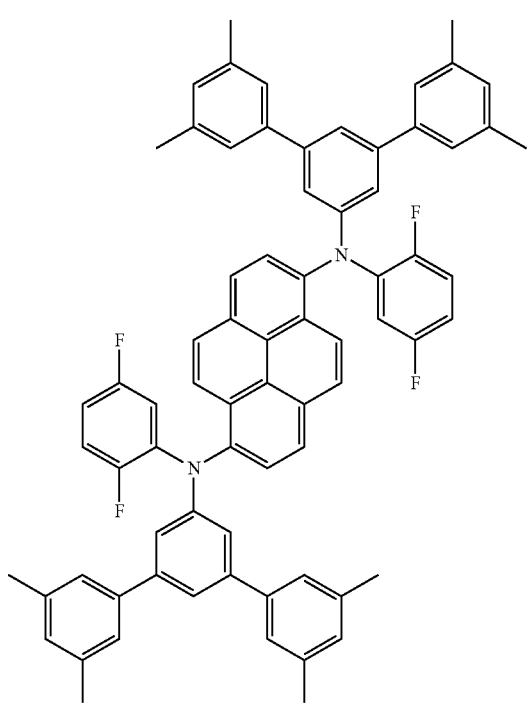
BD 217
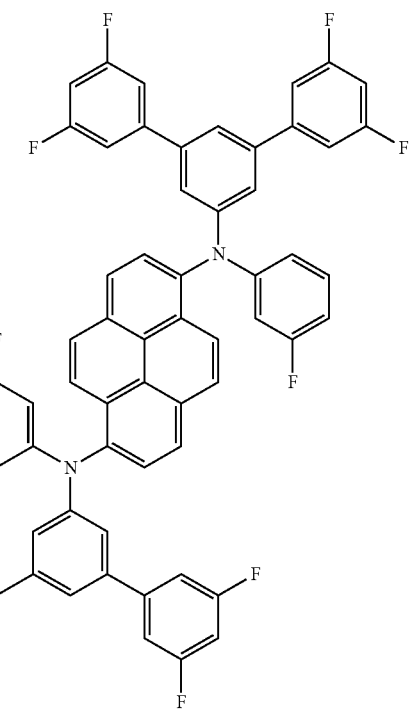
BD 218
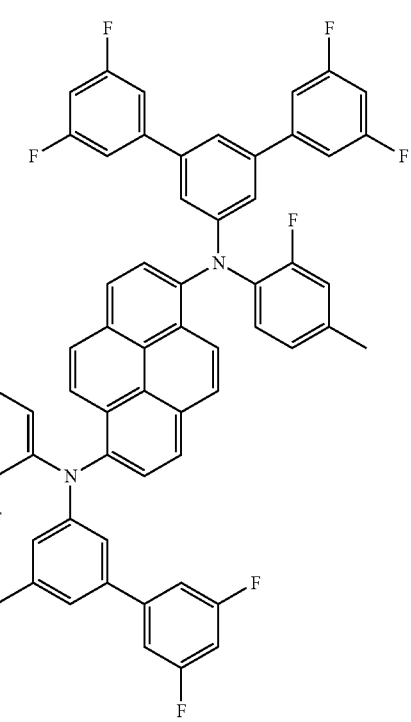

BD 219
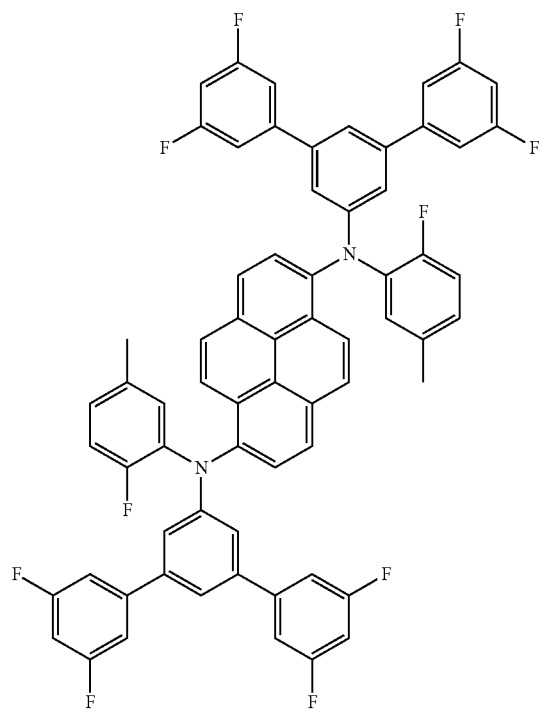
BD 221
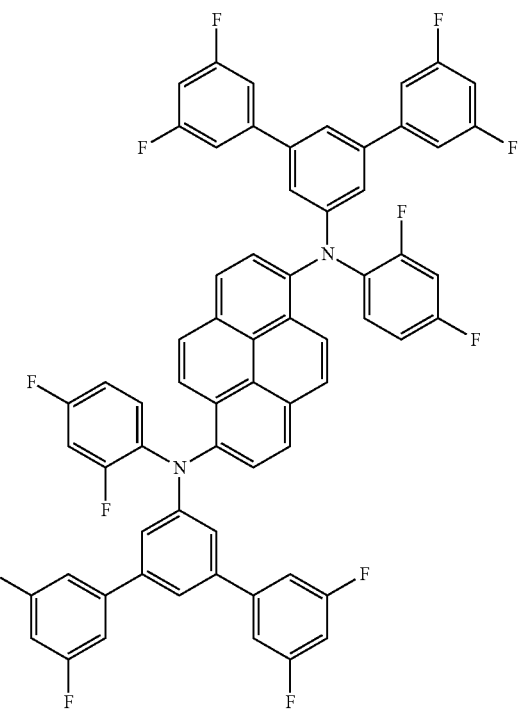
BD 220
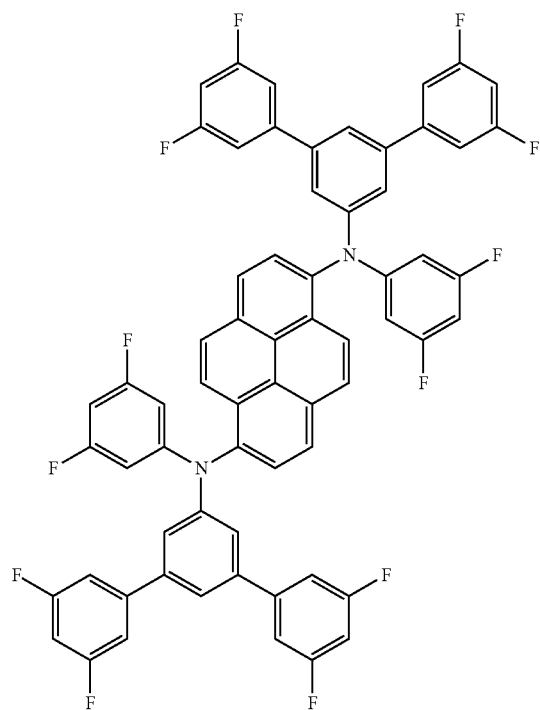
BD 222
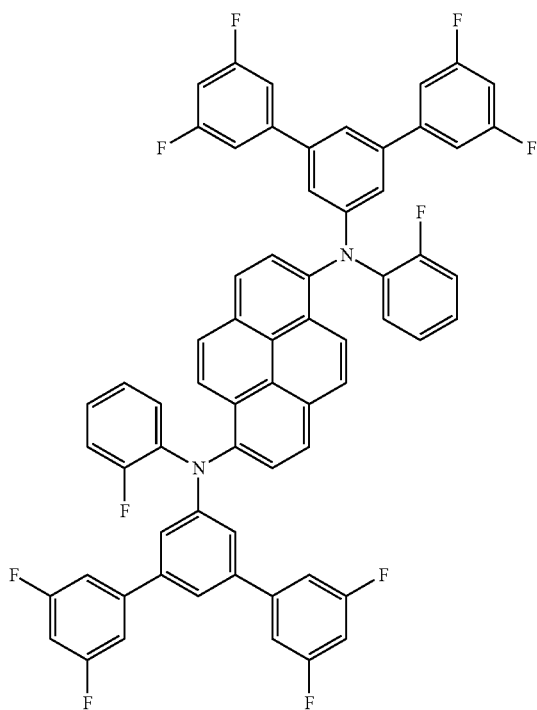

BD 223
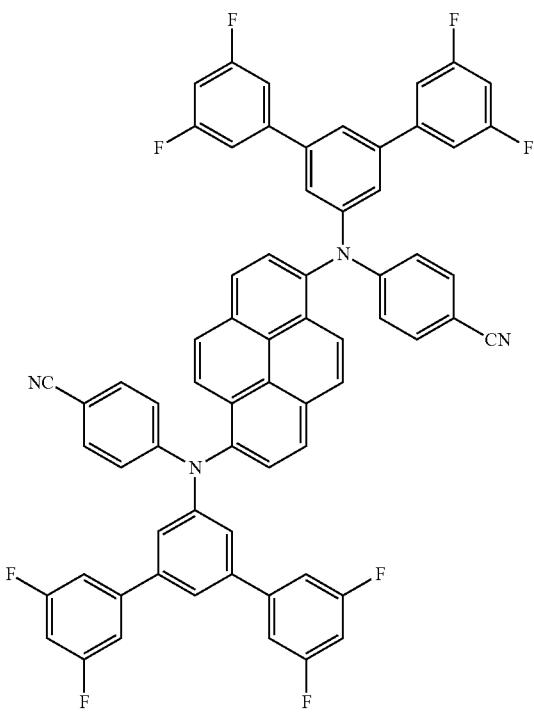
BD 224
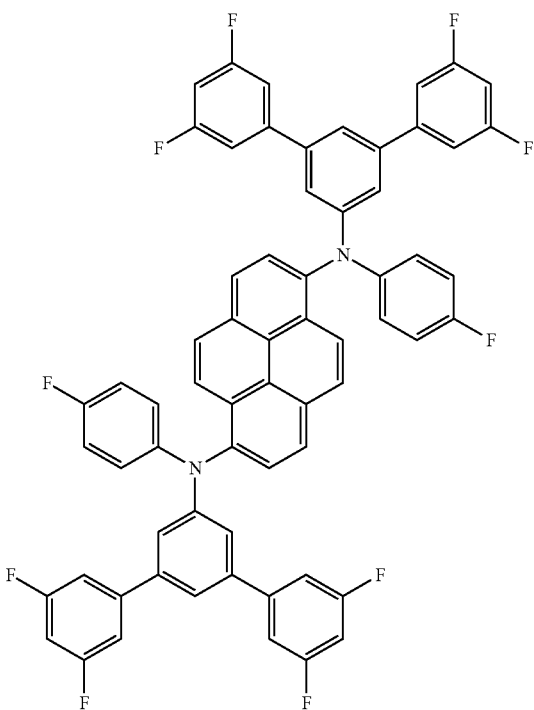
BD 225
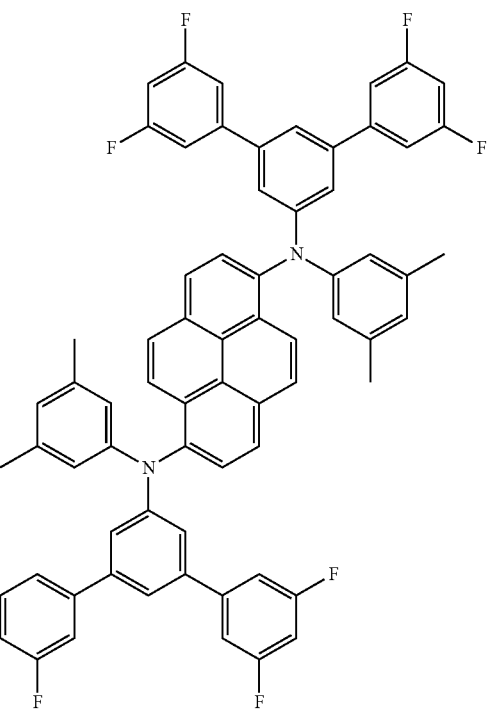
BD 226
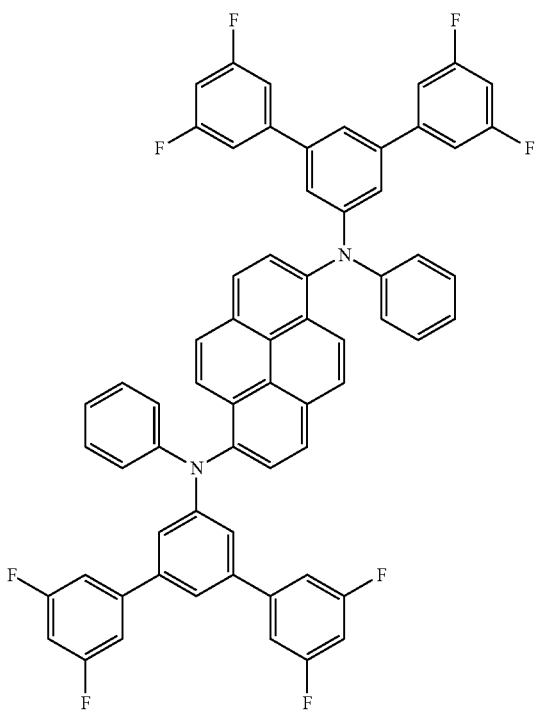

BD 227
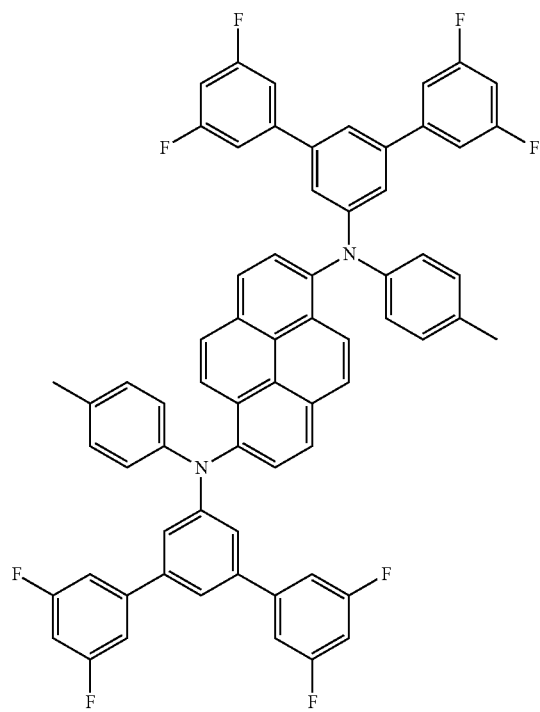
BD 229
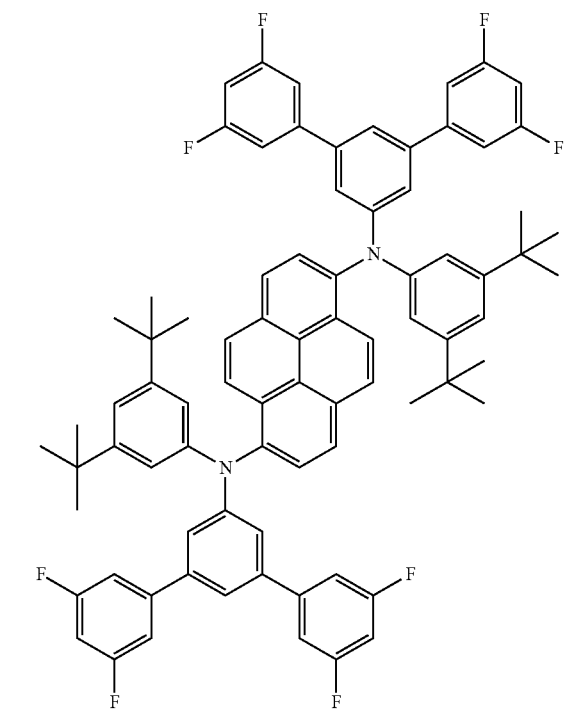
BD 228
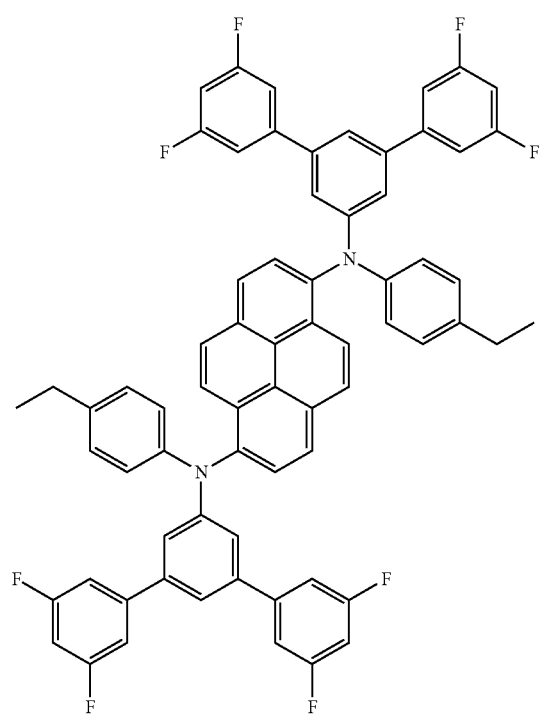
BD 230
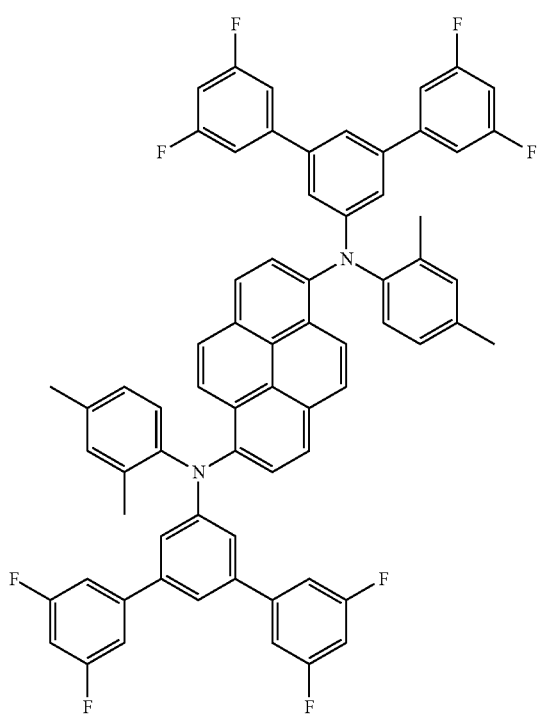

BD 231
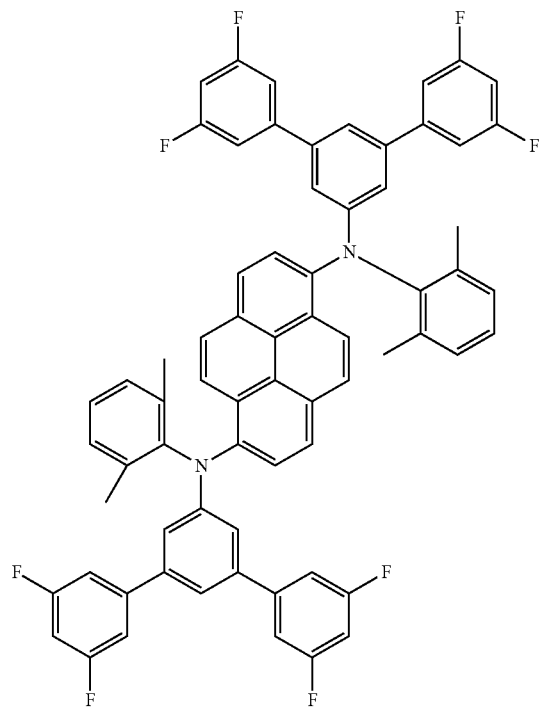
BD 233
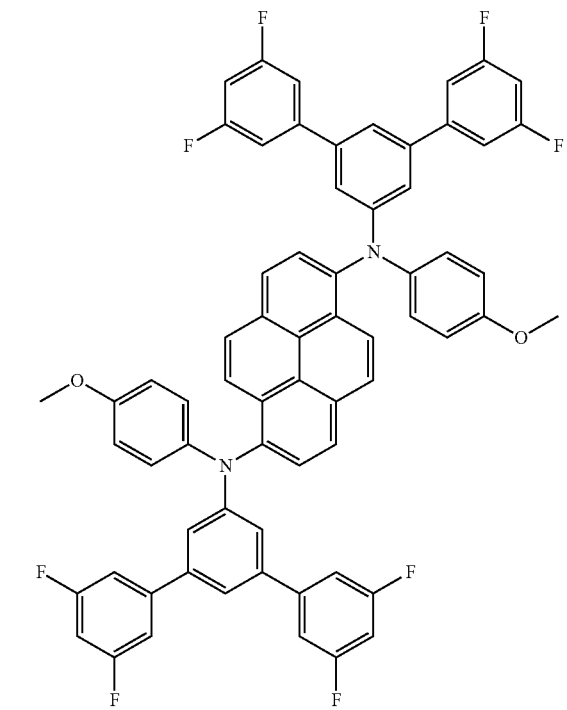
BD 232
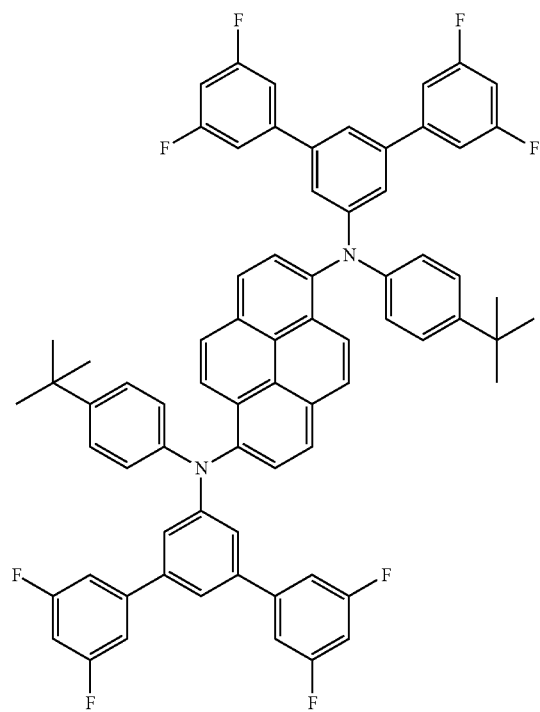
BD 234
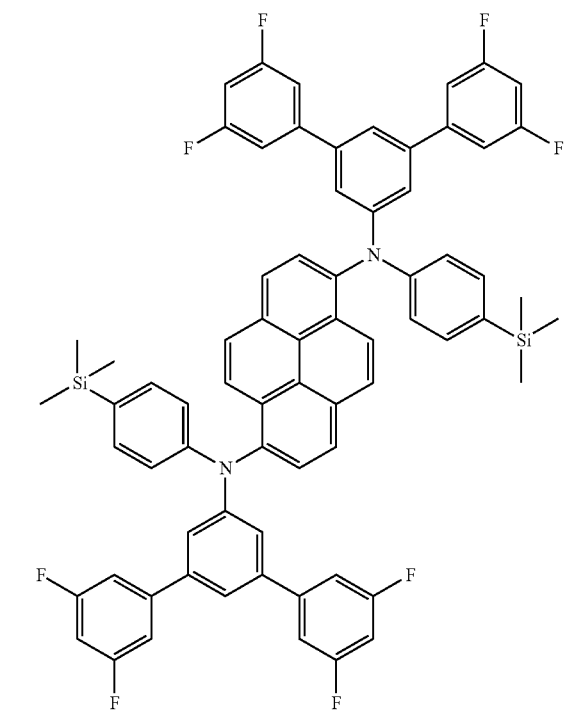

BD 235
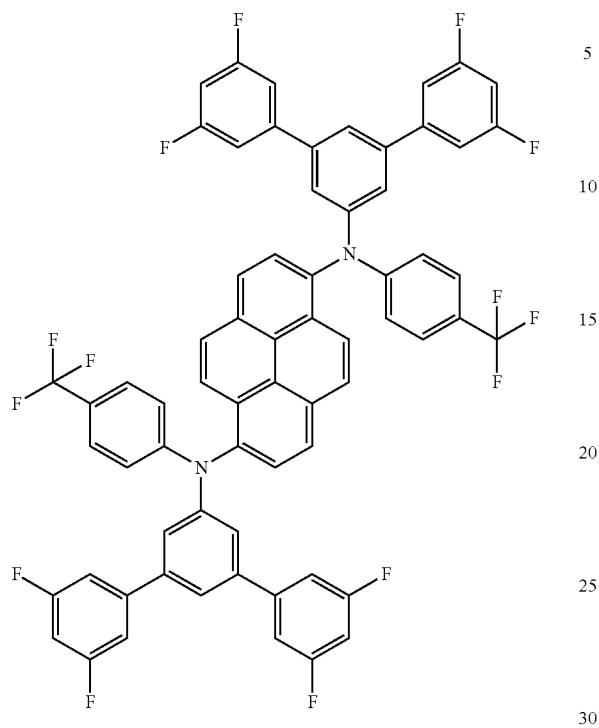
BD 237
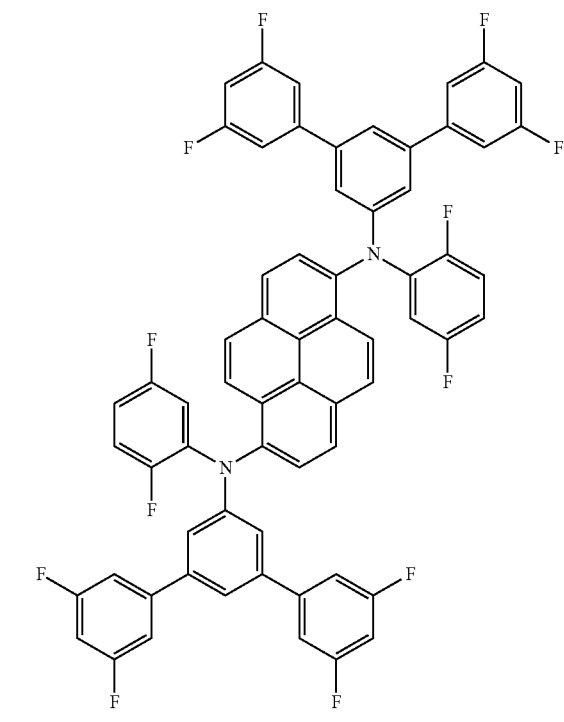
BD 236
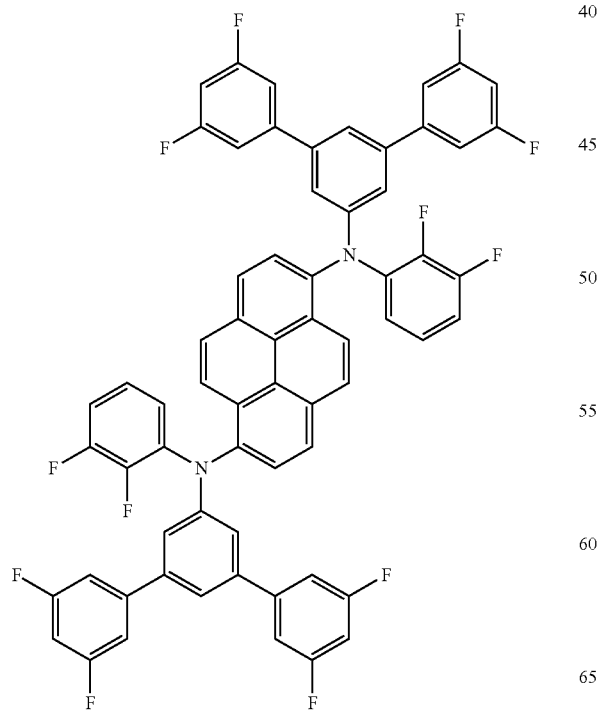
BD 238
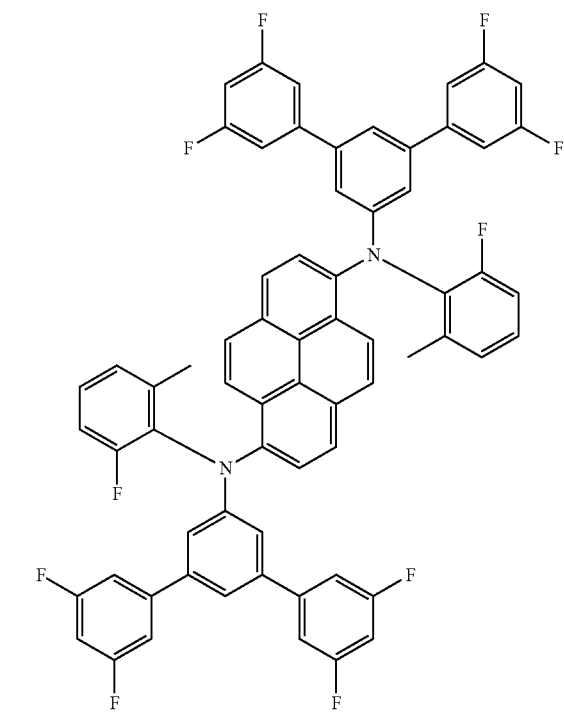

BD 239
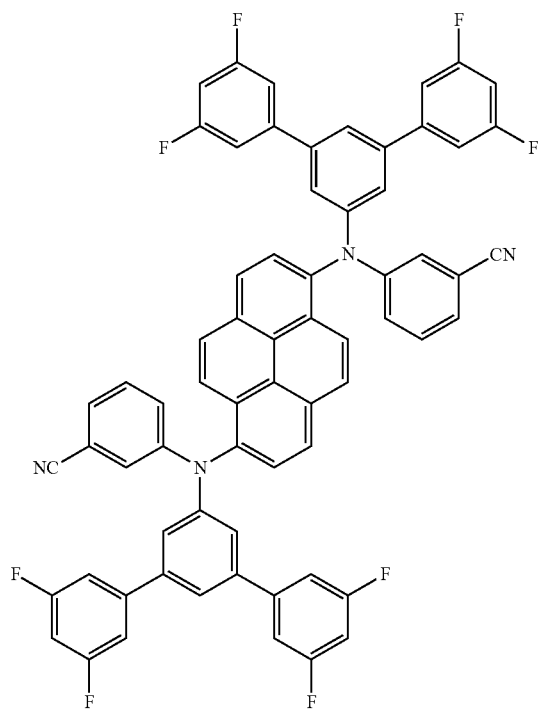
BD 241
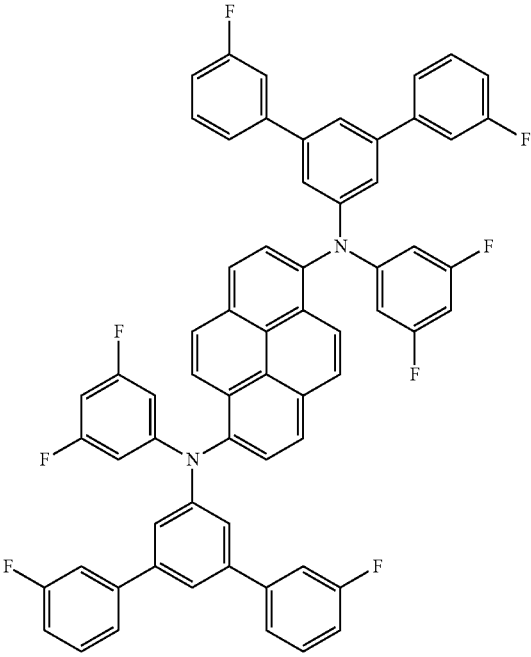
BD 240
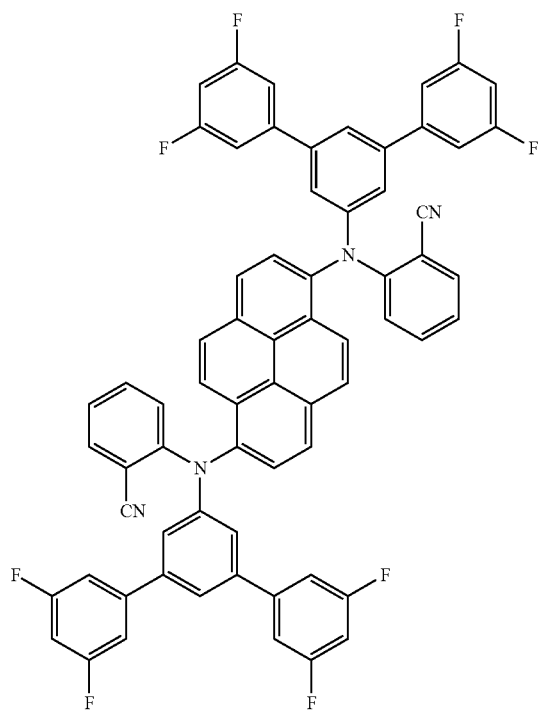
BD 242
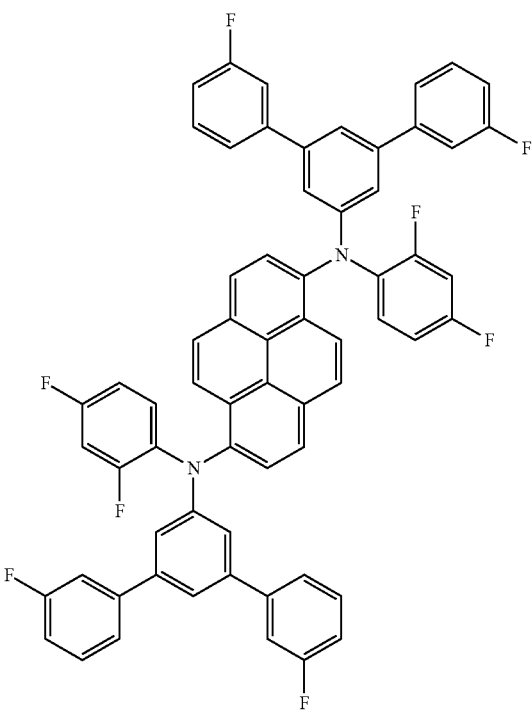

-continued
BD 243
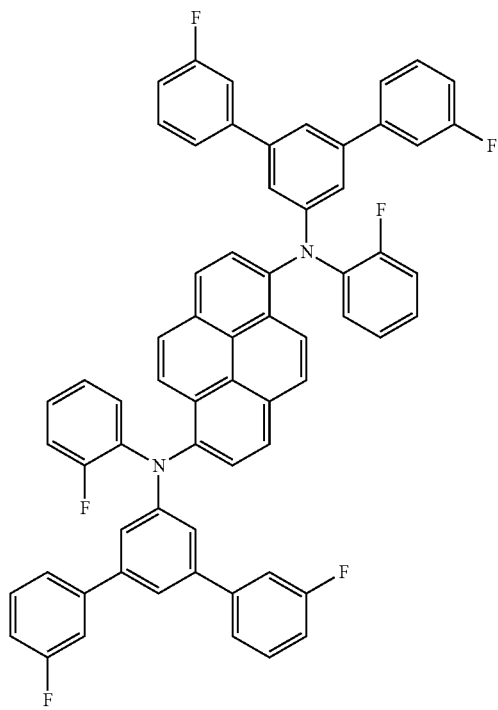
BD 245
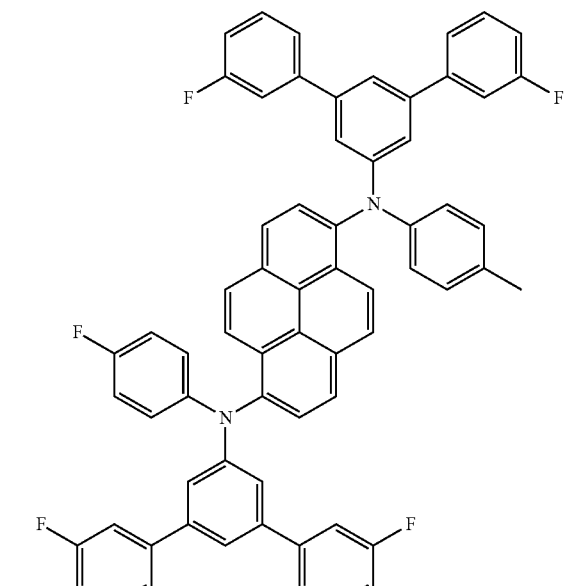
BD 244
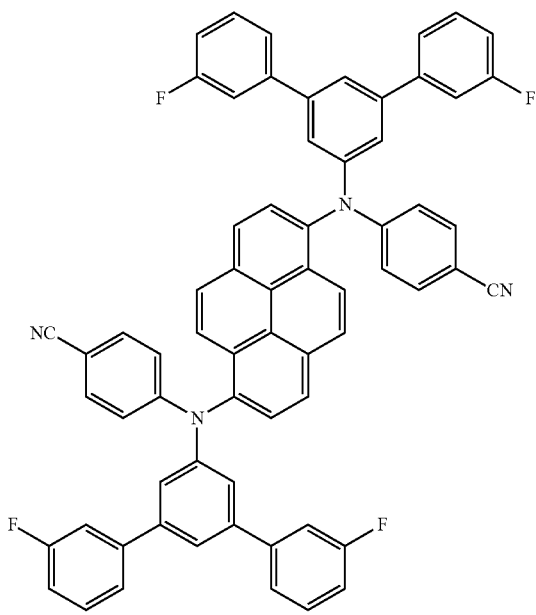
BD 246
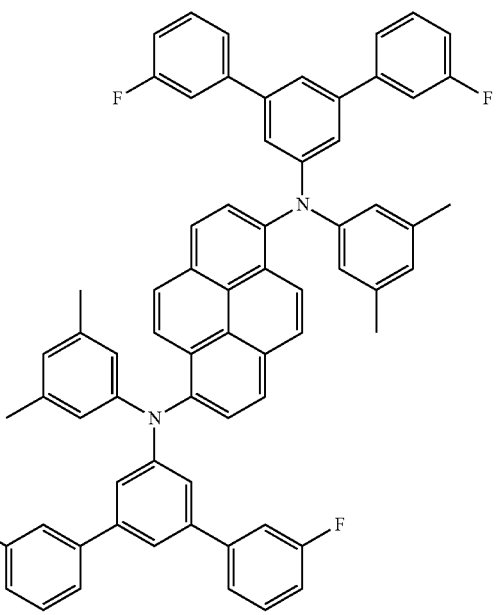

-continued
BD 247
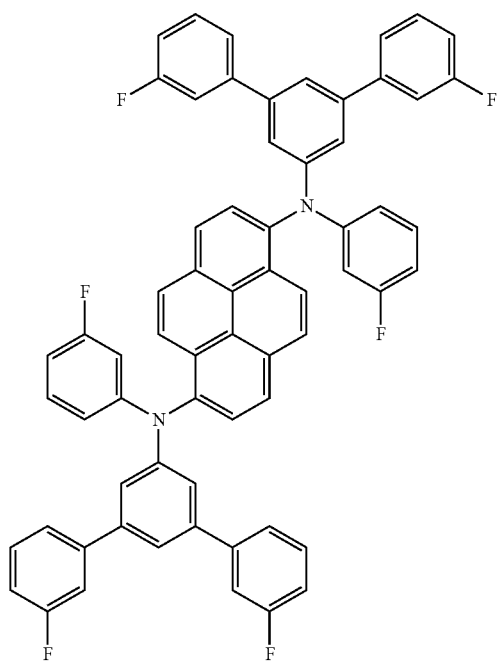
BD 249
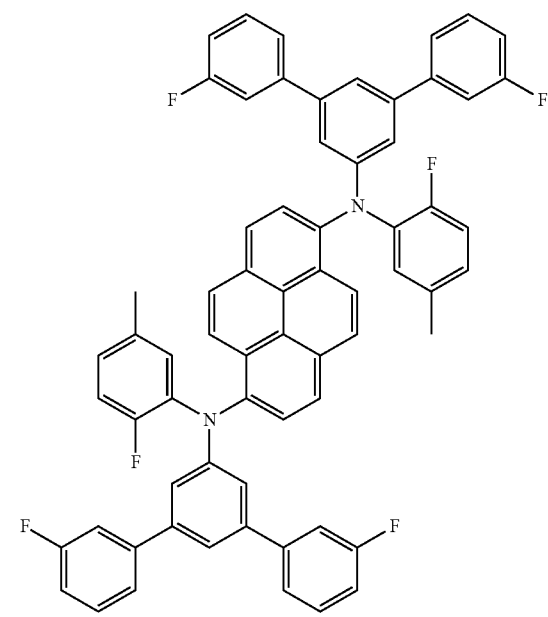
BD 248
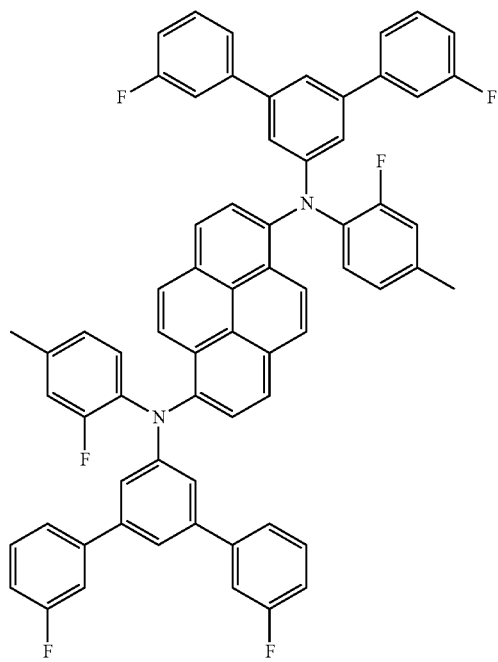
BD 250
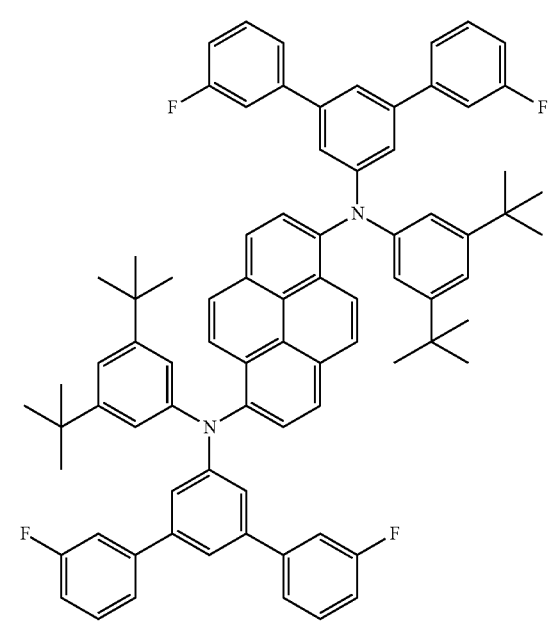

BD 251
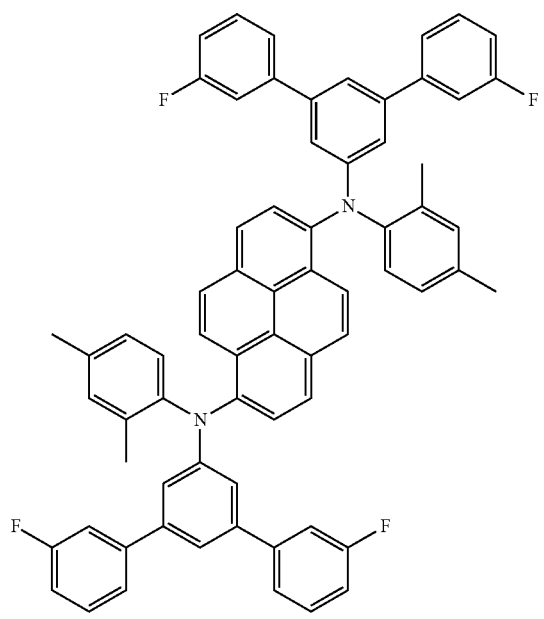
BD 253
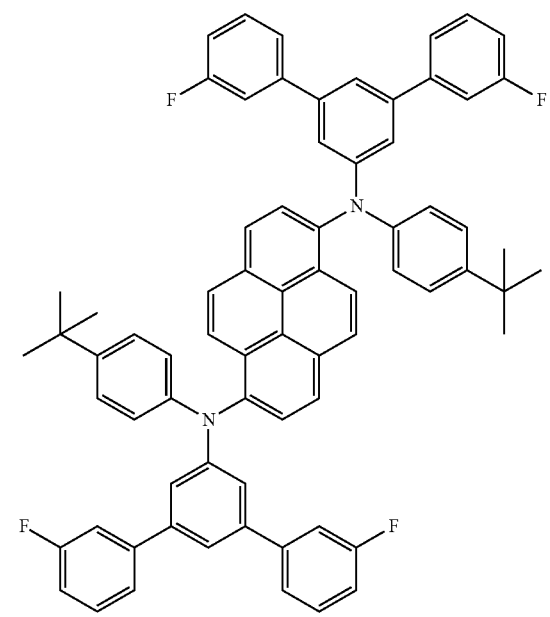
BD 252
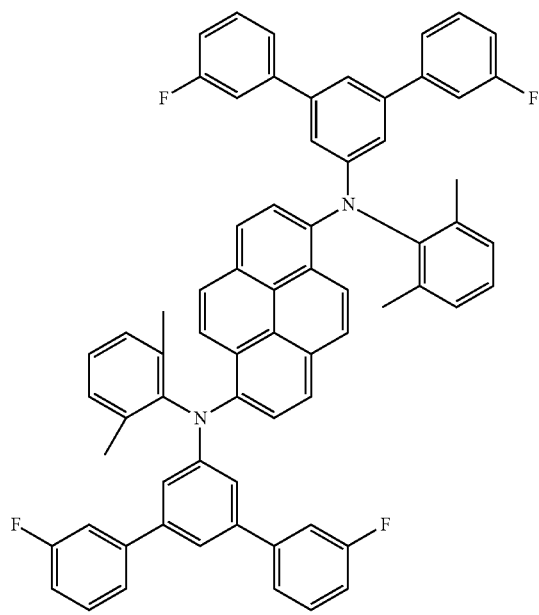
BD 254
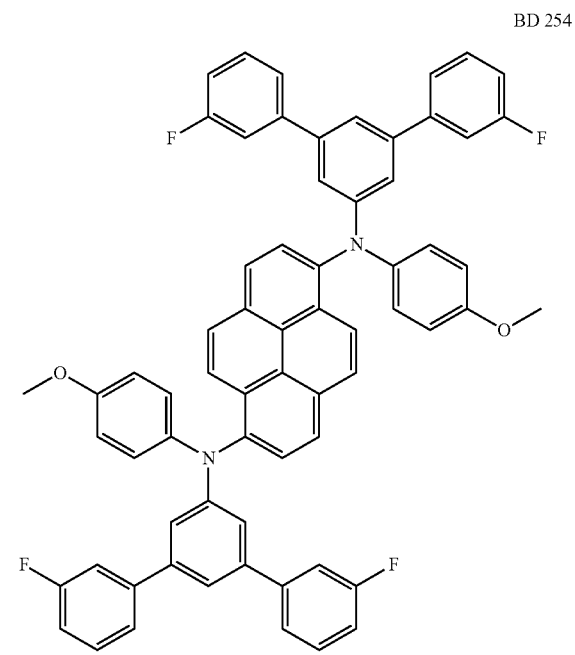

BD 255
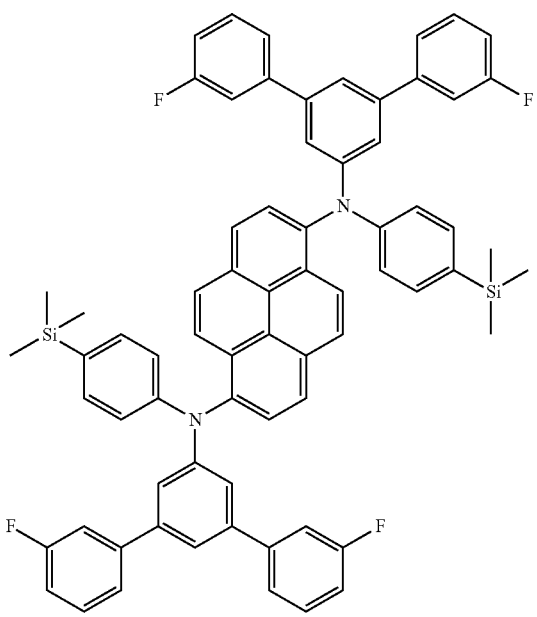
BD 257
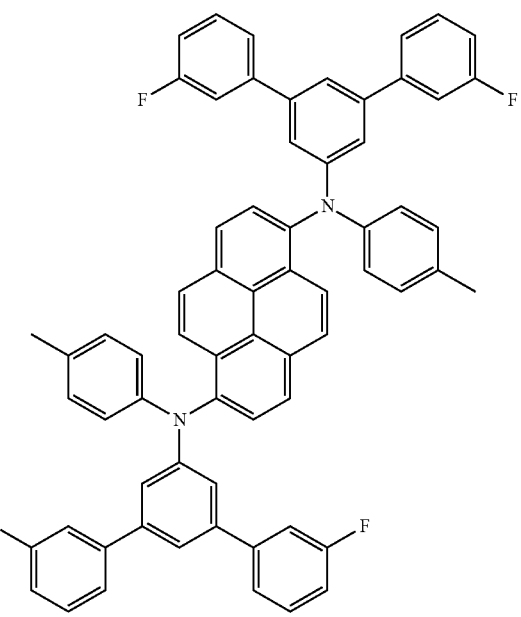
BD 256
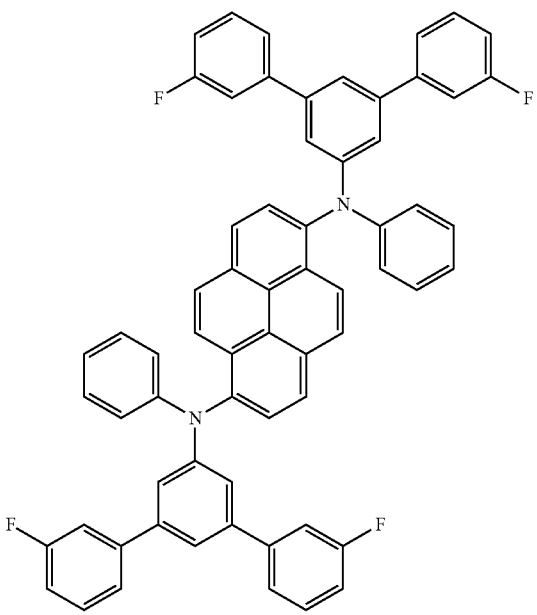
BD 258
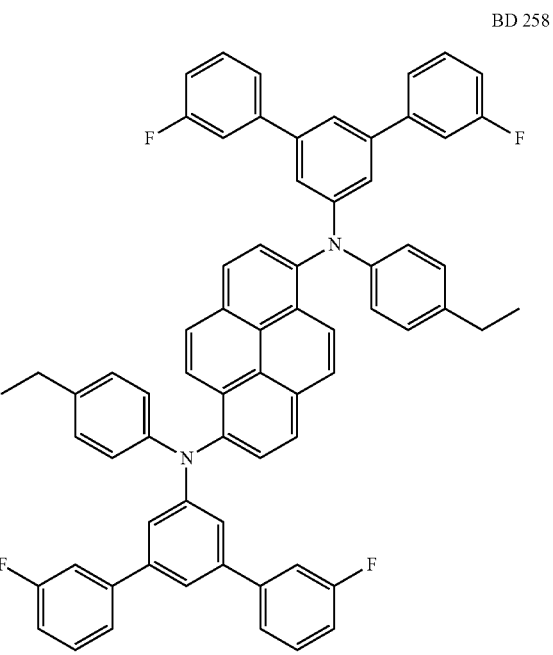

BD 259
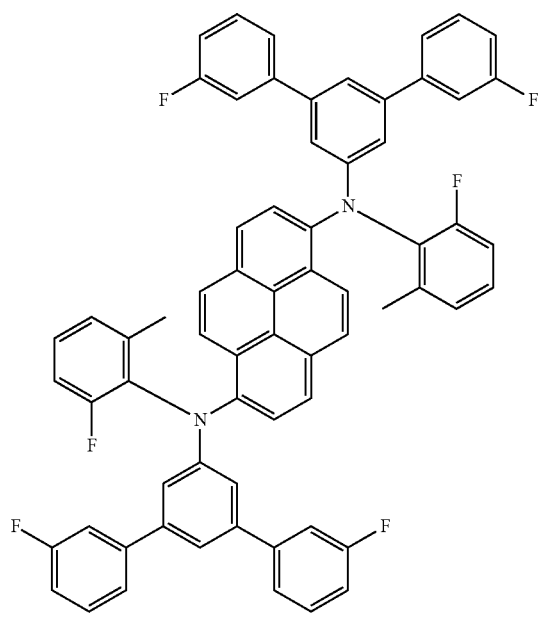
BD 261
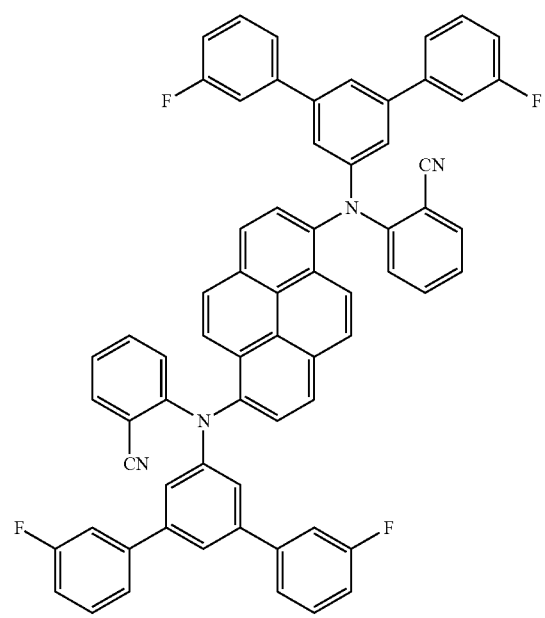
BD 260
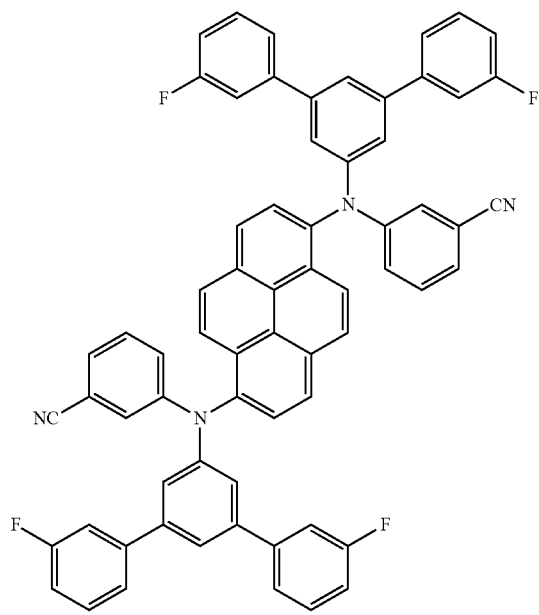
BD 262
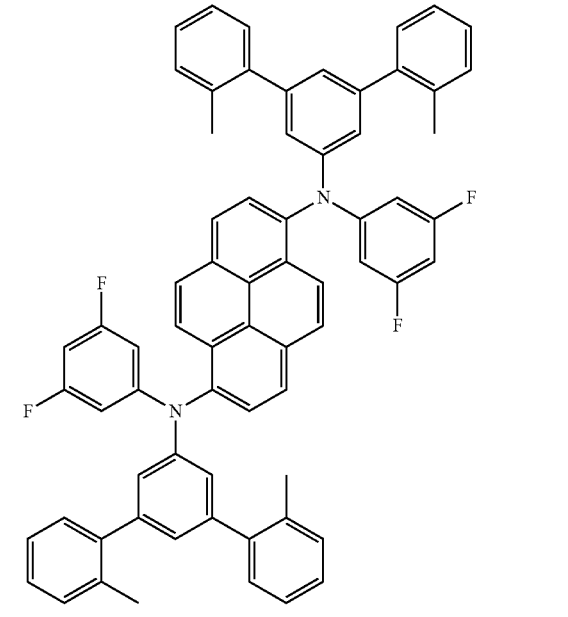

BD 263
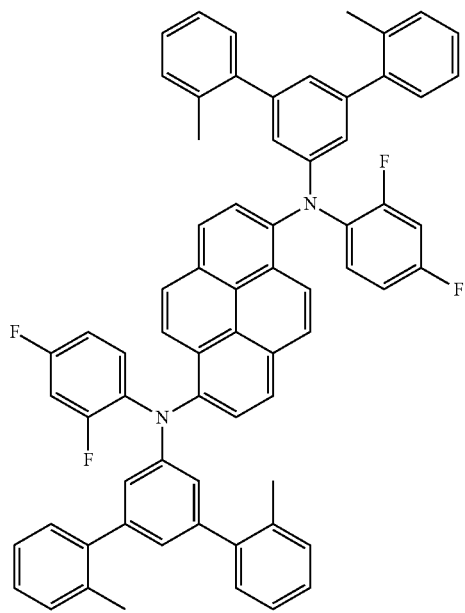
BD 265
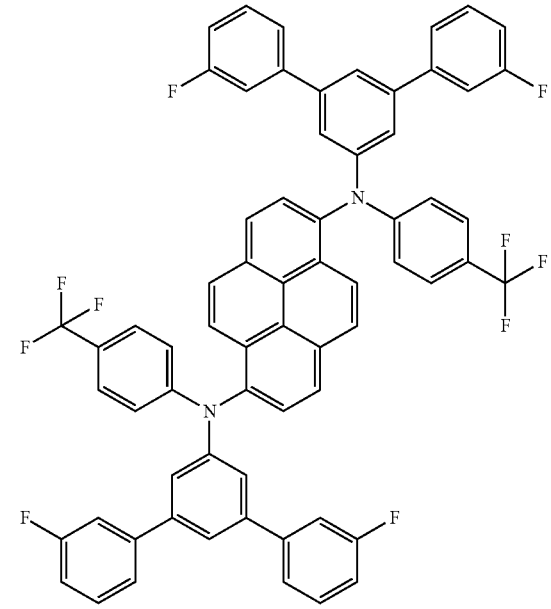
BD 264
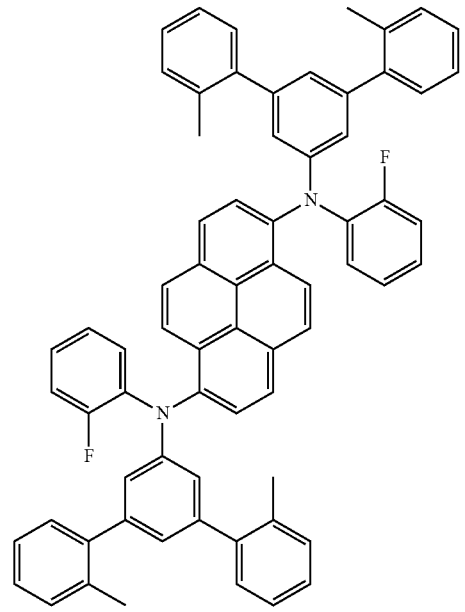
BD 266
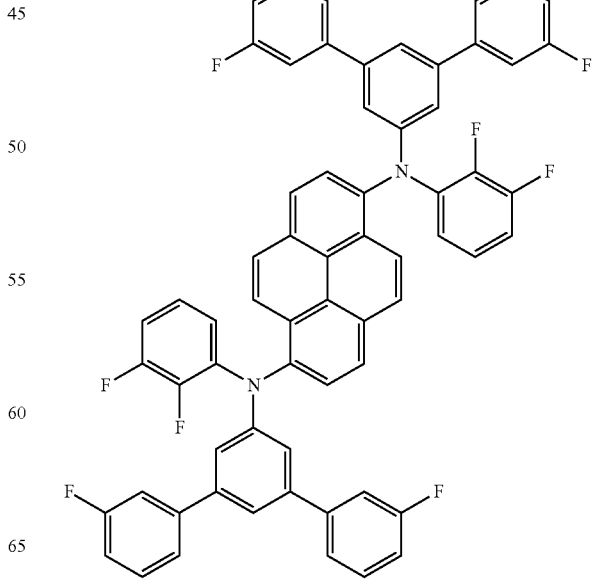

BD 267
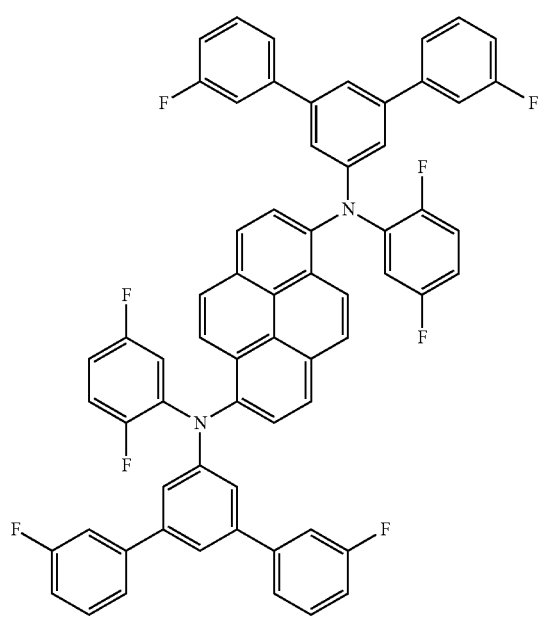
BD 269
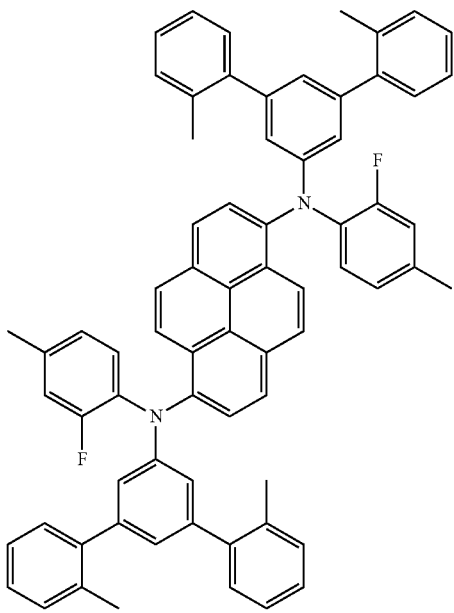
BD 268
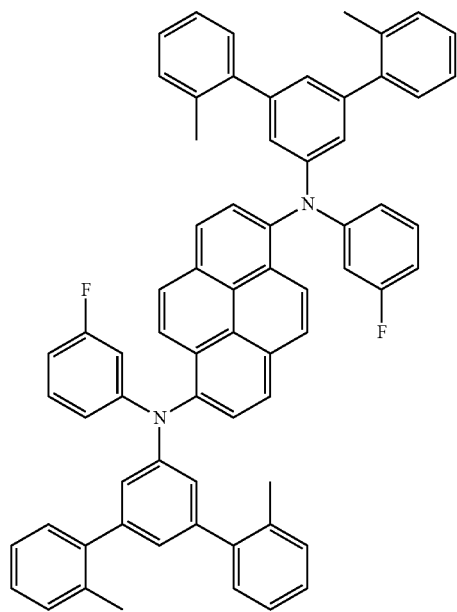
BD 270

BD 271
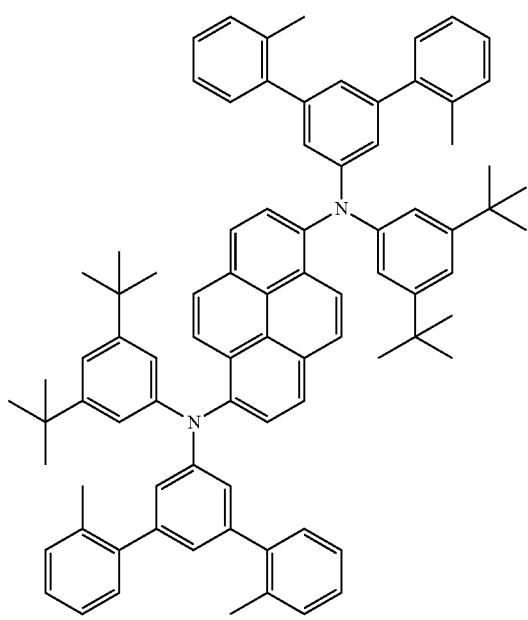
BD 273
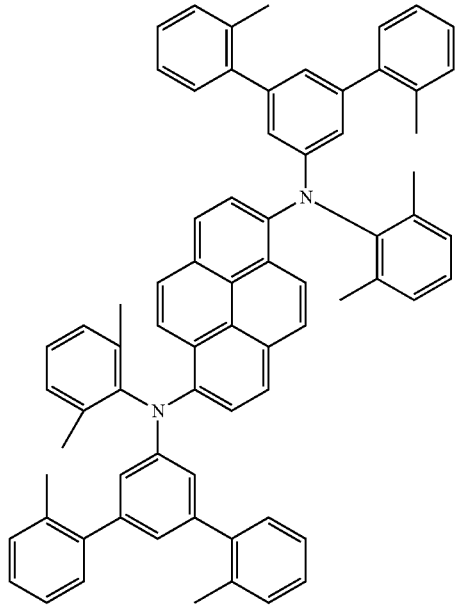
BD 272
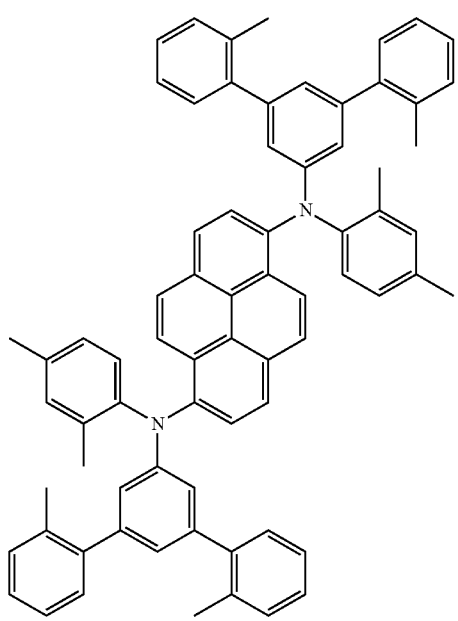
BD 274
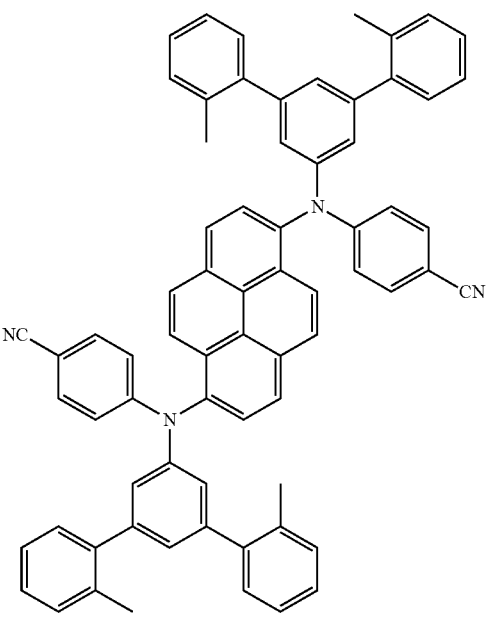

BD 275
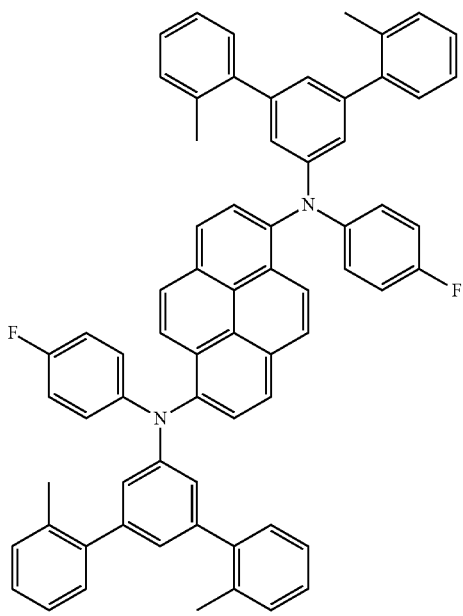
BD 277
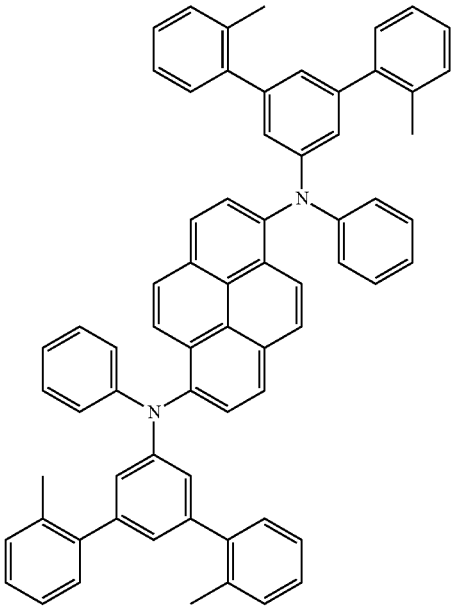
BD 276
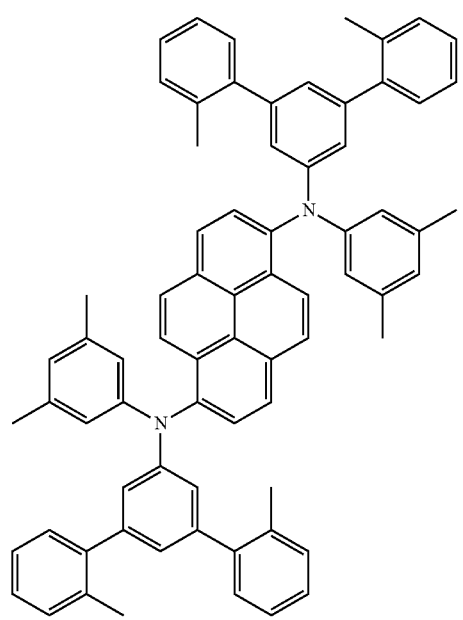
BD 278
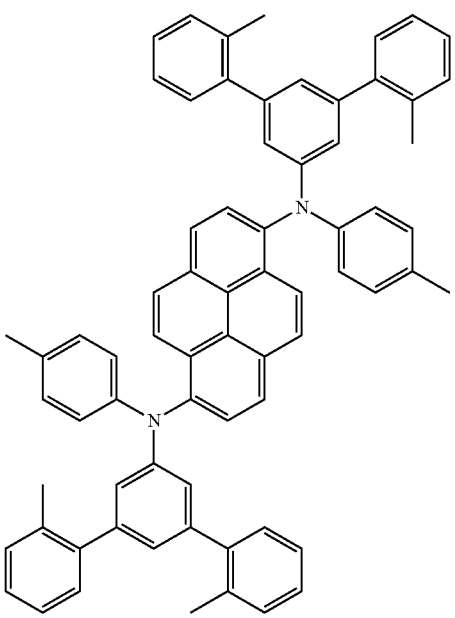

BD 279
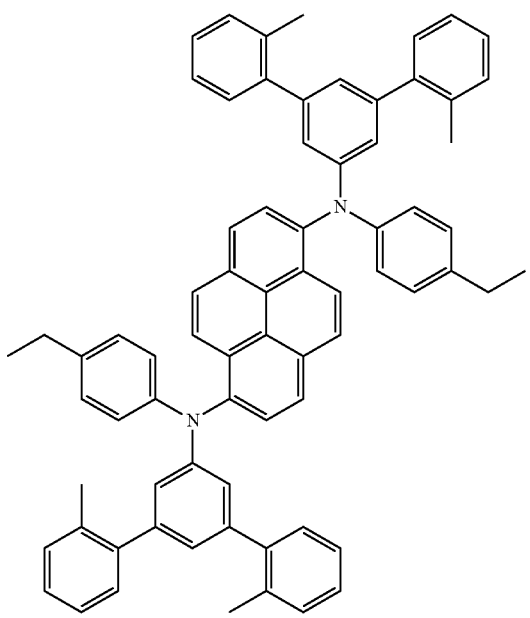
BD 280
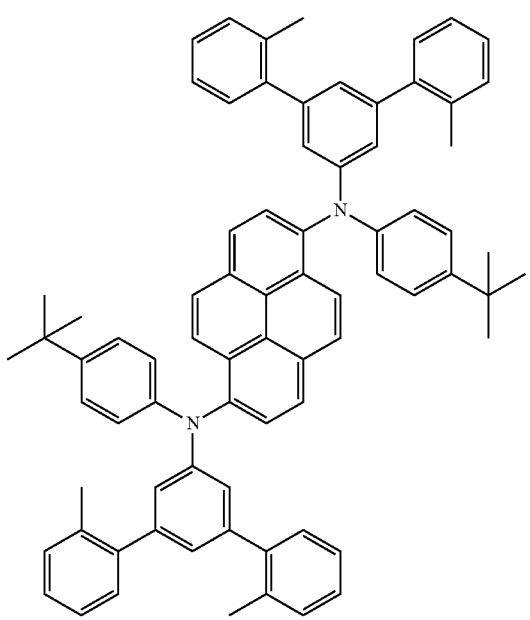
BD 281
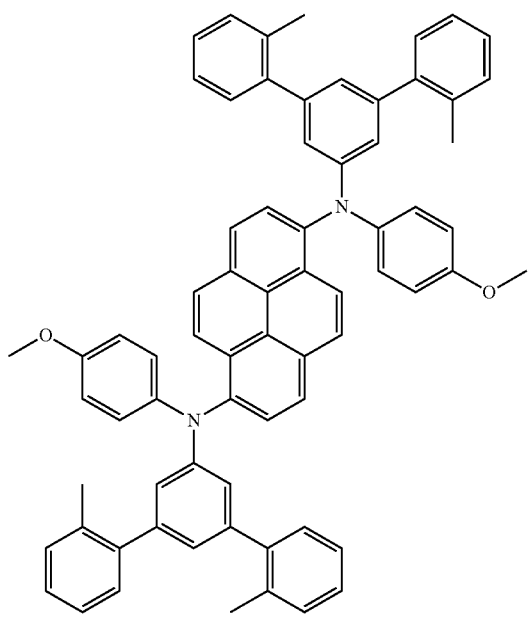
BD 282
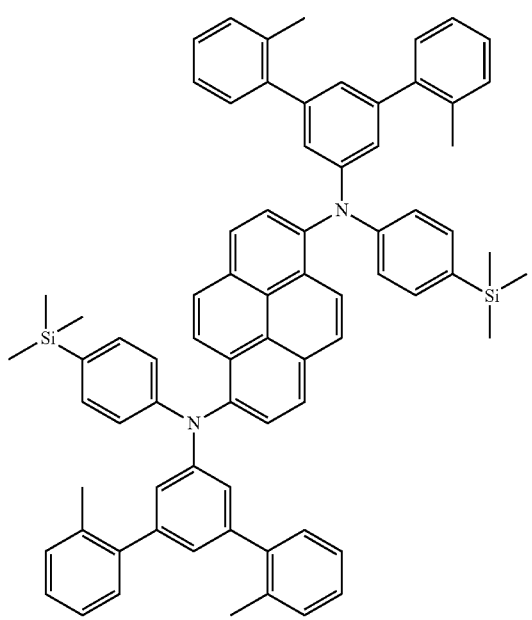

BD 283
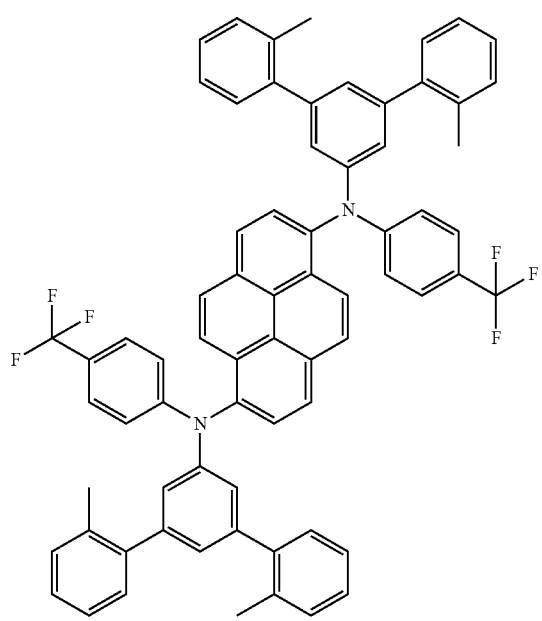
BD 285
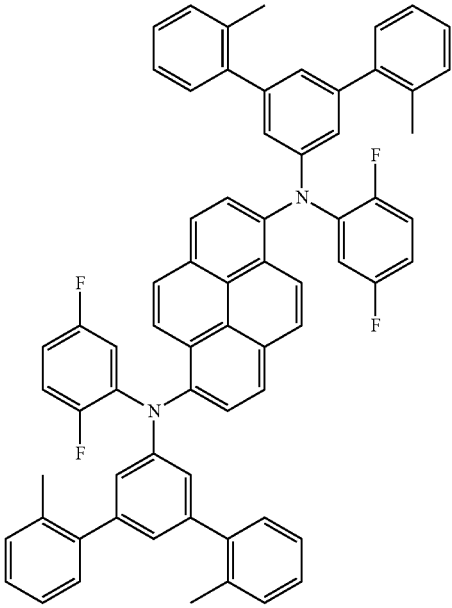
BD 284
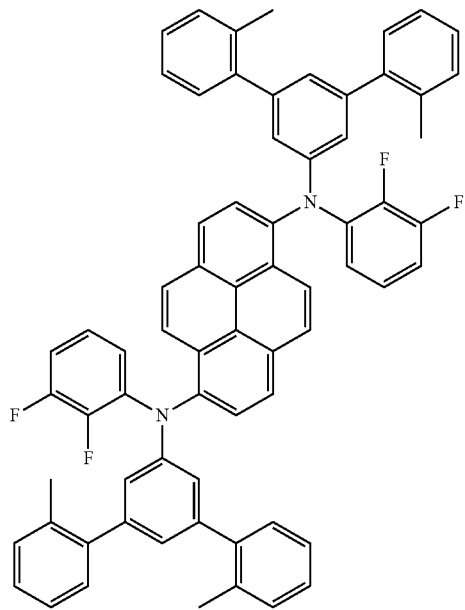
BD 286
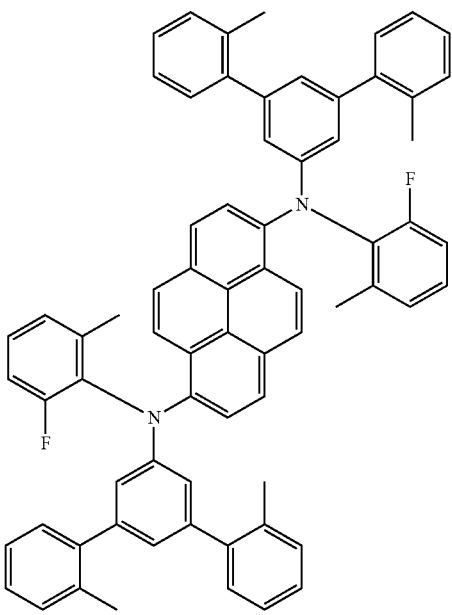

147
-continued
BD 287
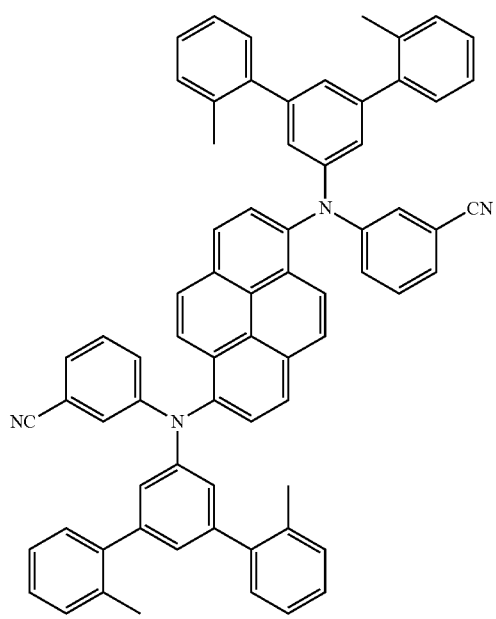
BD 288
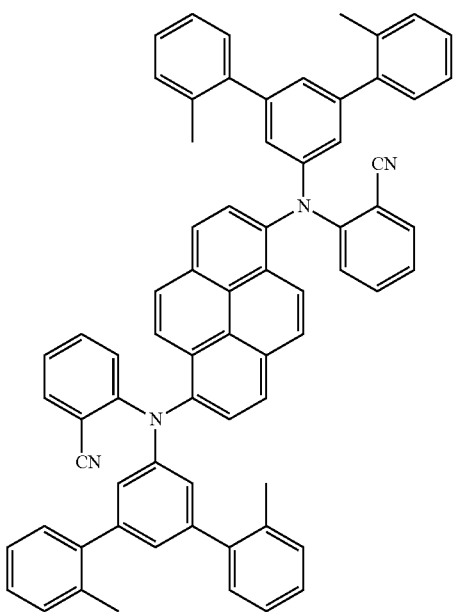
148
-continued
BD 289
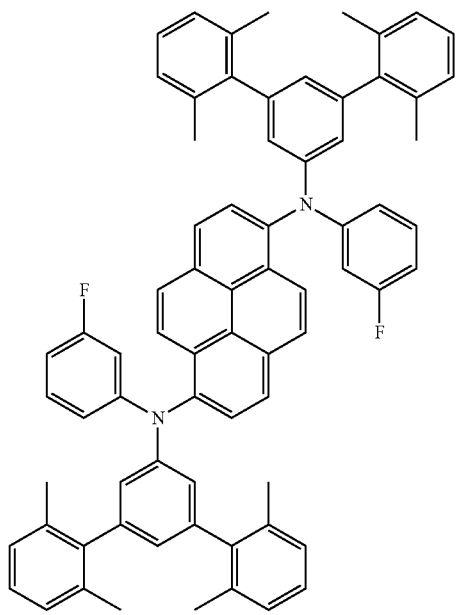
BD 290
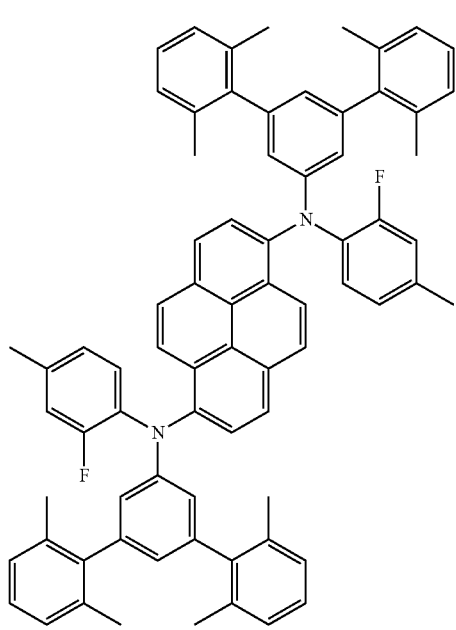

BD 291
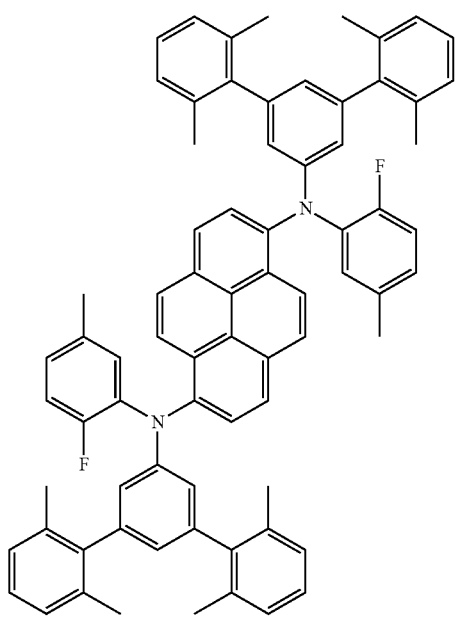
BD 293
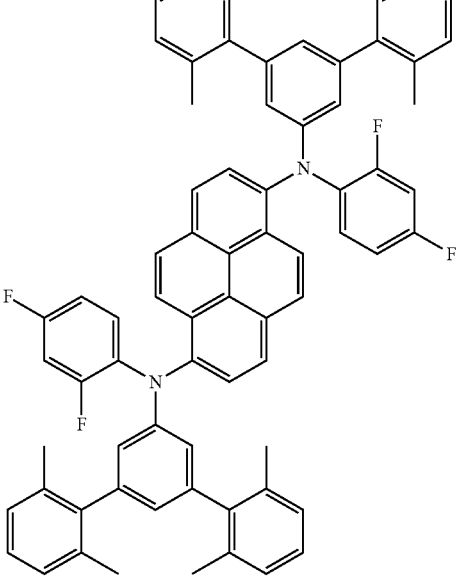
BD 292
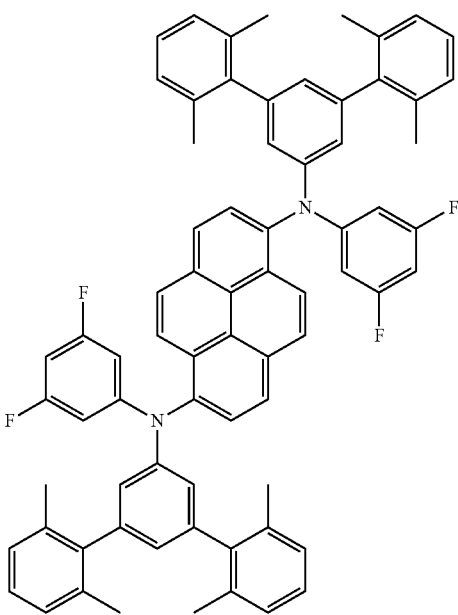
BD 294
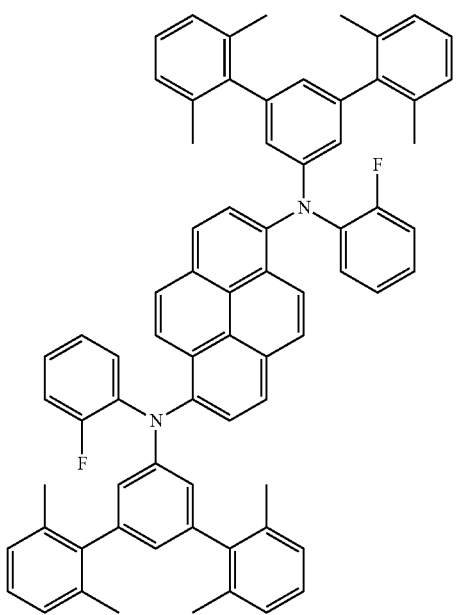

-continued
BD 295
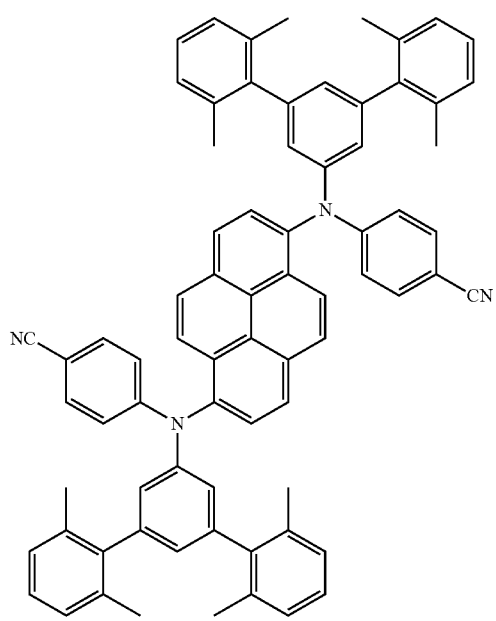
BD 297
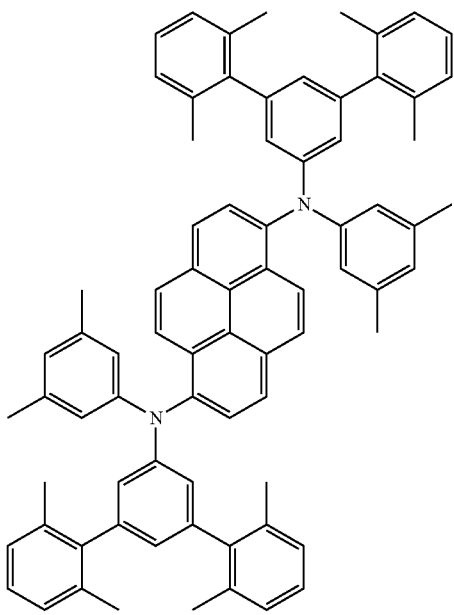
BD 296
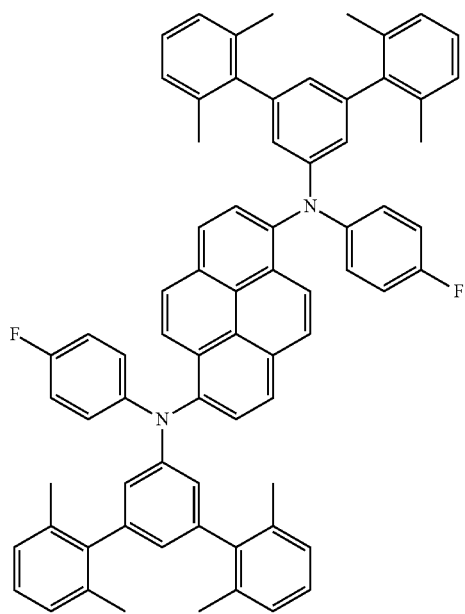
BD 298
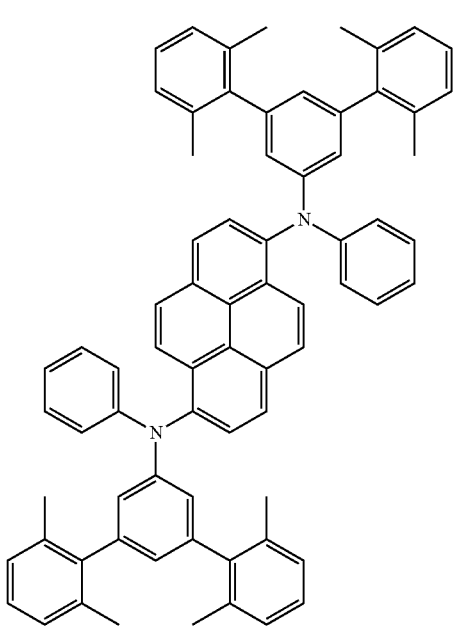

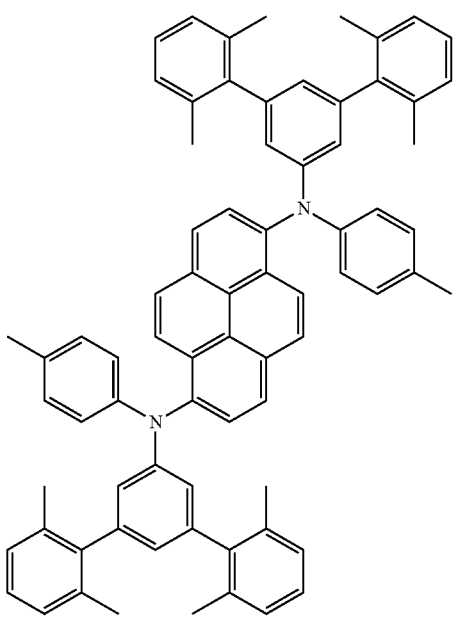
BD 299
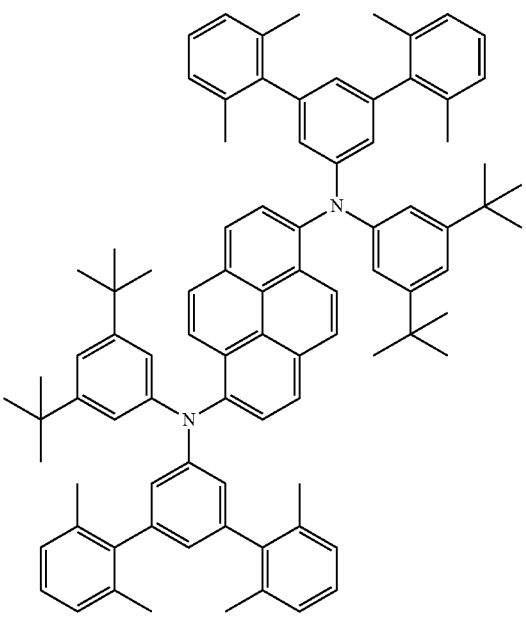
BD 301
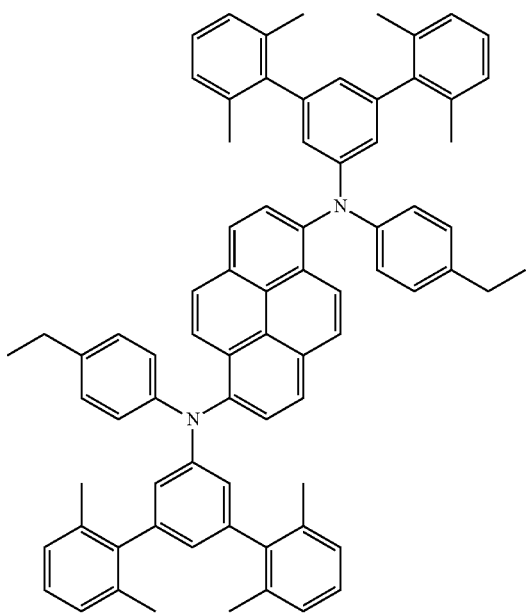
BD 300
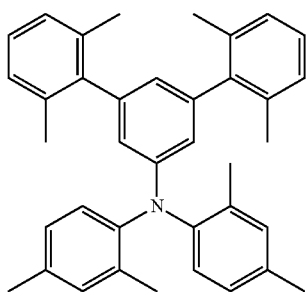
BD 302

BD 303
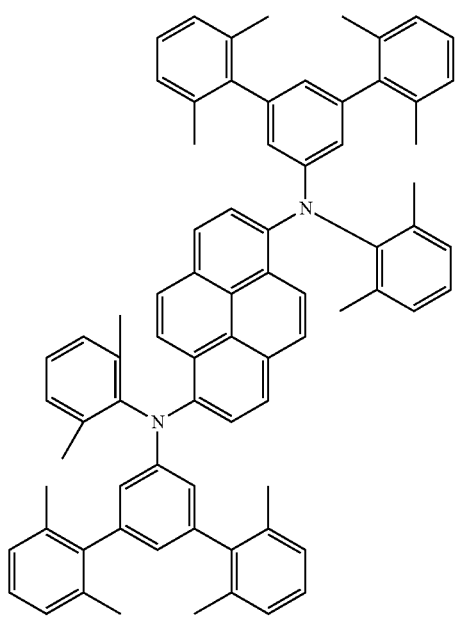
BD 304
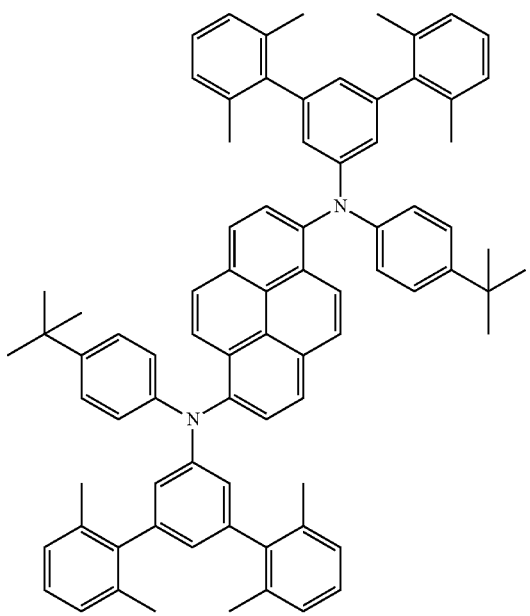
BD 305
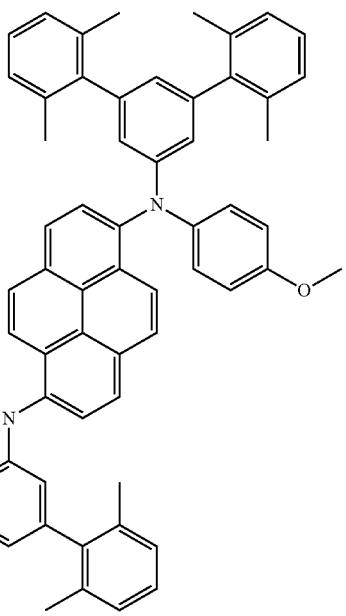
BD 306
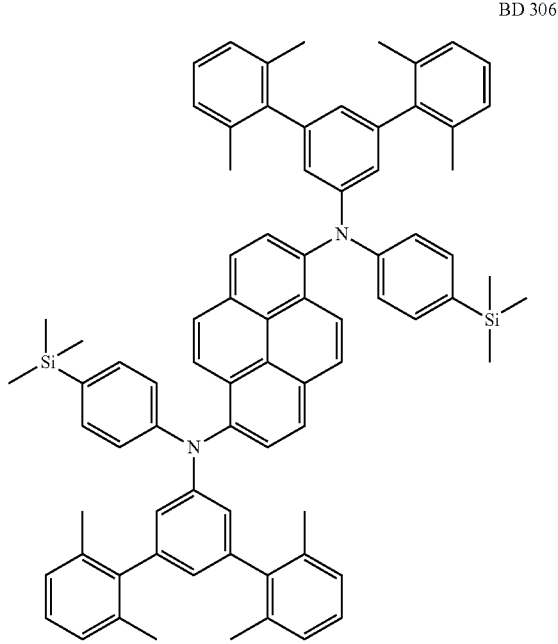

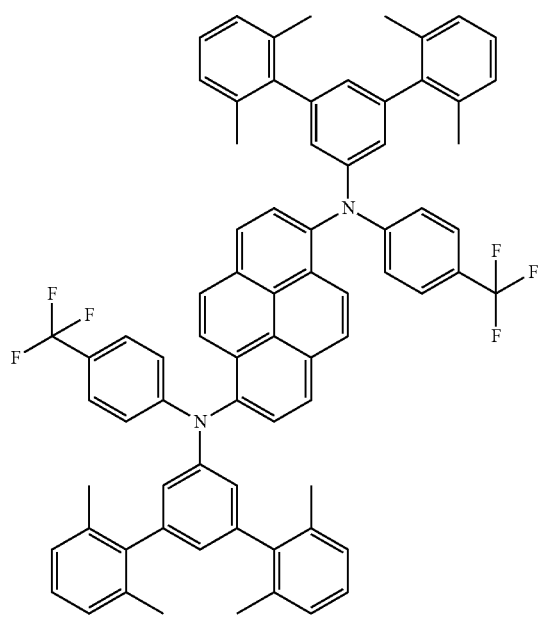
BD 307
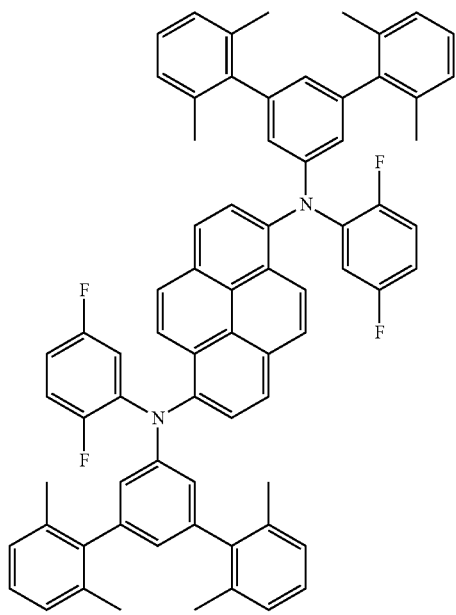
BD 309
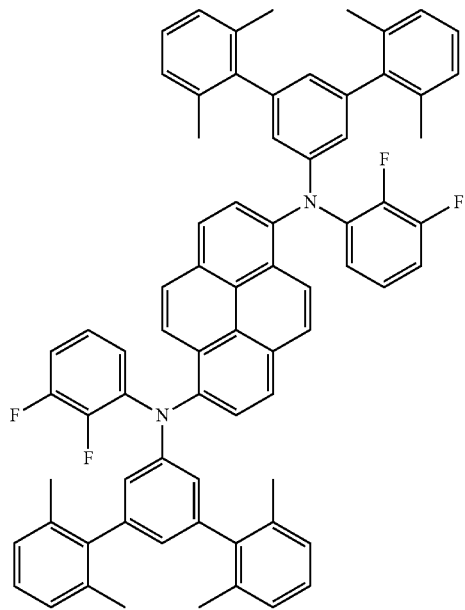
BD 308
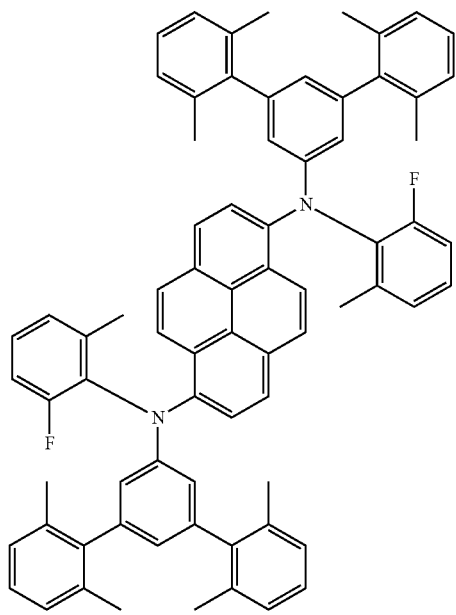
BD 310

BD 311
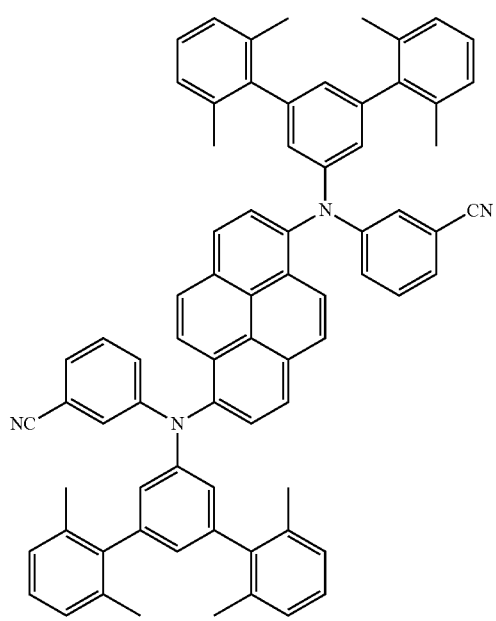
BD 312
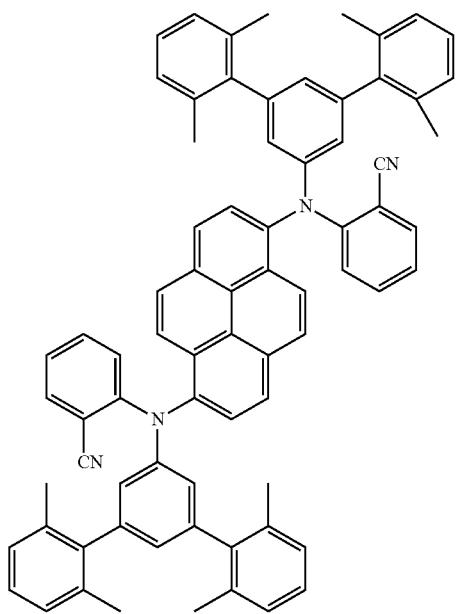
BD 313
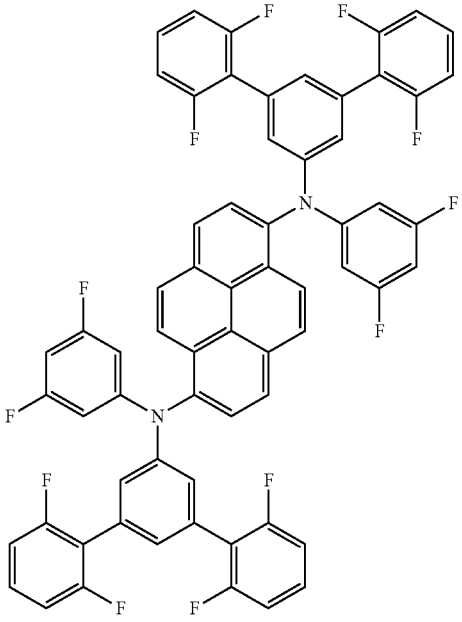
BD 314
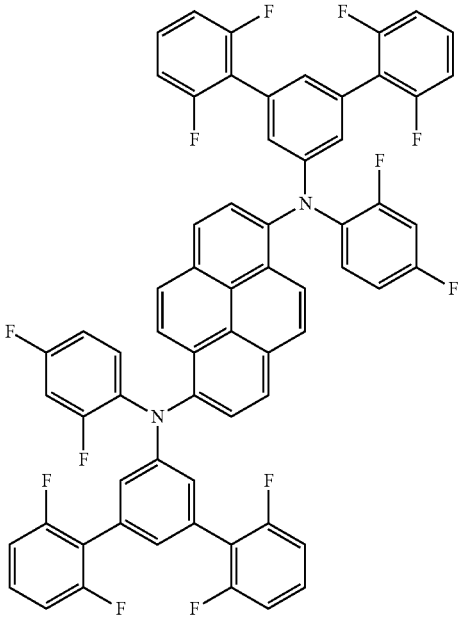

-continued
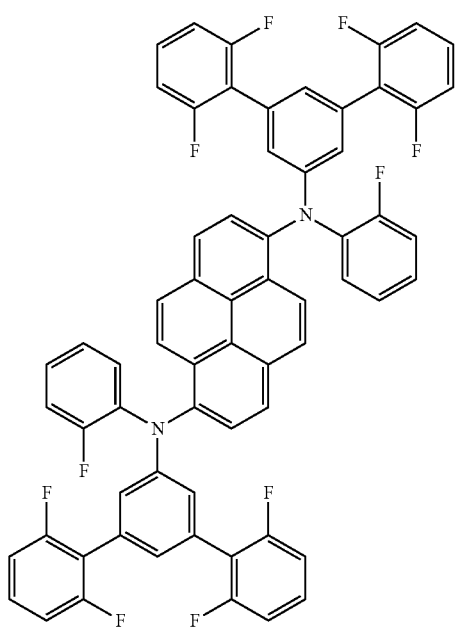
BD 315
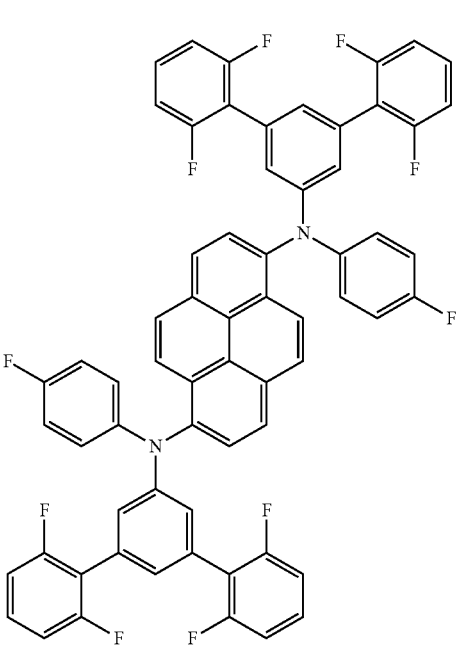
BD 317
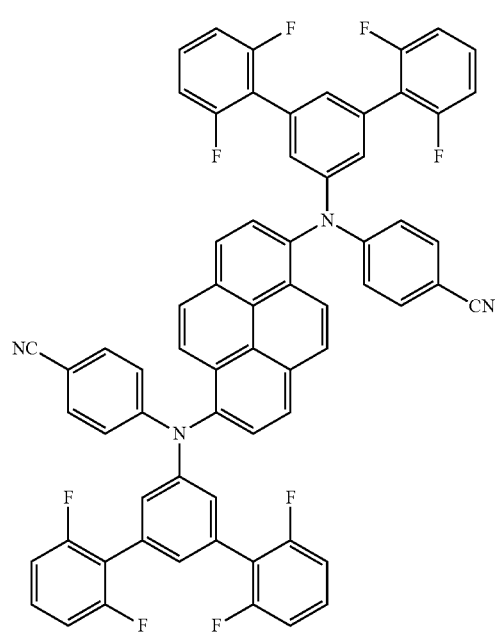
BD 316
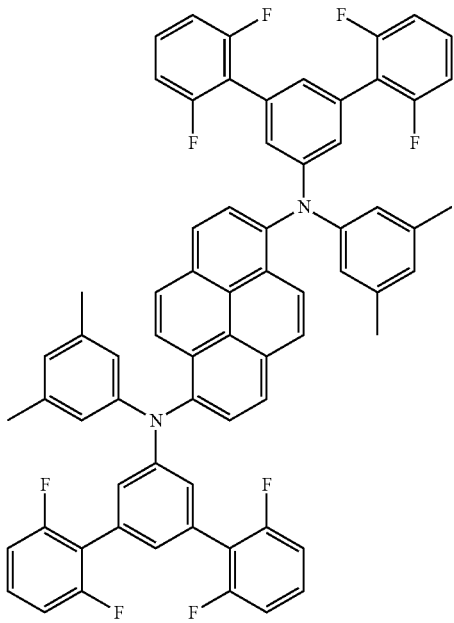
BD 318

BD 319
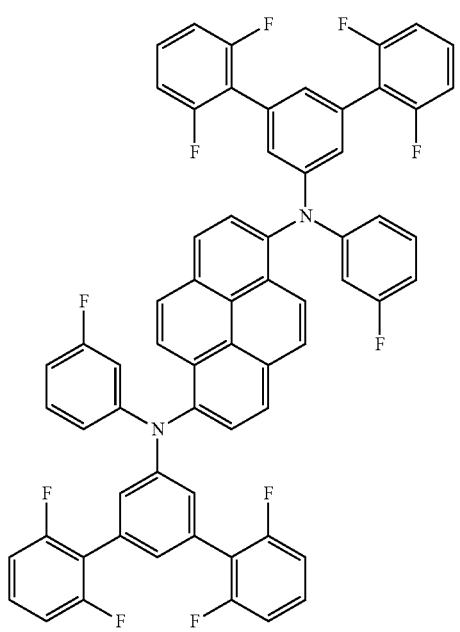
BD 320
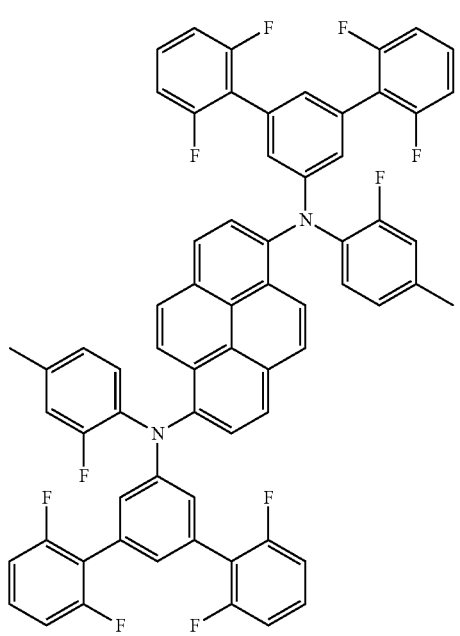
BD 321
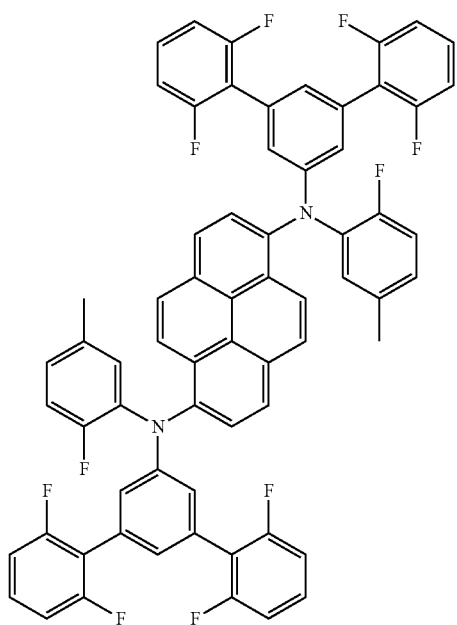
BD 322
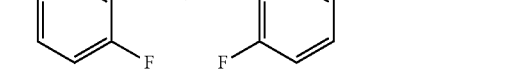

-continued
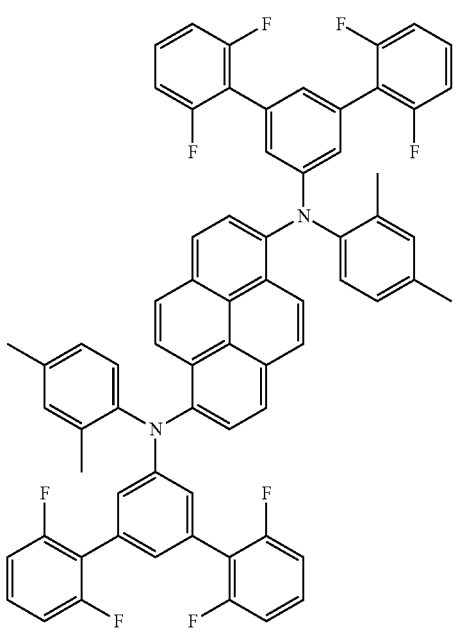
BD 323
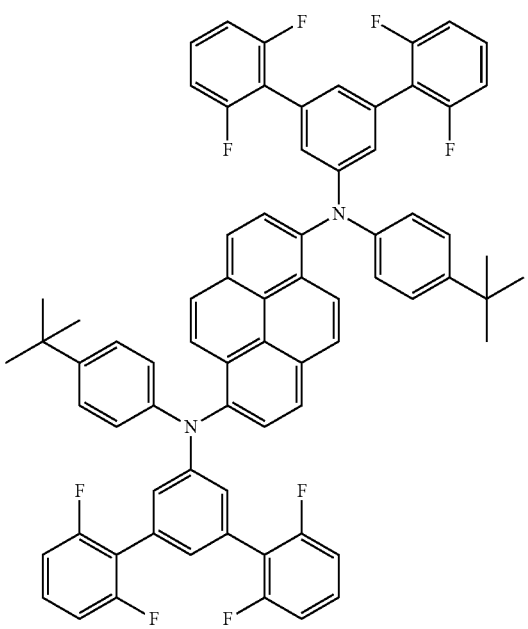
BD 325
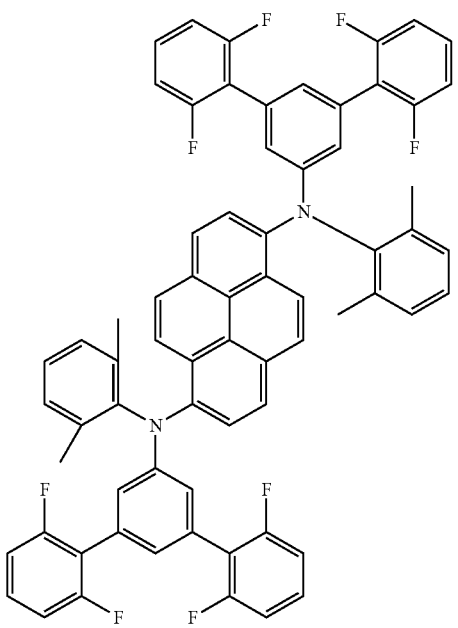
BD 324
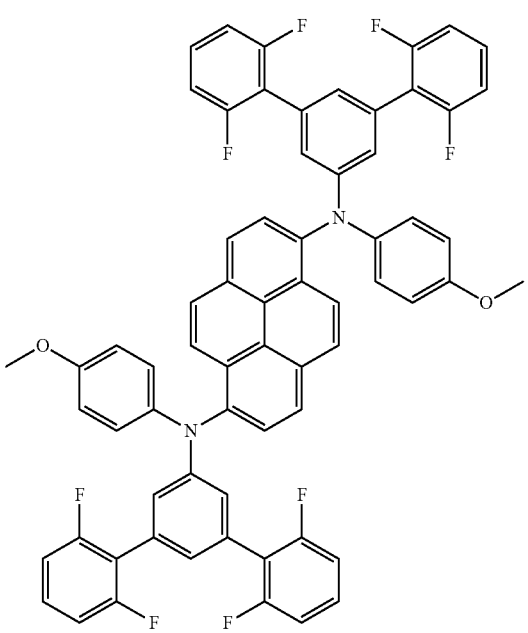
BD 326

BD 327
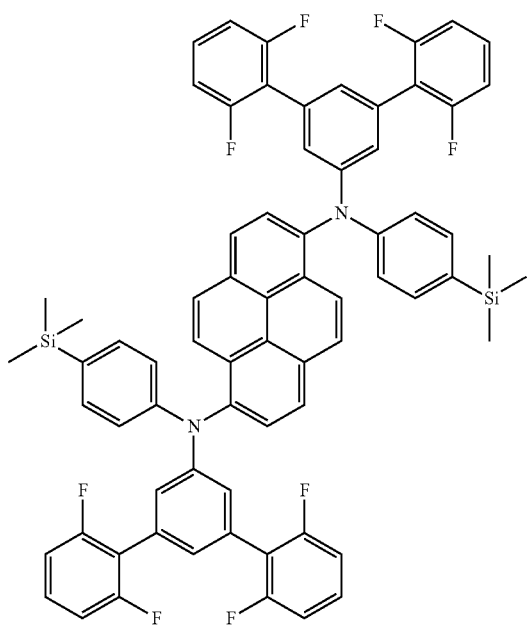
BD 329
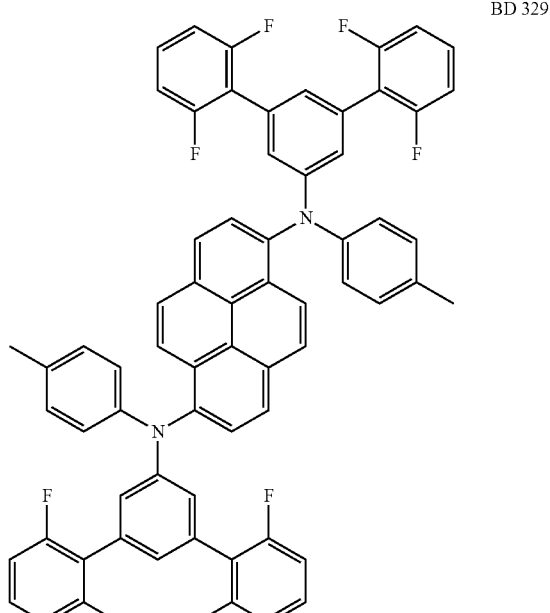
BD 328
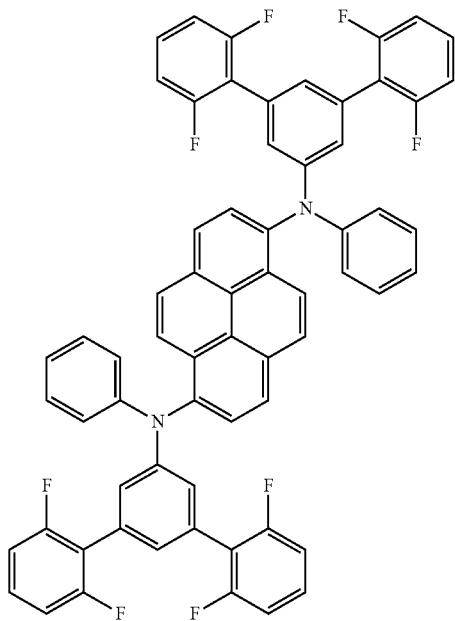
BD 330
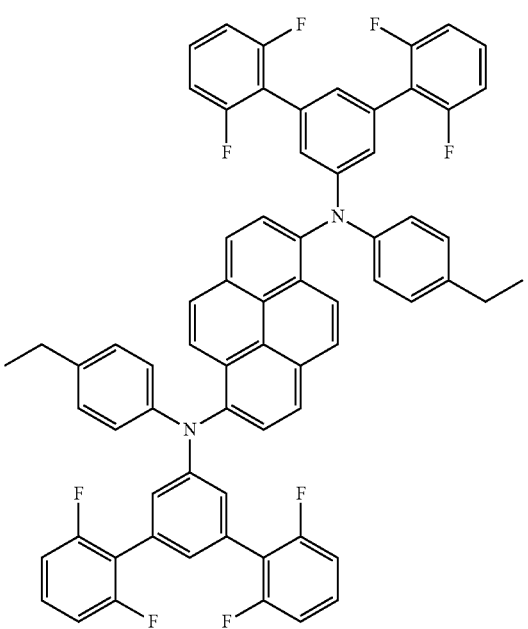

BD 331
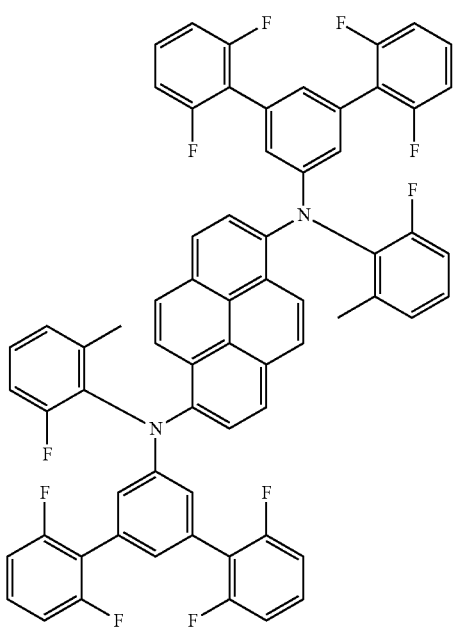
BD 333
BD 332
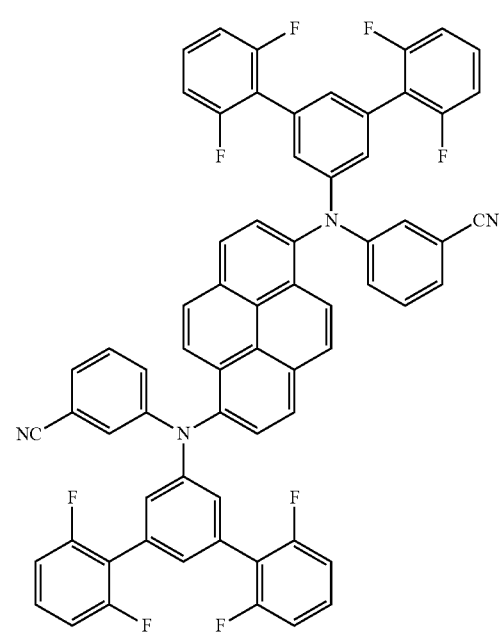
BD 334
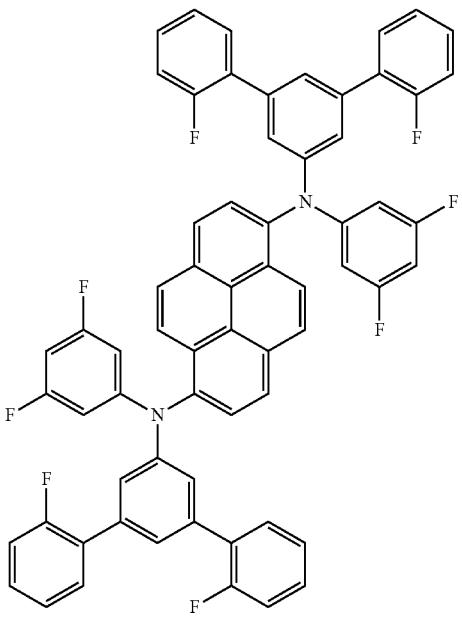

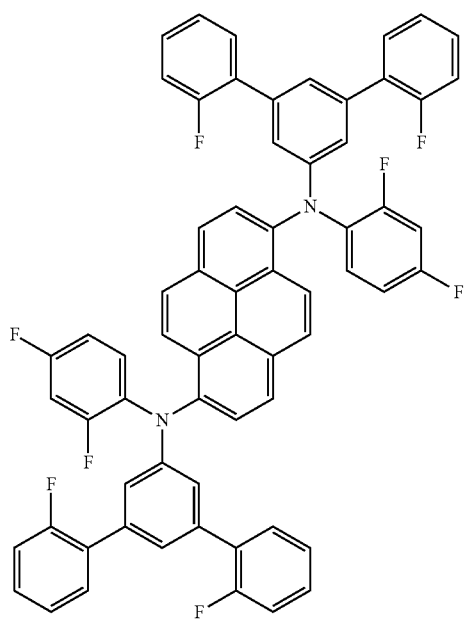
BD 335
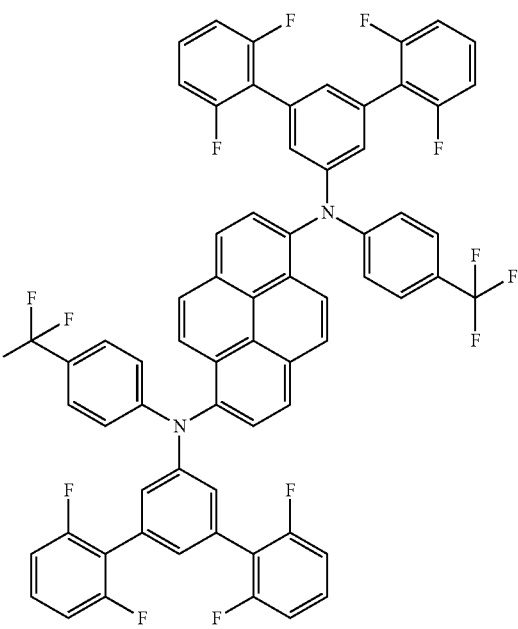
BD 337
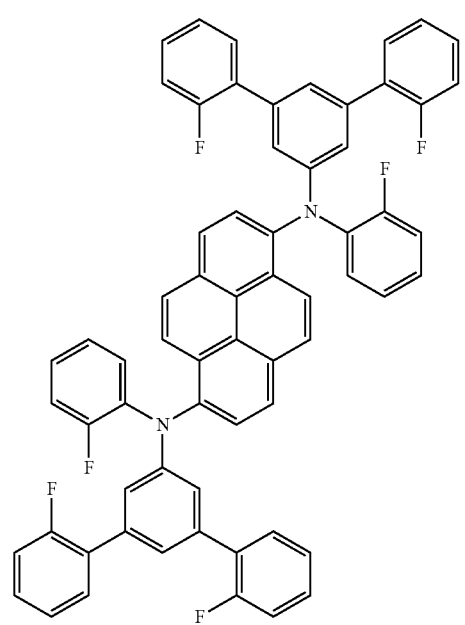
BD 336
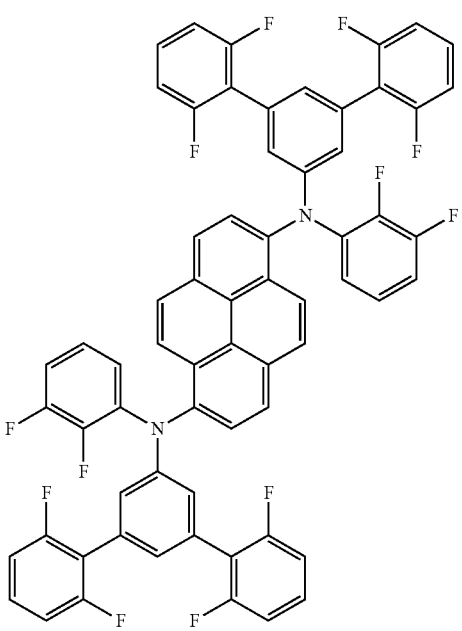
BD 338

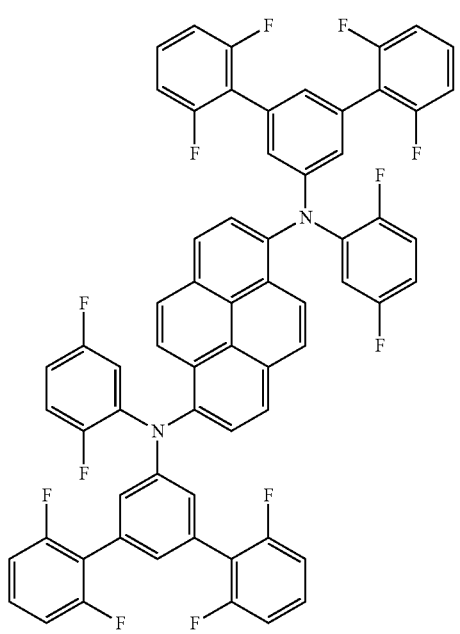
BD 339
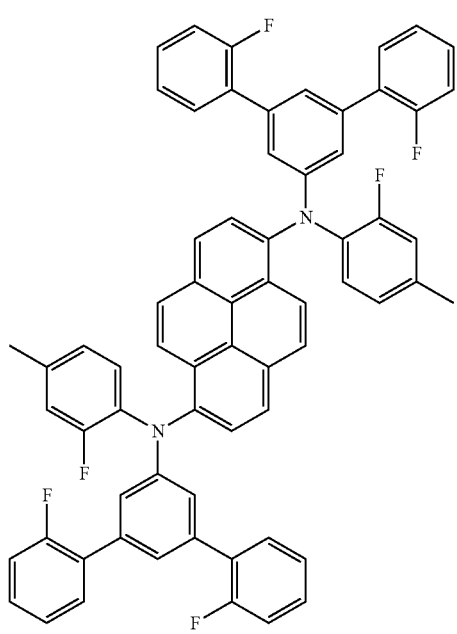
BD 341
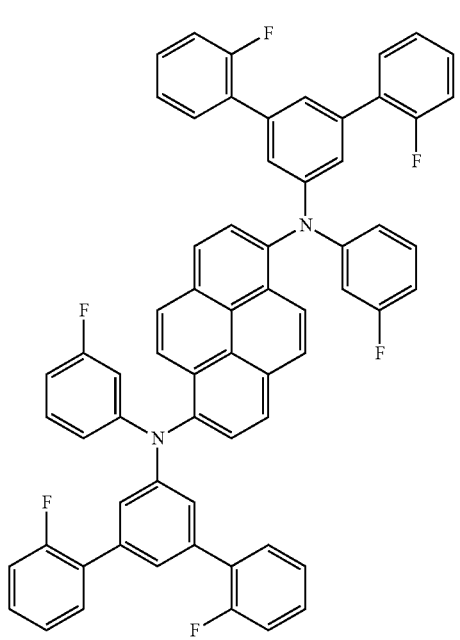
BD 340
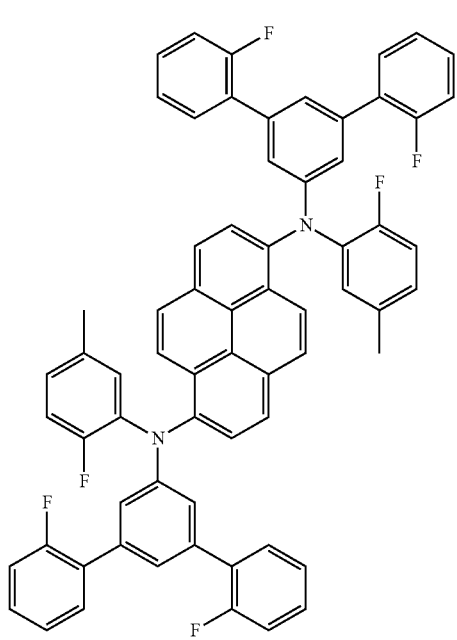
BD 342

BD 343
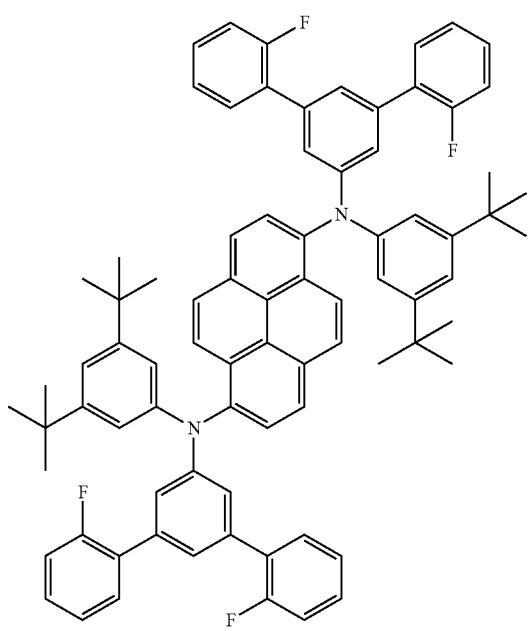
BD 344
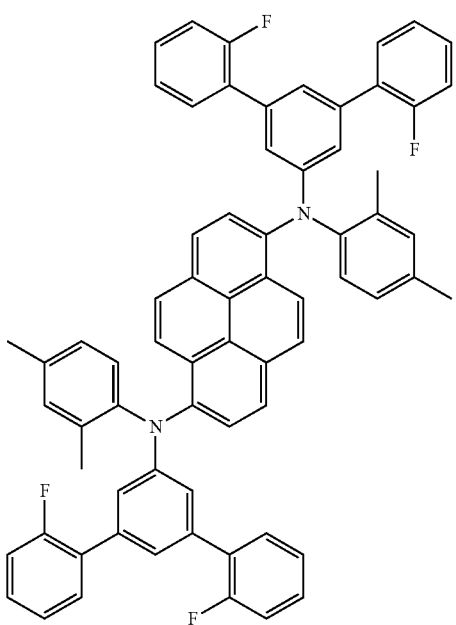
BD 345
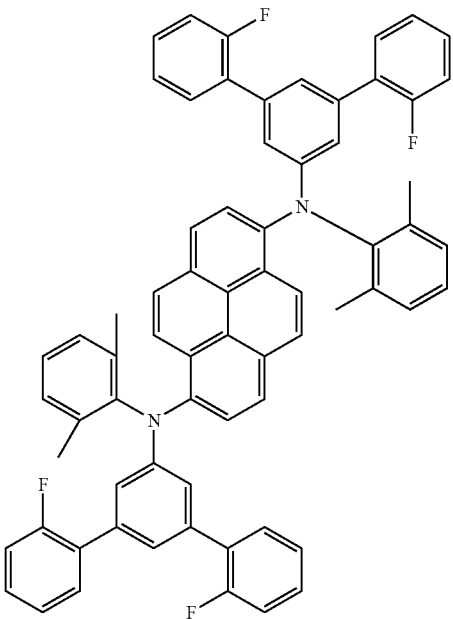
BD 346
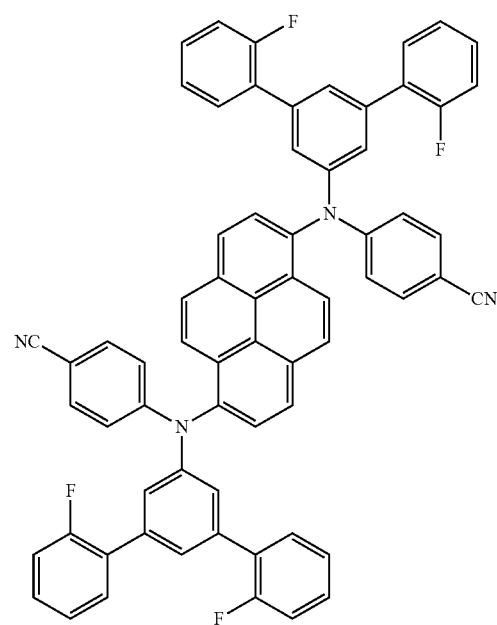

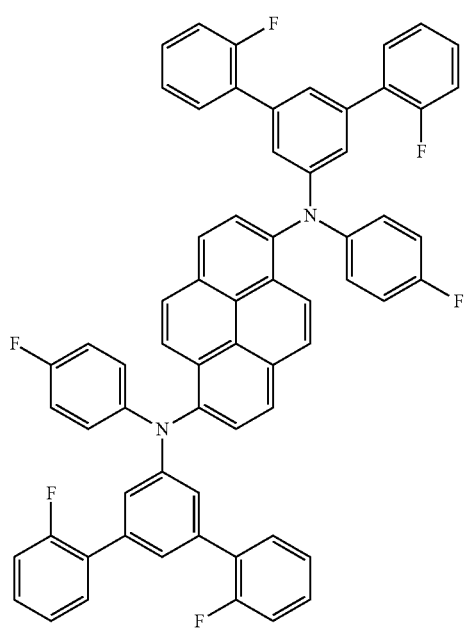
BD 347
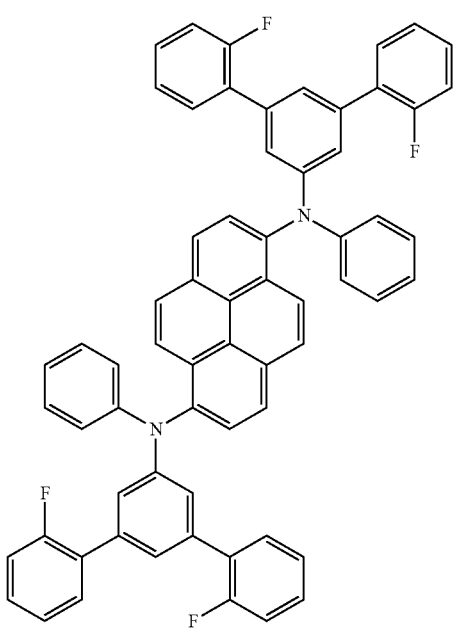
BD 349
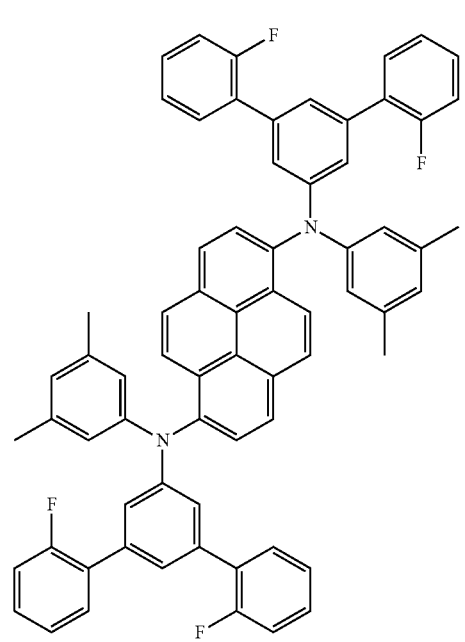
BD 348
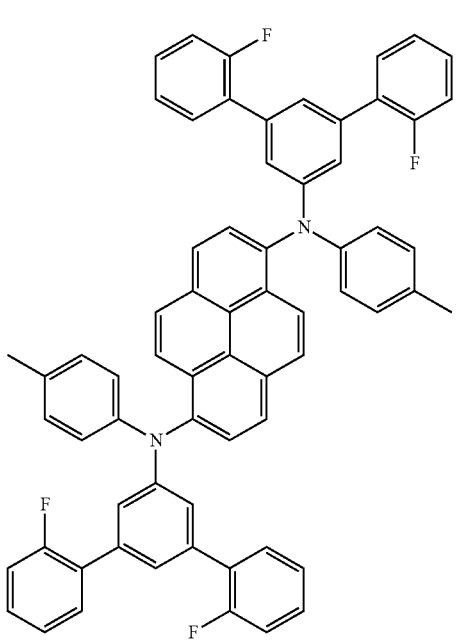
BD 350

-continued
BD 351
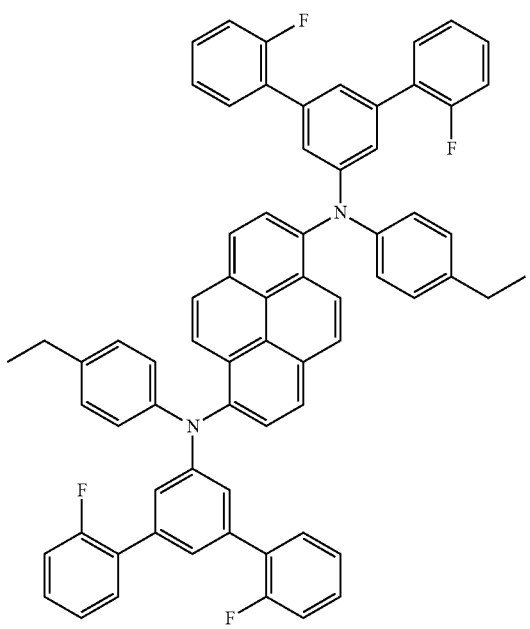
BD 353
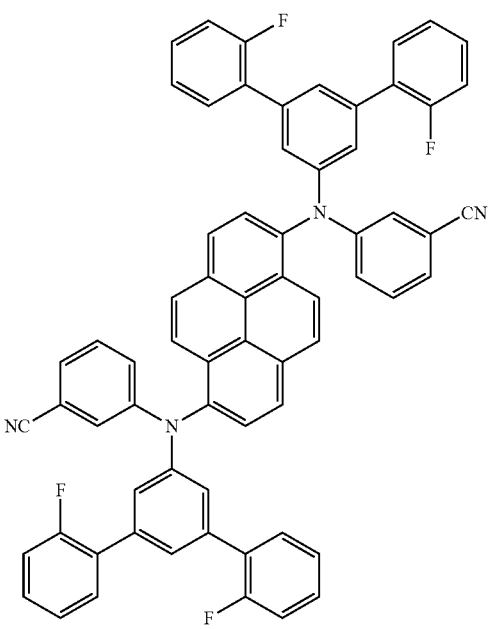
BD 352
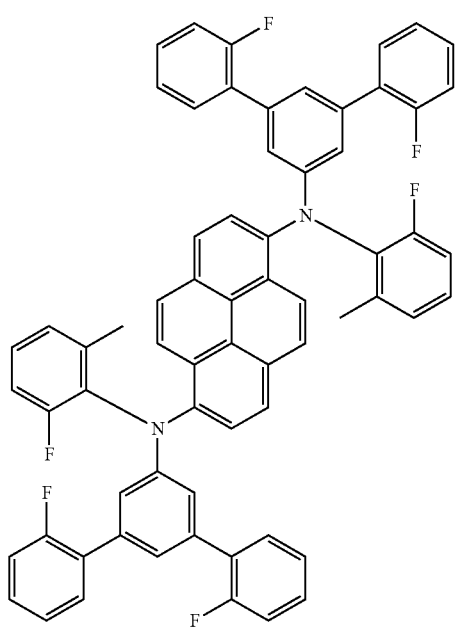
BD 354
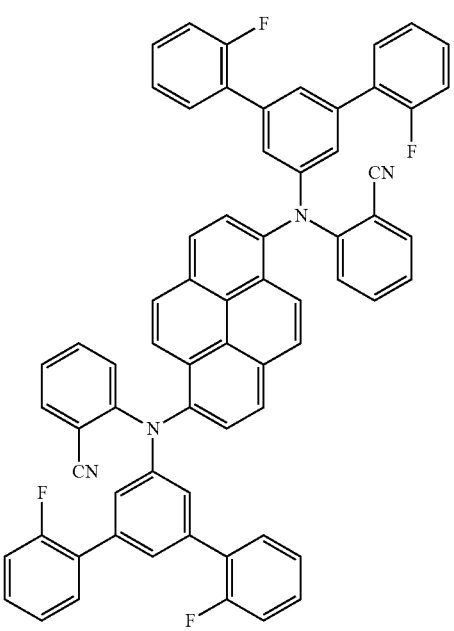

BD 355
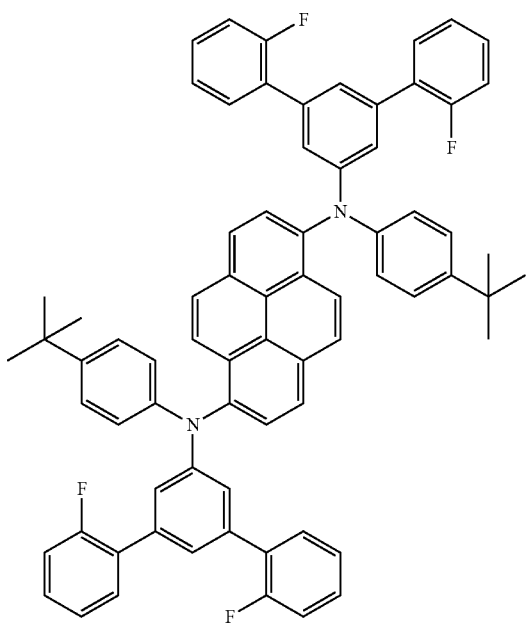
BD 357
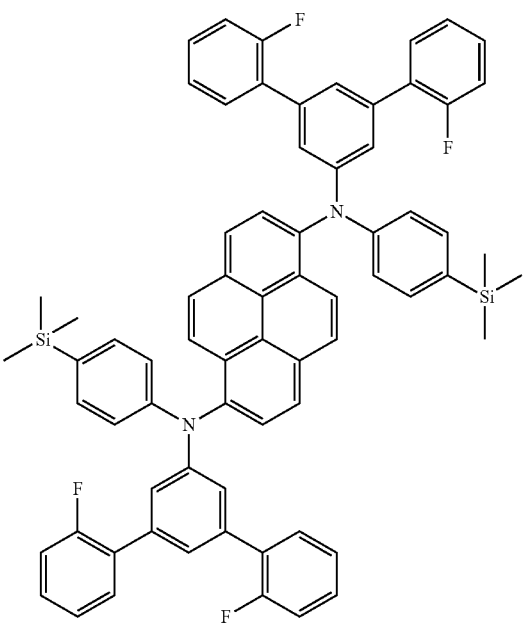
BD 356
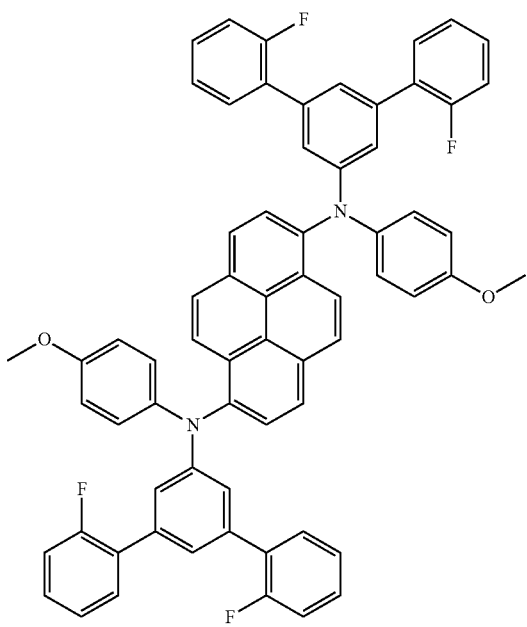
BD 358
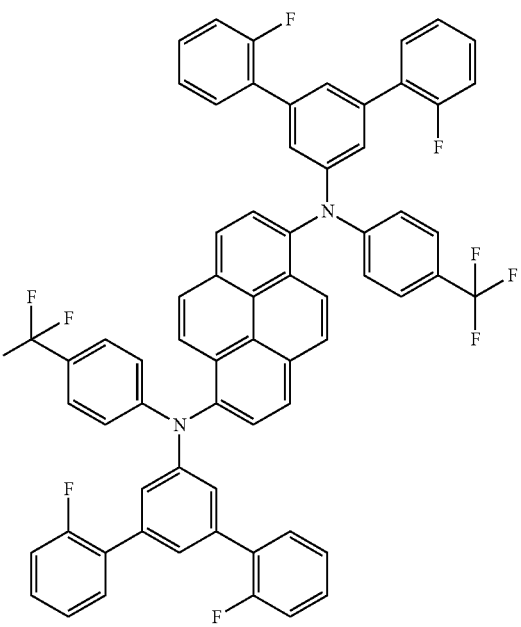

-continued

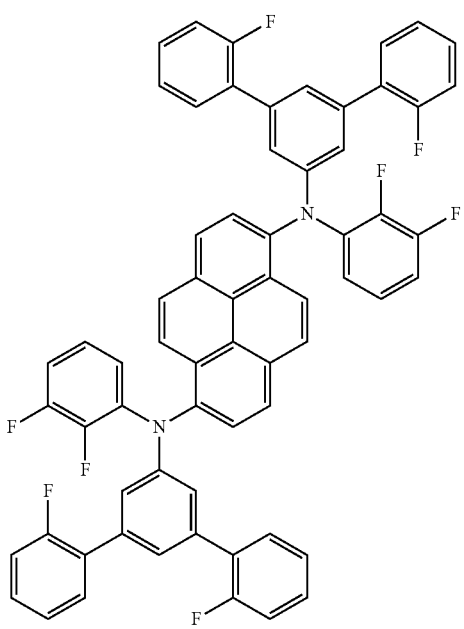
BD 359

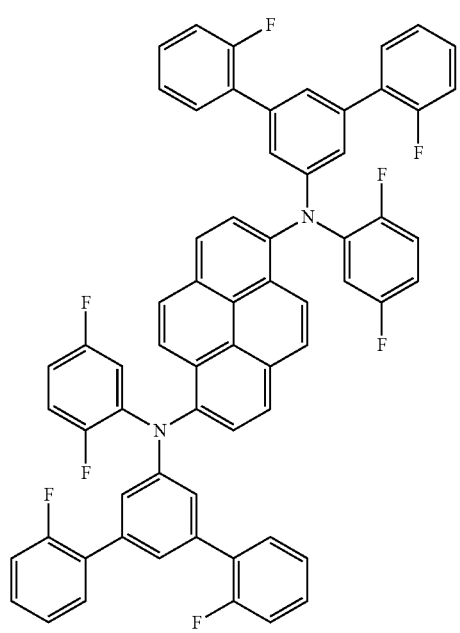
BD 360

A method for preparing the blue fluorescence compound of the present invention will be described taking a compound having a chemical formula BD-10 among the blue fluorescence compounds of the present invention.

An Example of Compounding

1) Compounding N-Phenyl-3,5-diphenylaniline

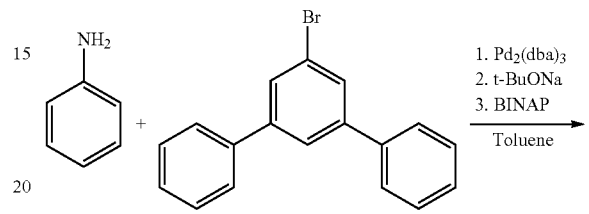

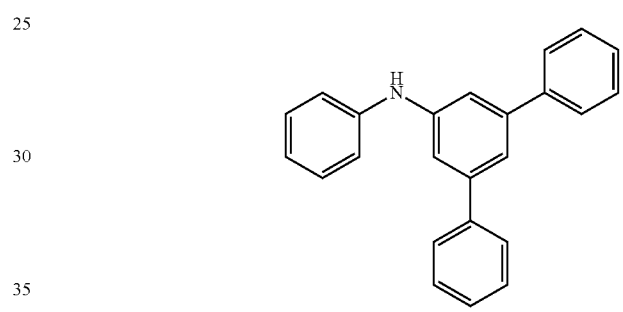

Aniline (3 g, 10.75 mmol), m-terphenyl (3.34 g, 10.85 mmol), Pd$_2$(dba)$_3$ (3 mol %), and t-BuONa (1.45 g, 15.05 mmol) is dissolved in toluene in a round flask, and a solution thereof is stirred at 100° C. Upon finishing reaction thereof, the toluene is removed from the solution, and a compound is extracted from the solution by using water and dichloromethane. The compound extracted thus is separated by using silica gel. The separated substance is re-crystallized by using dichloromethane and petroleum ether, and filtered, to obtain N-Phenyl-3,5-diphenylaniline (2.9 g, 84%).

2) Preparation of 1,6 di(N-Phenyl-N-(m)-terphenyl)pyrene

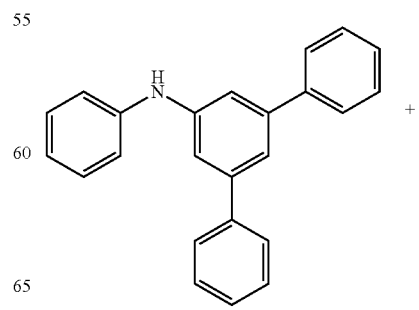

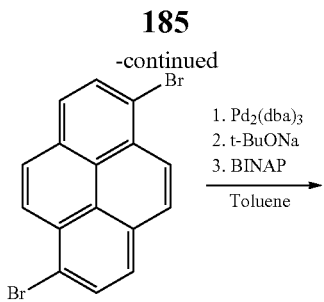

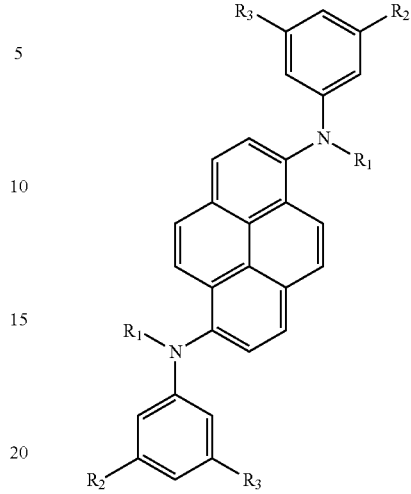

[Chemical Formula 1]

1.6 Dibromopyrene (1 g, 2.78 mmol), N-phenyl-3,5-diphenylaniline (1.87 g, 5.83 mmol), Pd₂(dba)₃ (3 mol %), BINAP (4 mol %), and t-BuONa (0.78 g, 8.16 mmol) is dissolved in toluene in a round flask, and a solution thereof is stirred at 100° C. Upon finishing reaction thereof, the toluene is removed from the solution, and a compound is extracted from the solution by using water and dichloromethane. The compound extracted thus is separated by using silica gel. The separated substance is re-crystallized by using dichloromethane and petroleum ether, and filtered, to obtain 1,6 di(N-phenyl-N-(m)-terphenyl)pyrene (BD-10; 4.27 g, 87%).

Referring to FIG. 1, the organic electroluminescence device 130 of the blue fluorescence compound of the present invention includes an anode 132, a cathode 138, and an electroluminescence layer formed between the anode 132 and the cathode 138 to have a host substance and a dopant substance. The dopant substance in the electroluminescence layer has the following chemical formula 1.

Where, each of R1, R2, and R3 are one of substances selected from aromatic groups, a heterocyclic, an aliphatic group and hydrogen which is substituted or not substituted, independently. The R1, R2, and R3 may or may not be identical substances.

In detail, the R1, R2, and R3 may be one of substances selected from the aromatic group including phenyl, biphenyl, naphthyl, phenanthrene, terphenyl, pyridine, quinoline, and deuterium, or a substituent thereof.

Or, each of the R1, R2, and R3 may be one of substances selected from aromatic compound having alkyl, alkoxy, halogen, cyano, and silyl groups.

The alkyl group is one selected from methyl, propyl, isopropyl, and t-butyl, and the alkoxy group is one selected from methoxy, ethoxy, and buthoxy. The halogen group is one selected from fluorine and chorine, and the silyl group may be trimethylsilyl.

In detail, the dopant substance of the electroluminescence layer 135 may be one of compounds having the following chemical formulae BD-1 to BD-360. However, the dopant substances are not limited to those. The host substance which forms the electroluminescence layer together with the dopant substance selected from BD-1 to BD-360 may be 4,4'-bis(2,2-diphenyl)-1,1' biphenyl(4,4'-bis(2,2-diphenylvinyl)-1,1'-biphenyl; DPVBi. However, the host substances are not limited to those, but any known substance may be used.

[Chemical Formula 2]

The organic electroluminescence device 130 may include a hole injection layer HIL 133 and a hole transport layer HTL 134 between the anode 132 and the electroluminescence layer 135, or an electron transport layer ETL 136 and an electron injection layer EIL 137 between the electroluminescence layer 135 and the cathode 138, additionally.

The anode 132 may be formed of ITO (Indium tin oxide) usually, and the hole injection layer 133 may be formed of copper phthalocyanine CuPc which has the following chemical formula 3 mainly.

[Chemical Formula 3]

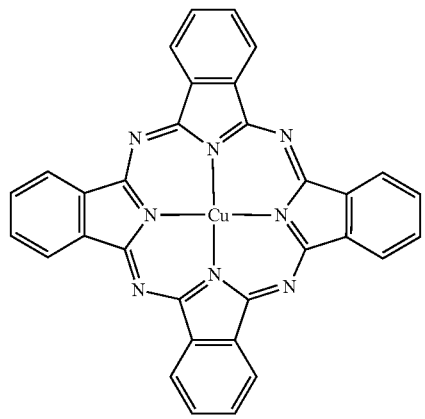

The hole transport layer 134 may be formed of 4,4'-bis[N-(1-naphthyl)-N-phenylamino]-biphenyl NPB having the following chemical formula 4. However, the material of the hole transport layer 134 is not limited this, but may be any known hole transport substance.

[Chemical Formula 4]

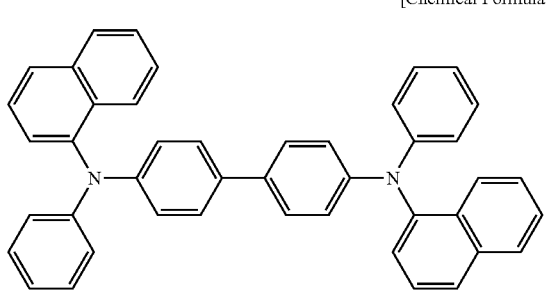

The electron transport layer 136 may be formed of 8-hydroxy-quinolate tris(8-hydroxy-quinolate)aluminum $Alq_3$ having the following chemical formula 5. However, the material of the electron transport layer 136 is not limited this, but may be any known electron transport substance.

[Chemical Formula 5]

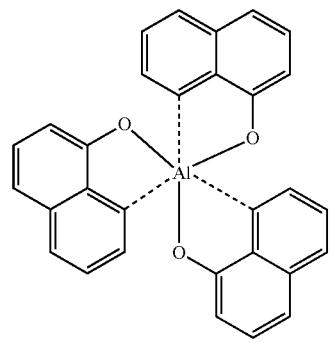

The electron injection layer 137 may be formed of LiF. However, the material of the electron injection layer 137 is not limited this, but may be any known electron injection substance. The cathode 138 may be formed of any known metal.

By using a blue fluorescent compound selected from the BD-1 to BD-360 as the dopant substance of the electroluminescence layer 135 of the organic electroluminescence device 130, the present invention permits to obtain a blue fluorescent organic electroluminescence device having high light emission efficiency, an excellent heat resistance, a long lifetime and high color purity.

In a method for fabricating an organic electroluminescence device of the blue fluorescent substance of the present invention, an anode is formed on a substrate, and a cathode is formed after forming a hole injection layer, a hole transport layer, an electroluminescence layer, an electron transport layer, and an electron injection layer on the anode in succession. In this instance, the electroluminescence layer includes a host substance and a dopant substance. The dopant substance of the electroluminescence layer may be a compound having above chemical formula 1, and in detail, a compound selected from compounds of BD-1 to BD-360.

The host substance may be DPVBi having above chemical formula 2, and the hole injection layer may be formed of CuPC having above chemical formula 3. The hole transport layer may be formed of NPB having above chemical formula 4, the electron transport layer may be formed of $Alq_3$ having above chemical formula 5, and the electron injection layer may be formed of LiF. The cathode may be formed of a known metal, such as aluminum Al.

However, materials of the hole injection layer, the hole transport layer, the electron transport layer, and the electron injection layer are not limited to above, but may be any known hole injection layer substance, any known hole transport layer substance, any known electron transport layer substance, and any known electron injection layer substance.

In the method for fabricating an organic electroluminescence device, by using a blue fluorescent compound selected from the BD-1 to BD-360 as the dopant substance, the present invention permits to obtain a blue fluorescent organic electroluminescence device having high light emission efficiency, an excellent heat resistance, a long lifetime and high color purity.

Embodiments of a method for fabricating an organic electroluminescence device of a blue fluorescent compound of the present invention will be described. However, the present invention is not limited to the following embodiments.

Embodiment 1

A sheet of ITO glass is patterned to have a 3 mm×3 mm sized light emission area and washed to from a substrate. After the substrate is mounted in a vacuum chamber and the vacuum chamber is evacuated to have a basic pressure of $1\times10^{-6}$ torr, organic substances are coated on the ITO in an order of CuPC (200 Å), NPB (400 Å), host DPVBi (200 Å)+dopant BD-4 (5%), Alq$_3$ (350 Å), LiF (5 Å), and Al (1000 Å), to fabricate the organic electroluminescence device. The organic electroluminescence device fabricated thus shows 616 cd/m$^2$ (5.82V) at 0.9 mA with CIE x=0.143, y=0.101.

Embodiment 2

A sheet of ITO glass is patterned to have a 3 mm×3 mm sized light emission area and washed to form a substrate. After the substrate is mounted in a vacuum chamber and the vacuum chamber is evacuated to have a basic pressure of $1\times10^{-6}$ torr, organic substances are coated on the ITO in an order of CuPC (200 Å), NPB (400 Å), host DPVBi (200 Å)+dopant BD-18 (5%), Alq$_3$ (350 Å), LiF (5 Å), and Al (1000 Å), to fabricate the organic electroluminescence device. The organic electroluminescence device fabricated thus shows 682 cd/m$^2$ (6.03V) at 0.9 mA with CIE x=0.146, y=0.110.

Embodiment 3

A sheet of ITO glass is patterned to have a 3 mm×3 mm sized light emission area and washed to form a substrate. After the substrate is mounted in a vacuum chamber and the vacuum chamber is evacuated to have a basic pressure of $1\times10^{-6}$ torr, organic substances are coated on the ITO in an order of CuPC (200 Å), NPB (400 Å), host DPVBi (200 Å)+dopant BD-24 (5%), Alq$_3$ (350 Å), LiF (5 Å), and Al (1000 Å), to fabricate the organic electroluminescence device. The organic electroluminescence device fabricated thus shows 623 cd/m$^2$ (5.95V) at 0.9 mA with CIE x=0.143, y=0.098.

Embodiment 4

A sheet of ITO glass is patterned to have a 3 mm×3 mm sized light emission area and washed to form a substrate. After the substrate is mounted in a vacuum chamber and the vacuum chamber is evacuated to have a basic pressure of $1\times10^{-6}$ torr, organic substances are coated on the ITO in an order of CuPC (200 Å), NPB (400 Å), host DPVBi (200 Å)+dopant BD-77 (5%), Alq$_3$ (350 Å), LiF (5 Å), and Al (1000 Å), to fabricate the organic electroluminescence device. The organic electroluminescence device fabricated thus shows 595 cd/m$^2$ (6.11V) at 0.9 mA with CIE x=0.140, y=0.088.

Embodiment 5

A sheet of ITO glass is patterned to have a 3 mm×3 mm sized light emission area and washed to form a substrate. After the substrate is mounted in a vacuum chamber and the vacuum chamber is evacuated to have a basic pressure of $1\times10^{-6}$ torr, organic substances are coated on the ITO in an order of CuPC (200 Å), NPB (400 Å), host DPVBi (200 Å)+dopant BD-134(5%), Alq$_3$ (350 Å), LiF (5 Å), and Al (1000 Å), to fabricate the organic electroluminescence device. The organic electroluminescence device fabricated thus shows 576 cd/m$^2$ (5.93V) at 0.9 mA with CIE x=0.139, y=0.084.

Comparative Example 1

A sheet of ITO glass is patterned to have a 3 mm×3 mm sized light emission area and washed to form a substrate. After the substrate is mounted in a vacuum chamber and the vacuum chamber is evacuated to have a basic pressure of $1\times10^{-6}$ torr, organic substances are coated on the ITO in an order of CuPC (200 Å), NPB (400 Å), host DPVBi (200 Å)+dopant BD-a (1%), Alq$_3$ (350 Å), LiF (5 Å), and Al (1000 Å), to fabricate the organic electroluminescence device. The organic electroluminescence device fabricated thus shows 526 cd/m$^2$ (6.7V) at 0.9 mA with CIE x=0.136, y=0.188.

Results of the embodiments 1 to 5 and the comparative example 5 are shown in table 1, below.

TABLE 1

| DEVICE | VOLTAGE (V) | CURRENT (mA) | BRIGHTNESS (cd/m$^2$) | CIE (x) | CIE (Y) |
|---|---|---|---|---|---|
| EMBODIMENT 1 | 5.82 | 0.9 | 616 | 0.143 | 0.101 |
| EMBODIMENT 2 | 6.03 | 0.9 | 682 | 0.146 | 0.110 |
| EMBODIMENT 3 | 5.95 | 0.9 | 623 | 0.143 | 0.098 |
| EMBODIMENT 4 | 6.11 | 0.9 | 595 | 0.140 | 0.088 |
| EMBODIMENT 5 | 5.93 | 0.9 | 576 | 0.139 | 0.084 |
| COMPARATIVE EXAMPLE 1 | 6.7 | 0.9 | 526 | 0.136 | 0.188 |

It can be known that, as shown in above embodiments, by introducing a compound selected from BD-1 to BD-360 as the dopant substance of the electroluminescence layer of the present invention, the organic electroluminescence device can be driven at a voltage 0.59V~0.88V lower than the related art dopant substance, with low CIE coordinates improving color purity. Along with this, the organic electroluminescence device of the blue fluorescence compound of the present invention has high light emission efficiency and a long light emission life.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. A blue fluorescence compound comprising a compound selected from the group consisting of BD 1-8, BD 18-29, BD 31-33, BD 39, BD 43-108, BD 111, BD 115, BD 116, BD 118-120, BD 124-173, BD 175-177, BD 179, BD 180, BD 183, BD 187-198, BD 202, BD 203, BD 208-210, BD 213-270, BD 274, BD 275, BD 282-296 and BD 306-360:

BD 1
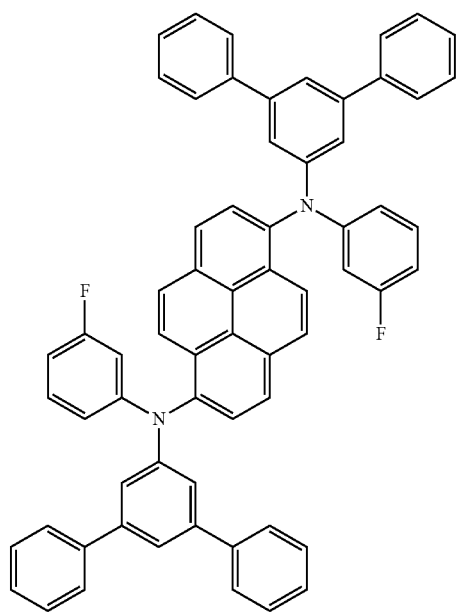
BD 2
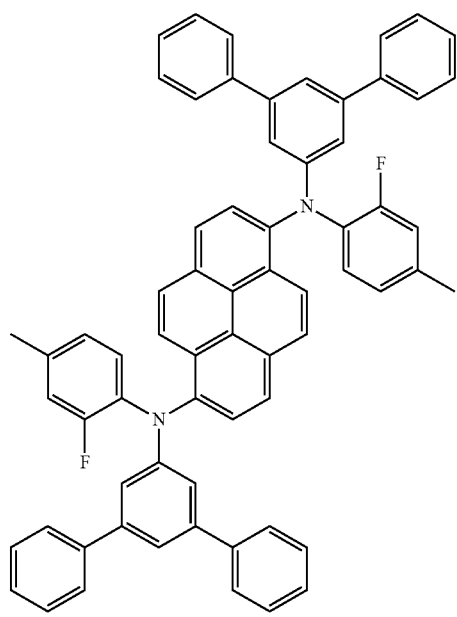
-continued
BD 3
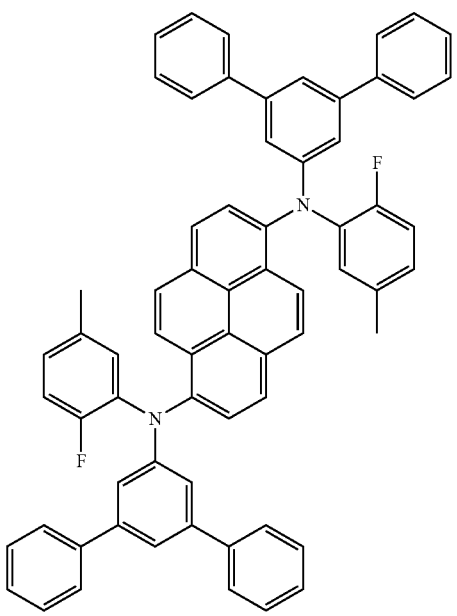
BD 4
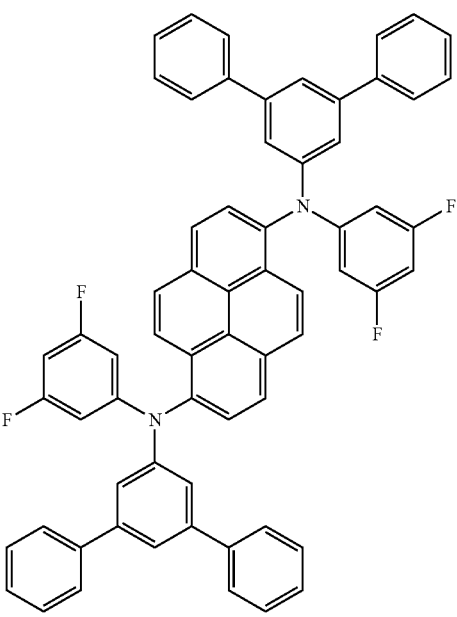

BD 5
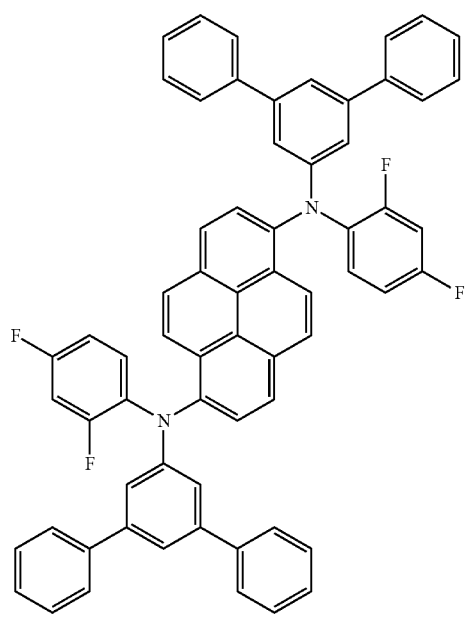
BD 6
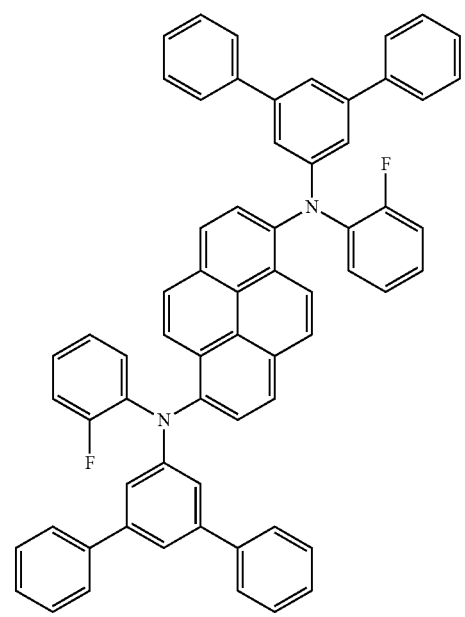
BD 7
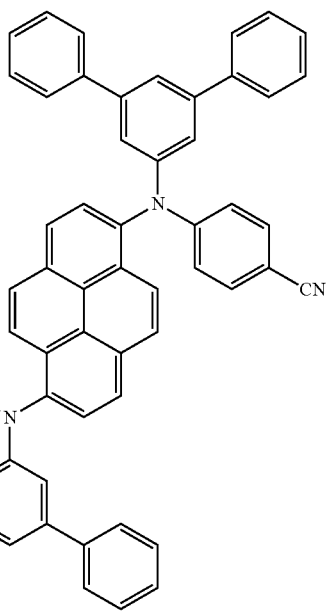
BD 8
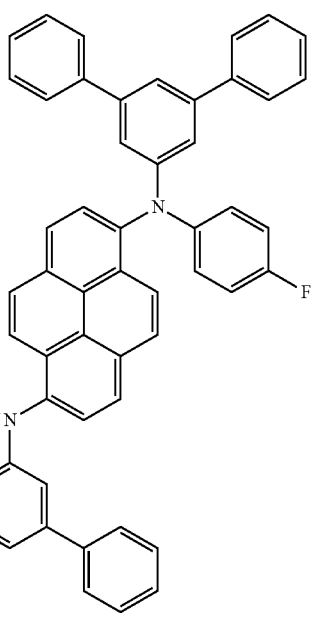

BD 18
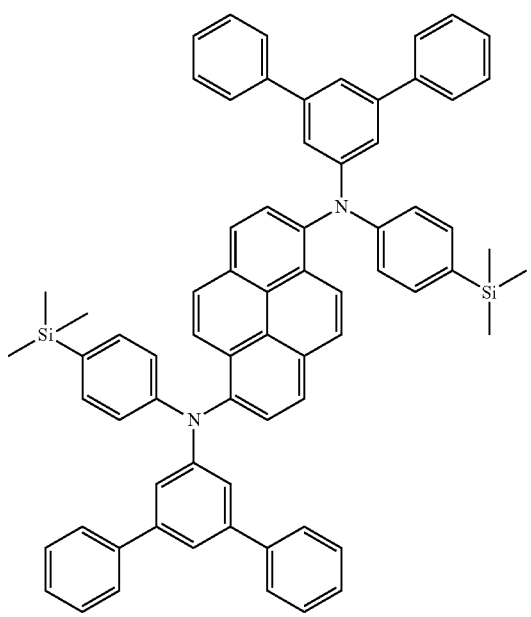
BD 19
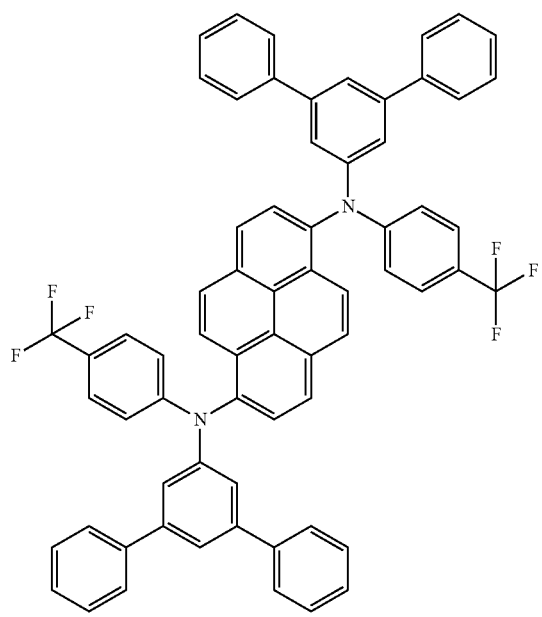
BD 20
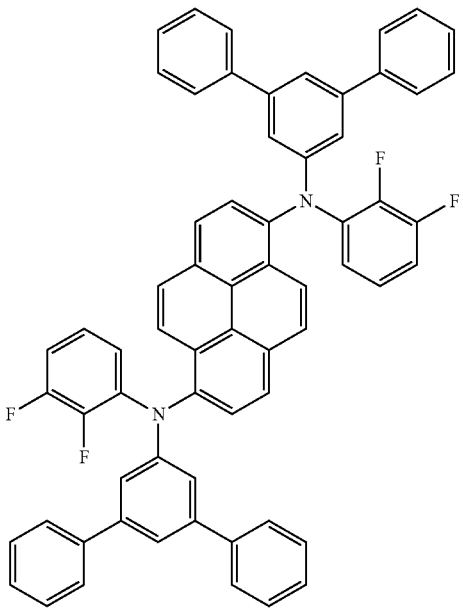
BD 21
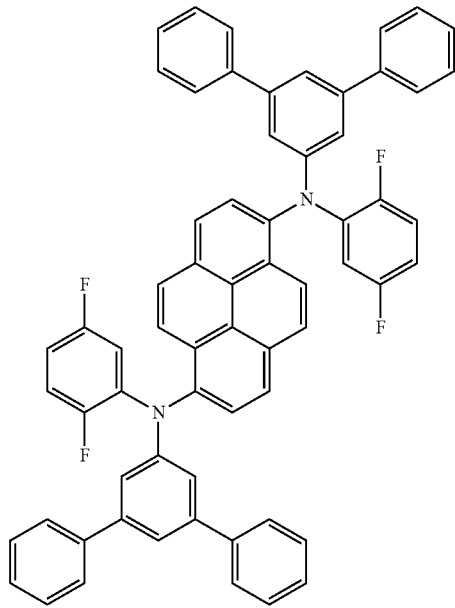

BD 22
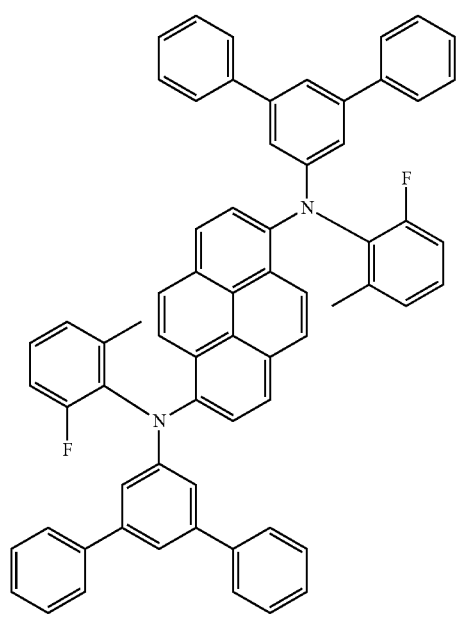
BD 24
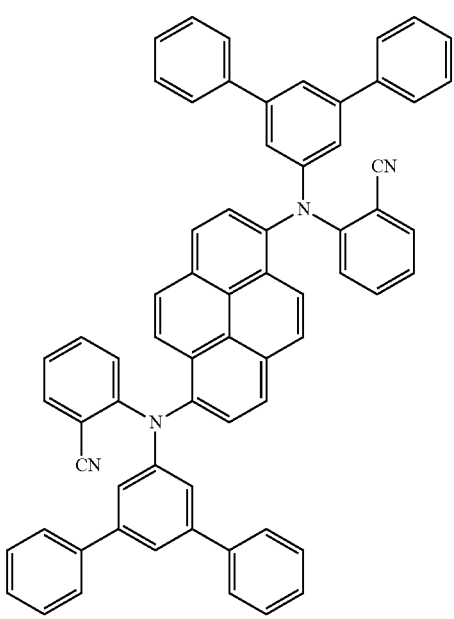
BD 23
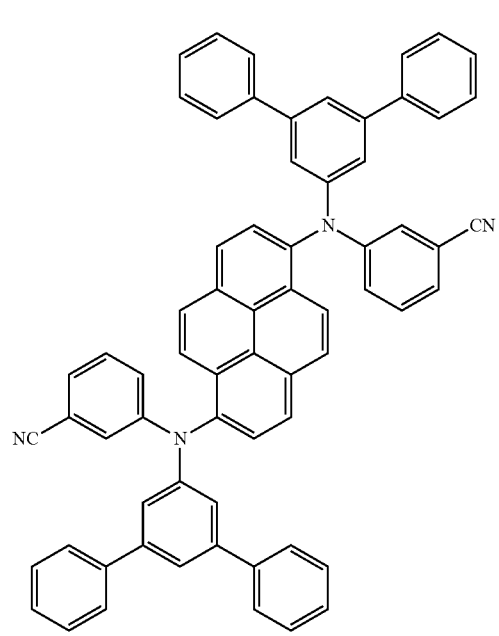
BD 25
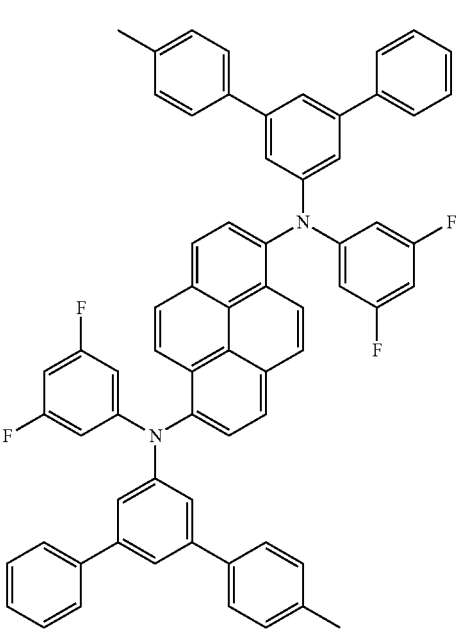

199
-continued
BD 26
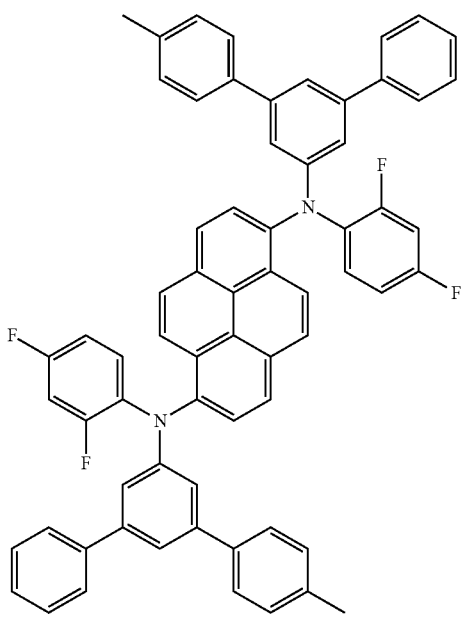
BD 27
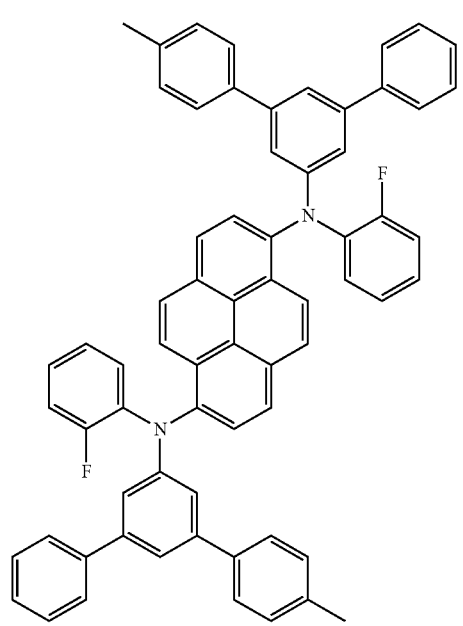
200
-continued
BD 28
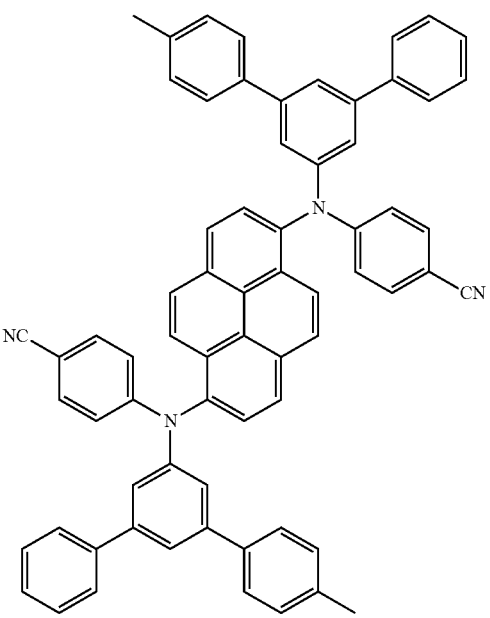
BD 29
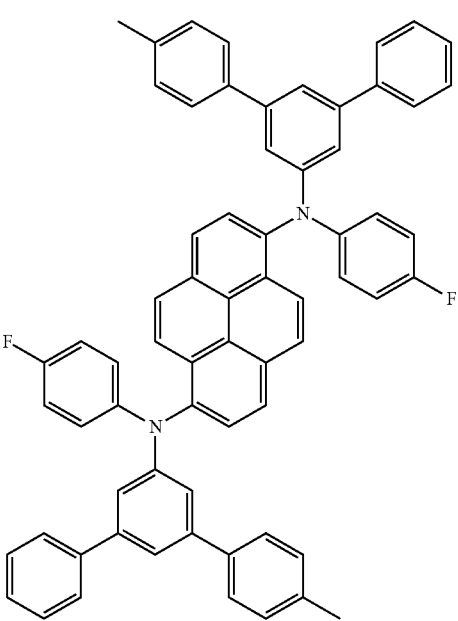

BD 31
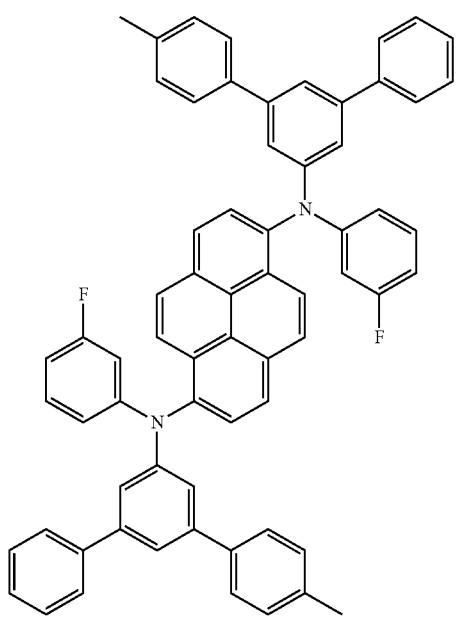
BD 32
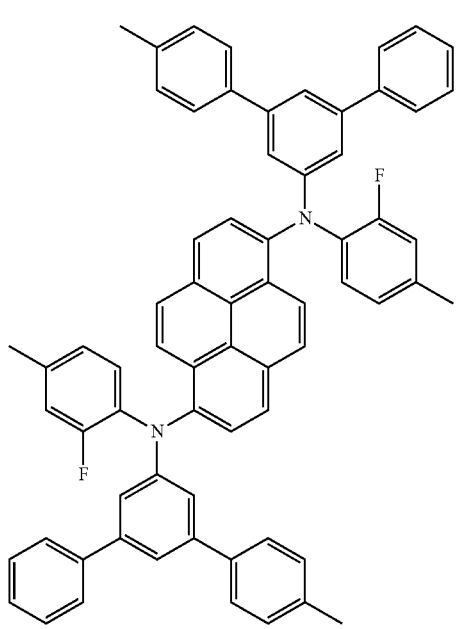
BD 33
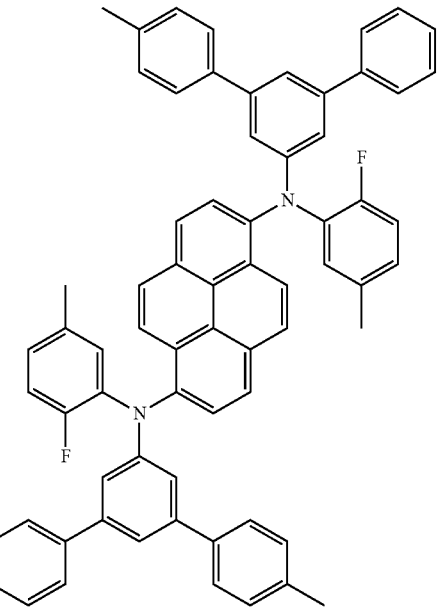
BD 39
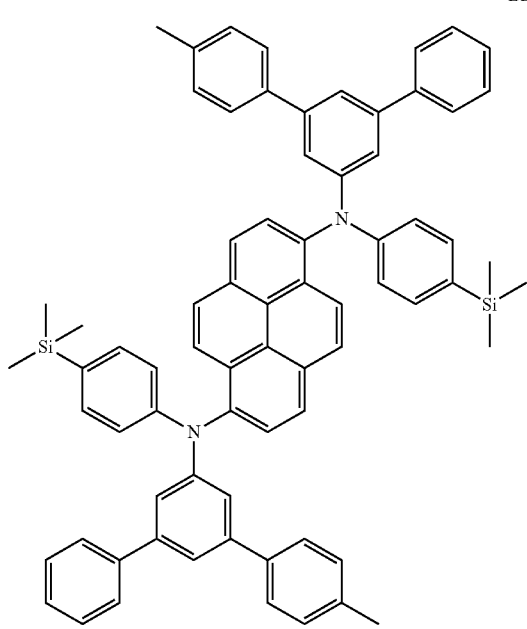

BD 43
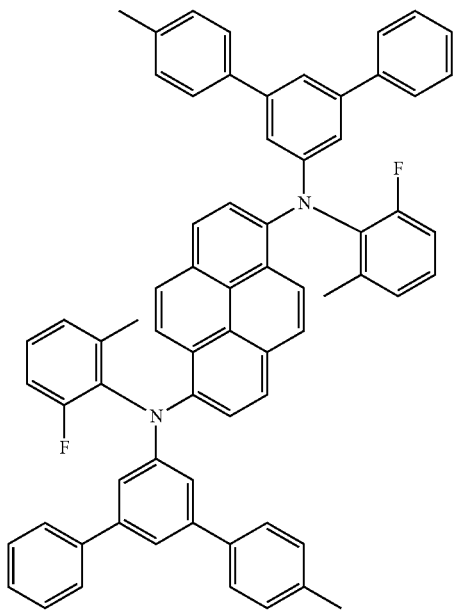
BD 44
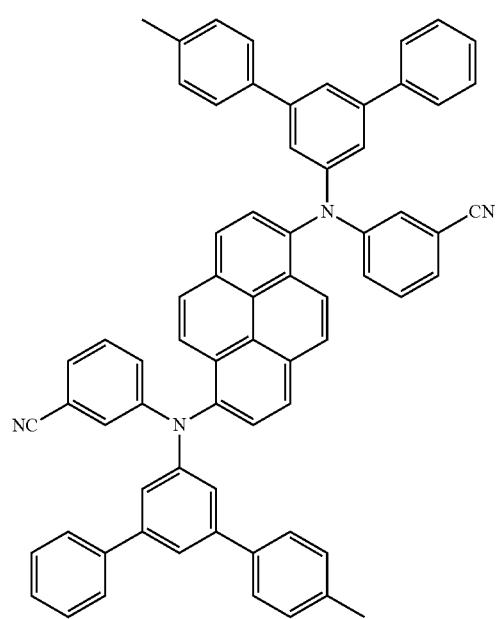
BD 45
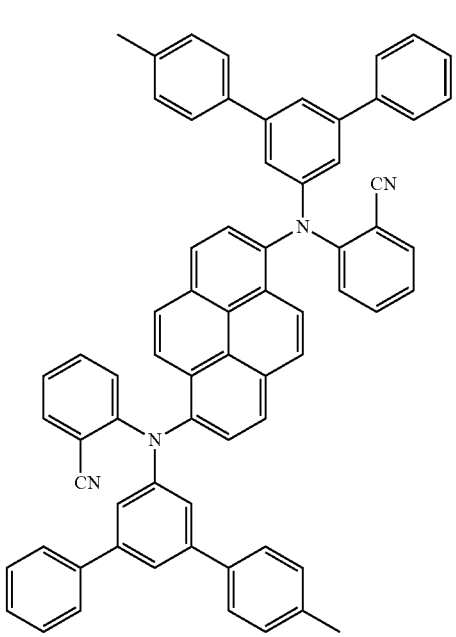
BD 46
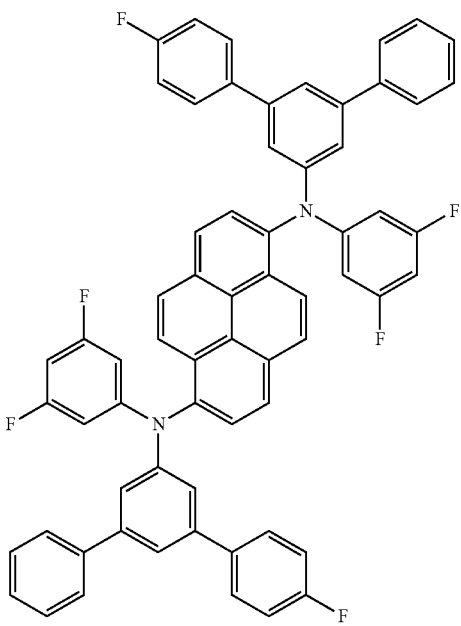

BD 47
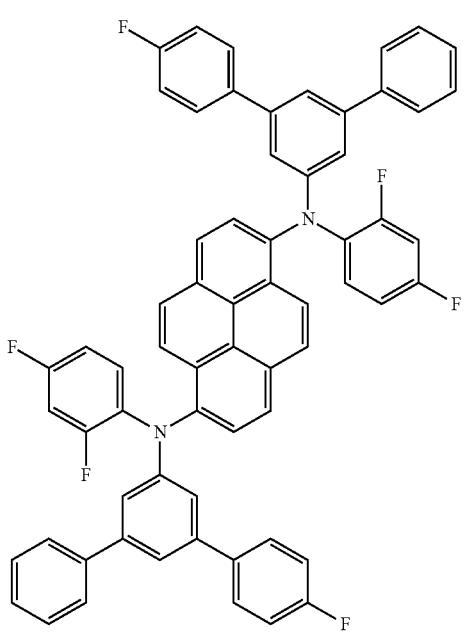
BD 48
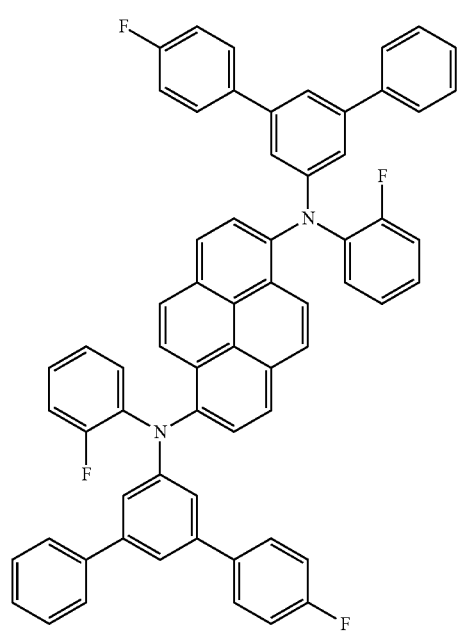
BD 49
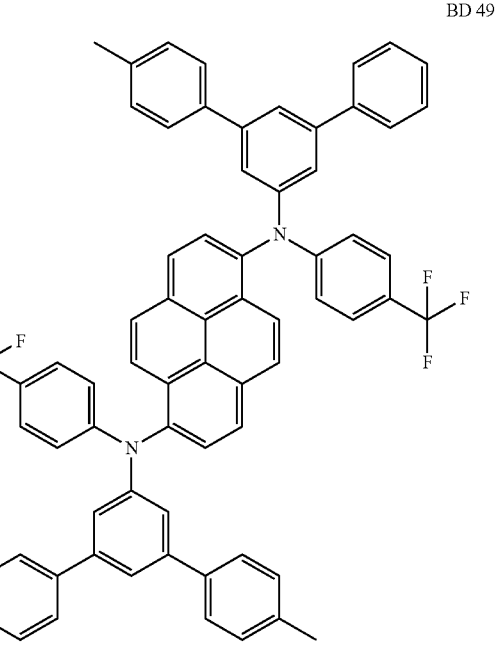
BD 50
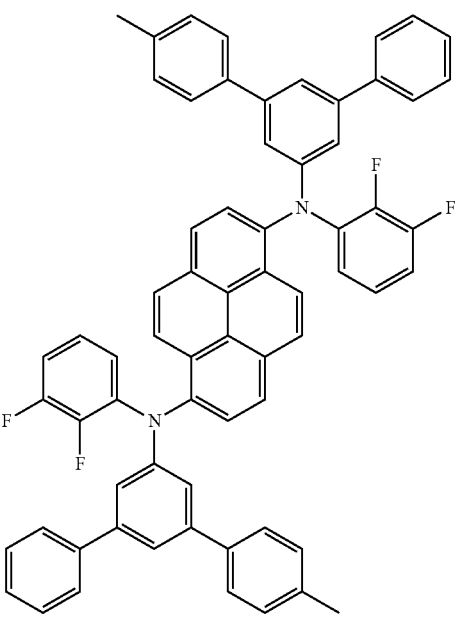

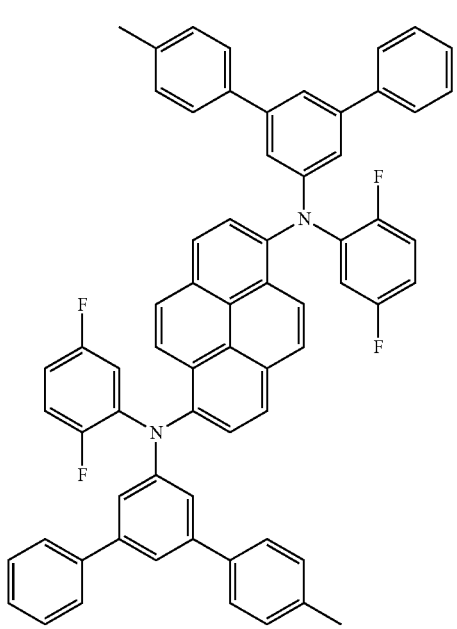
BD 51
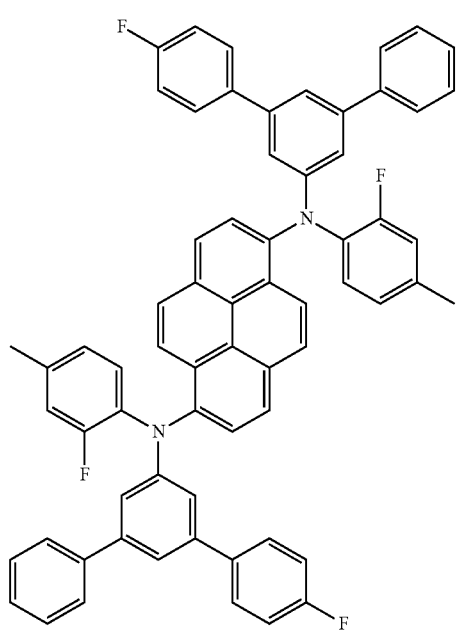
BD 53
BD 52
BD 54

BD 55
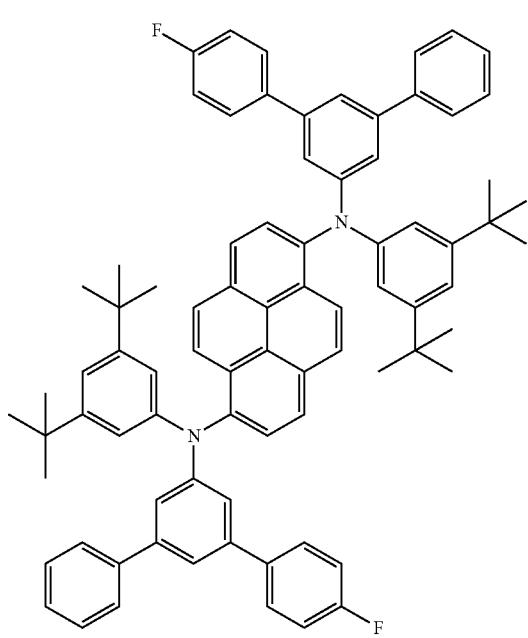
BD 56
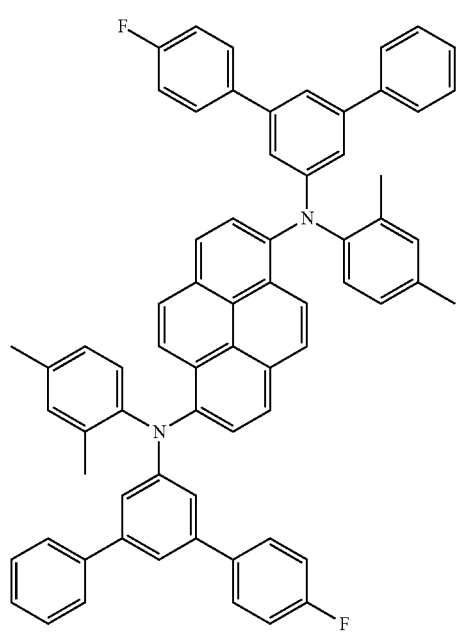
BD 57
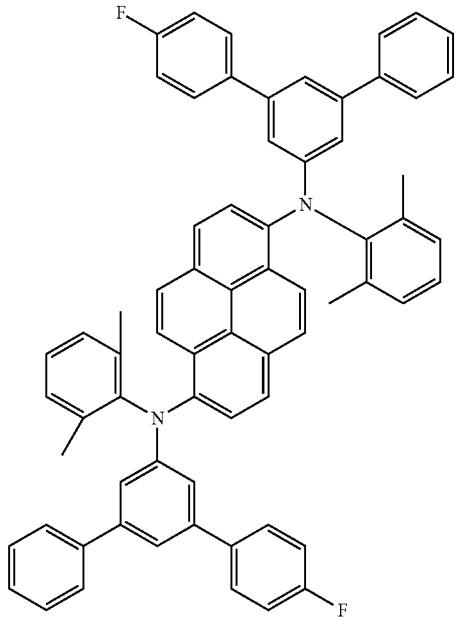
BD 58
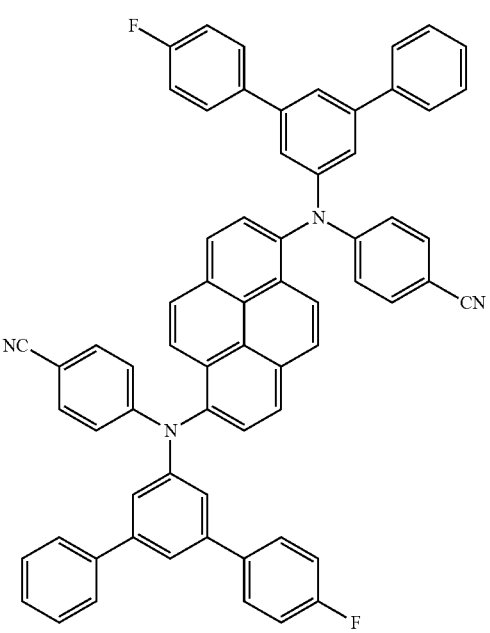

-continued
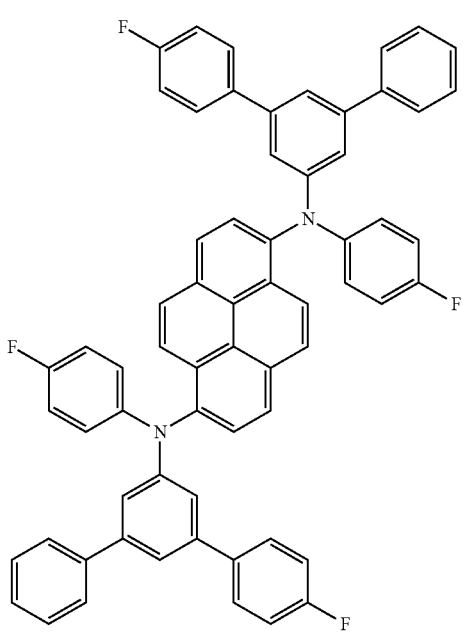
BD 59
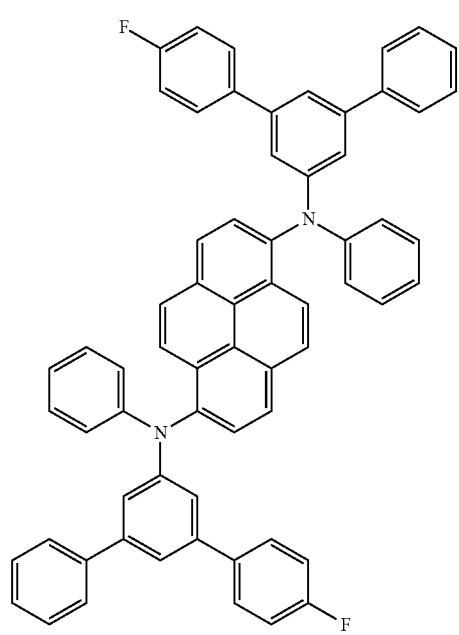
BD 61
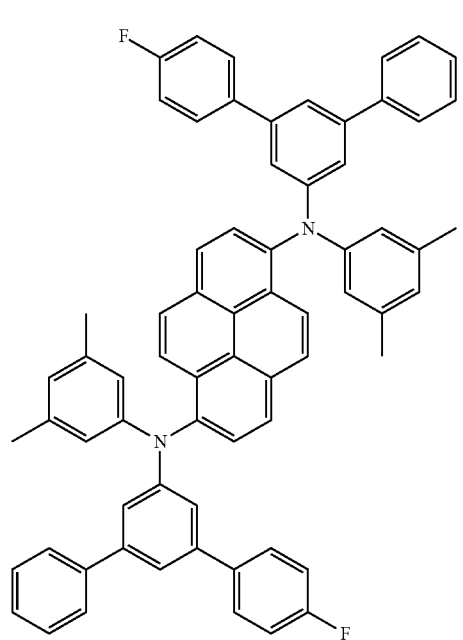
BD 60
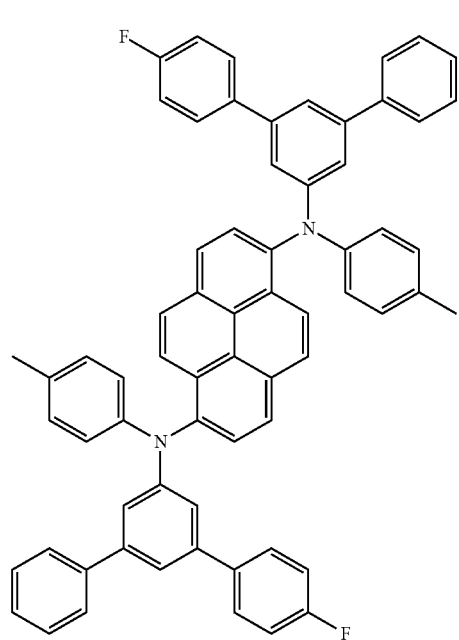
BD 62

213
-continued
BD 63
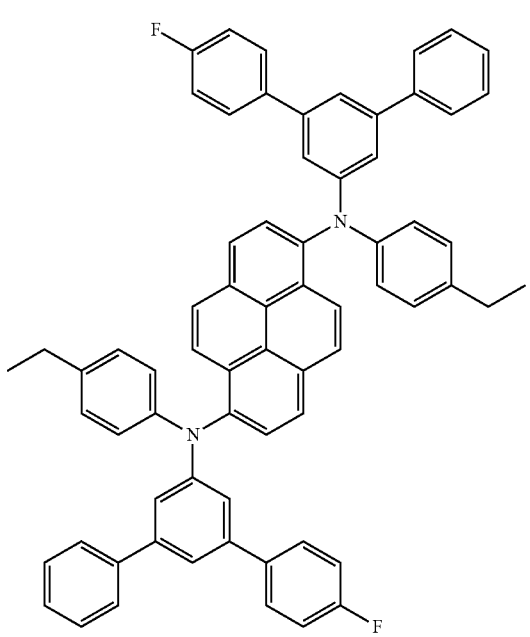
214
-continued
BD 65
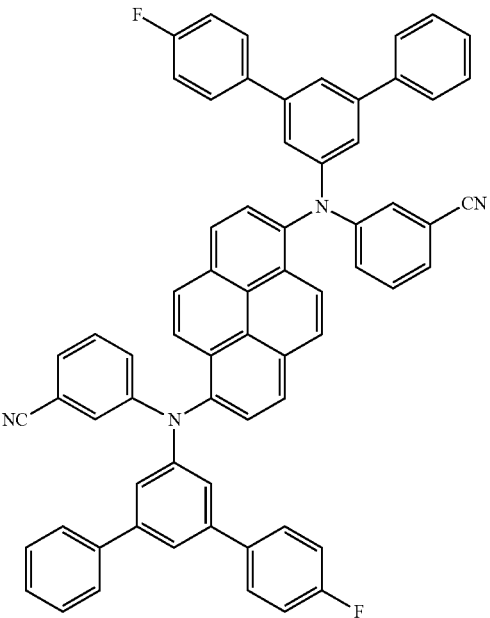
BD 64
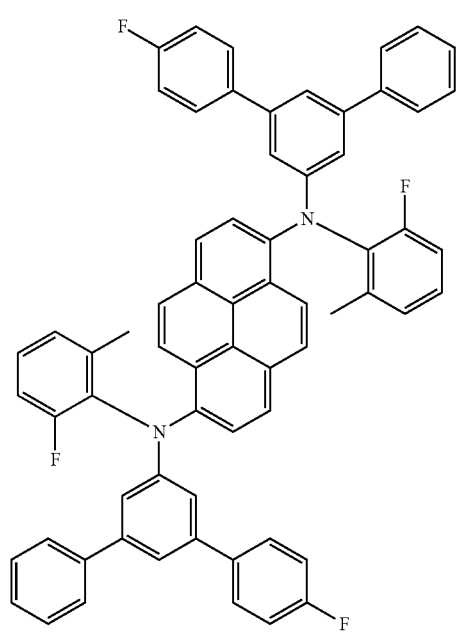
BD 66
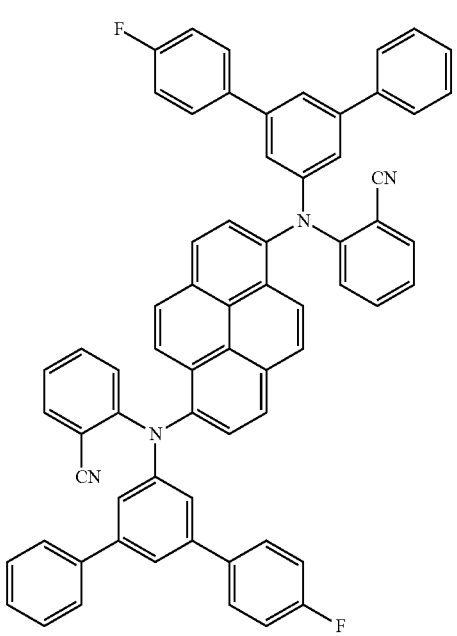

215
-continued
BD 67
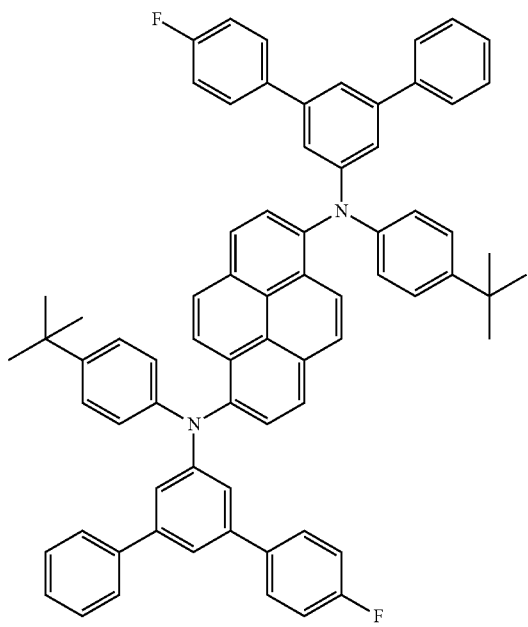
BD 68
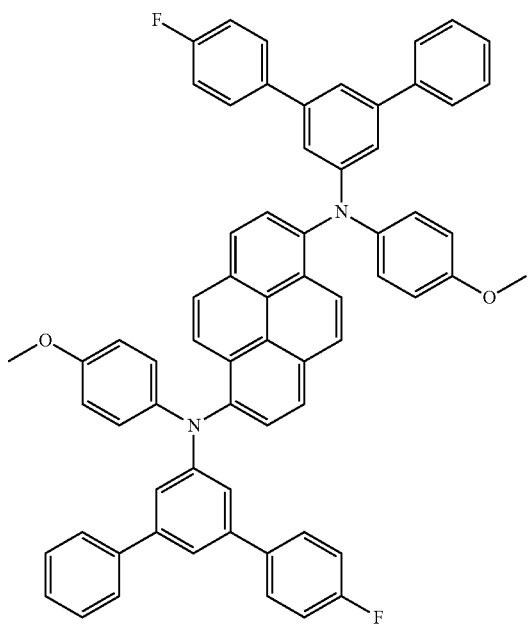
216
-continued
BD 69
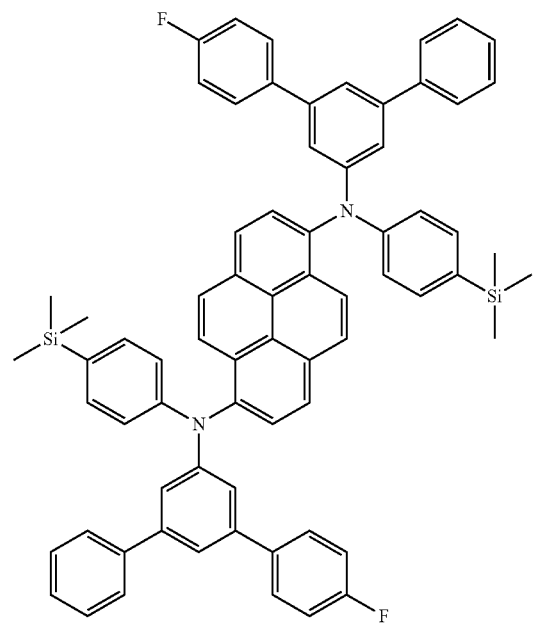
BD 70
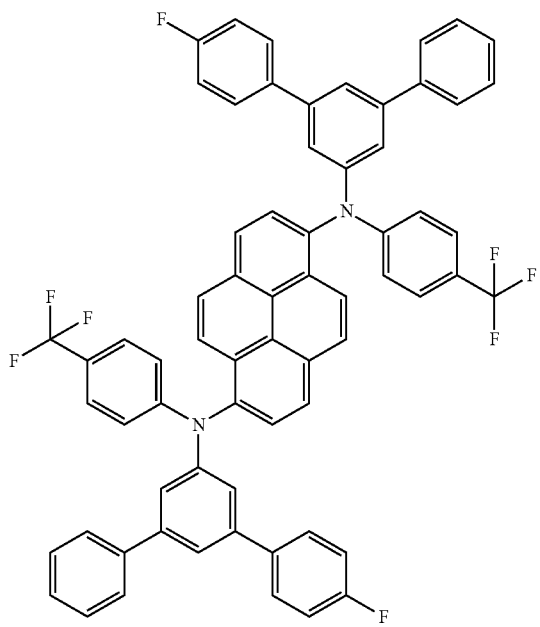

BD 71
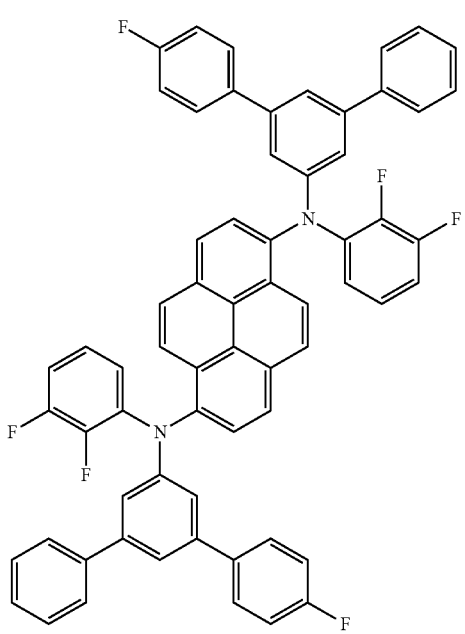
BD 72
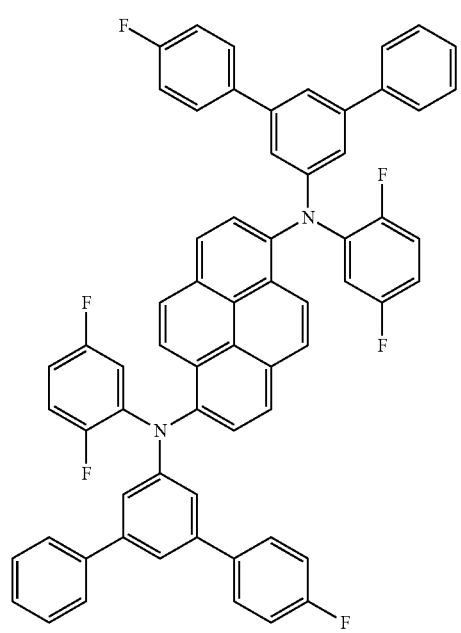
BD 73
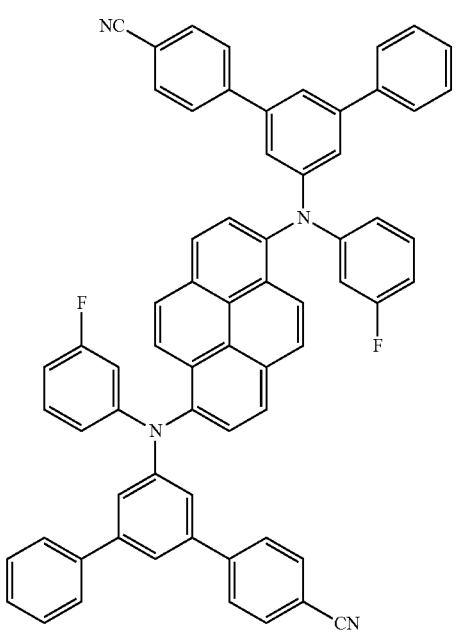
BD 74
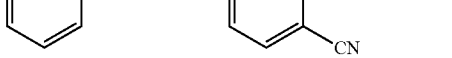

BD 75
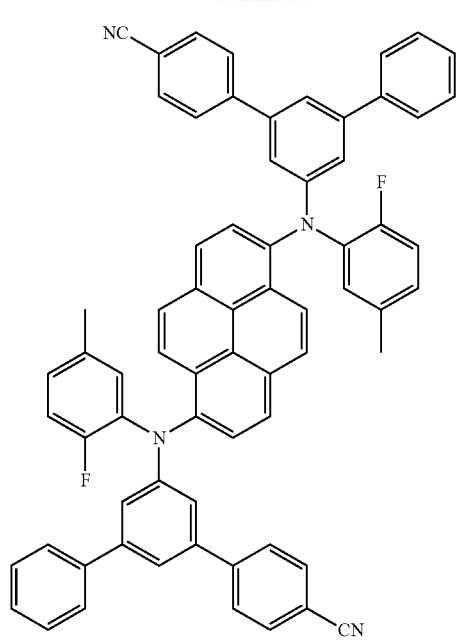
BD 77
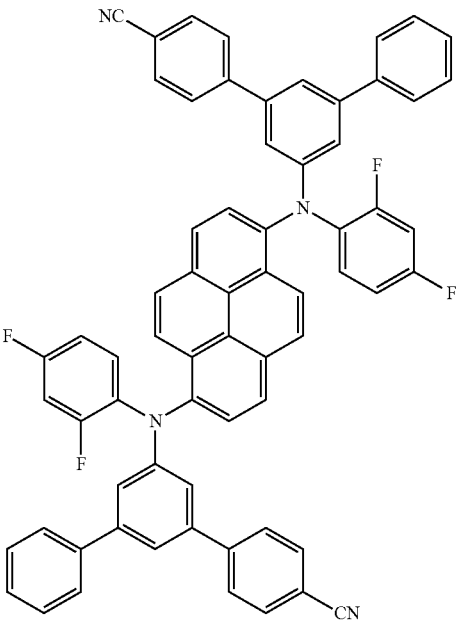
BD 76
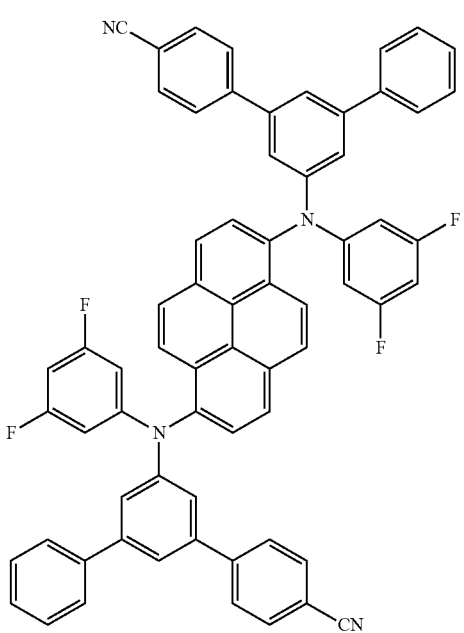
BD 78
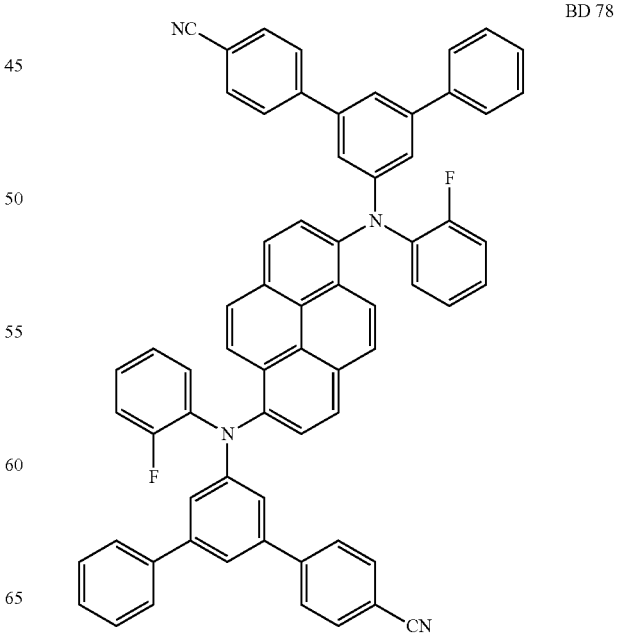

-continued
BD 79
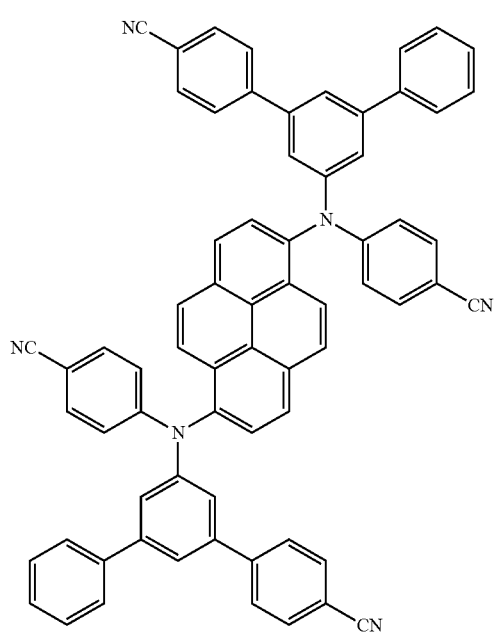
BD 80
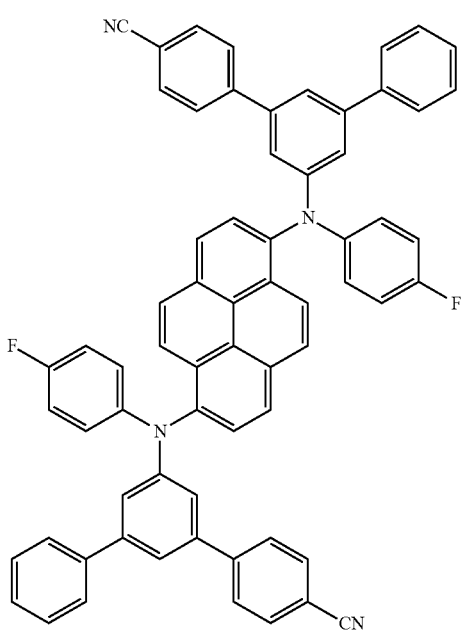
-continued
BD 81
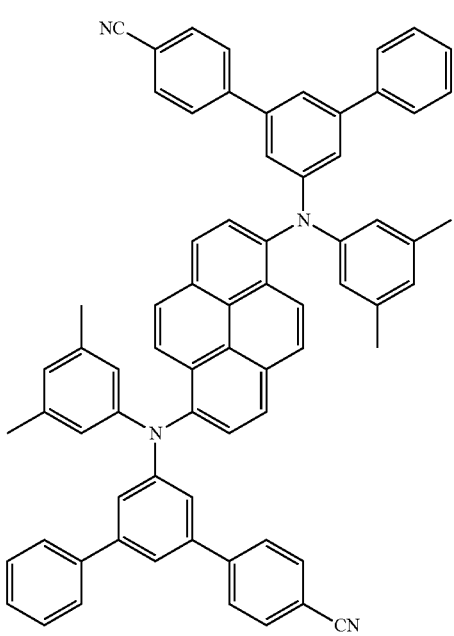
BD 82
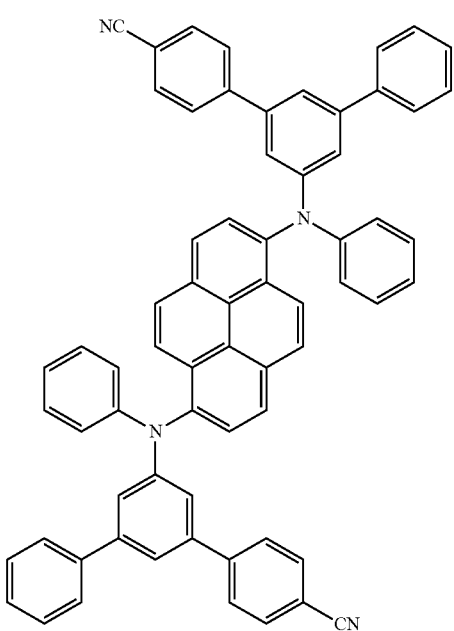

-continued
BD 83
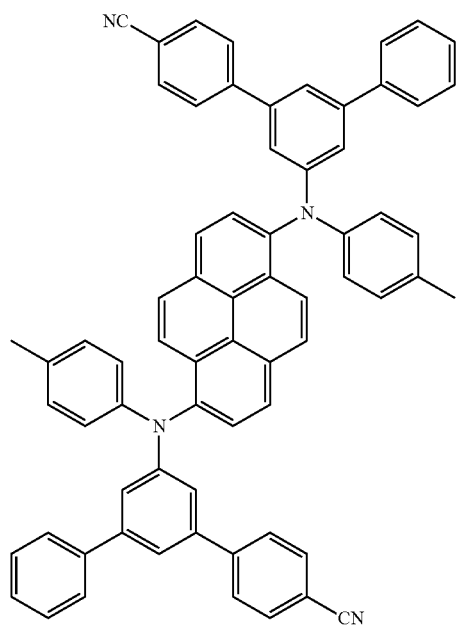
BD 85
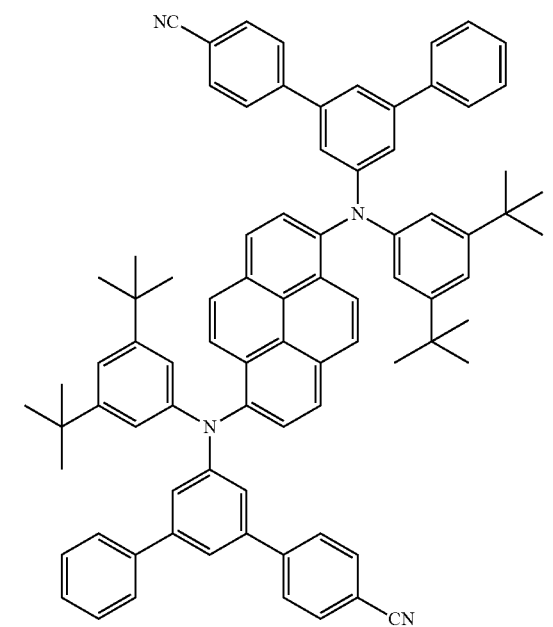
BD 84
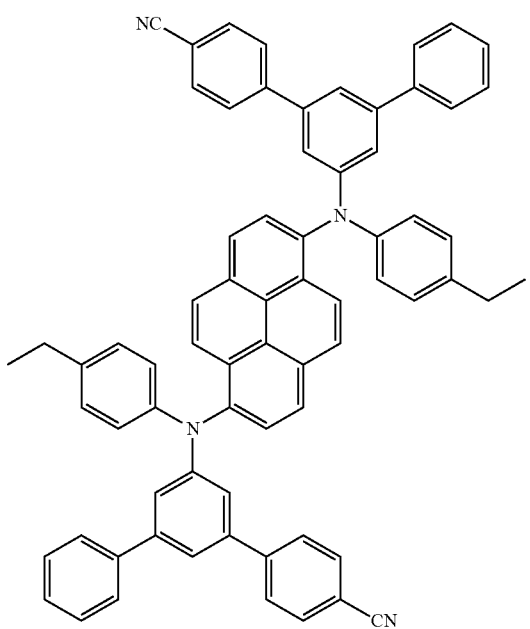
BD 86
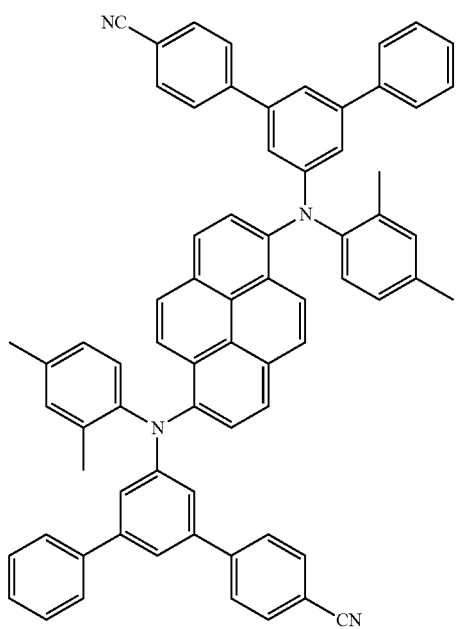

225
-continued
BD 87
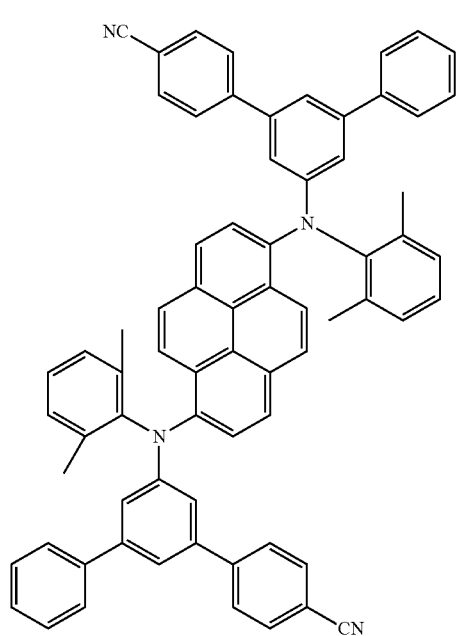
BD 88
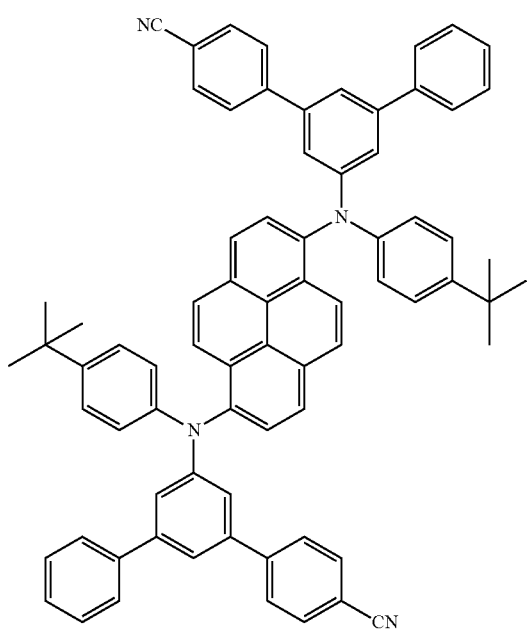
226
-continued
BD 89
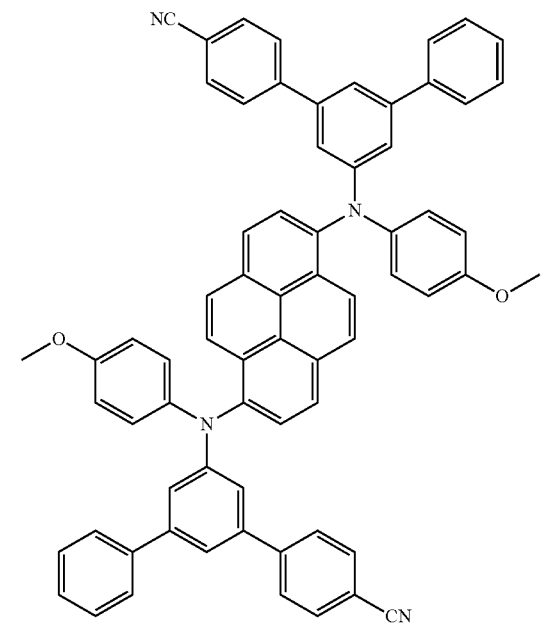
BD 90
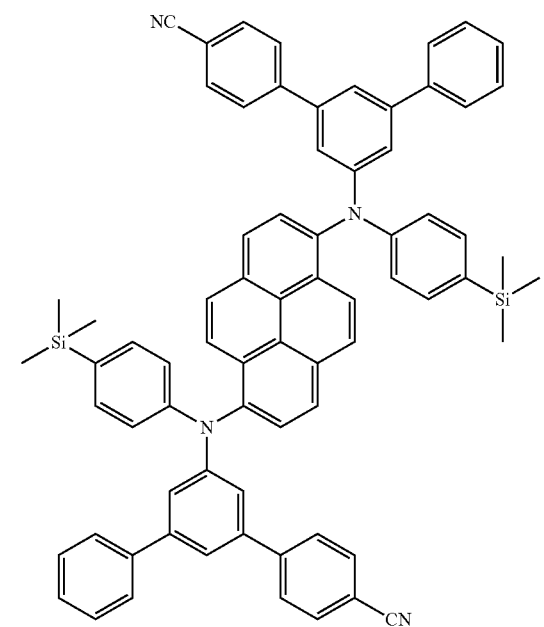

-continued
BD 91
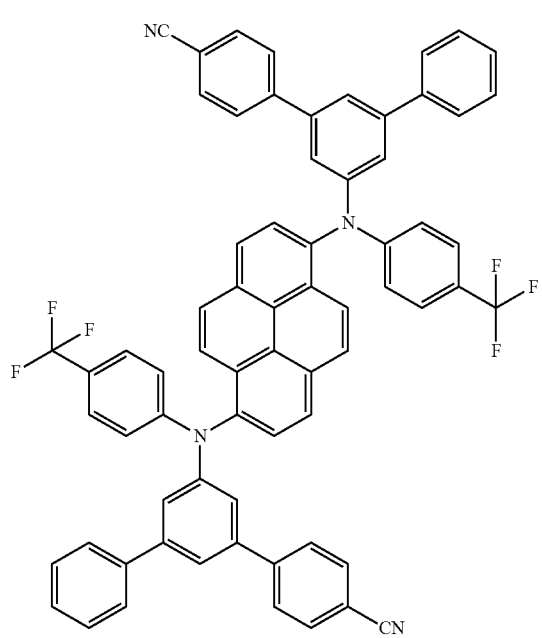
BD 93
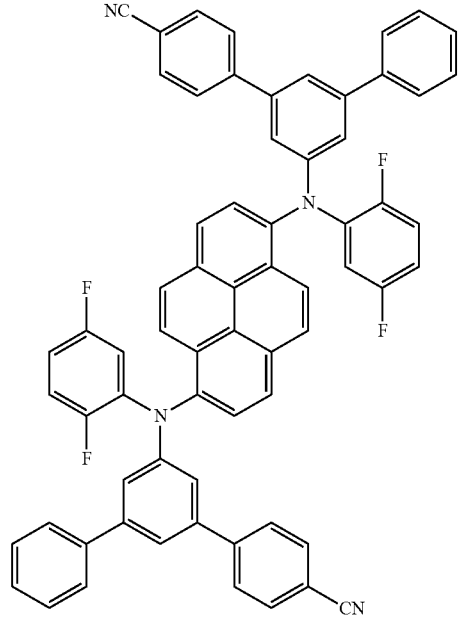
BD 92
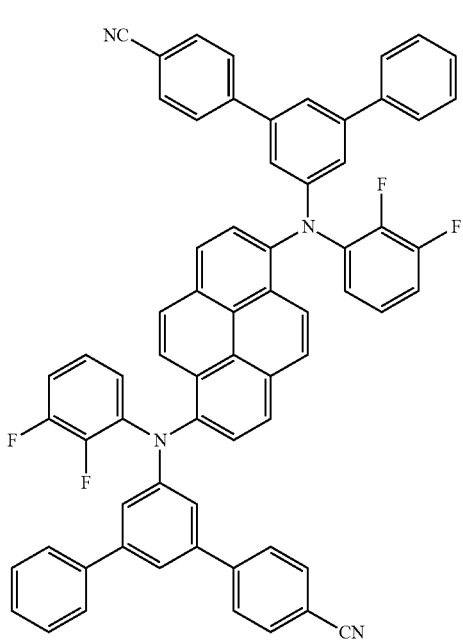
BD 94
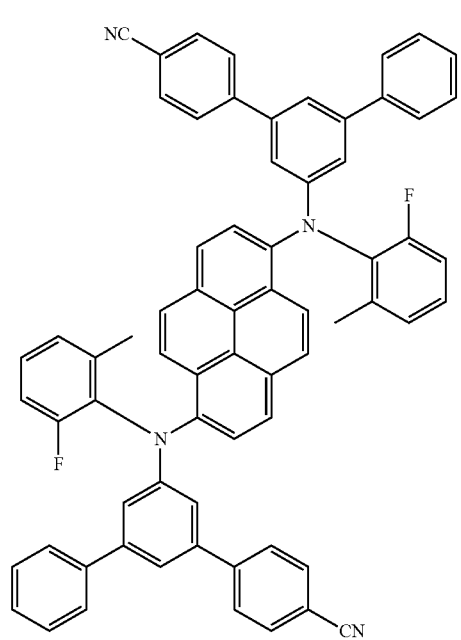

BD 95
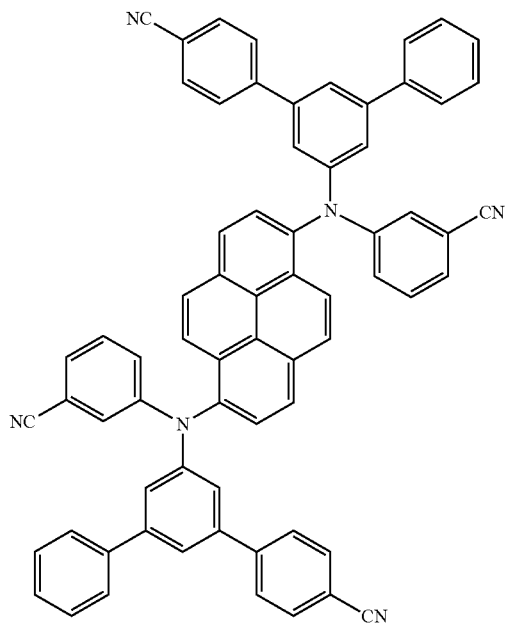
BD 96
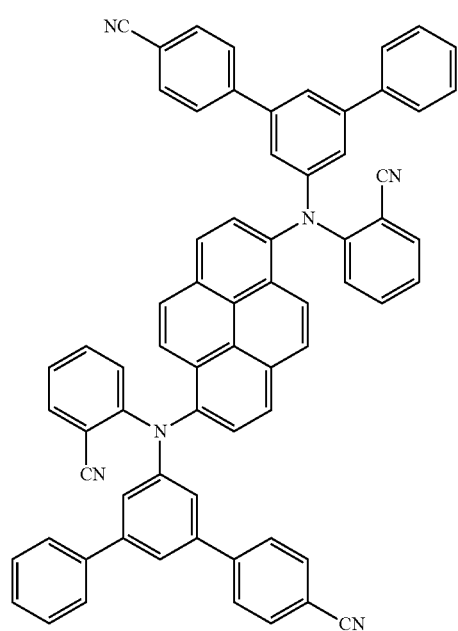
BD 97
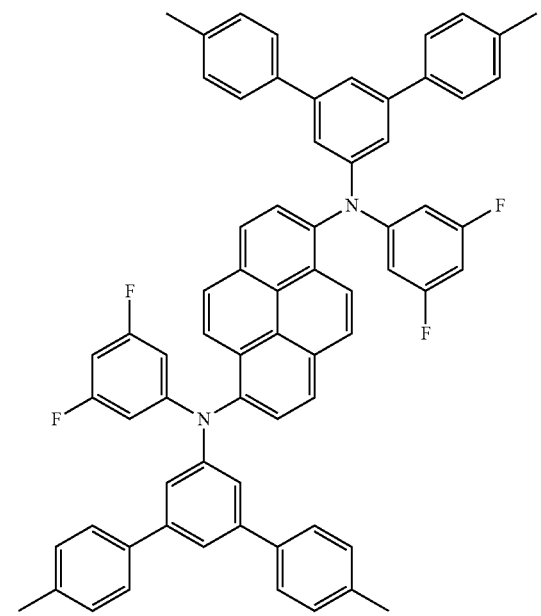
BD 98
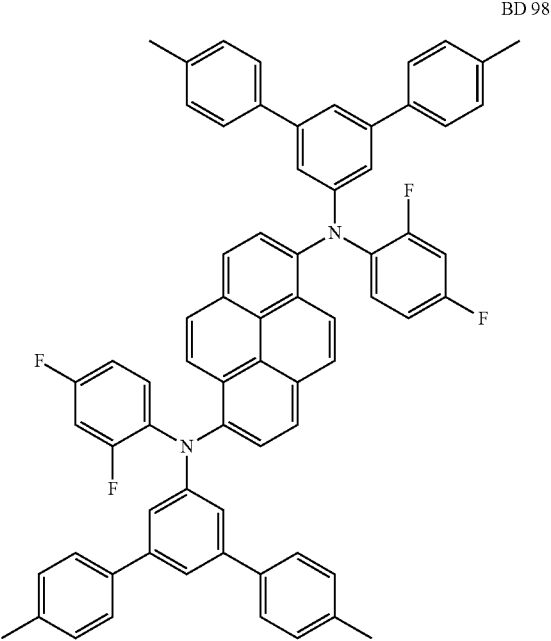

BD 99
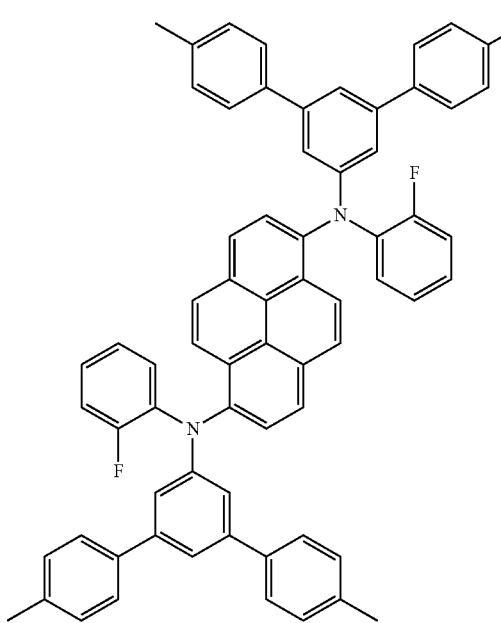
BD 100
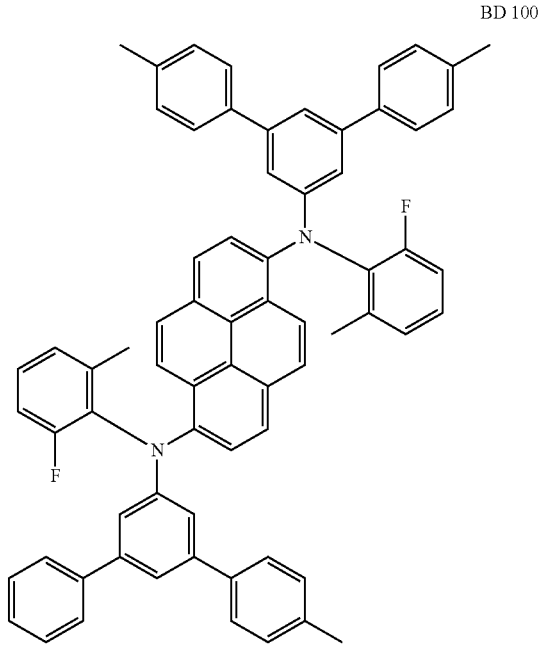
BD 101
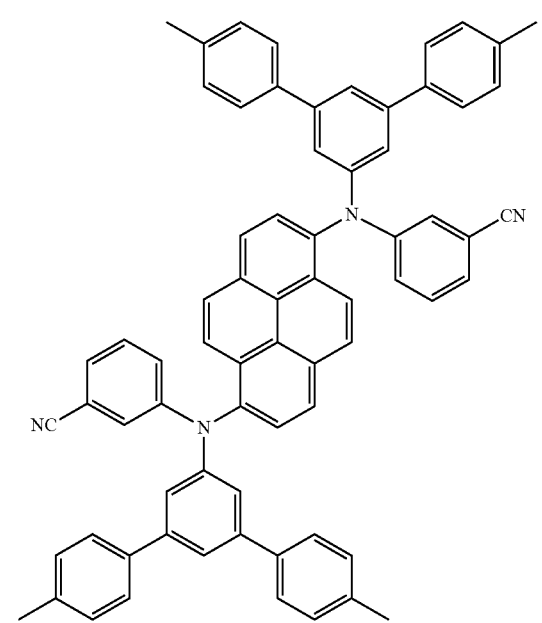
BD 102
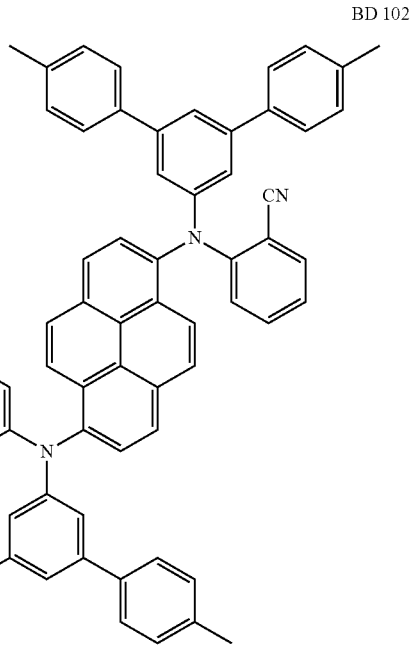

BD 103
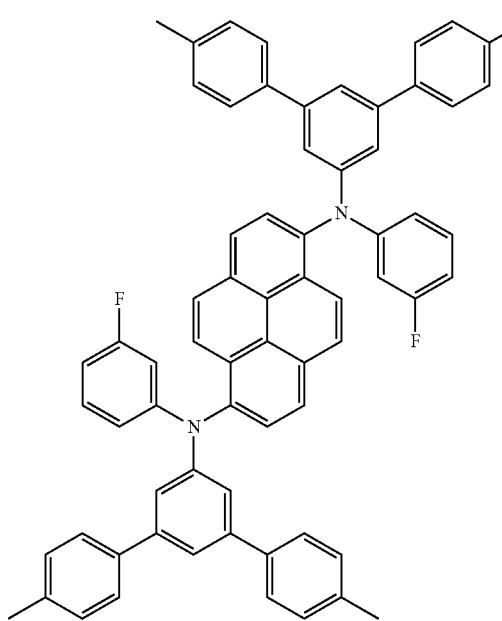
BD 104
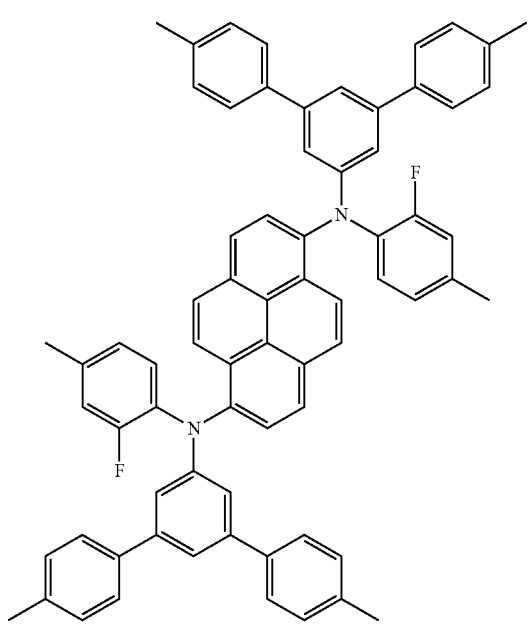
BD 105
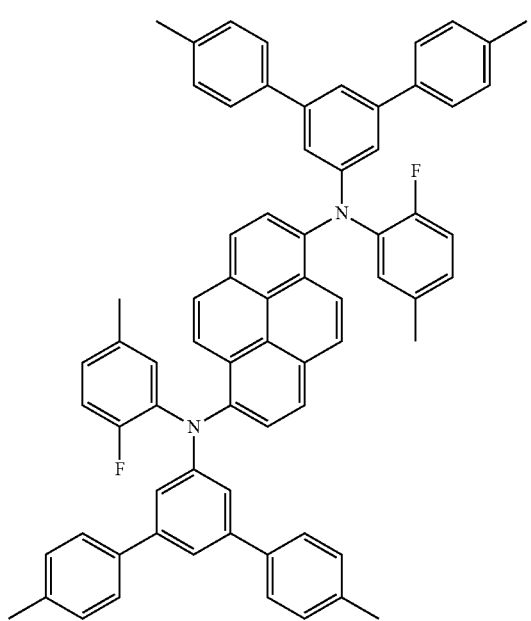
BD 106
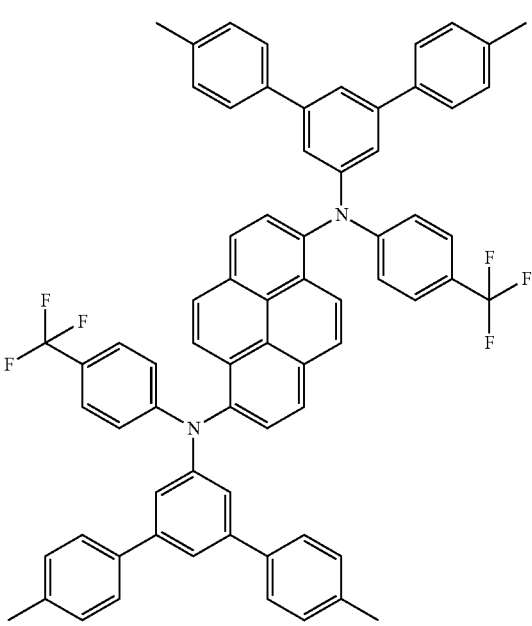

-continued
BD 107
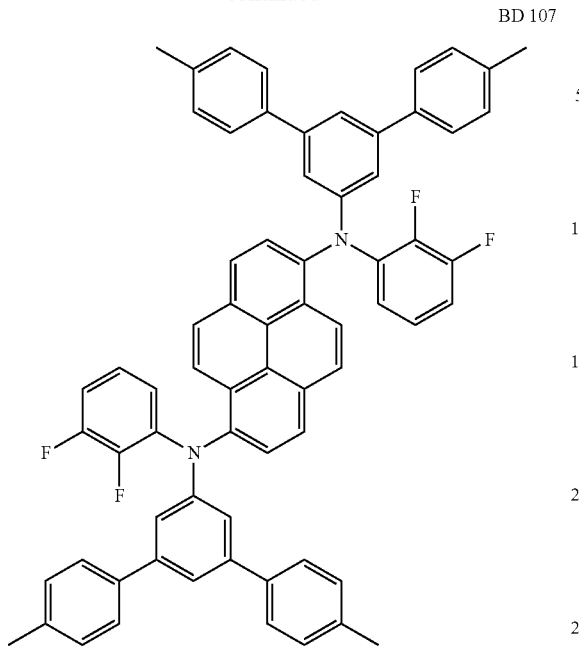
BD 113
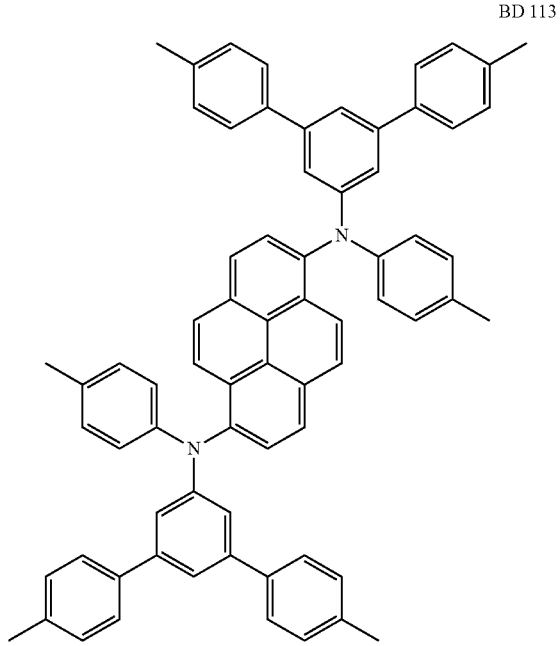
BD 108
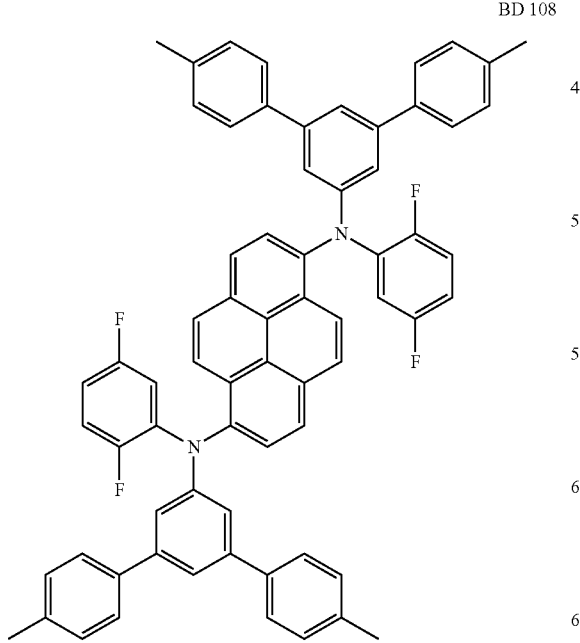
BD 115
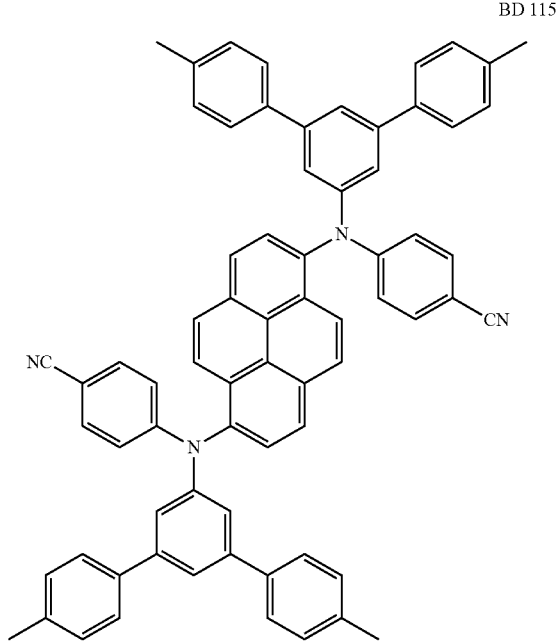

237
-continued
BD 115
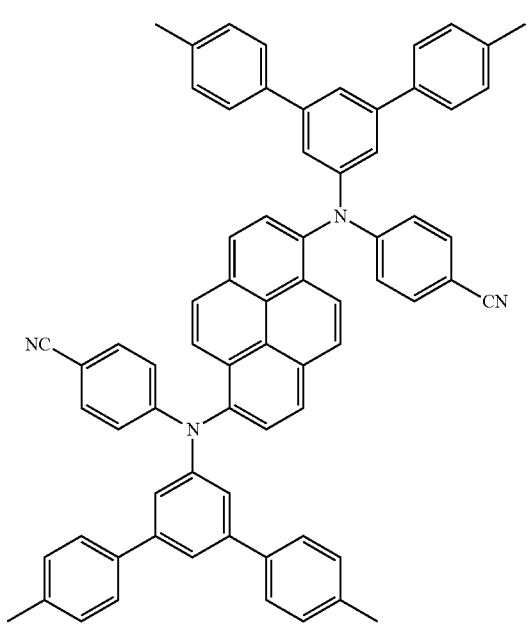
BD 116
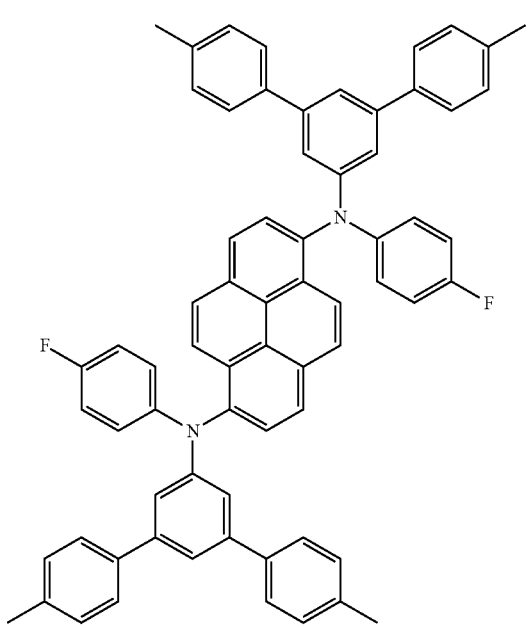
238
-continued
BD 117
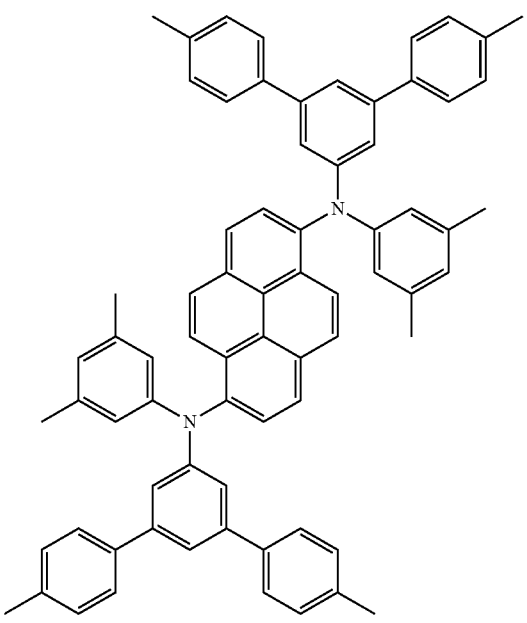
BD 118
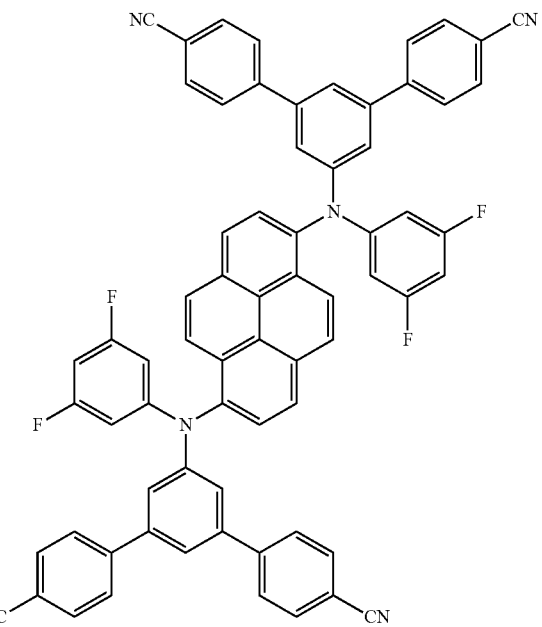

BD 119
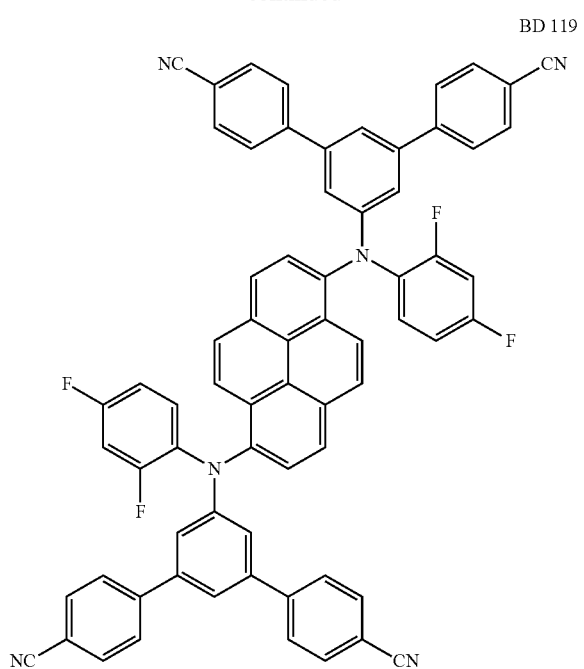
BD 121
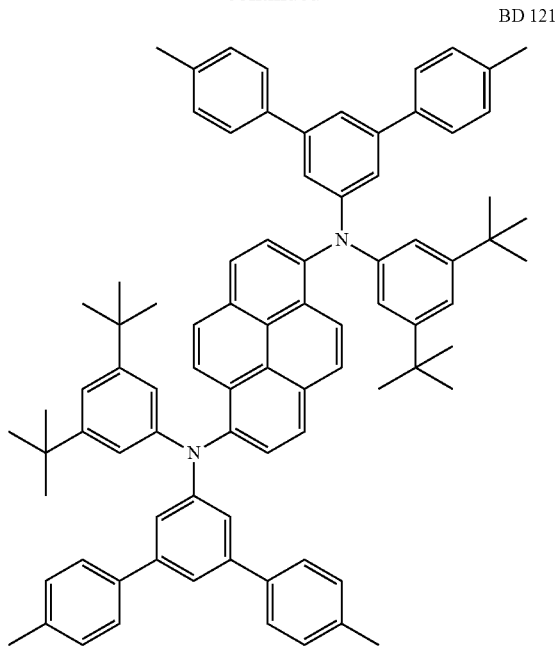
BD 120
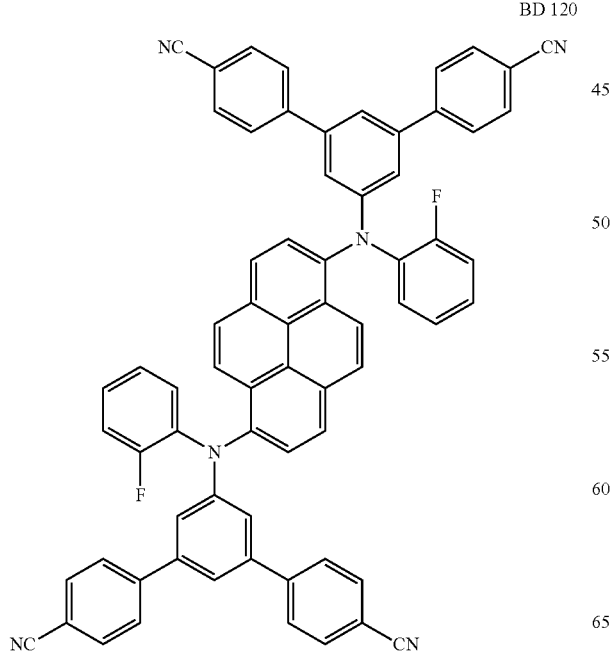
BD 123
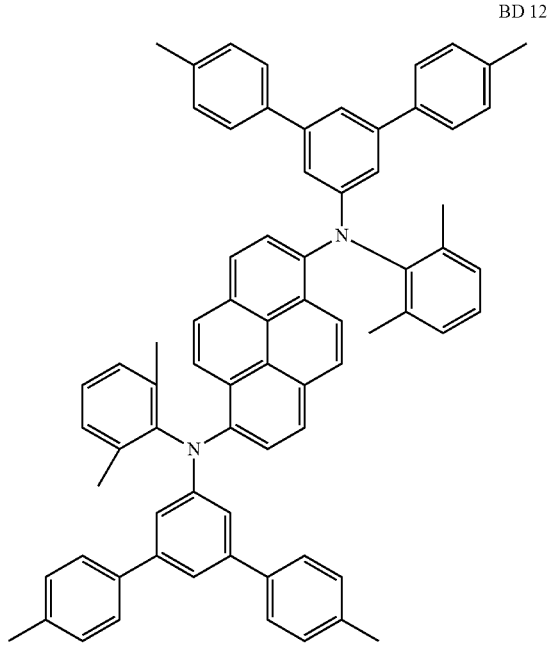

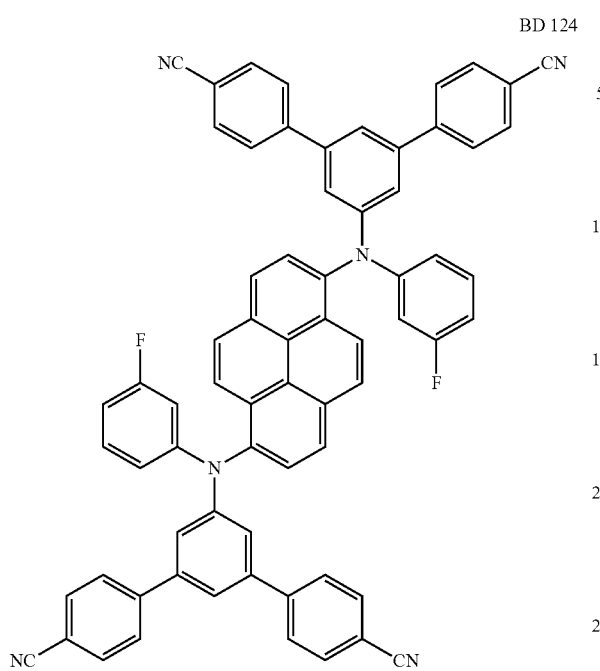
BD 124
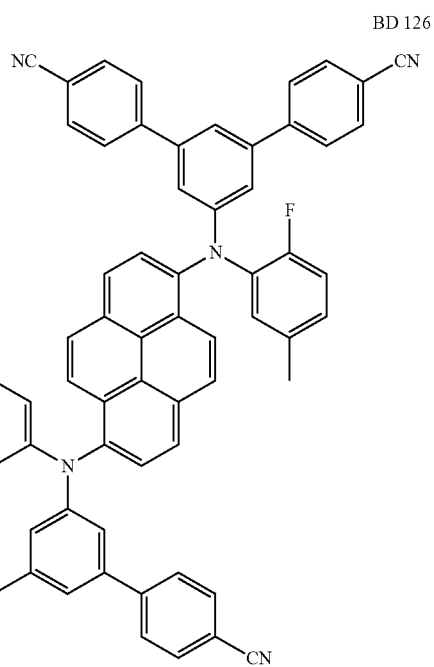
BD 126
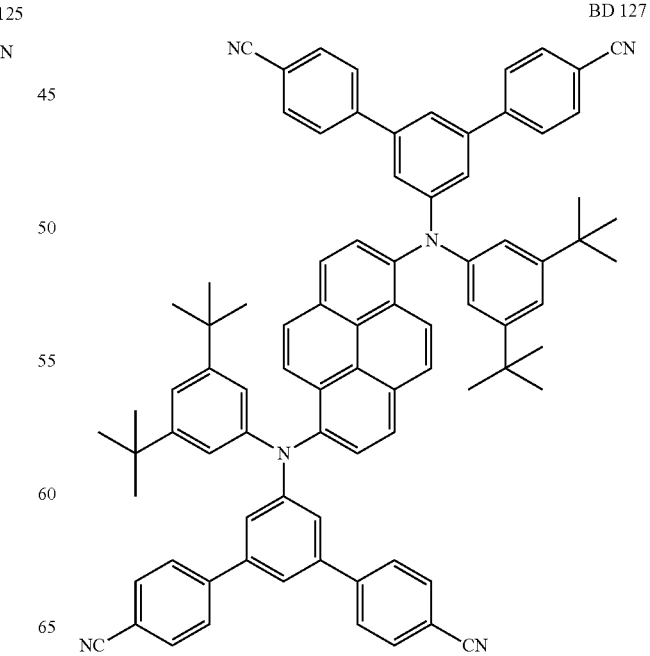
BD 127
BD 125

-continued
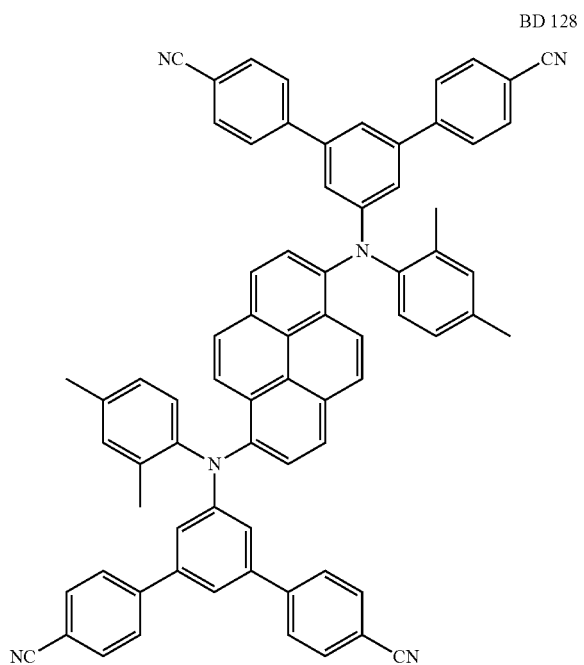
BD 128
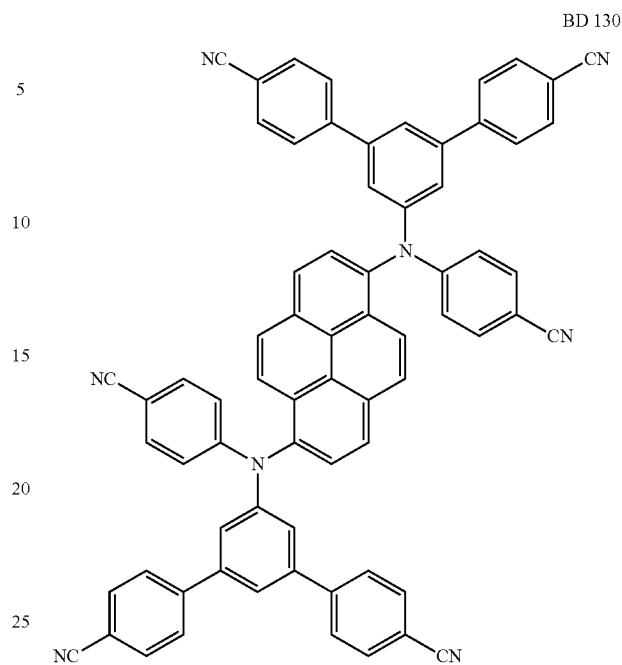
BD 130
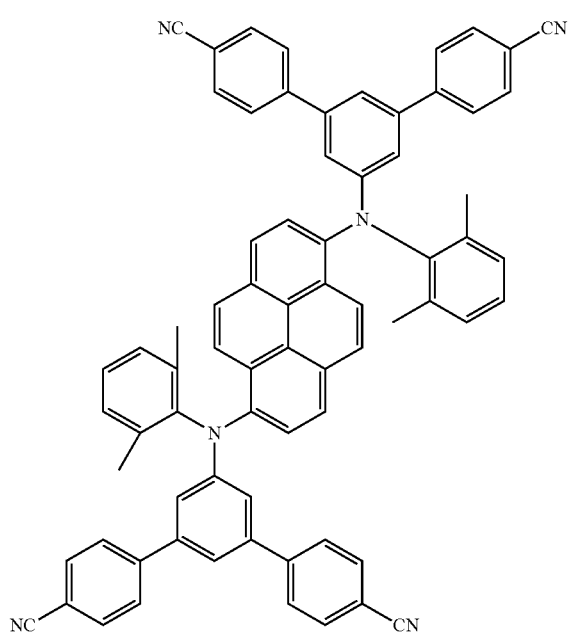
BD 129
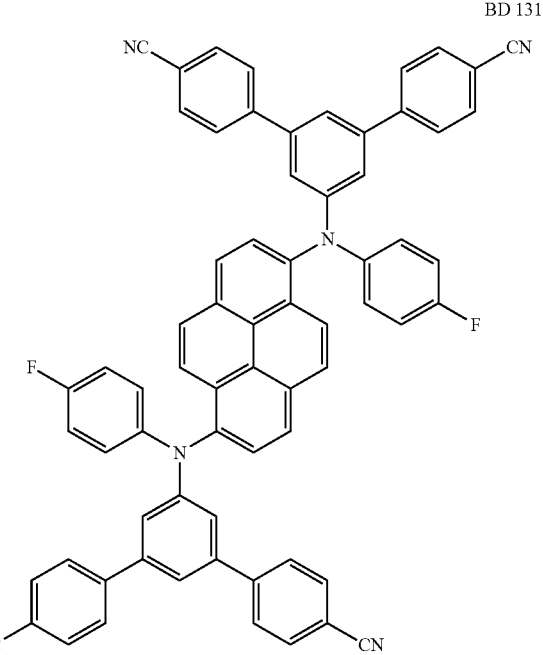
BD 131

245
-continued
BD 132
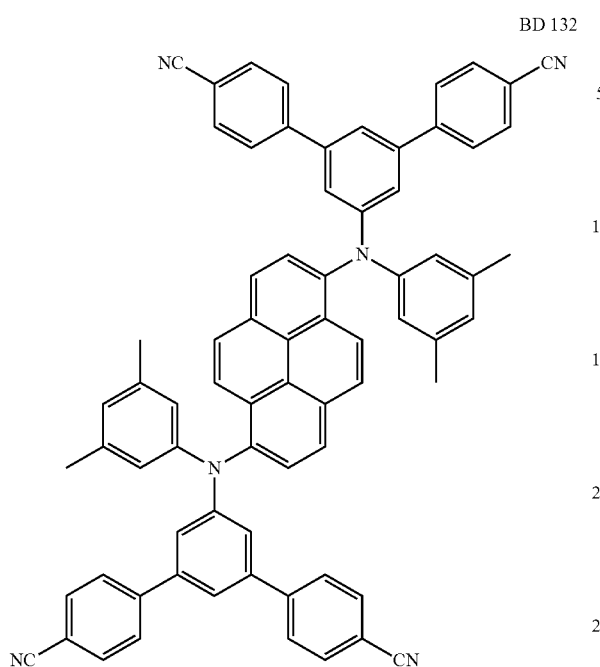
BD 133
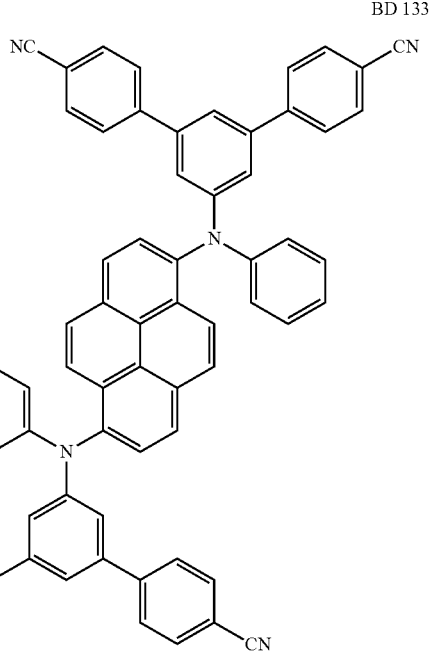
246
-continued
BD 134
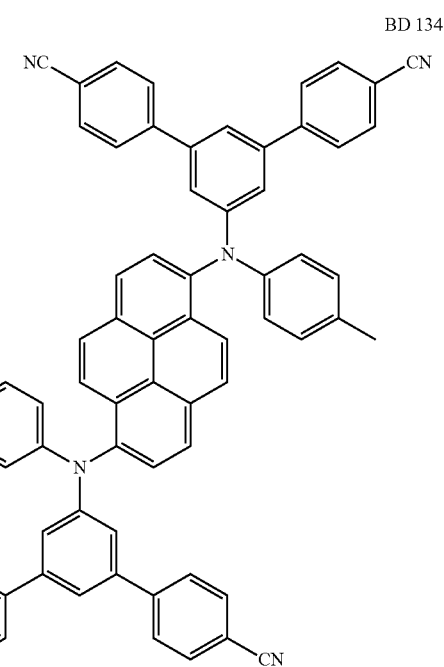
BD 135
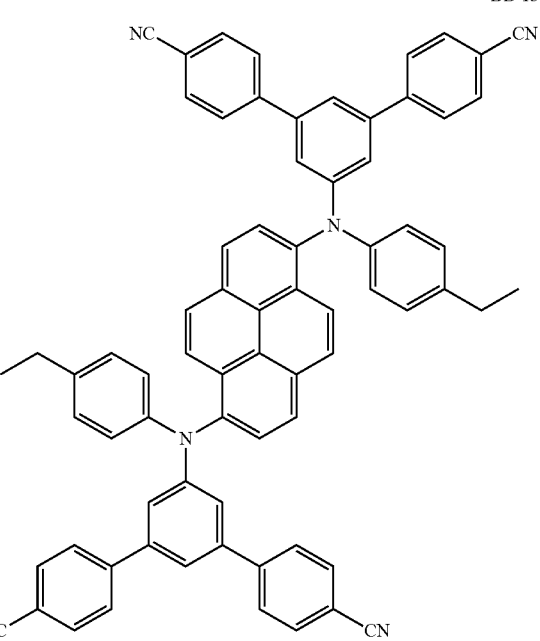

BD 136
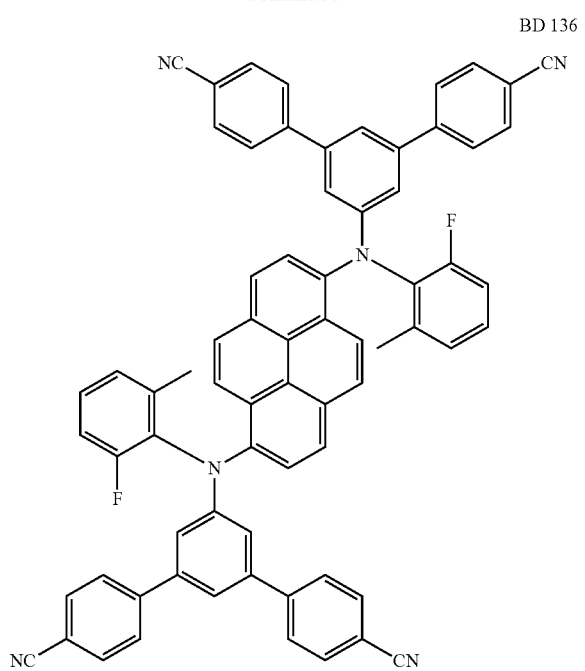
BD 138
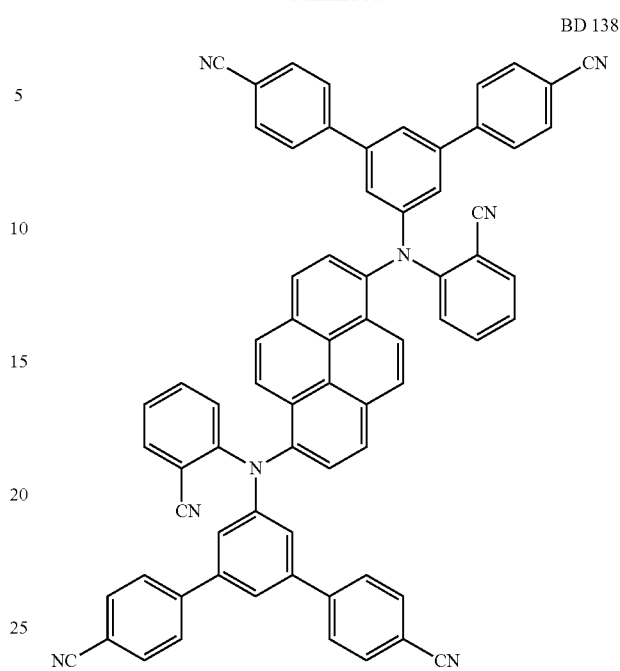
BD 137
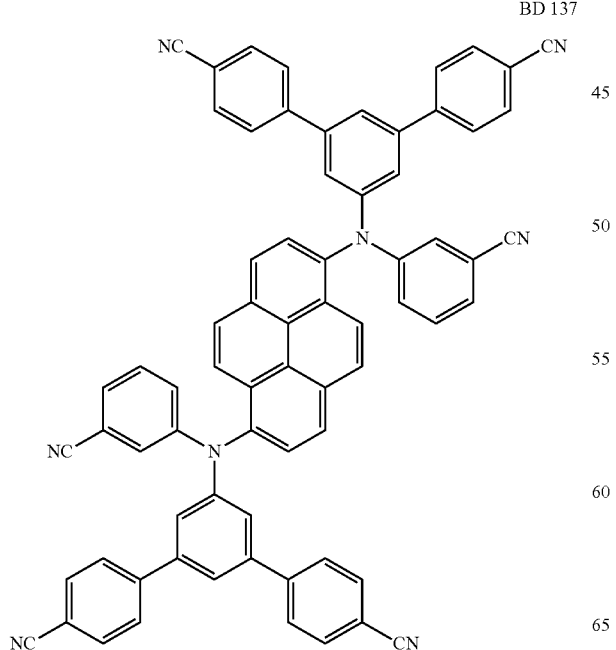
BD 139
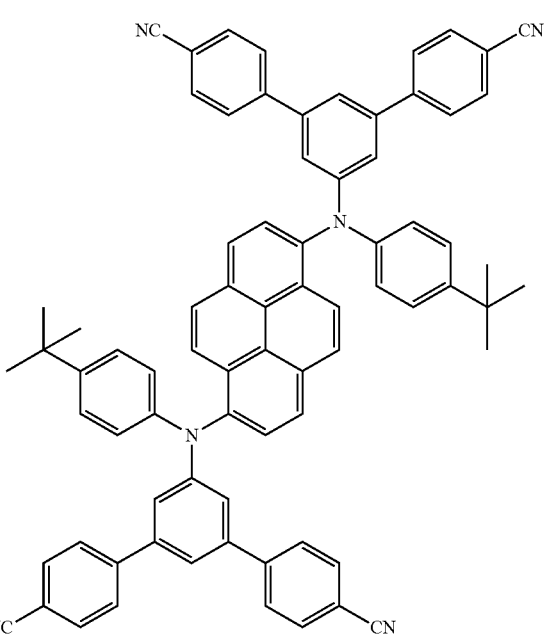

BD 140
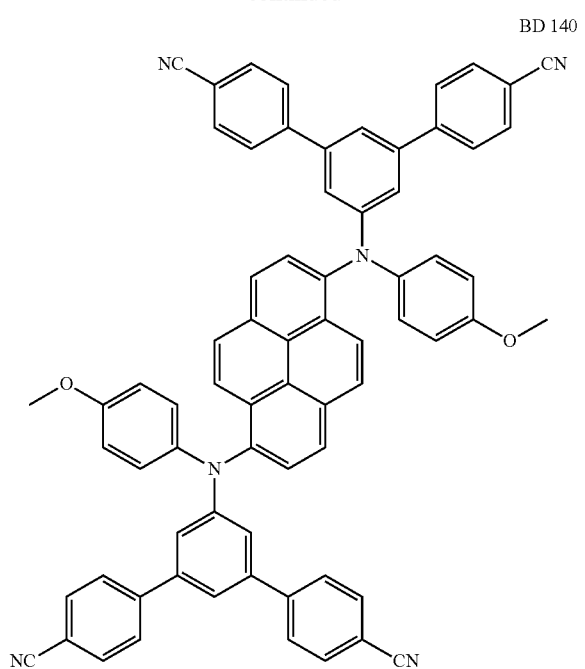
BD 141
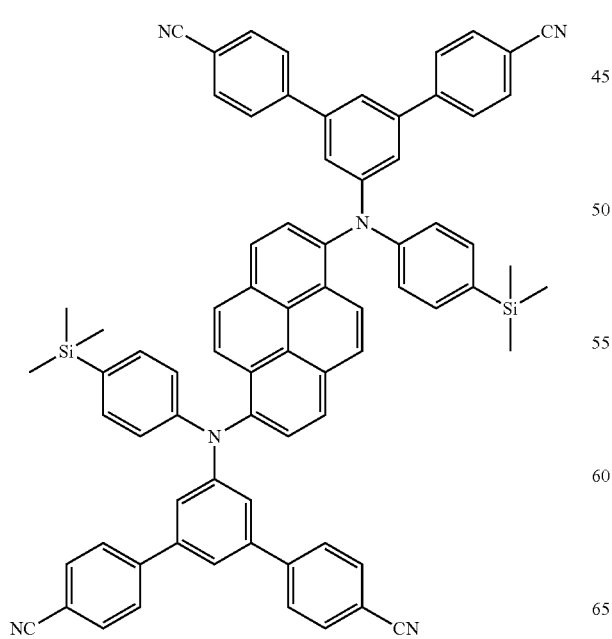
BD 142
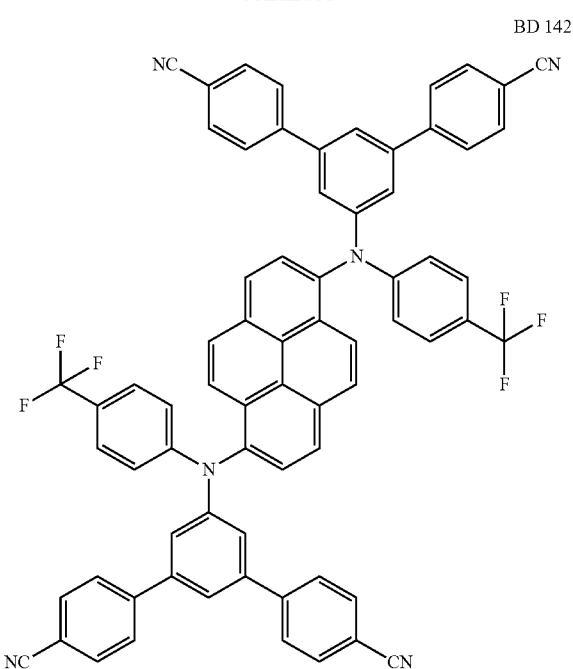
BD 143
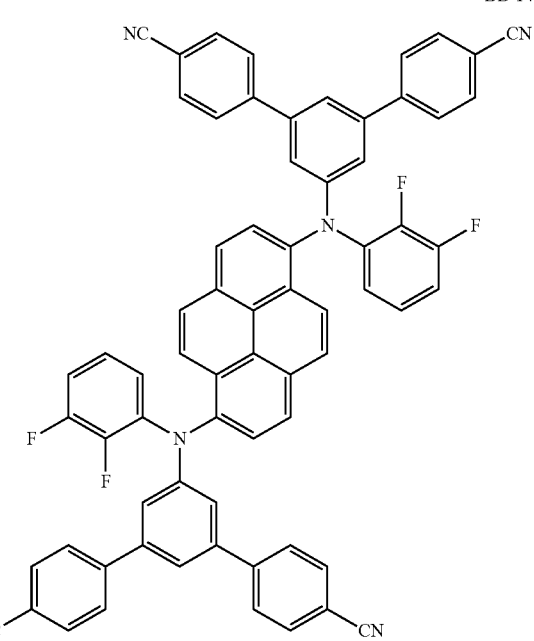

251
-continued
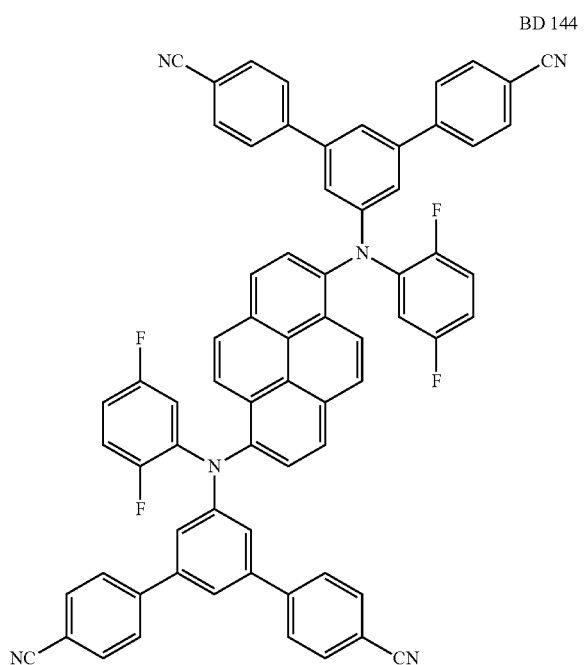 [SMILES: N#Cc1ccc(-c2cc(-c3ccc(C#N)cc3)cc(N(c3ccccc3F)c3ccc4ccc5c(N(c6cc(-c7ccc(C#N)cc7)cc(-c7ccc(C#N)cc7)c6)c6ccccc6F)ccc6ccc3c4c65)c2)cc1]
BD 144
252
-continued
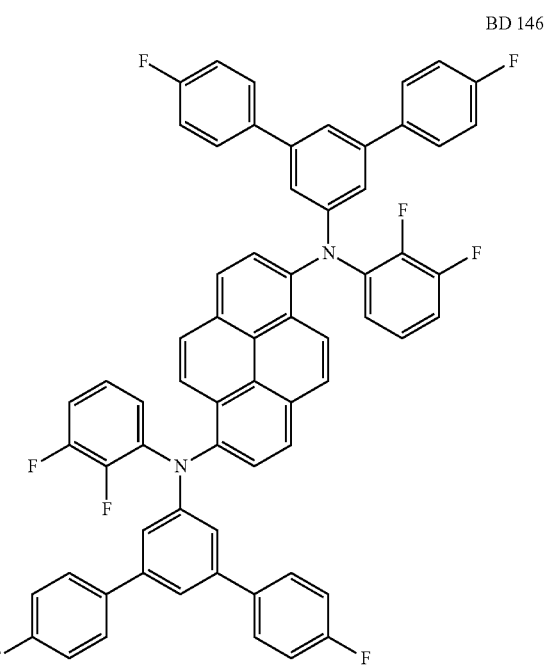
BD 146
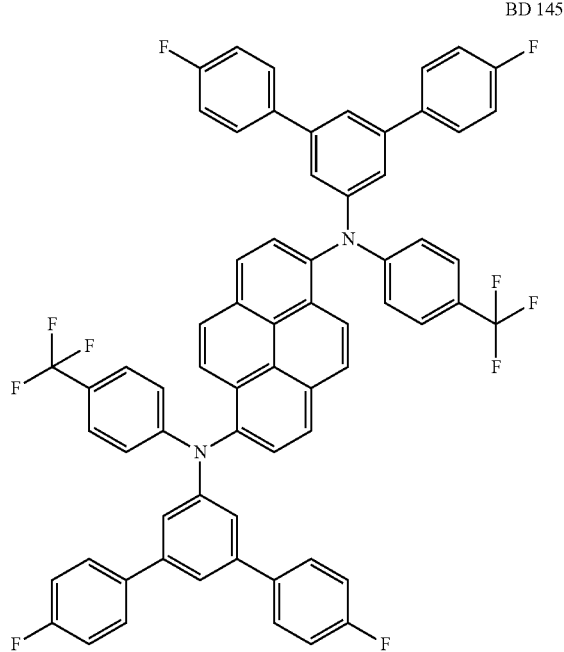
BD 145
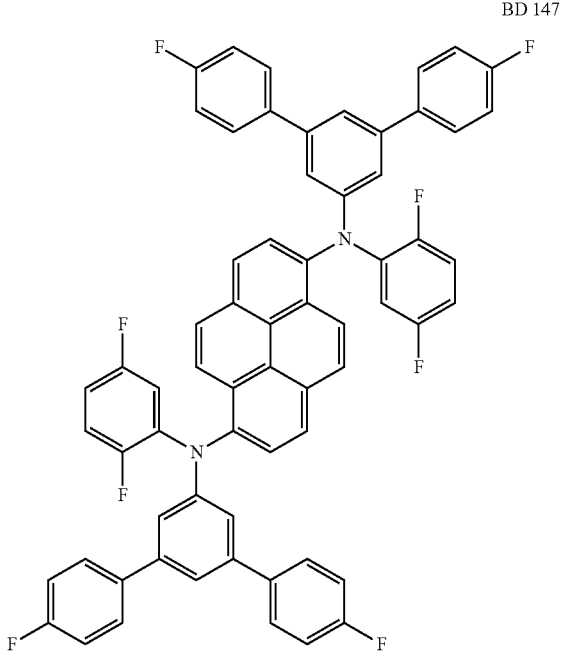
BD 147

BD 148
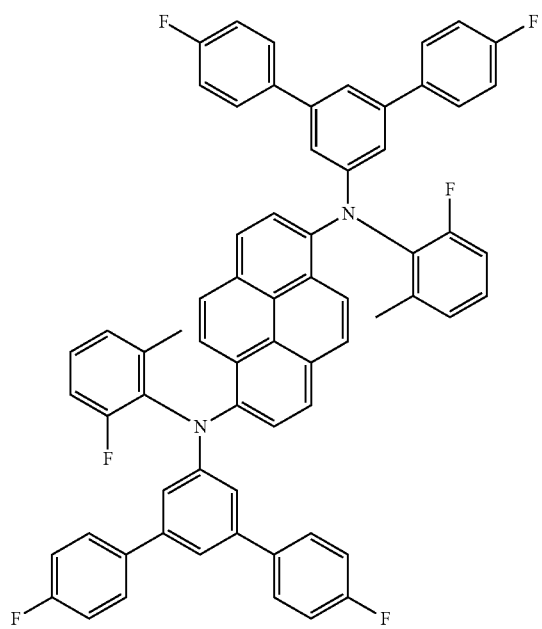
BD 150
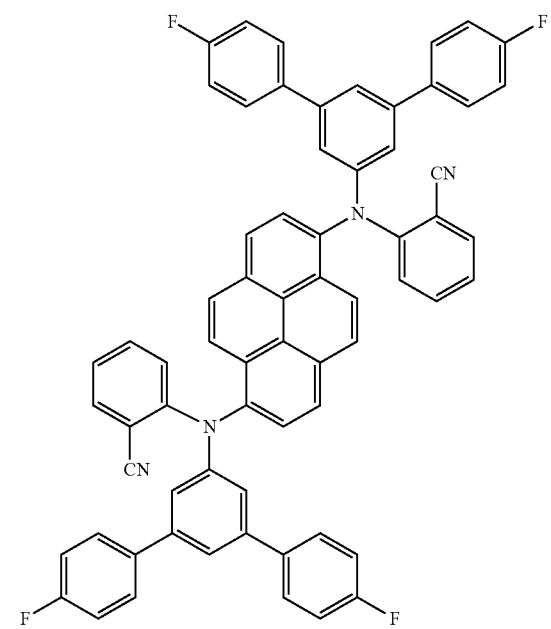
BD 149
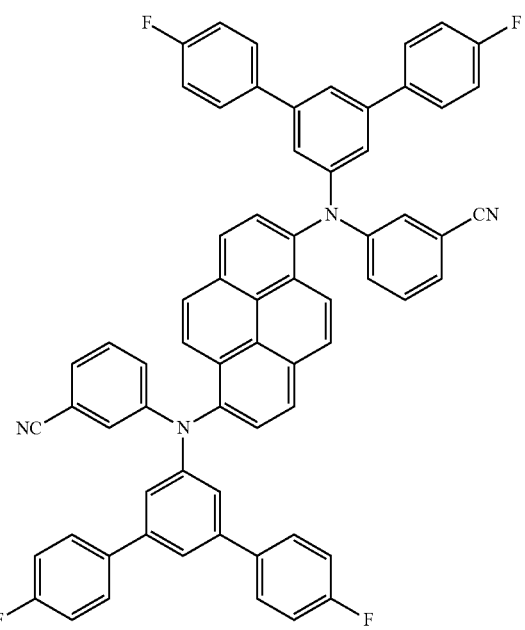
BD 151
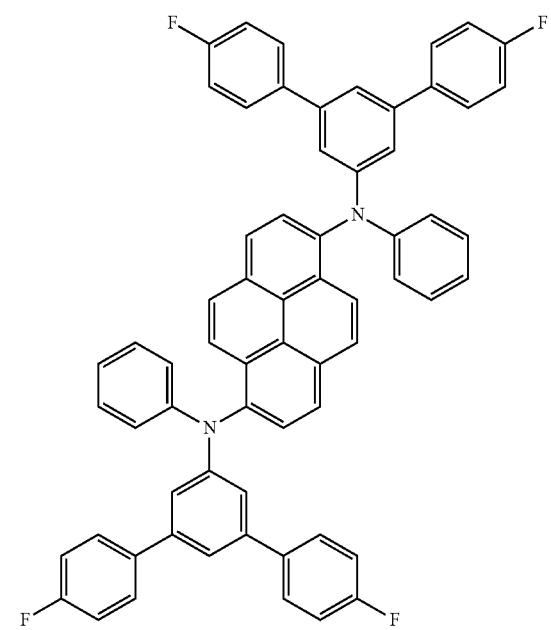

-continued
BD 152
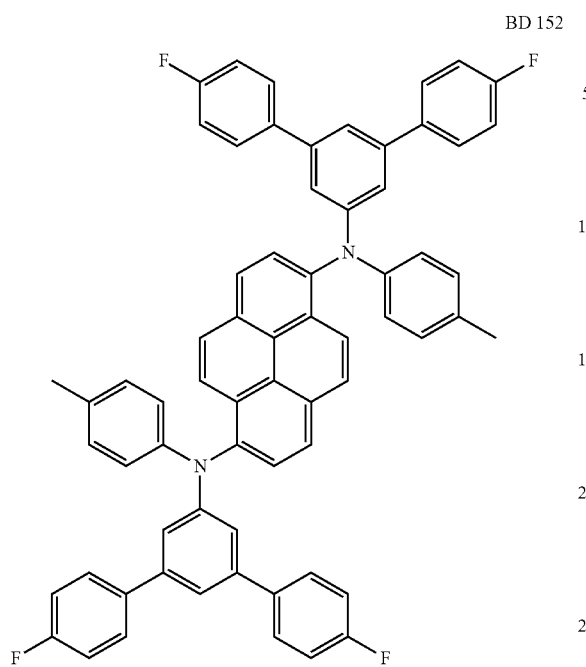
BD 154
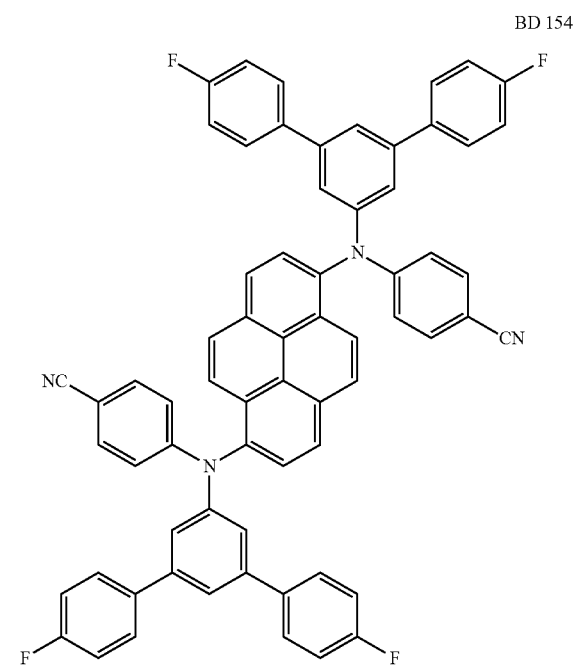
BD 153
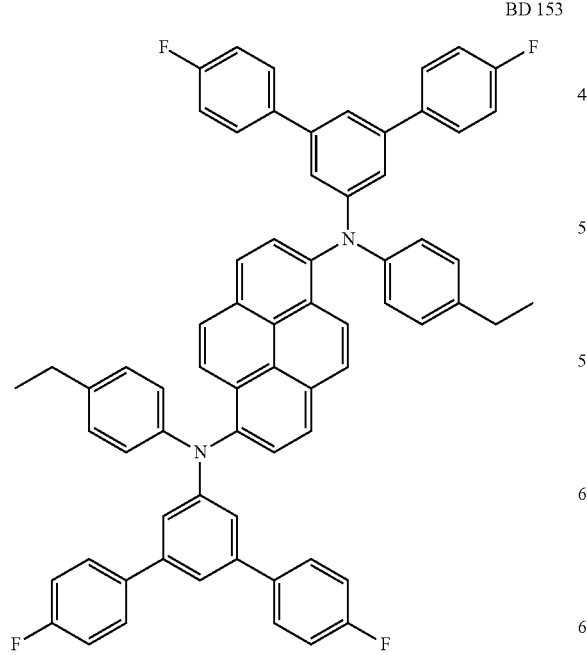
BD 155
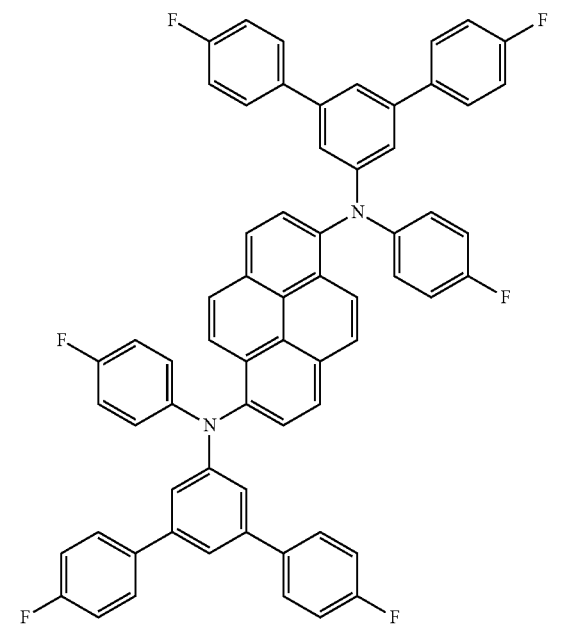

BD 156
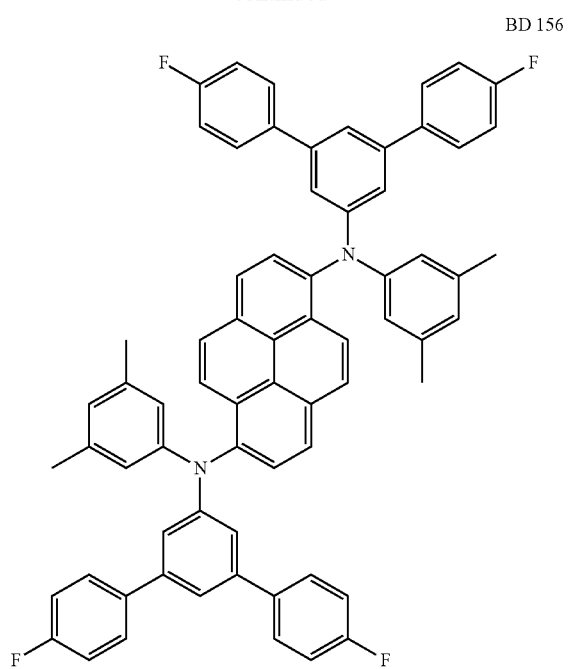
BD 157
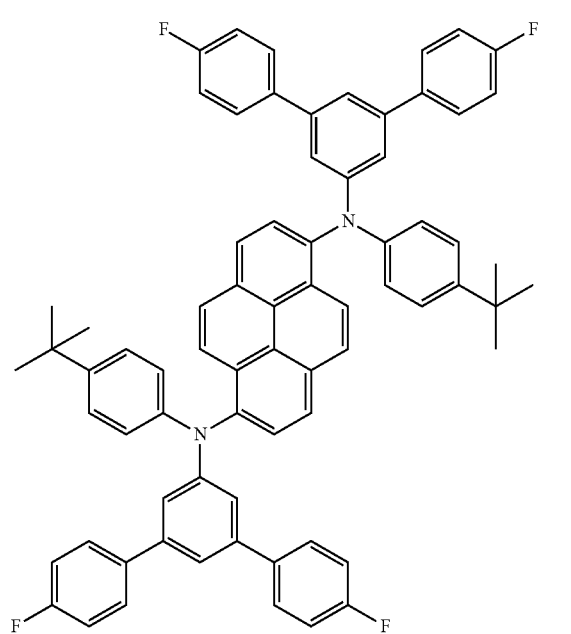
BD 158
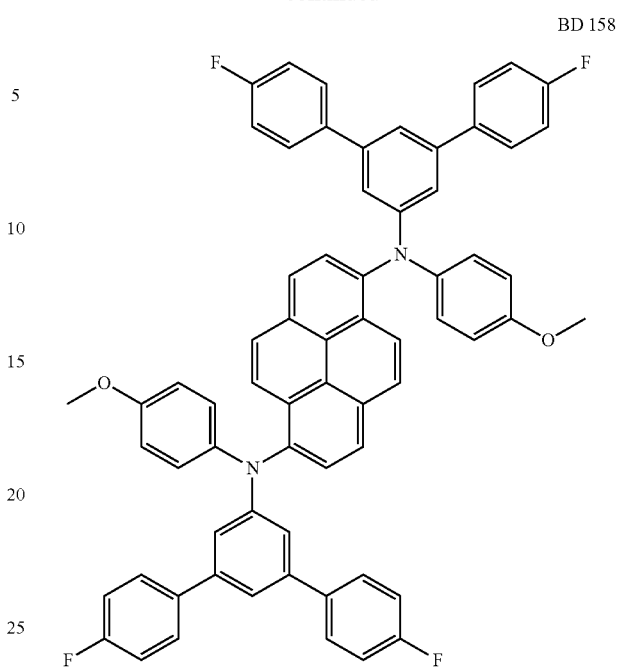
BD 159
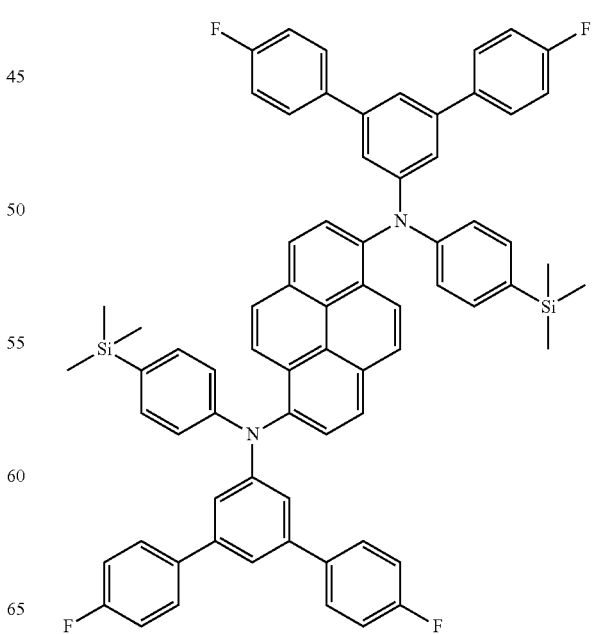

-continued
BD 160
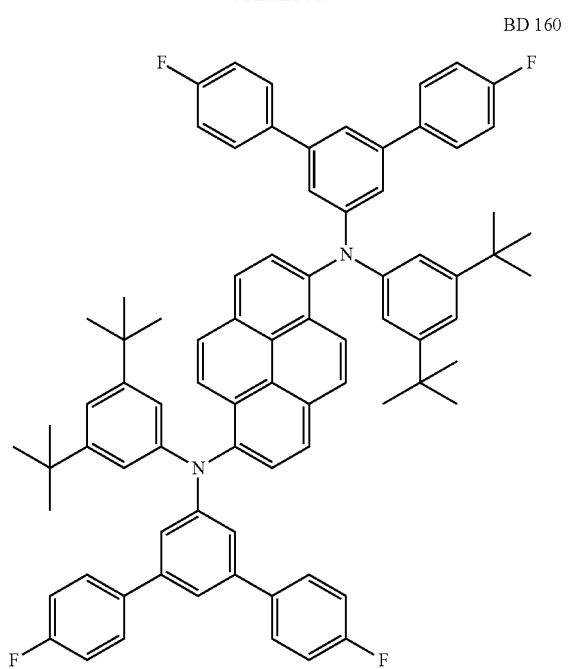
BD 162
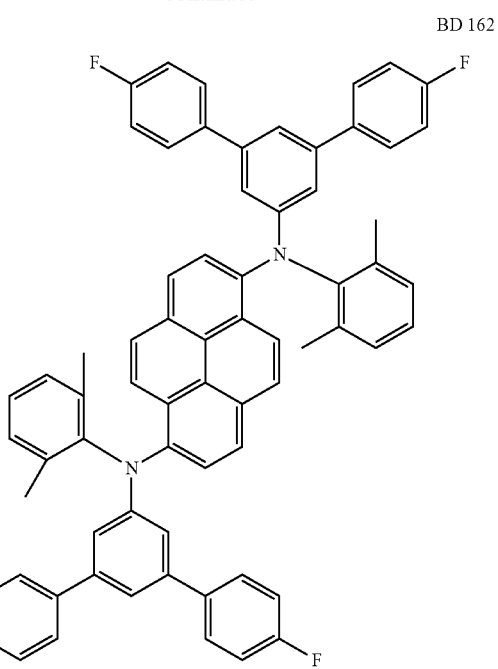
BD 161
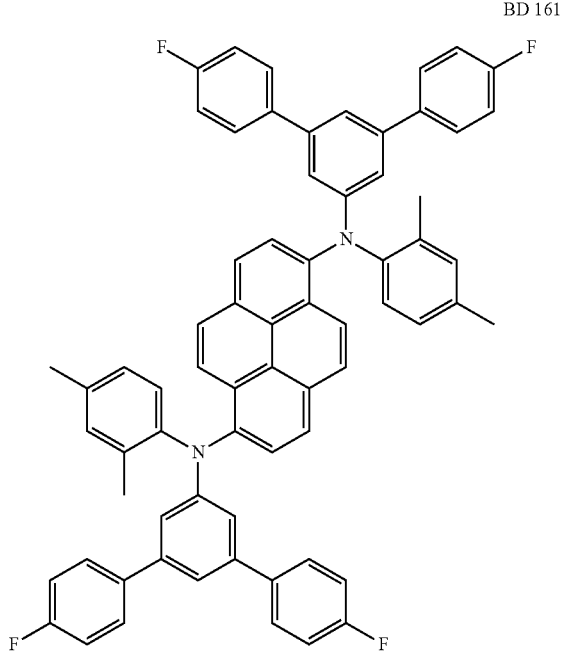
BD 163
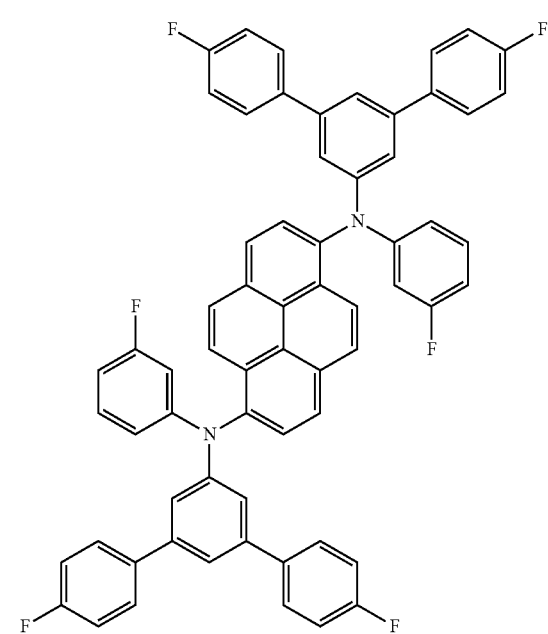

BD 164
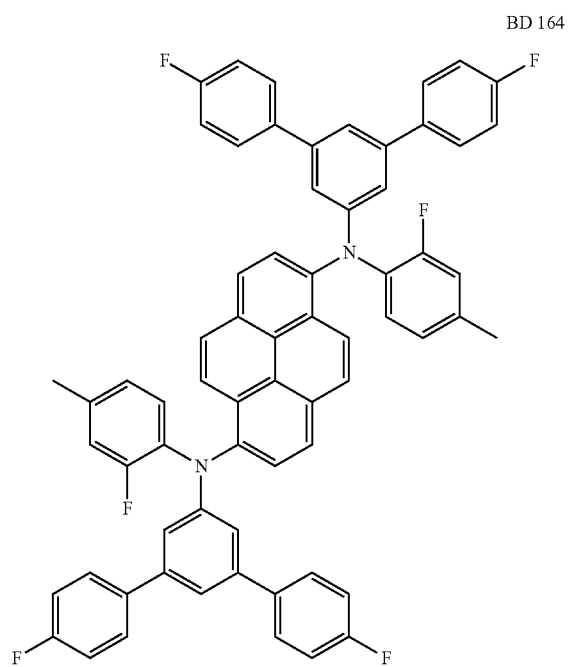
BD 166
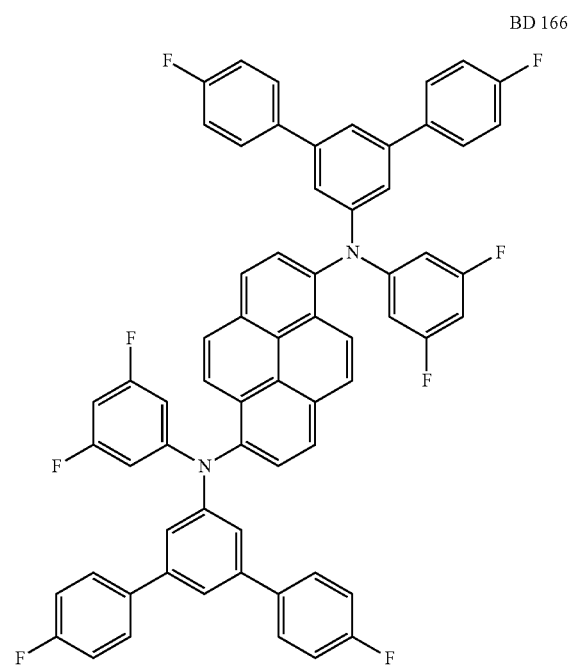
BD 165
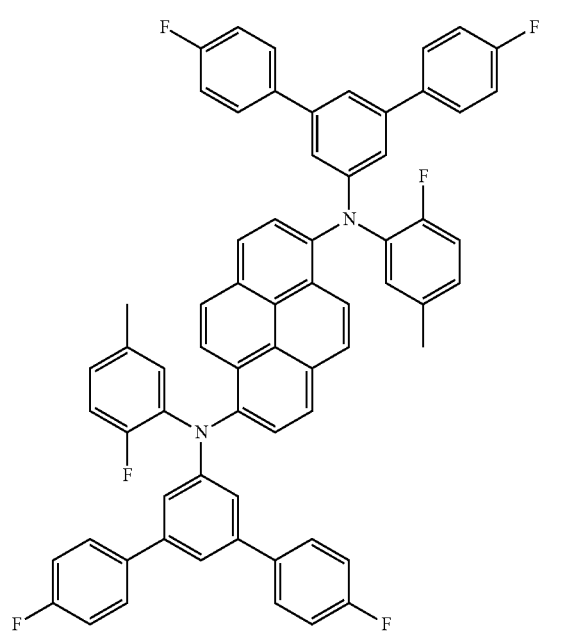
BD 167
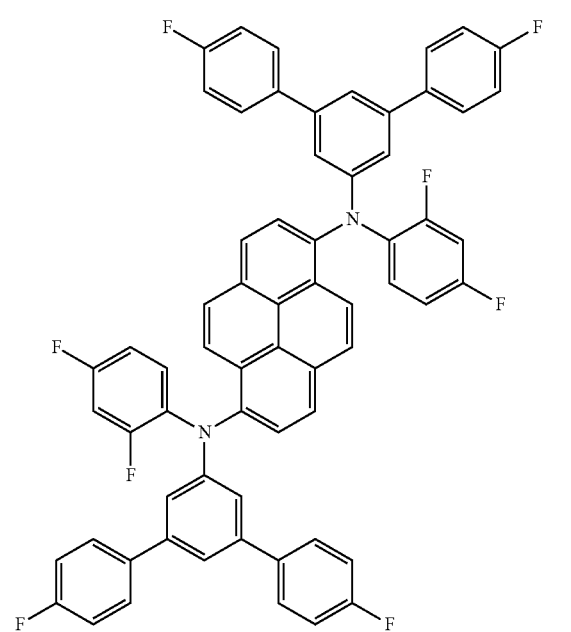

263
-continued
BD 168
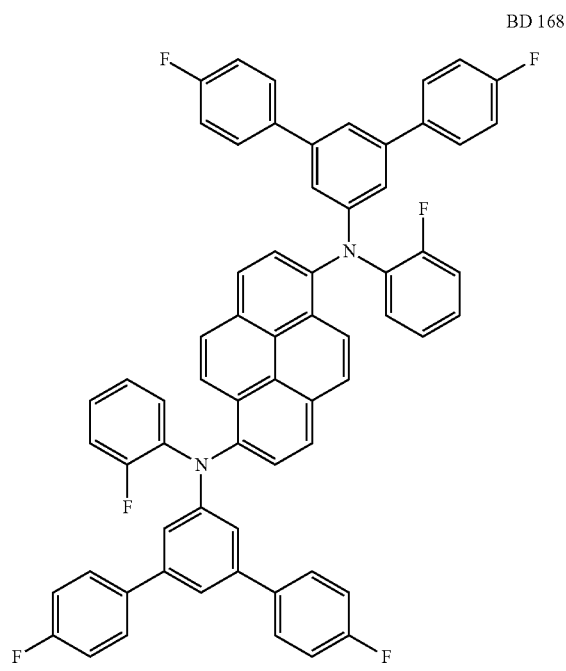
BD 169
264
-continued
BD 170
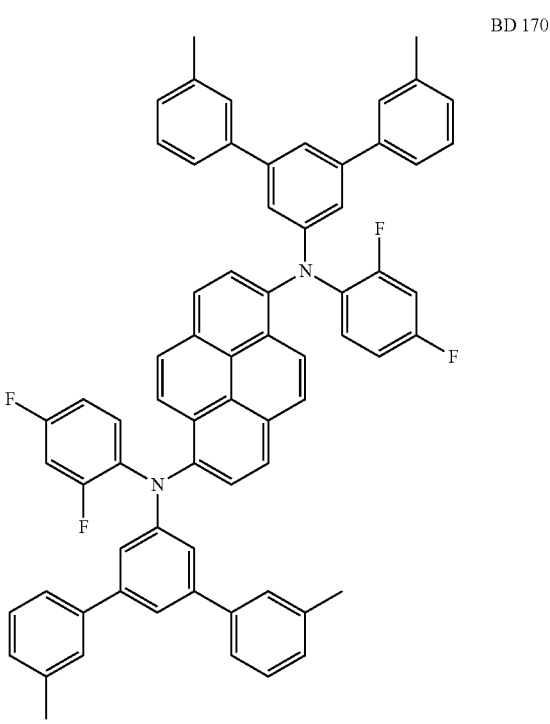
BD 171
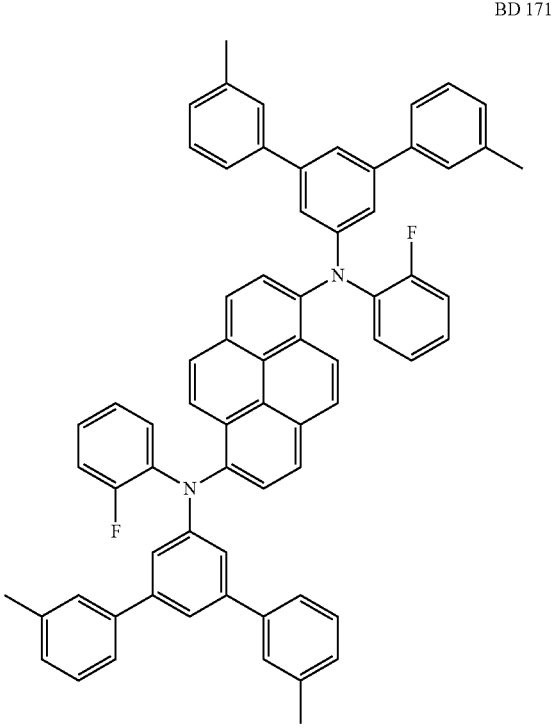

-continued
BD 172
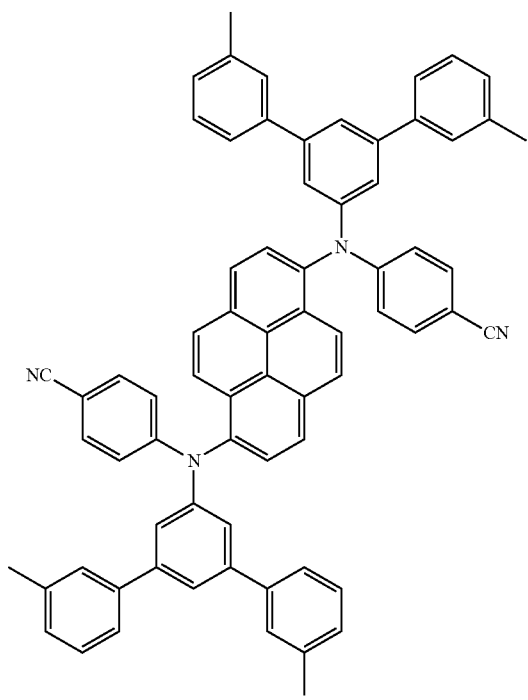
BD 175
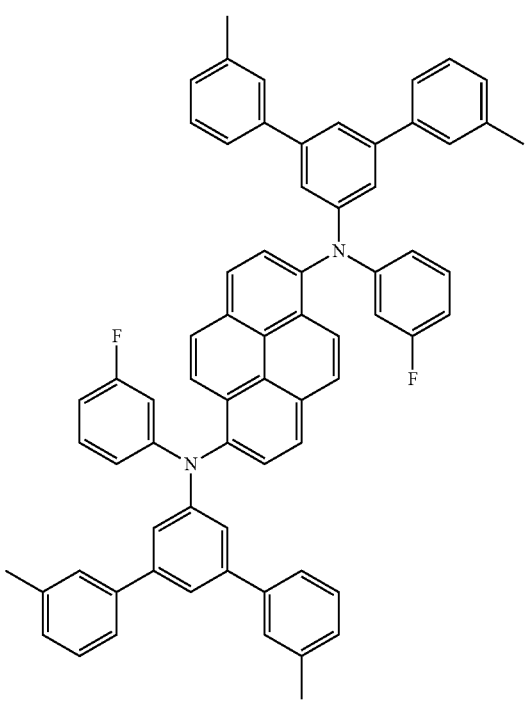
BD 173
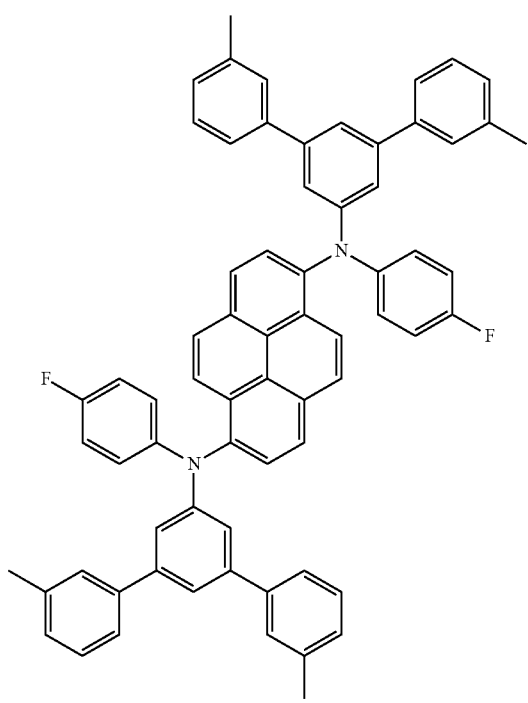
BD 176
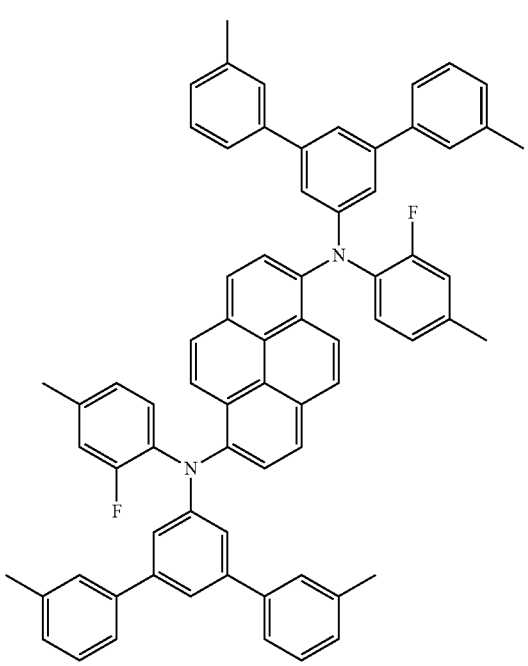

BD 177
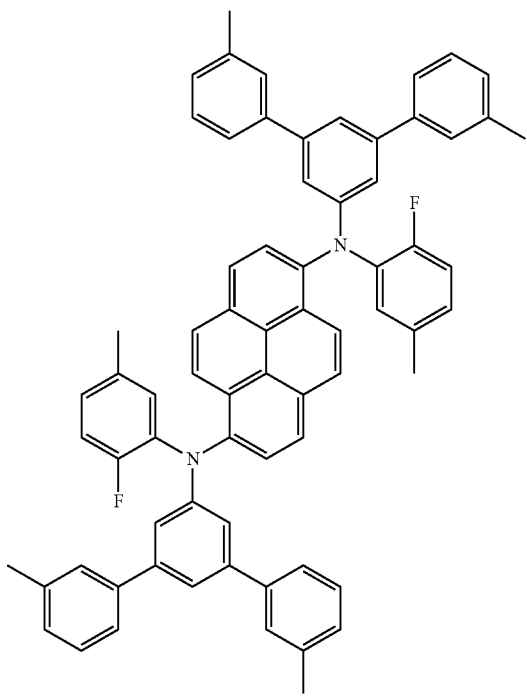
BD 180
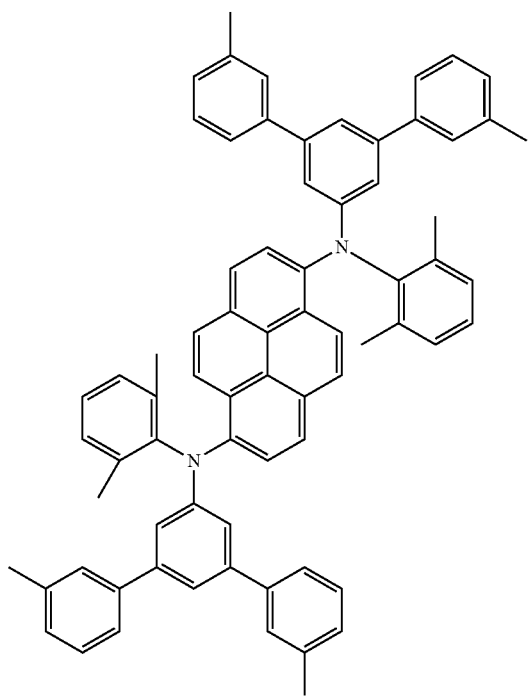
BD 179
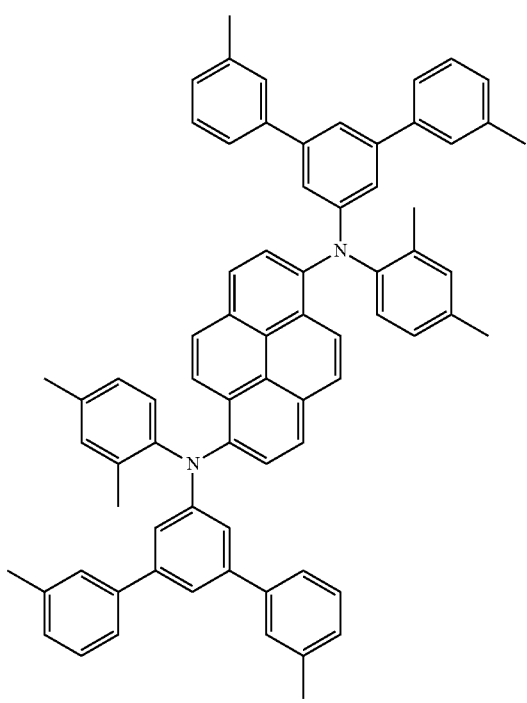
BD 183
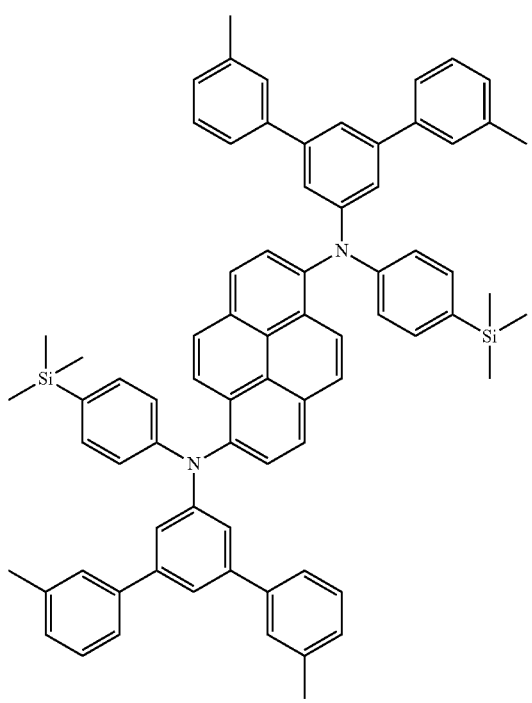

269
-continued
BD 187
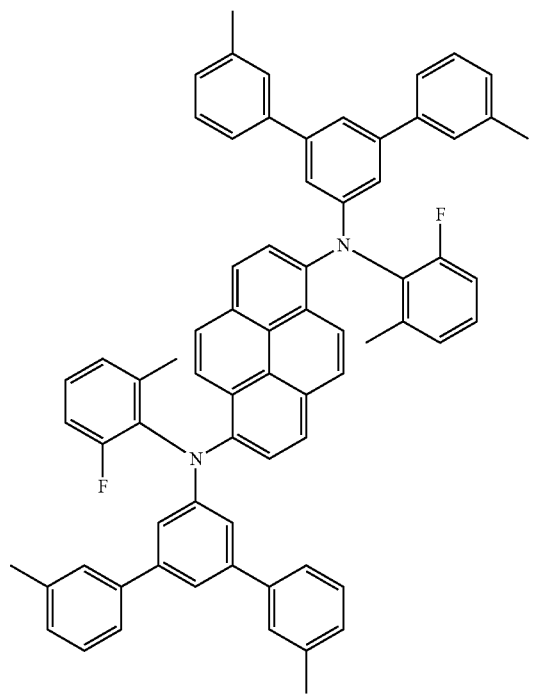
BD 188
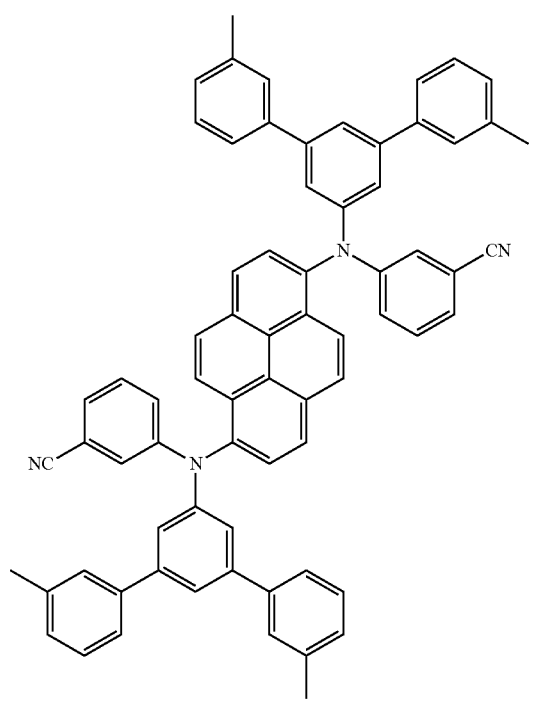
270
-continued
BD 189
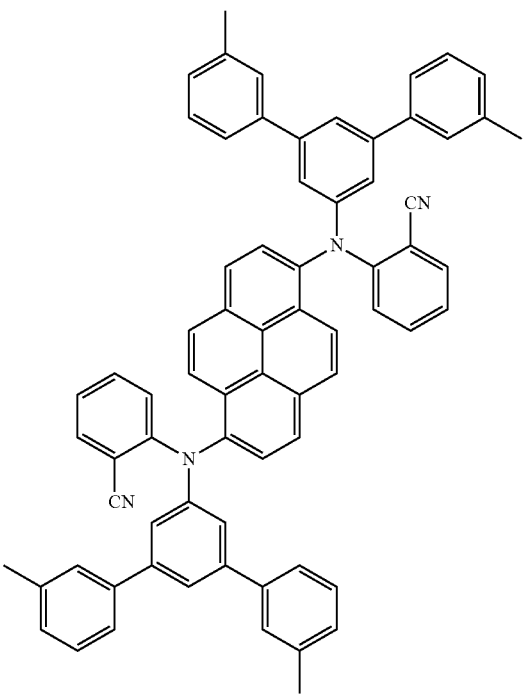
BD 190
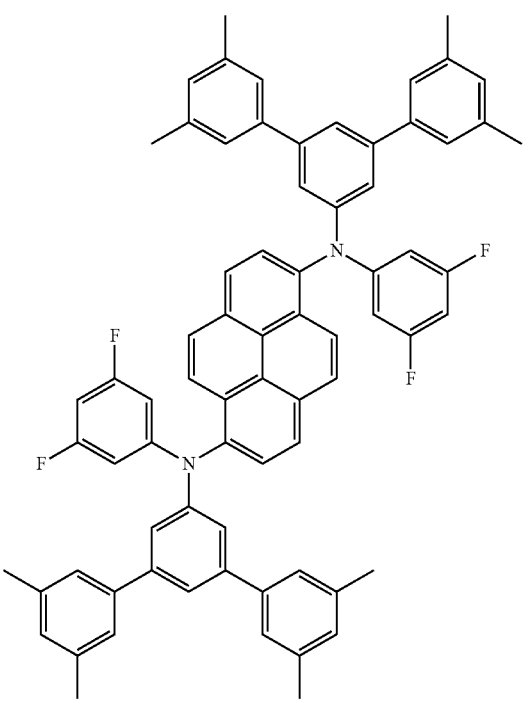

BD 191
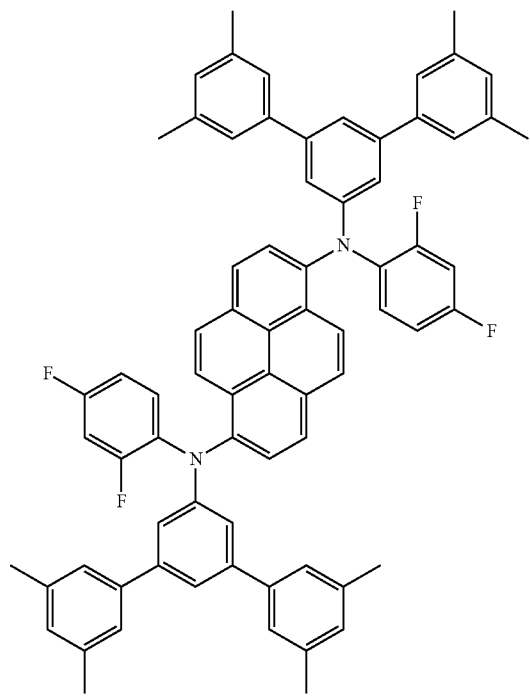
BD 193
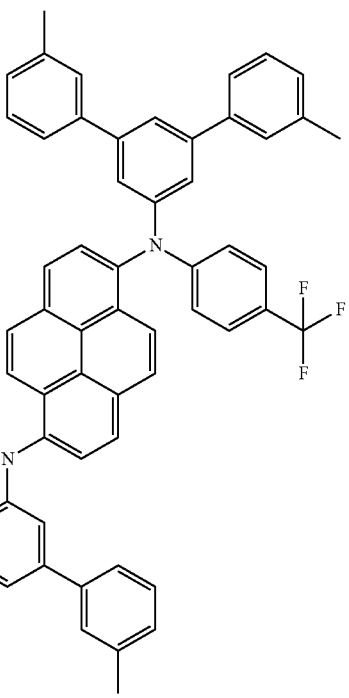
BD 192
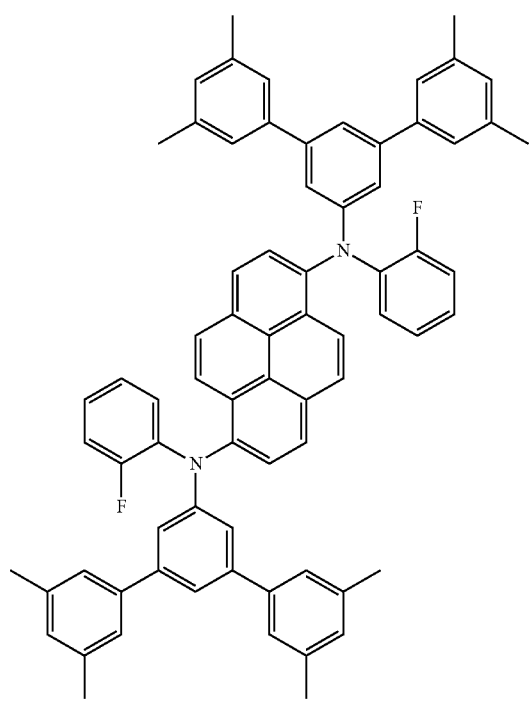
BD 194
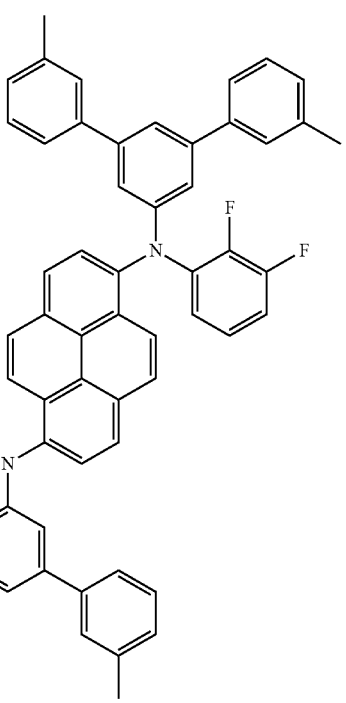

BD 195
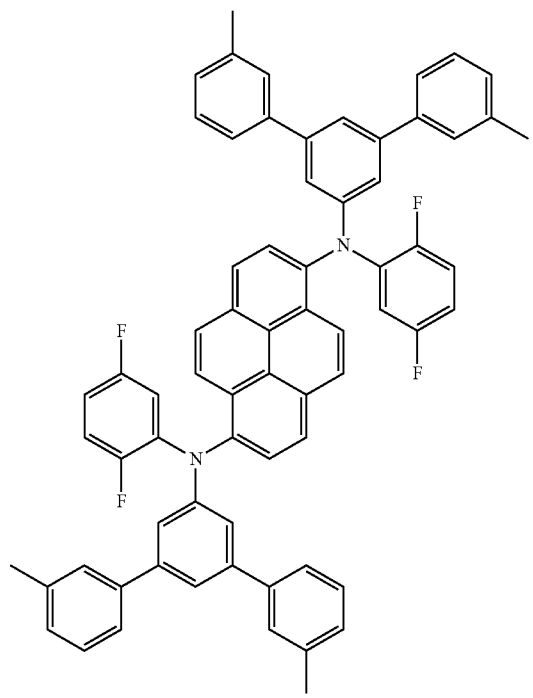
BD 197
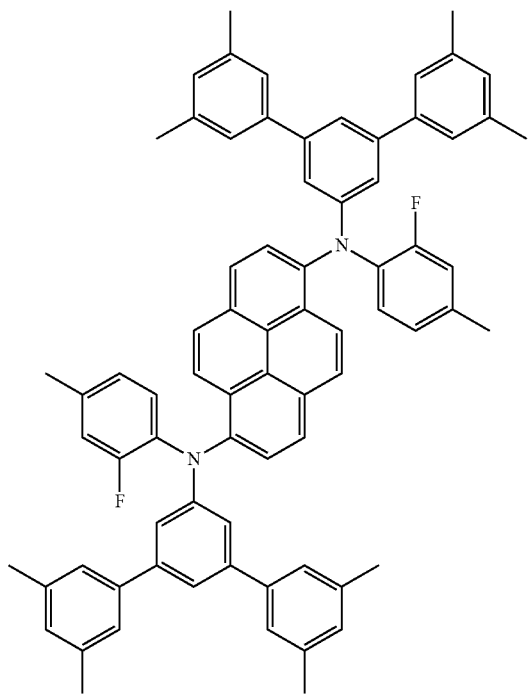
BD 196
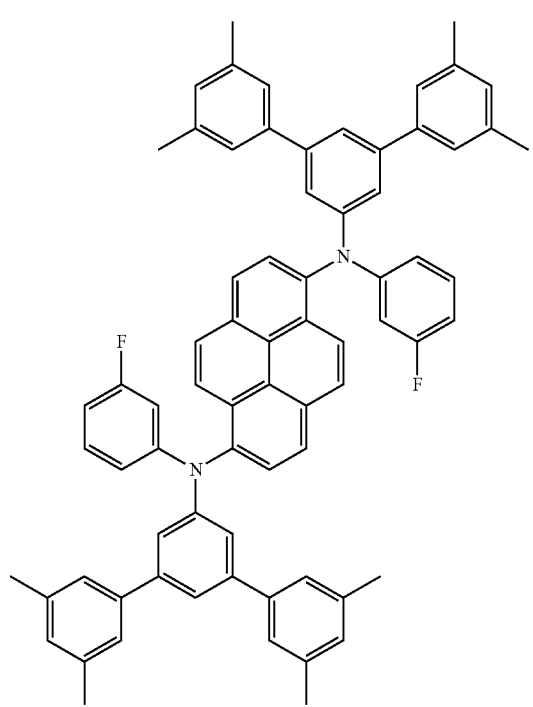
BD 198
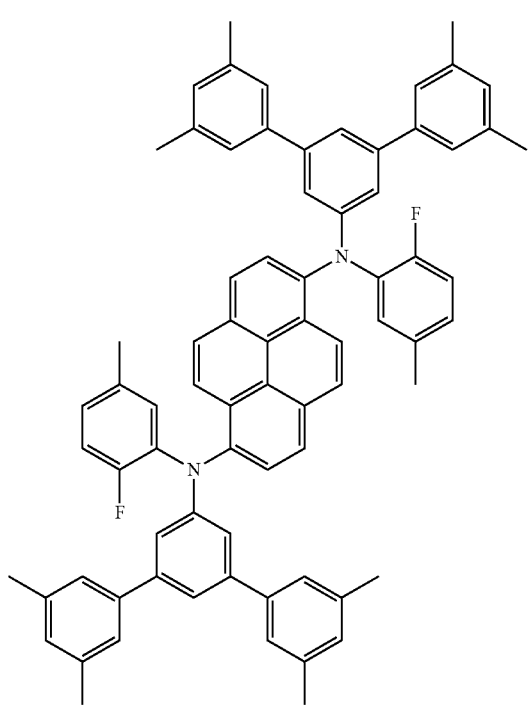

BD 202
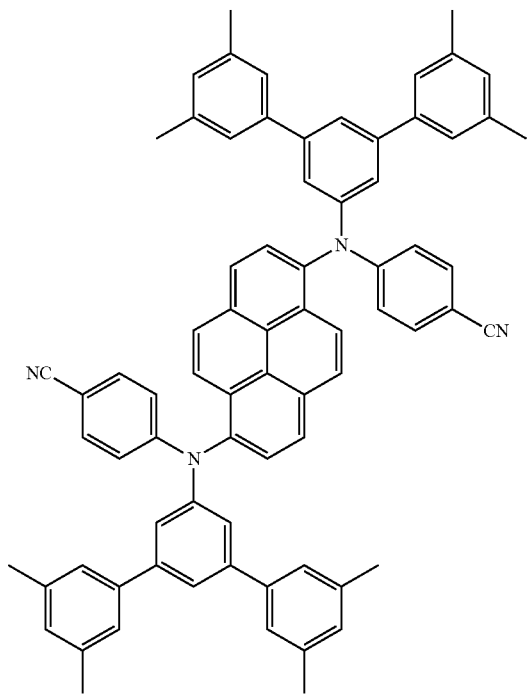
BD 203
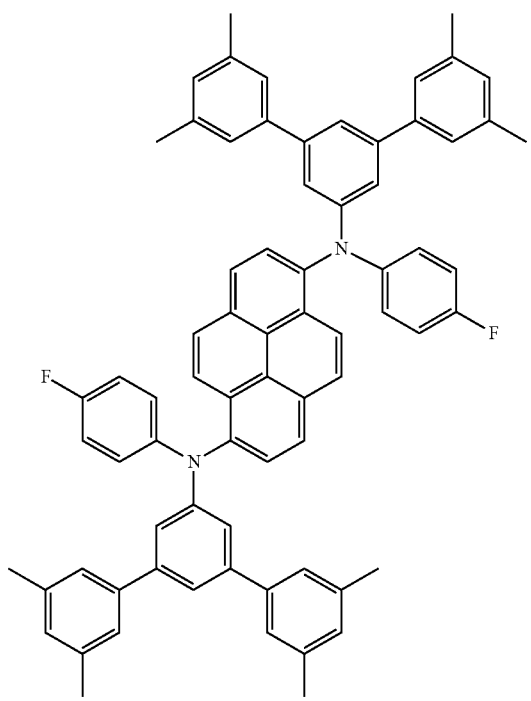
BD 208
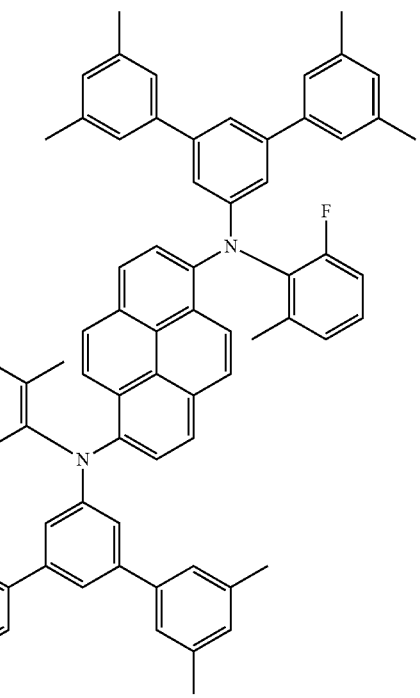
BD 209
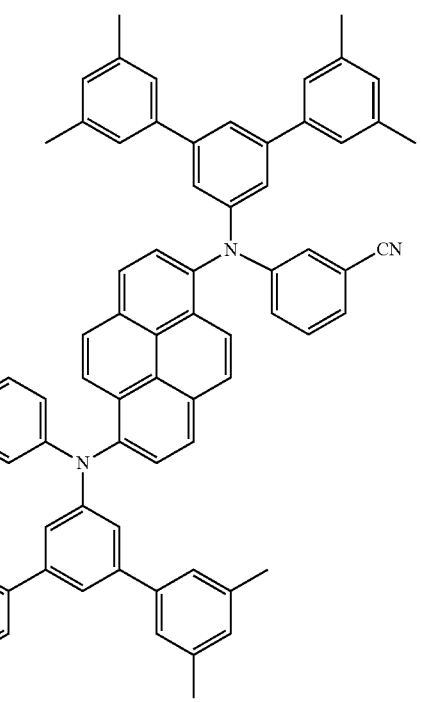

BD 210
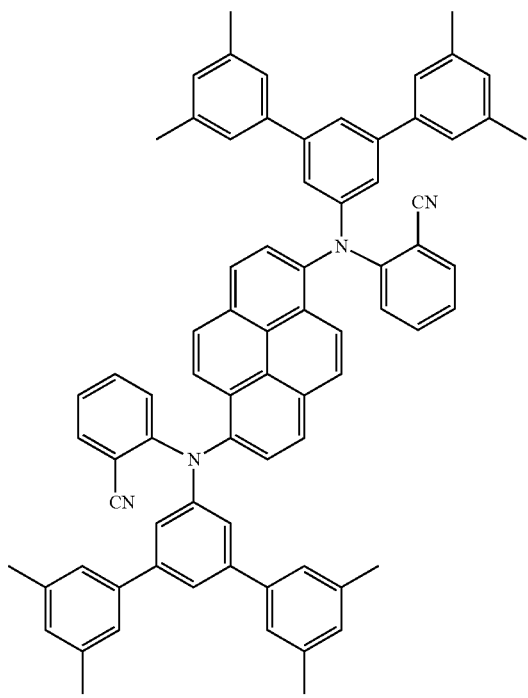
BD 213
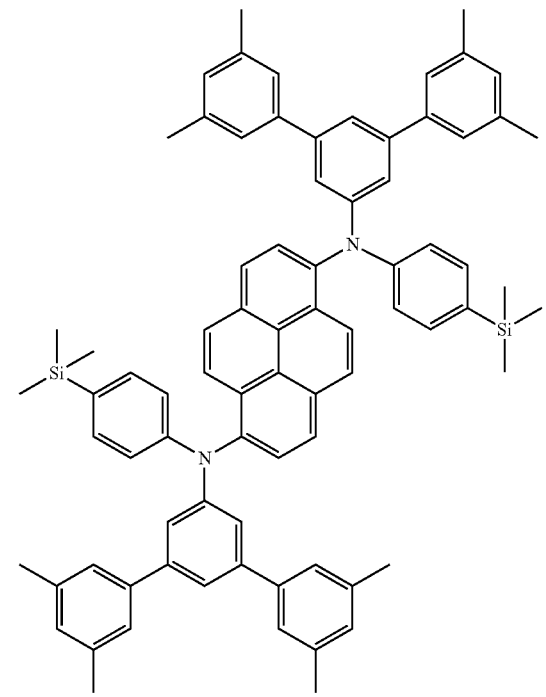
BD 213
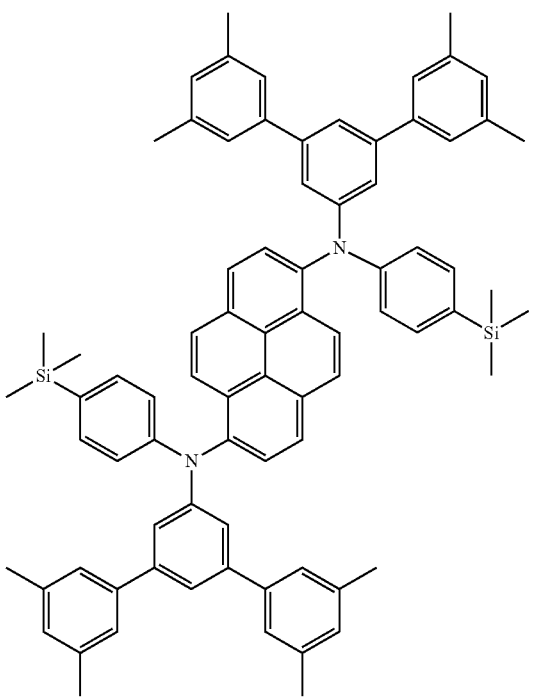
BD 214
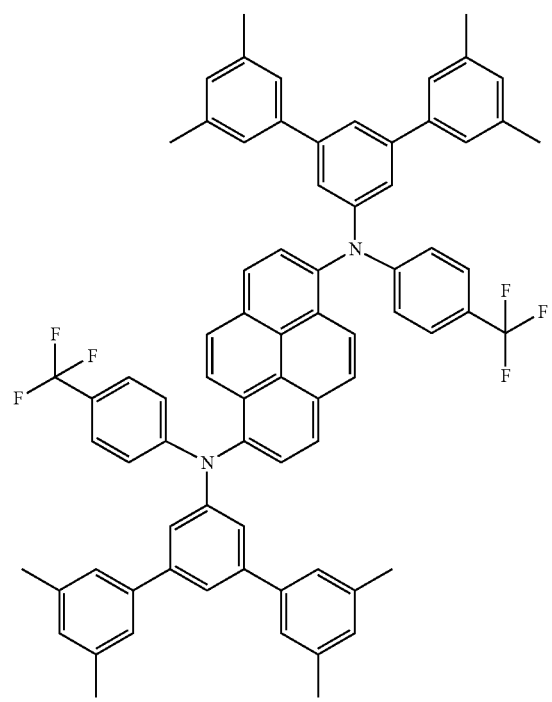

BD 215
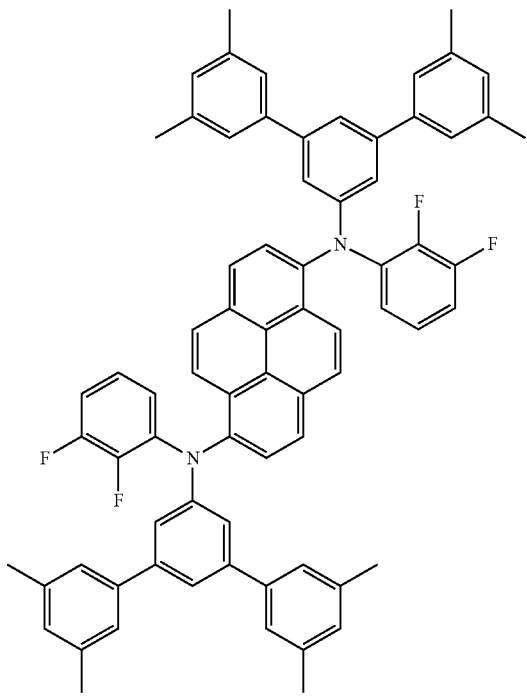
BD 216
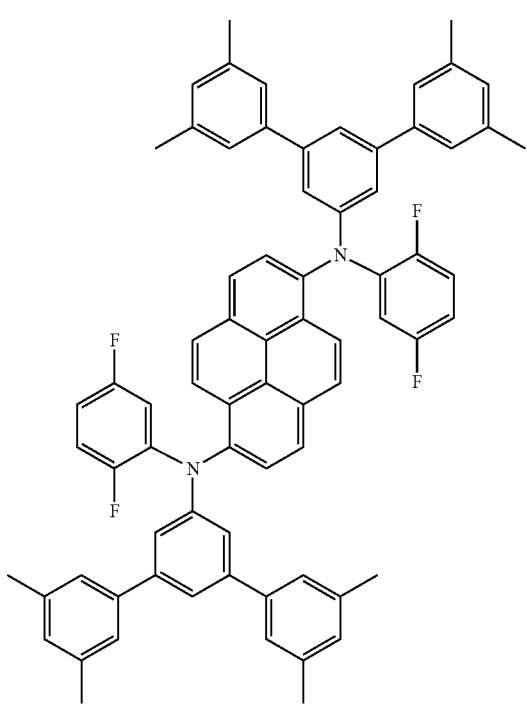
BD 217
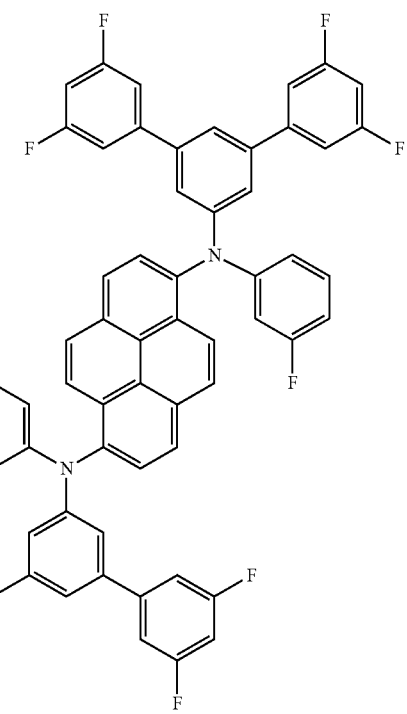
BD 218
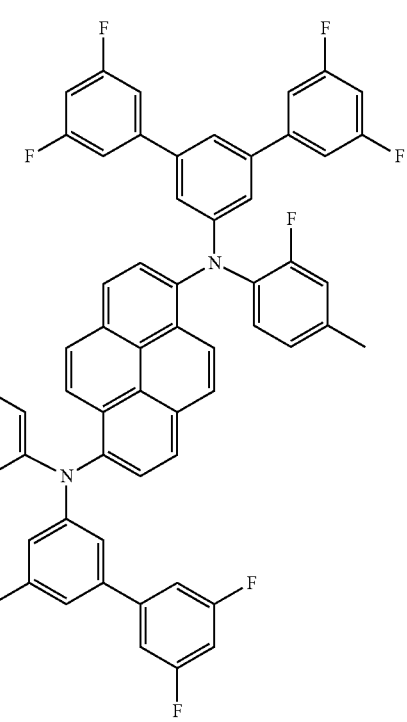

BD 219
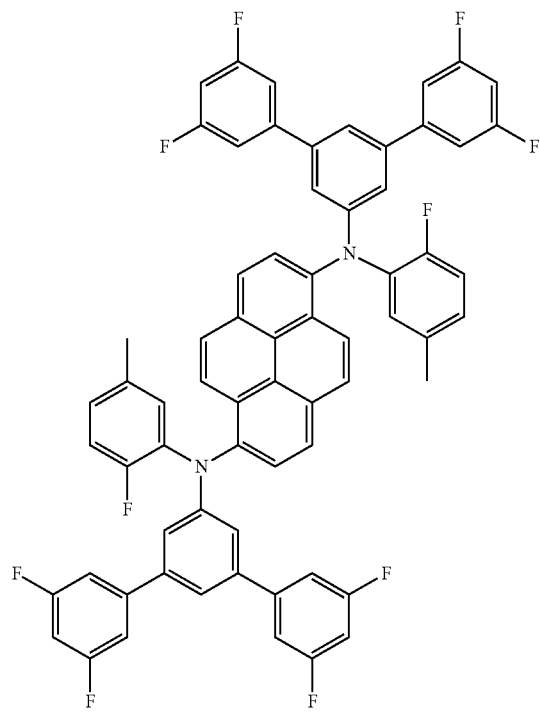
BD 221
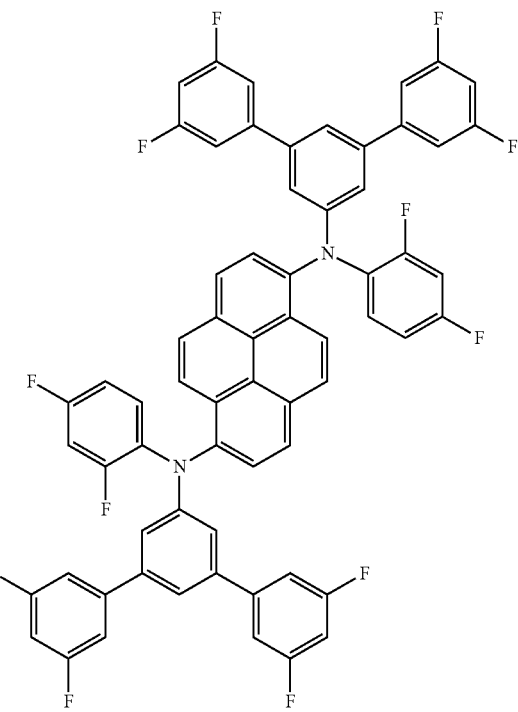
BD 220
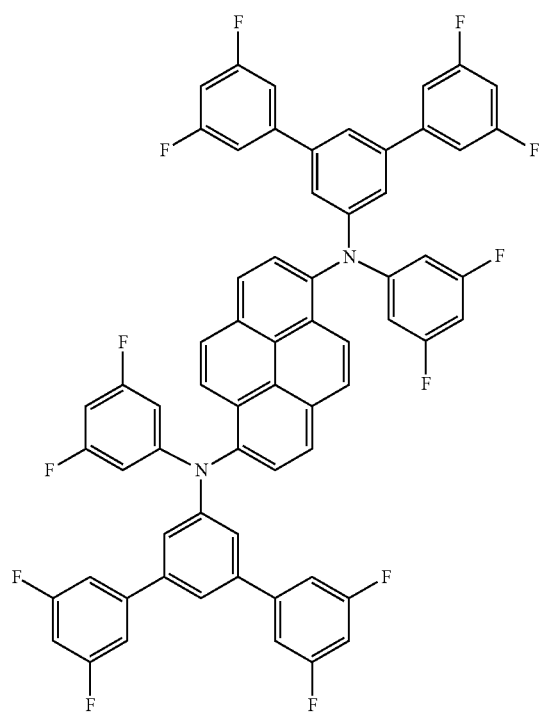
BD 222
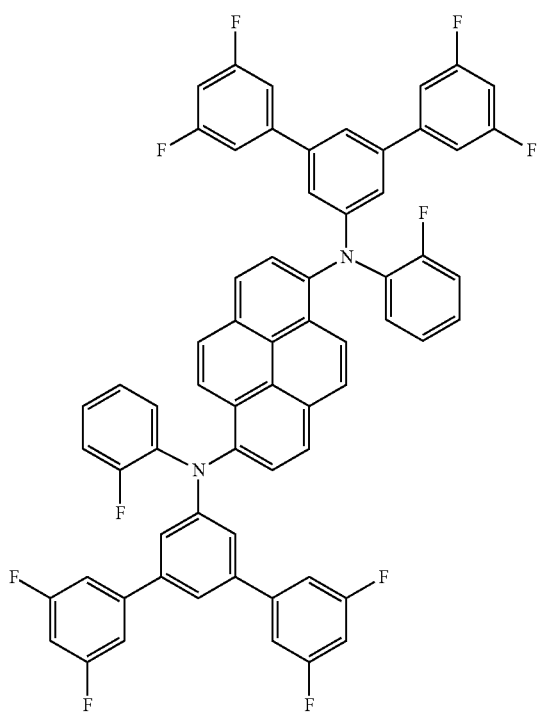

BD 223
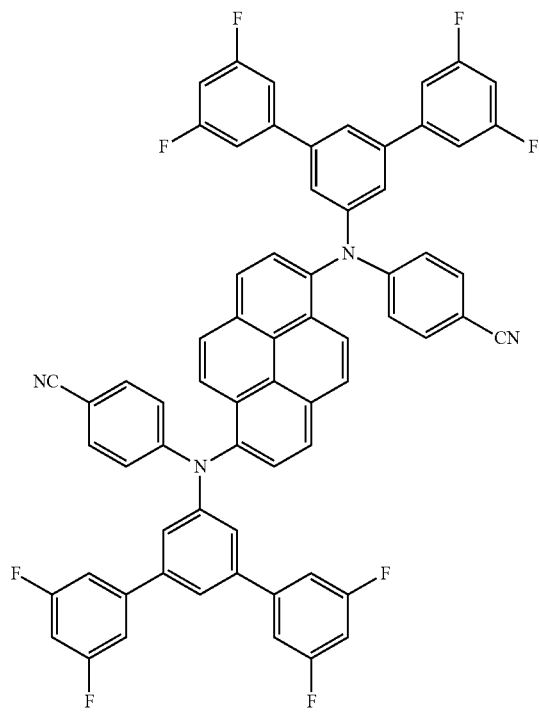
BD 225
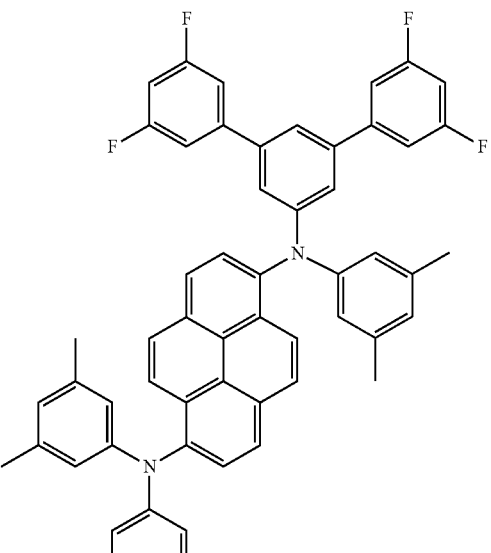
BD 224
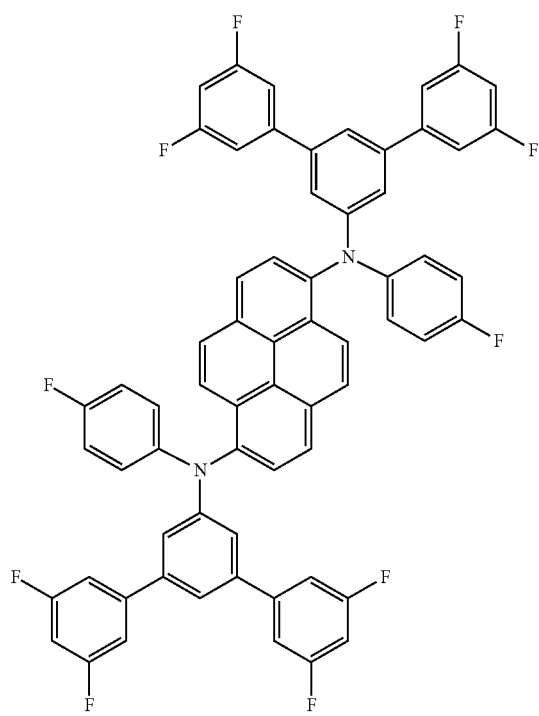
BD 226
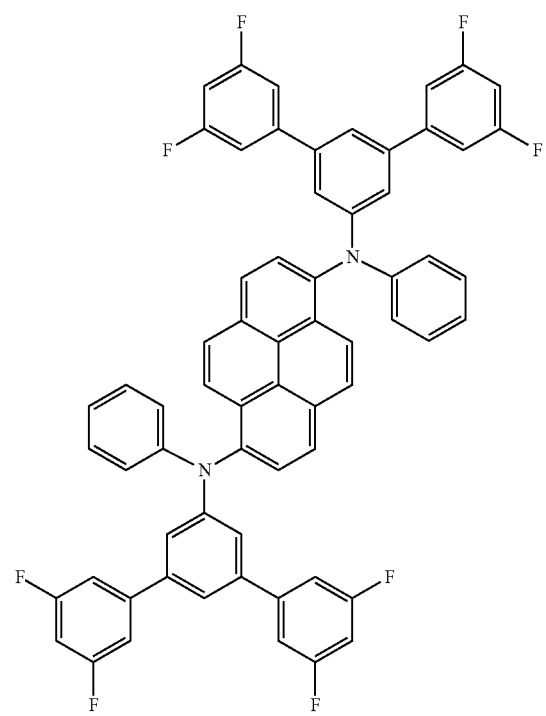

BD 227
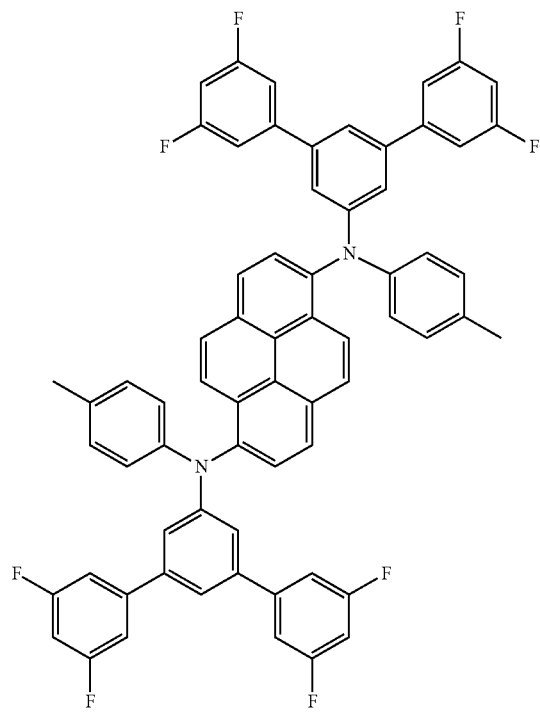
BD 229
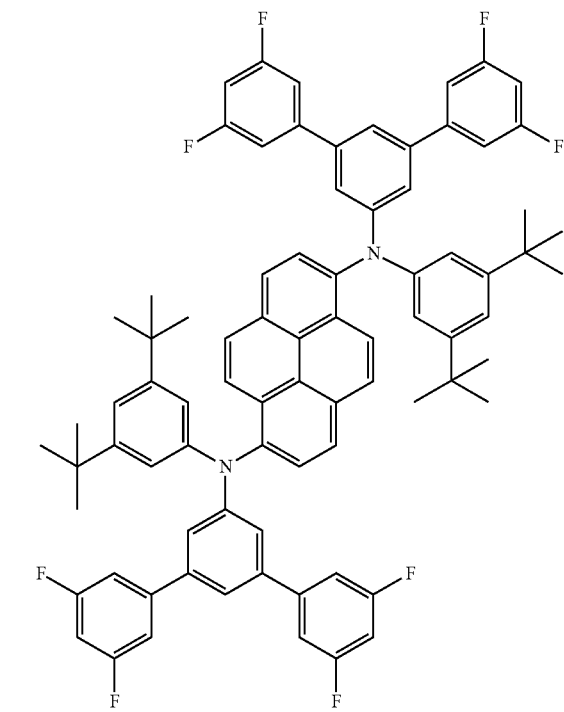
BD 228
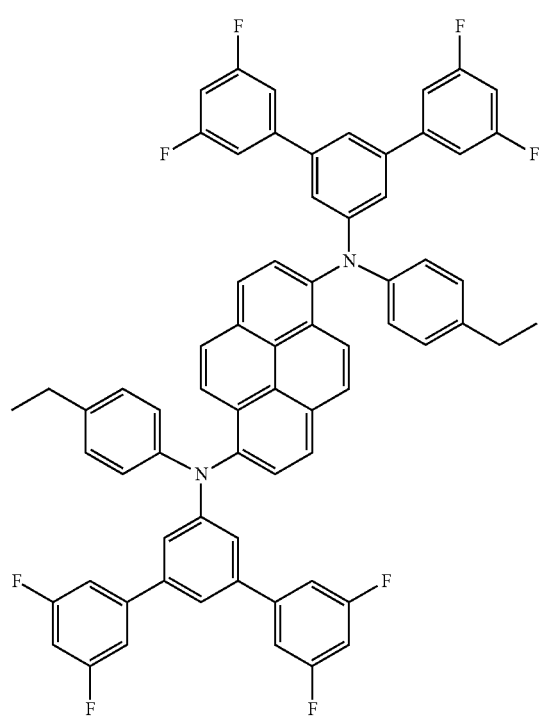
BD 230
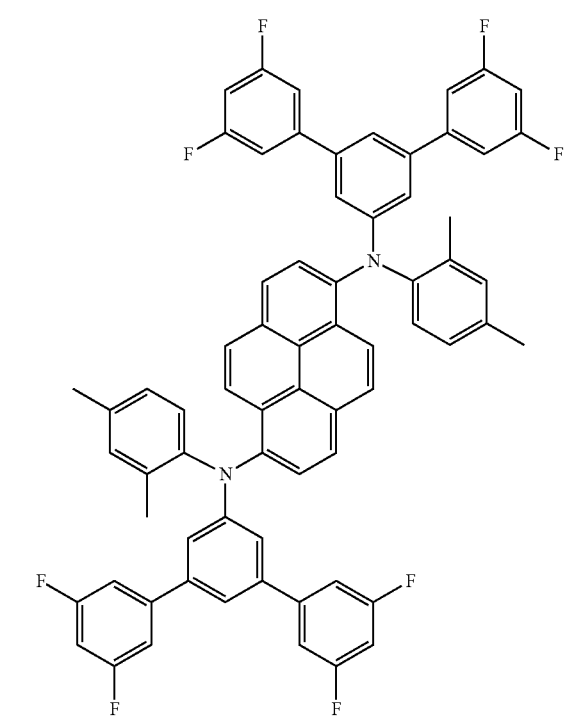

BD 231
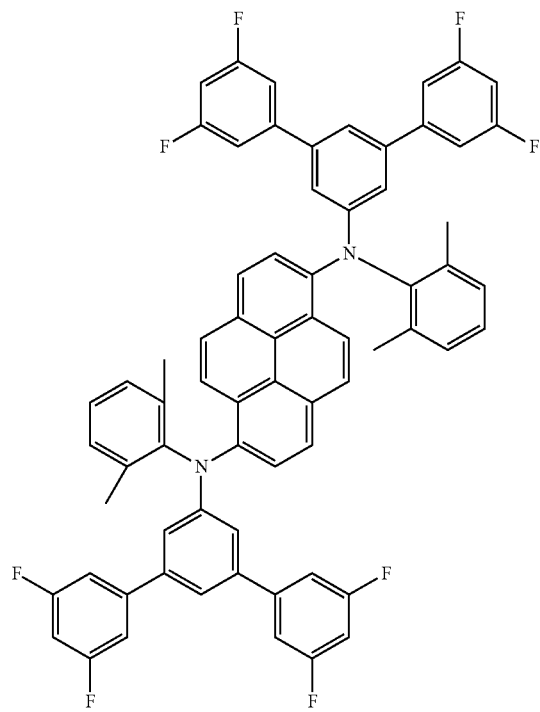
BD 233
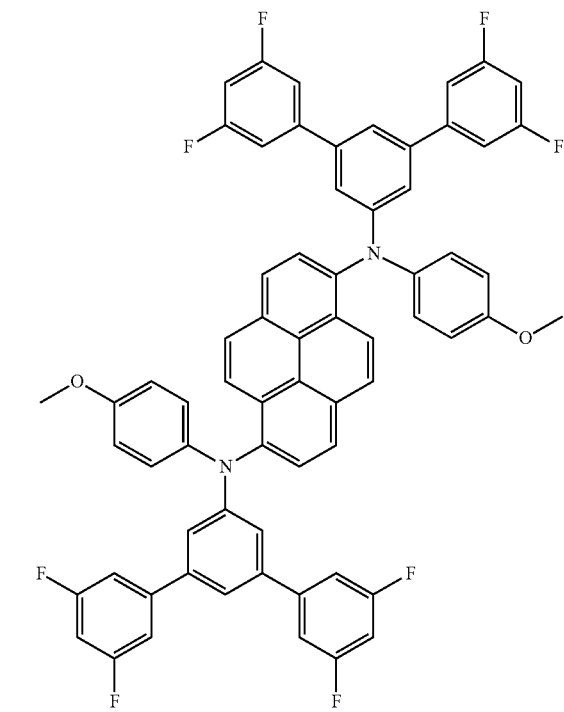
BD 232
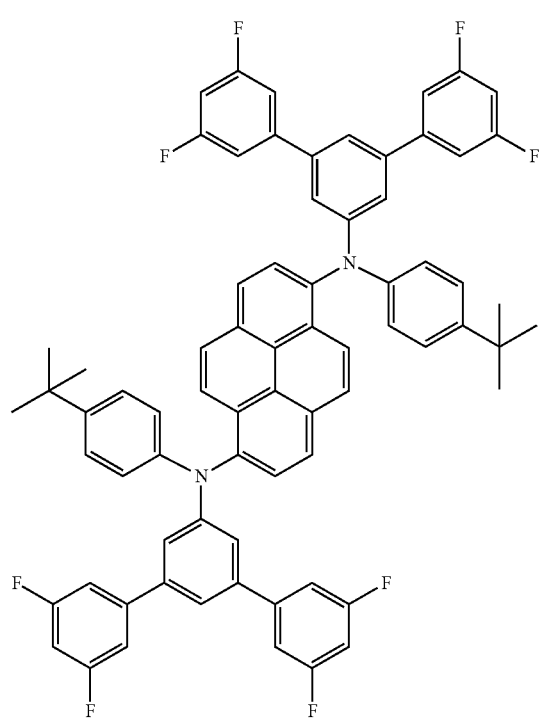
BD 234
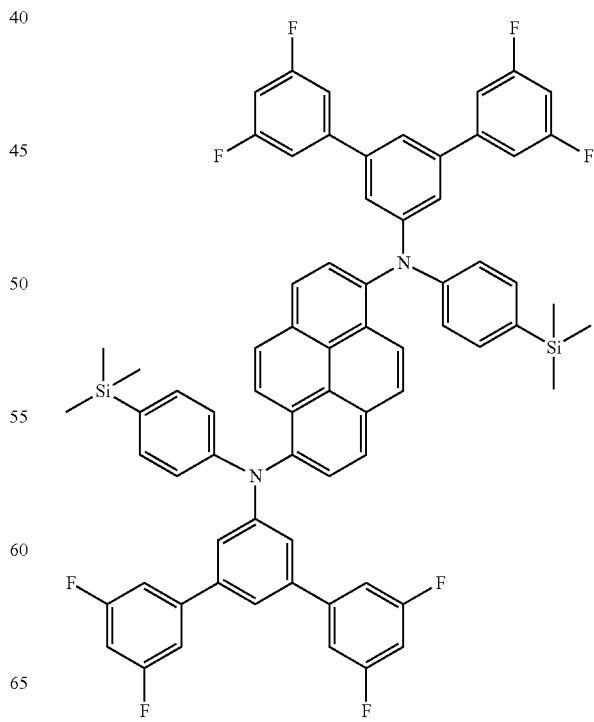

BD 235
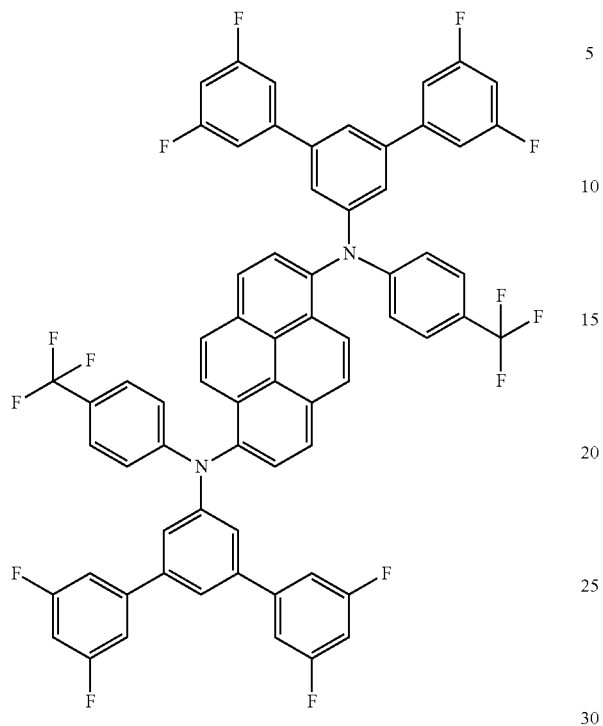
BD 237
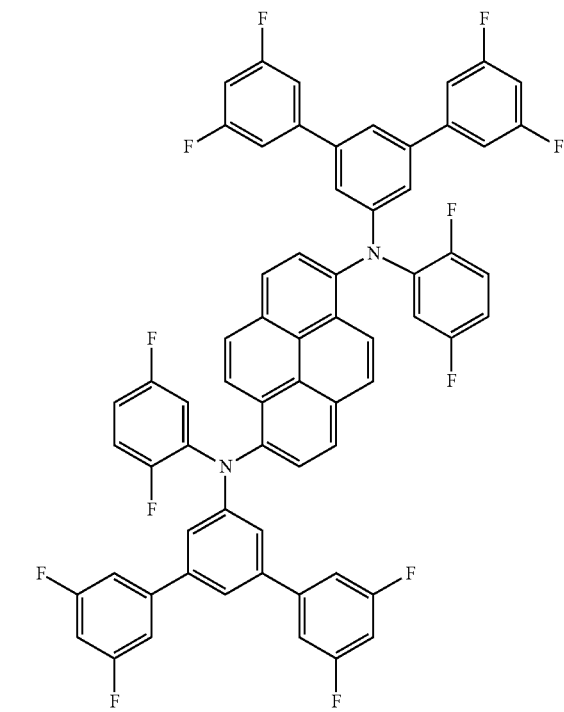
BD 236
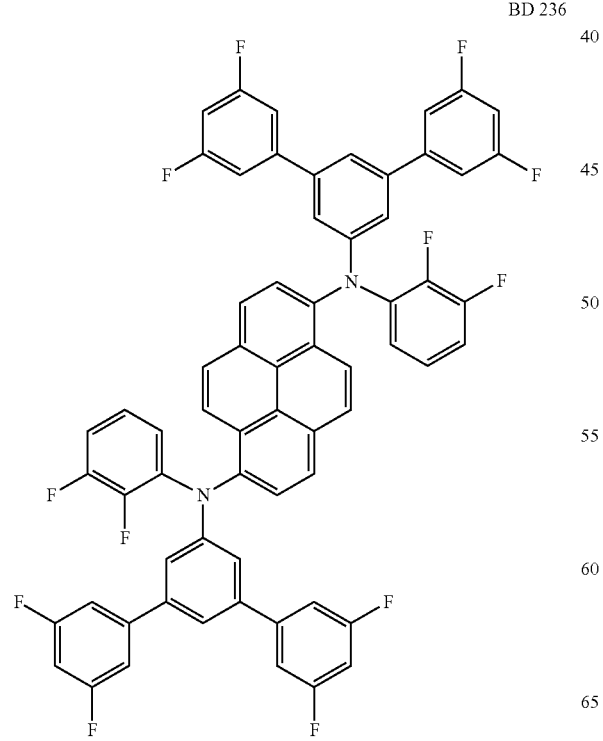
BD 238
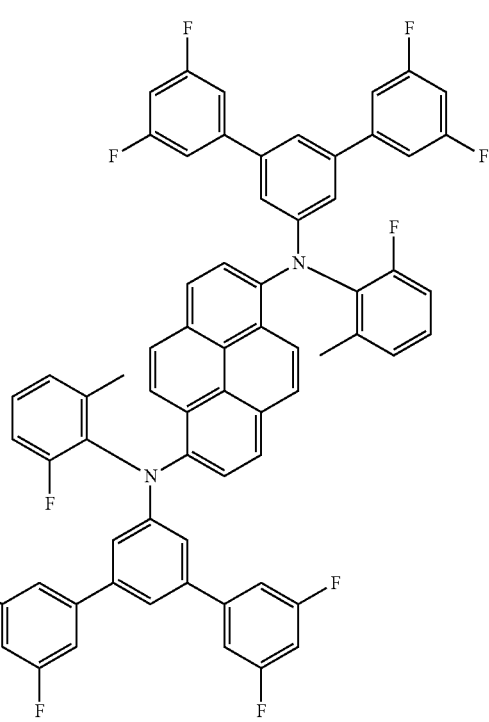

BD 239
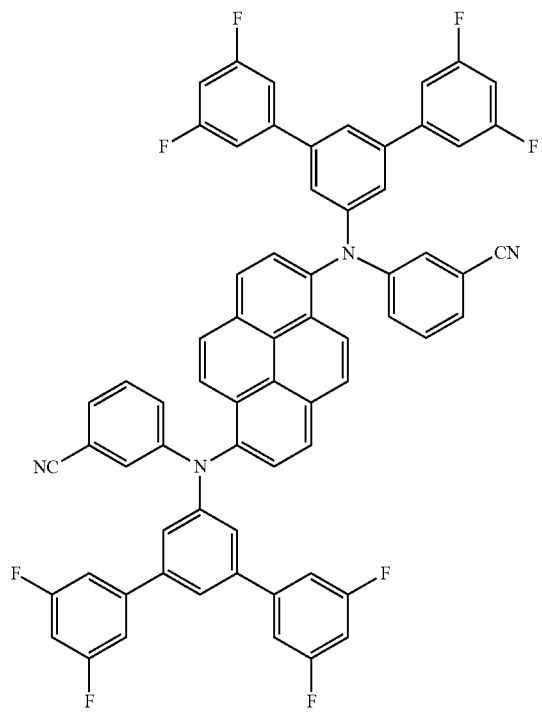
BD 241
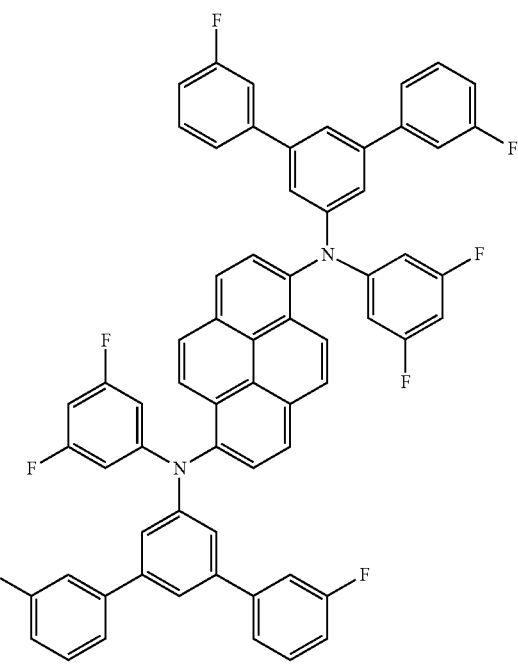
BD 240
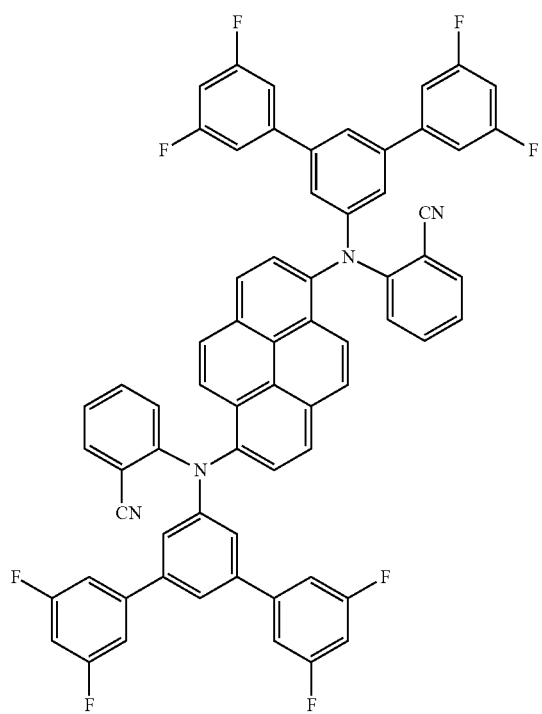
BD 242
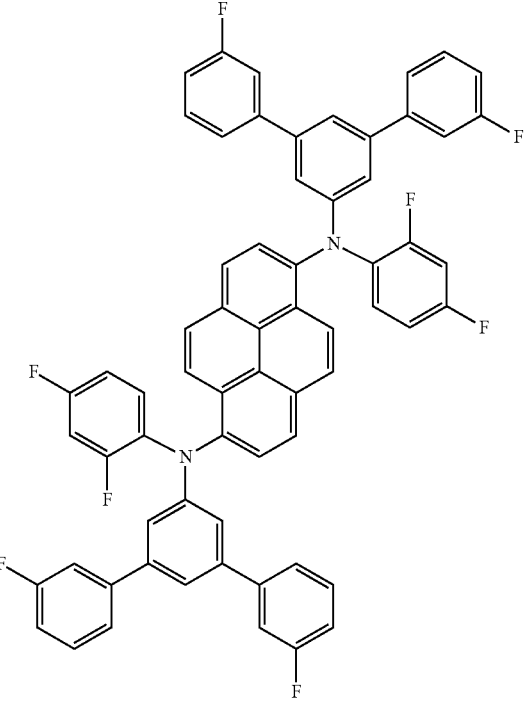

BD 243
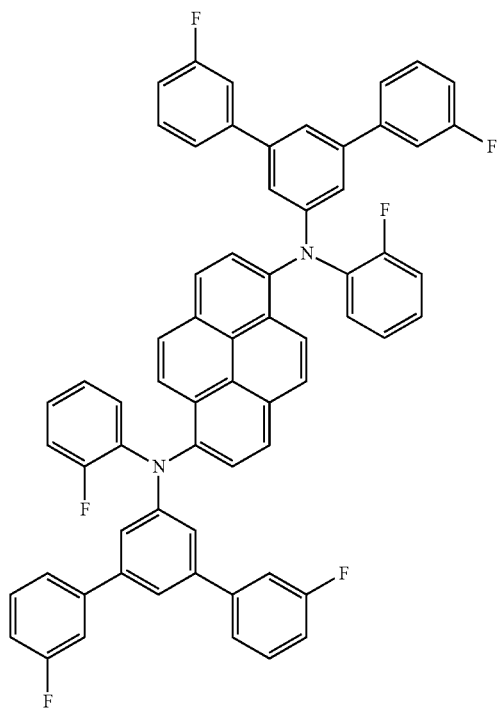
BD 245
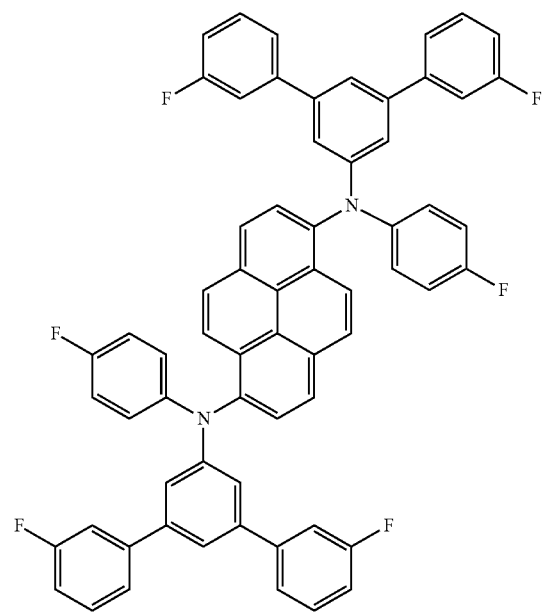
BD 244
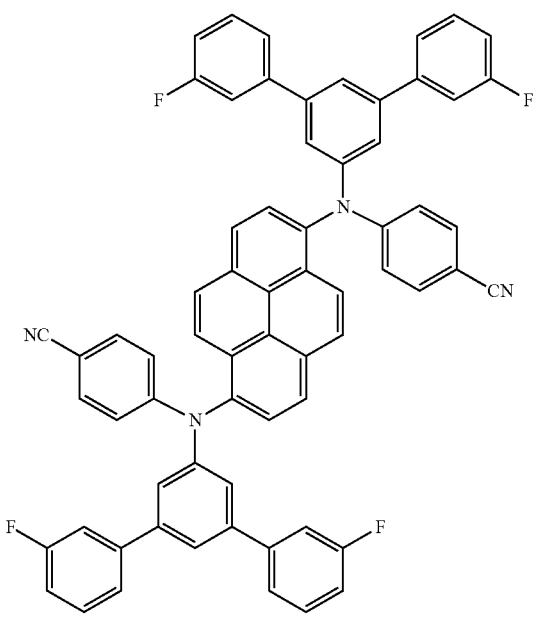
BD 246
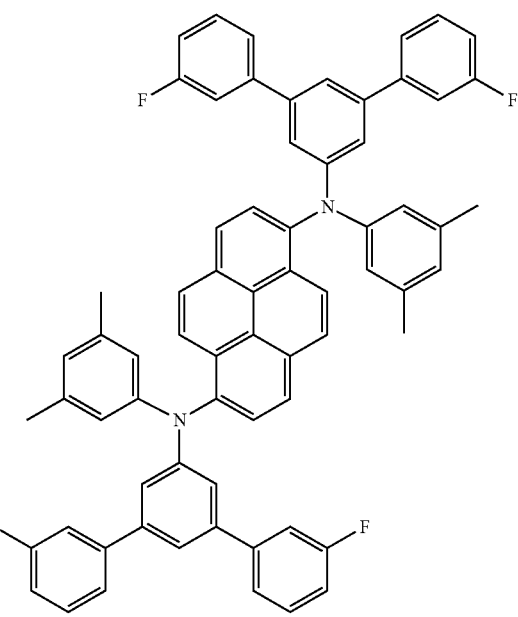

BD 247
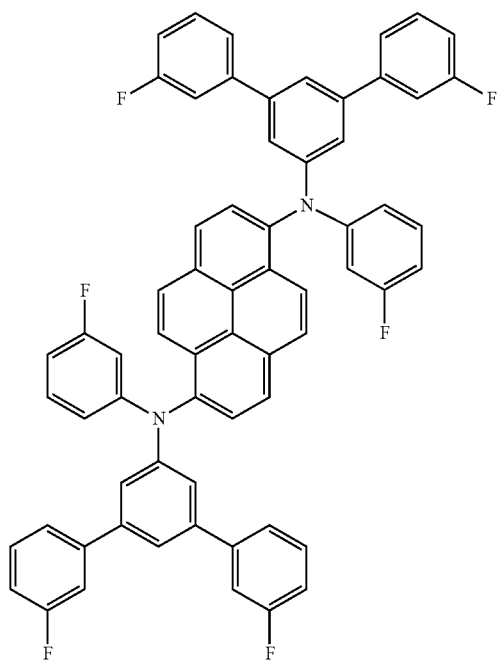
BD 248
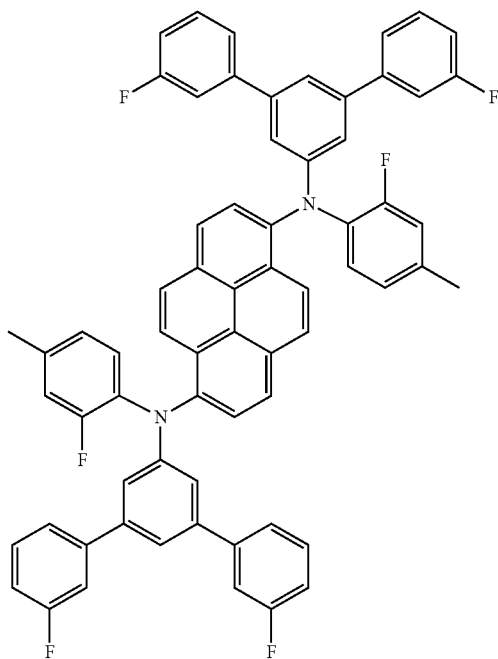
BD 249
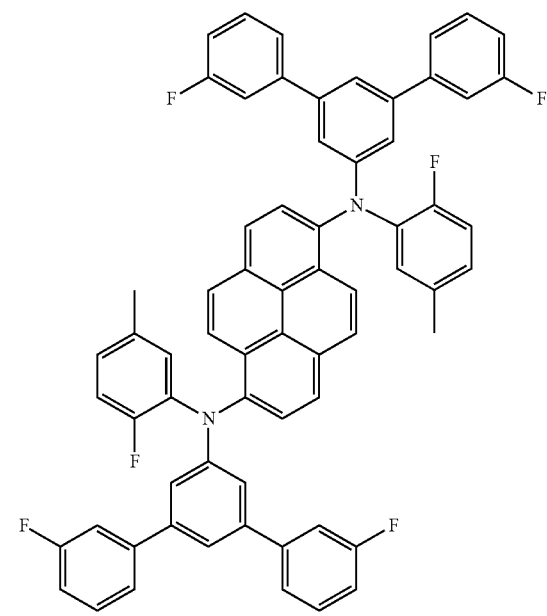
BD 250
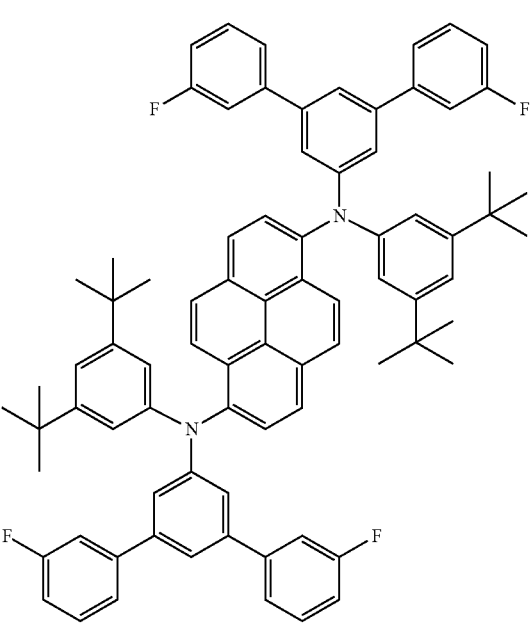

-continued
BD 251
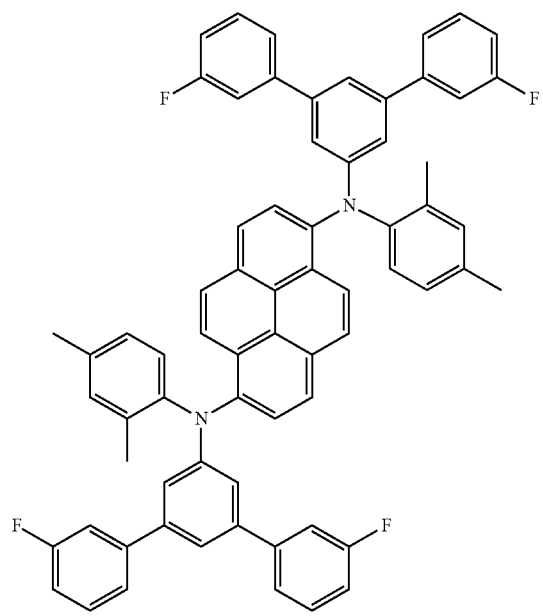
BD 252
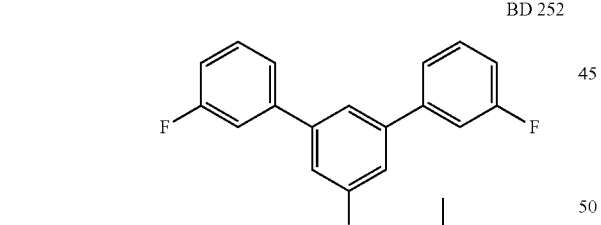
BD 253
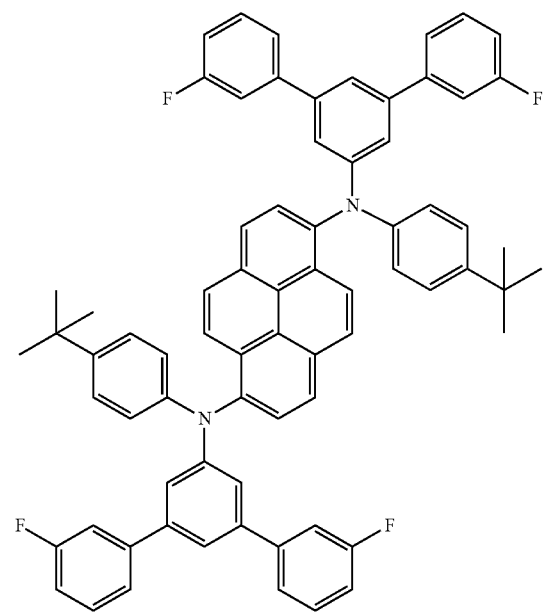
BD 254
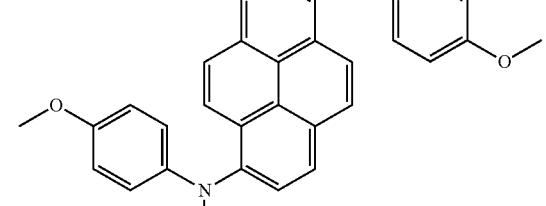

BD 255
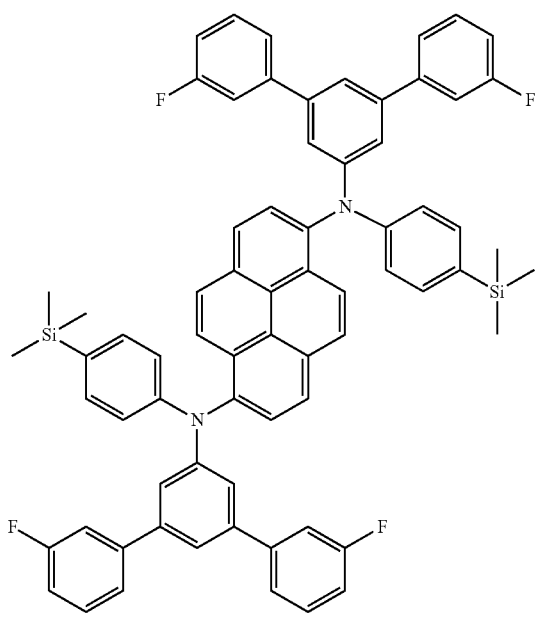
BD 257
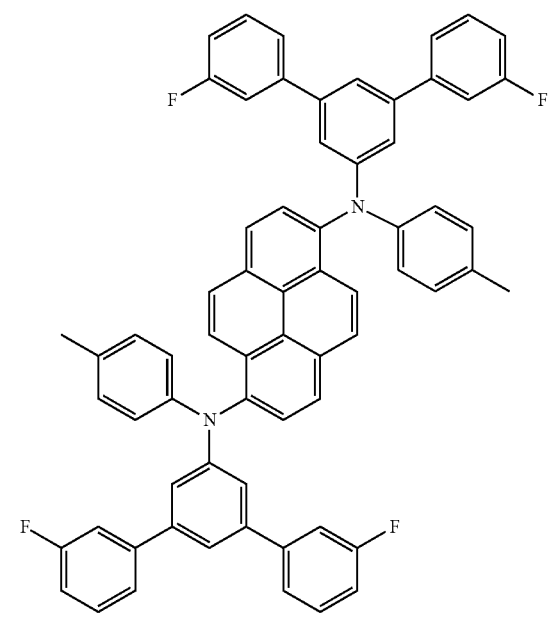
BD 256
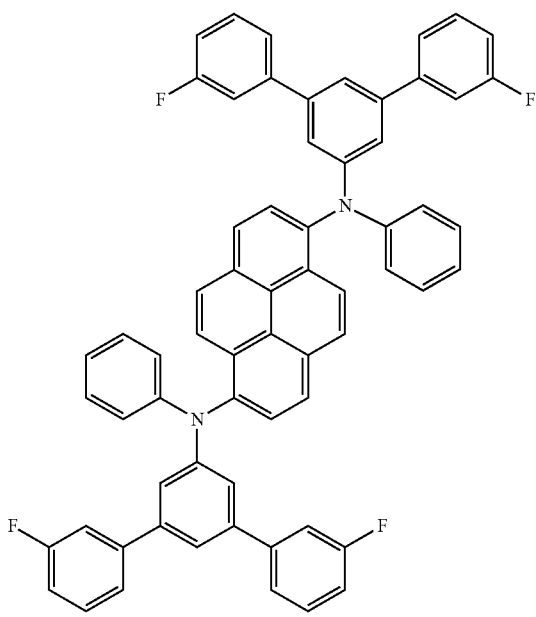
BD 258
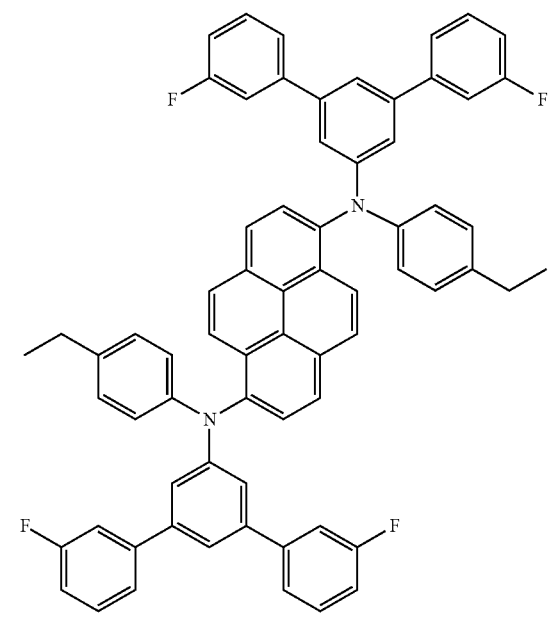

301
-continued
BD 259
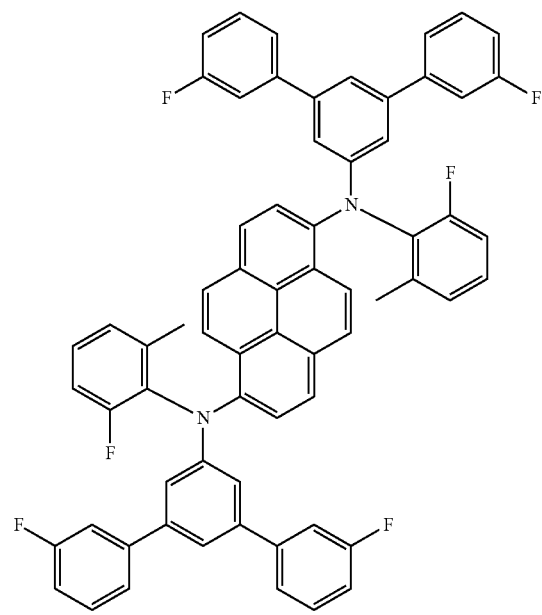
BD 260
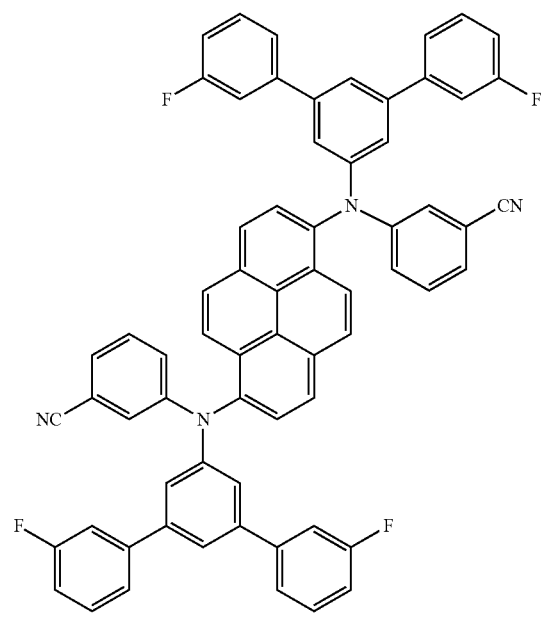
302
-continued
BD 261
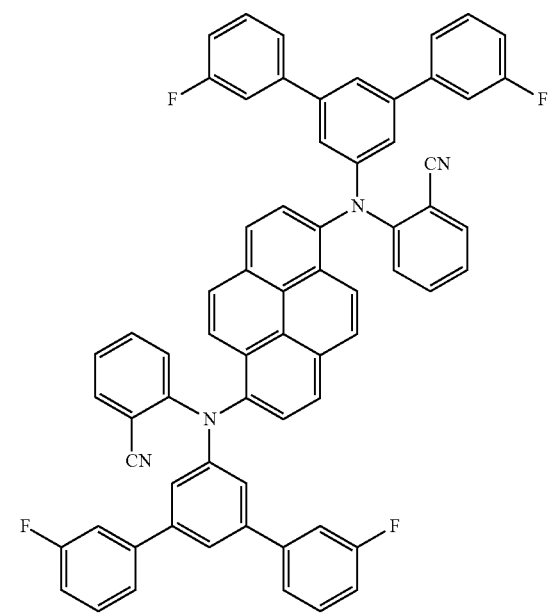
BD 262
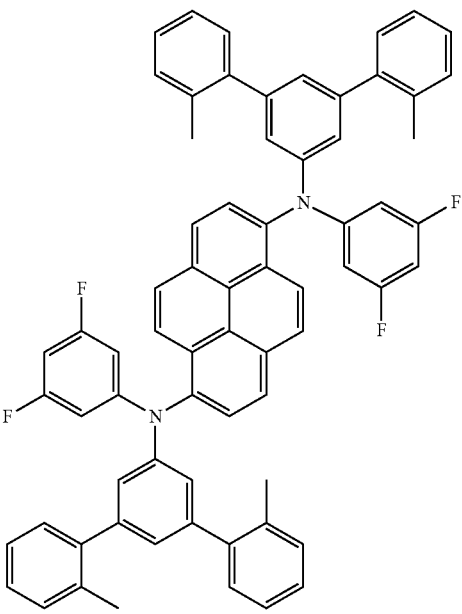

BD 263
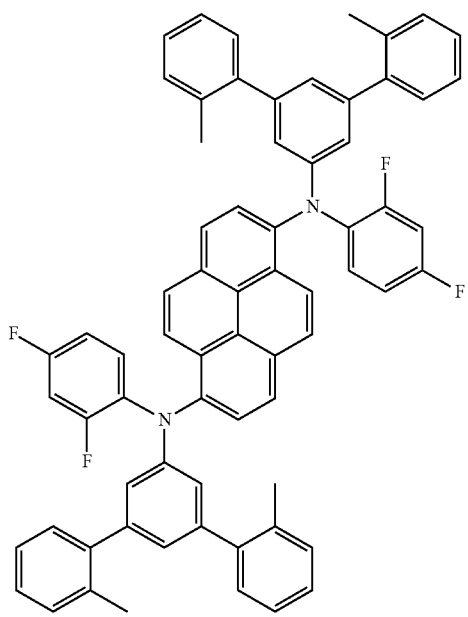
BD 264
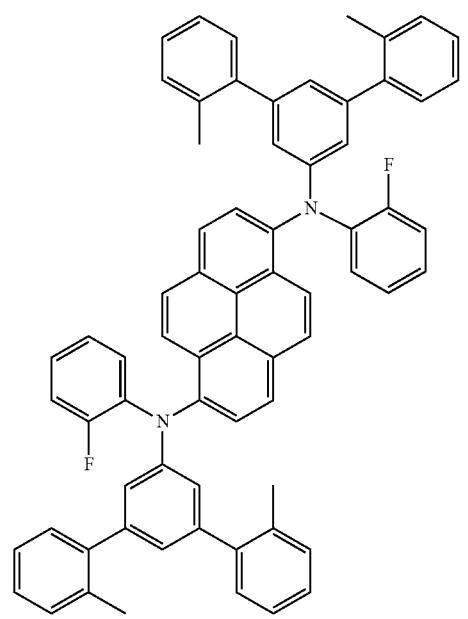
BD 265
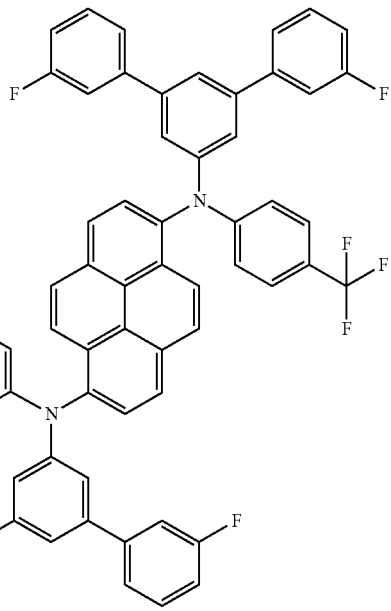
BD 266
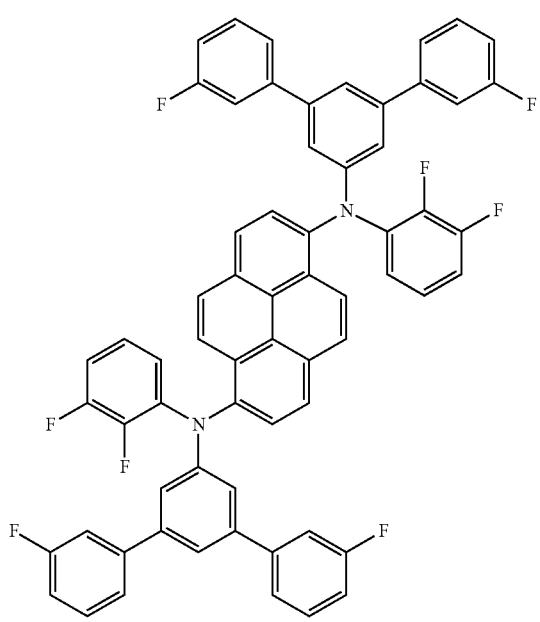

305
-continued
BD 267
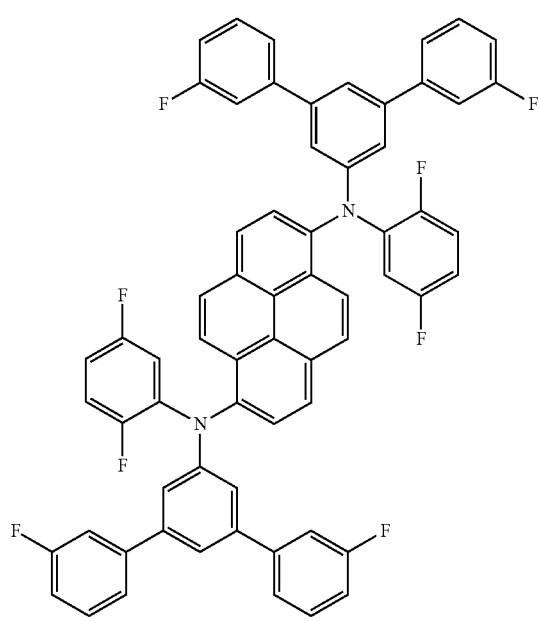
BD 267
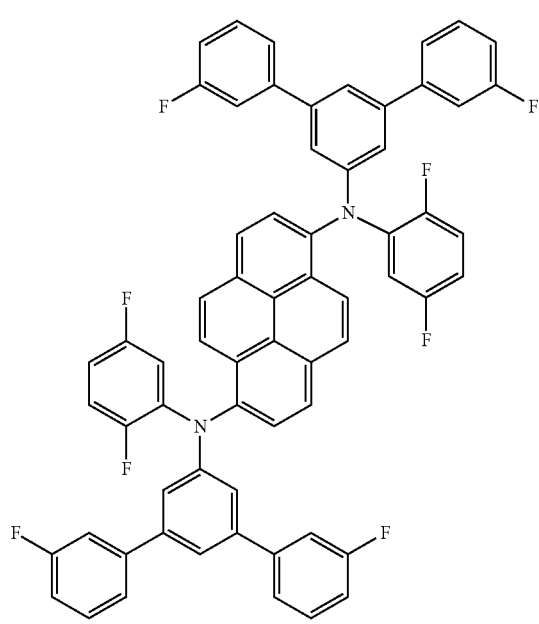
306
-continued
BD 268
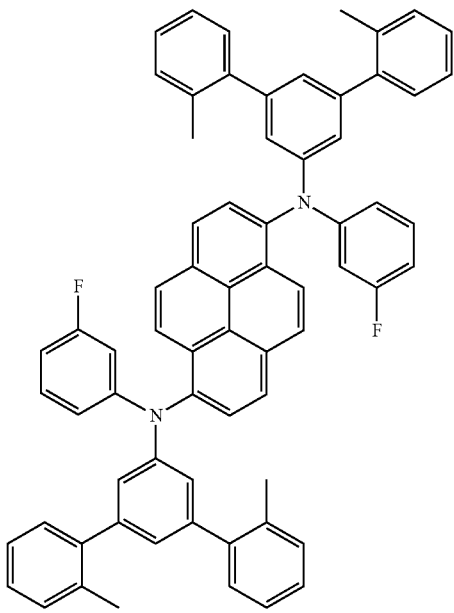
BD 269
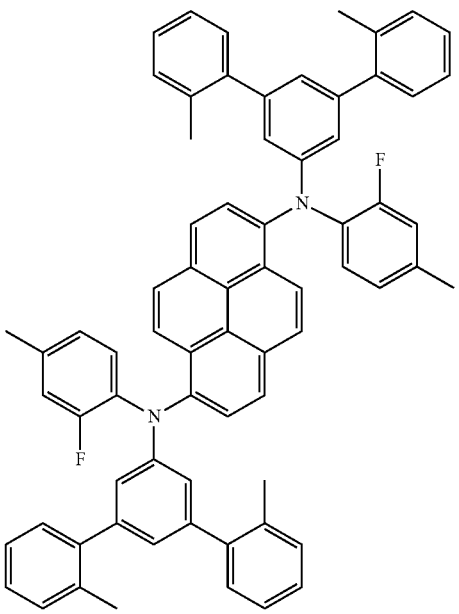

BD 270
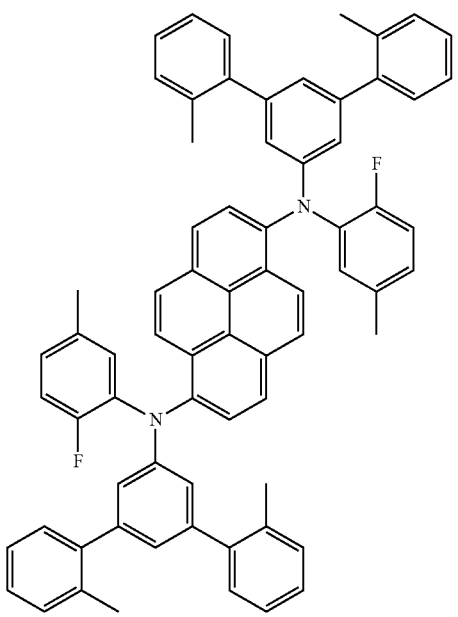
BD 275
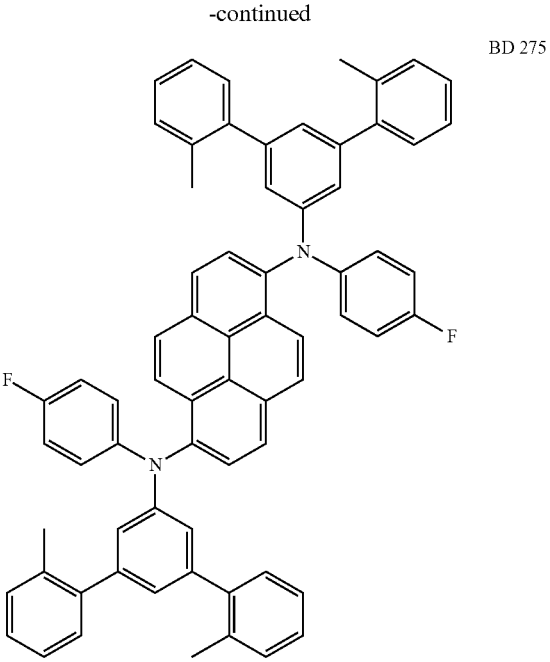
BD 274
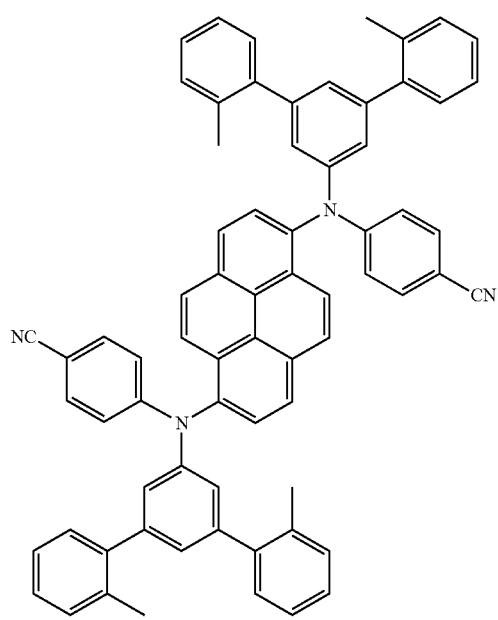
BD 282
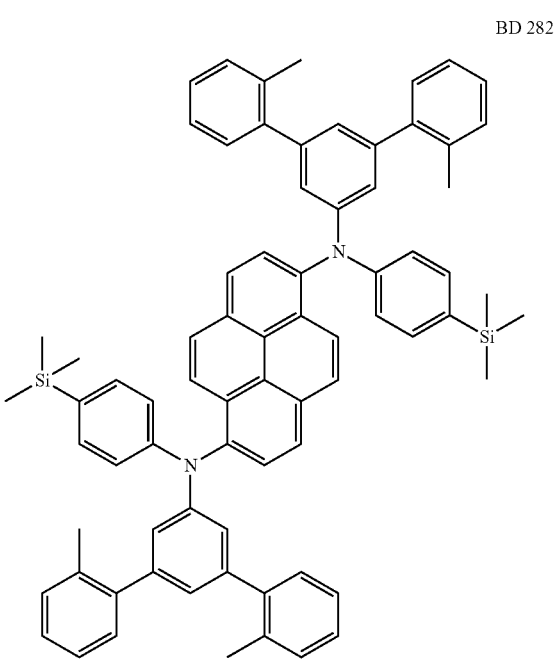

BD 283
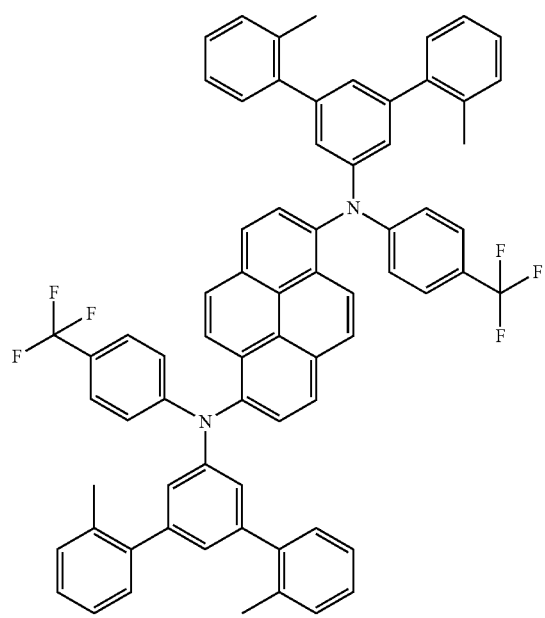
BD 285
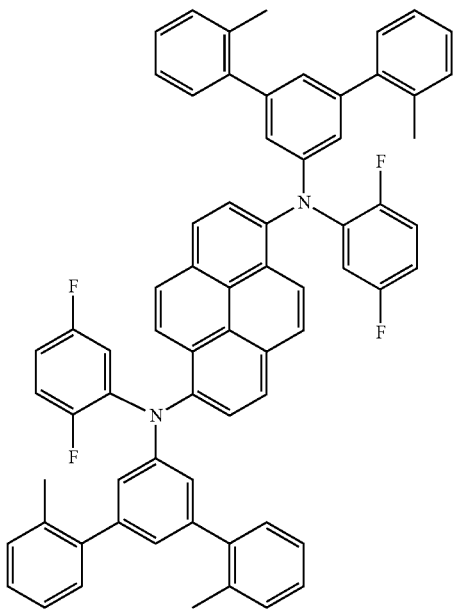
BD 284
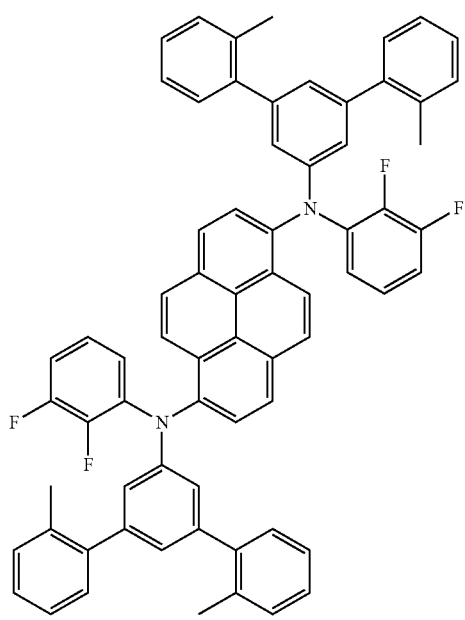
BD 286
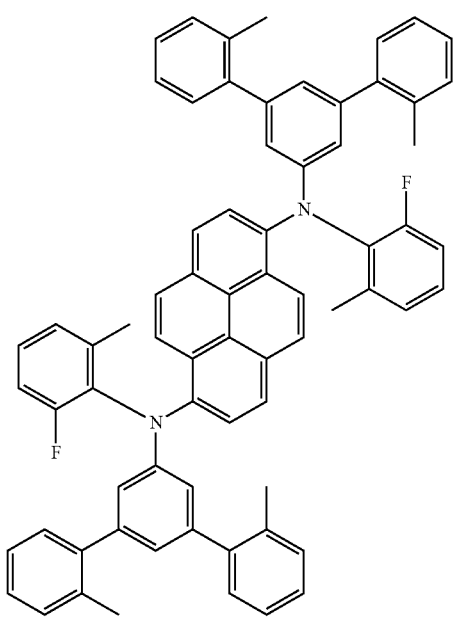

BD 287
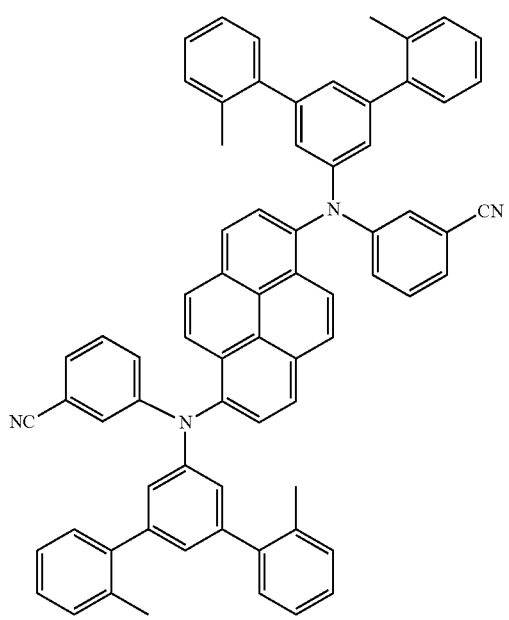
BD 289
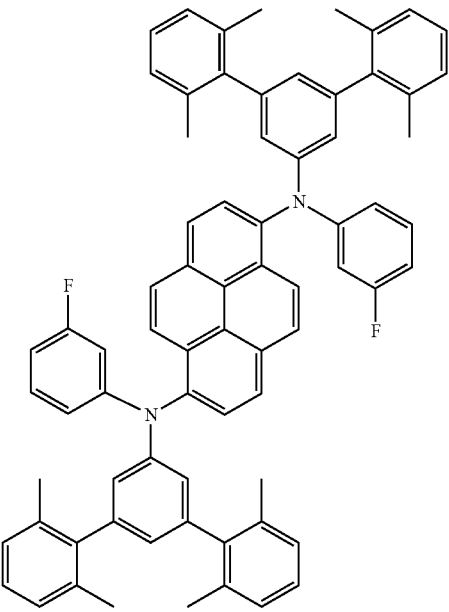
BD 288
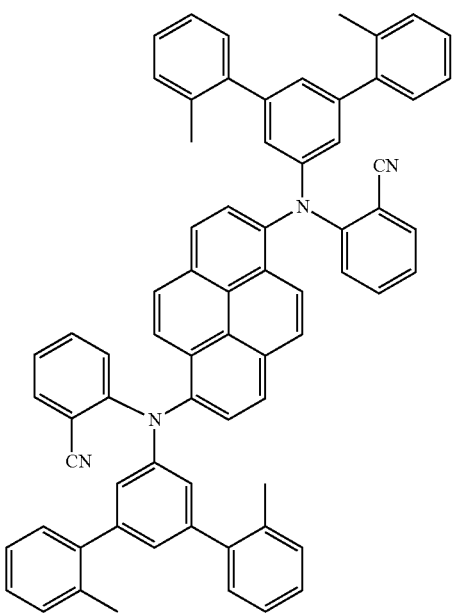
BD 290
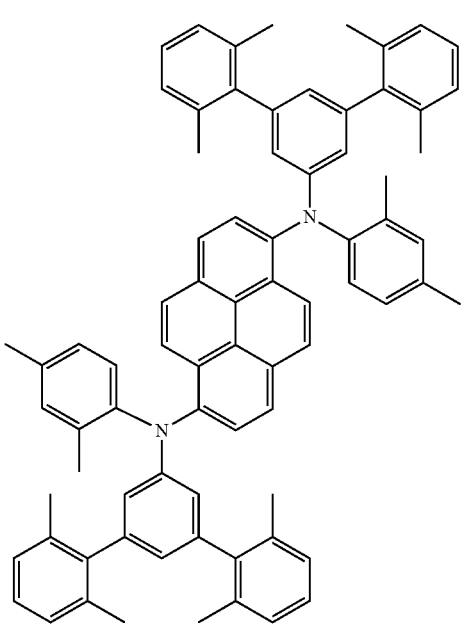

BD 291
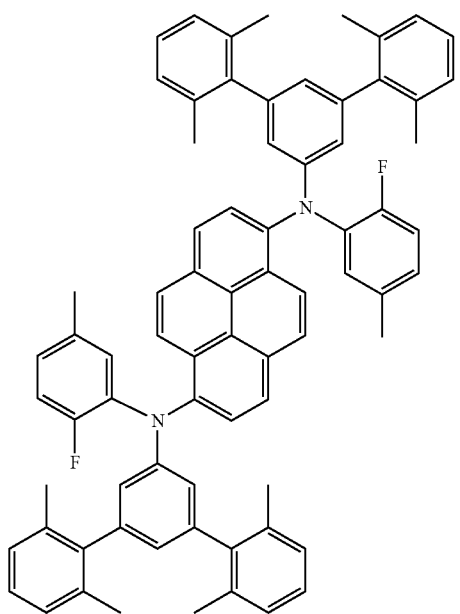
BD 293
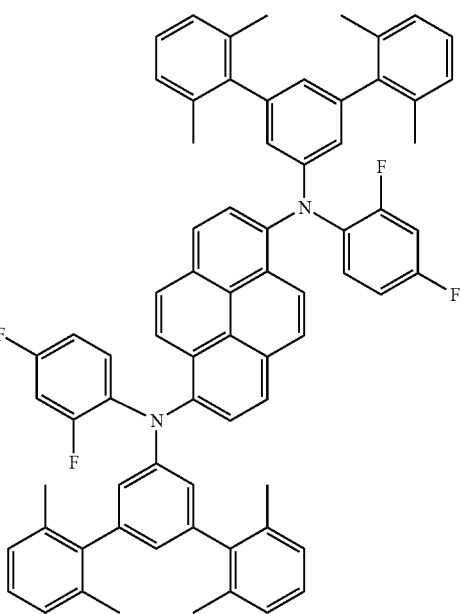
BD 292
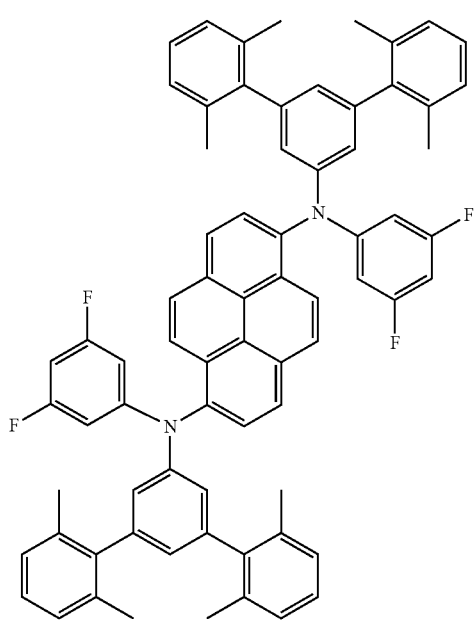
BD 294
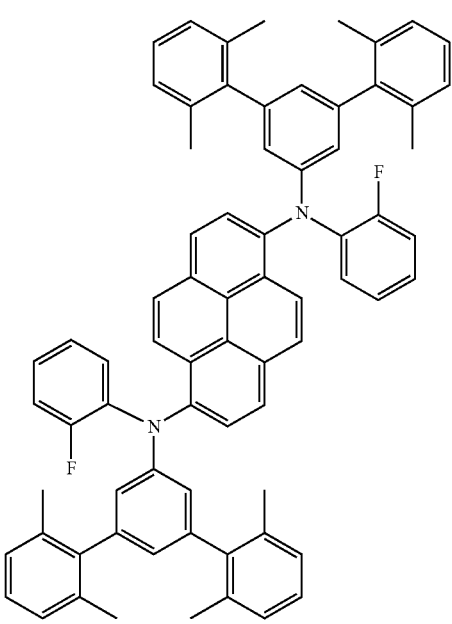

315
-continued
BD 295
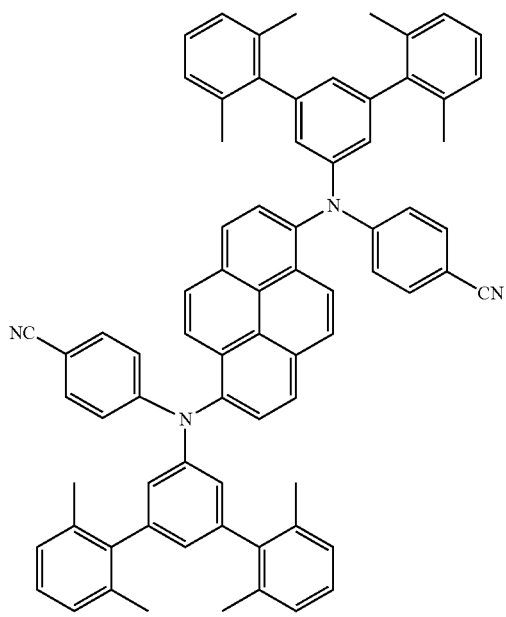
BD 296
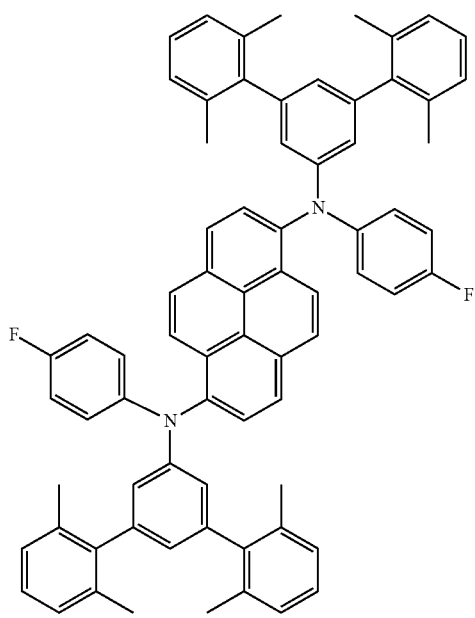
316
-continued
BD 306
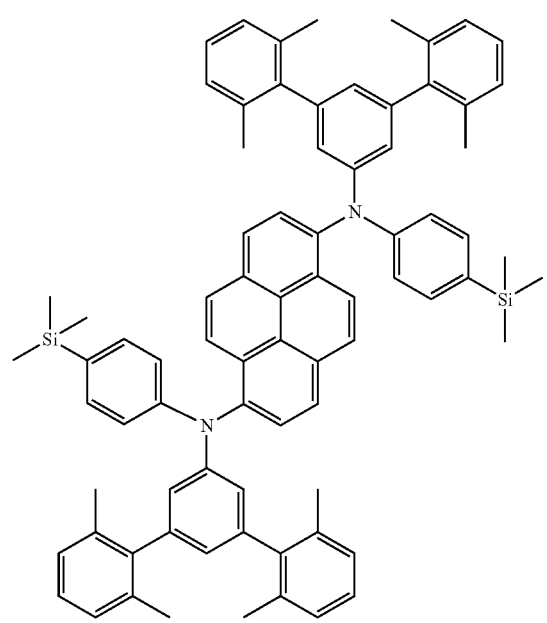
BD 307
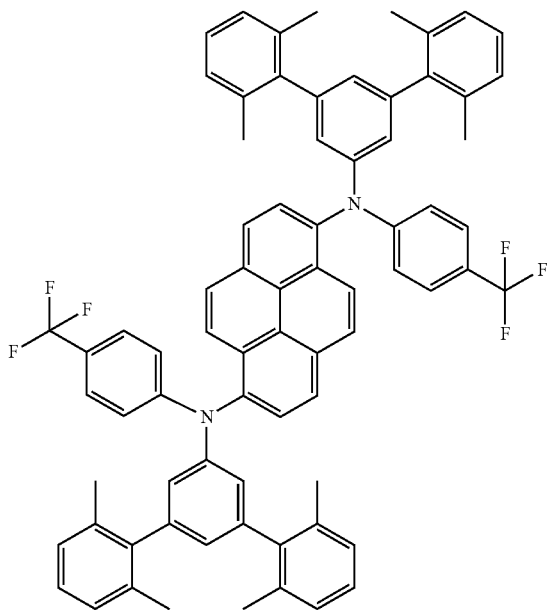

BD 308
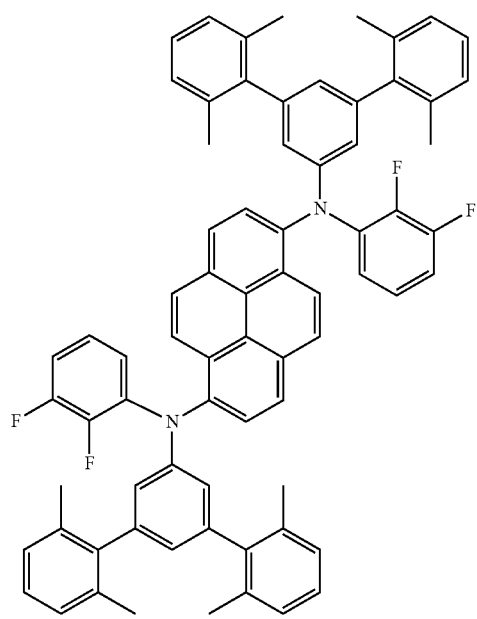
BD 310
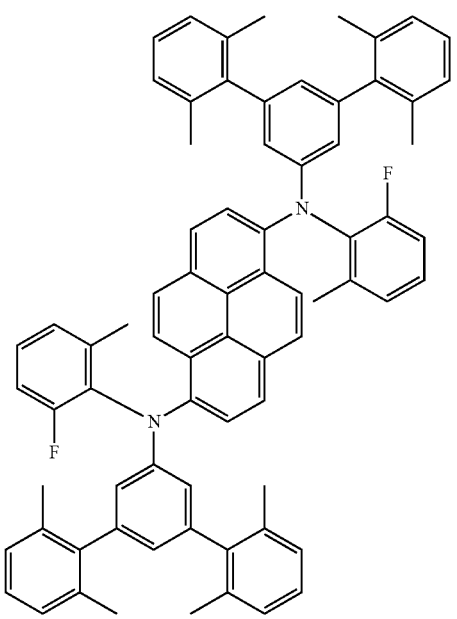
BD 309
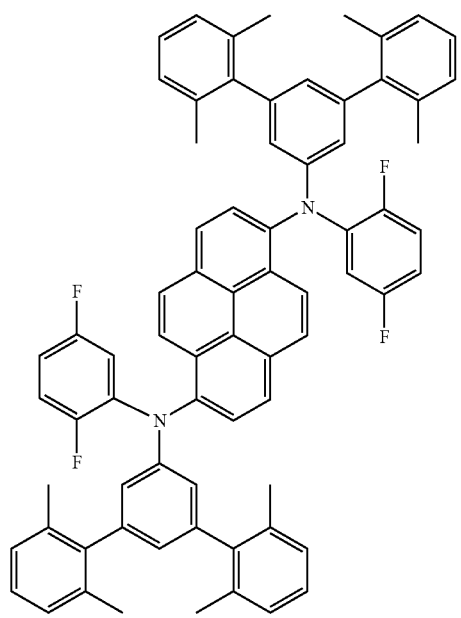
BD 311
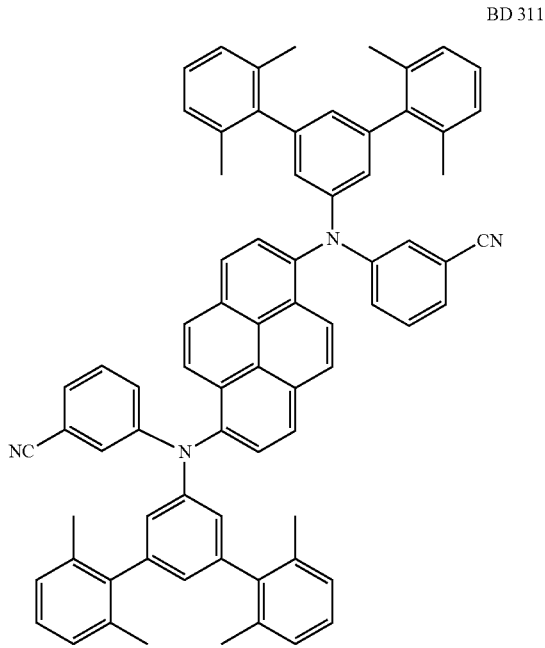

BD 312
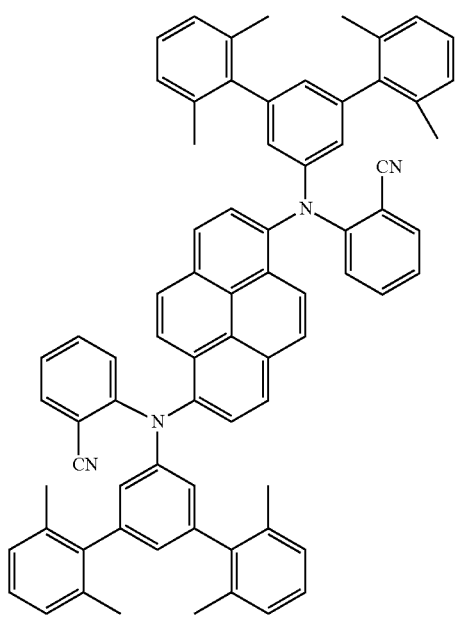
BD 314
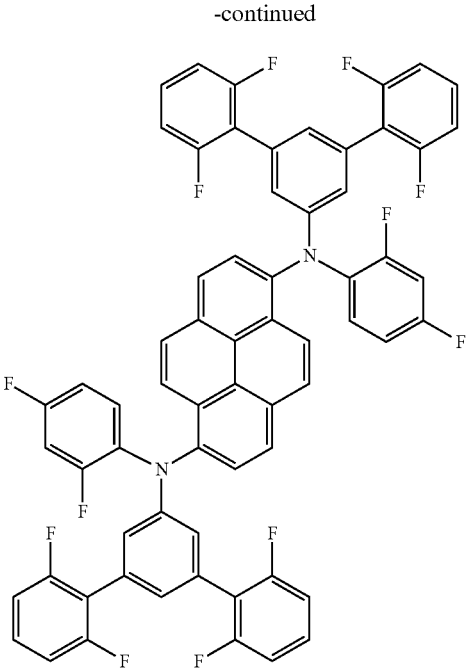
BD 313
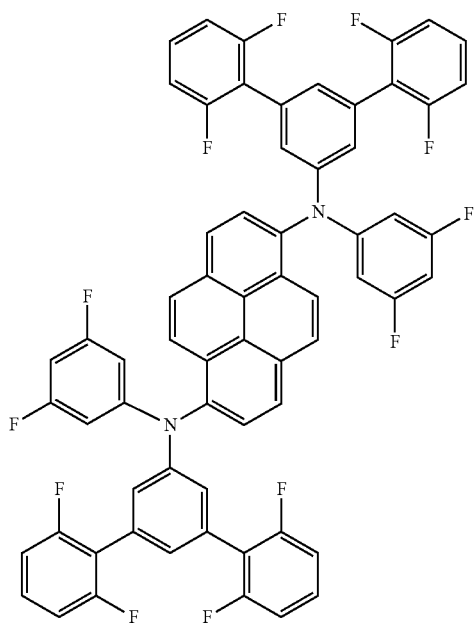
BD 315
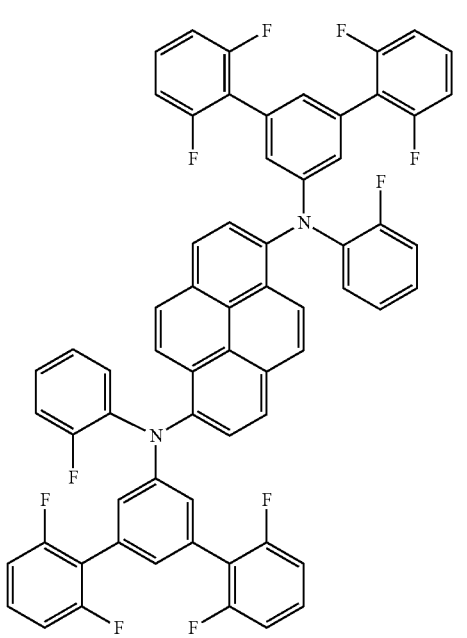

-continued
BD 316
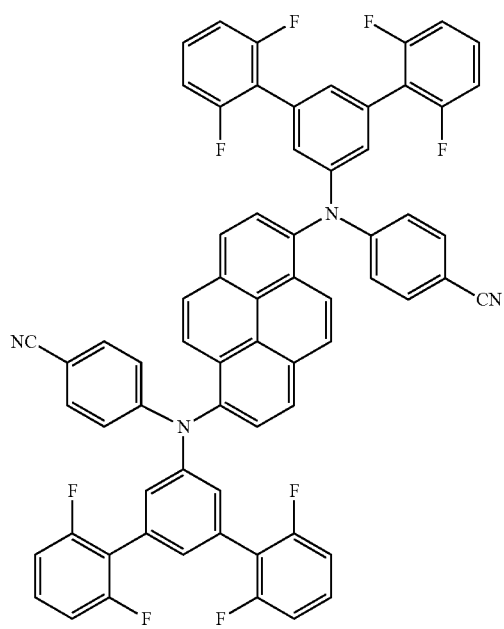
BD 317
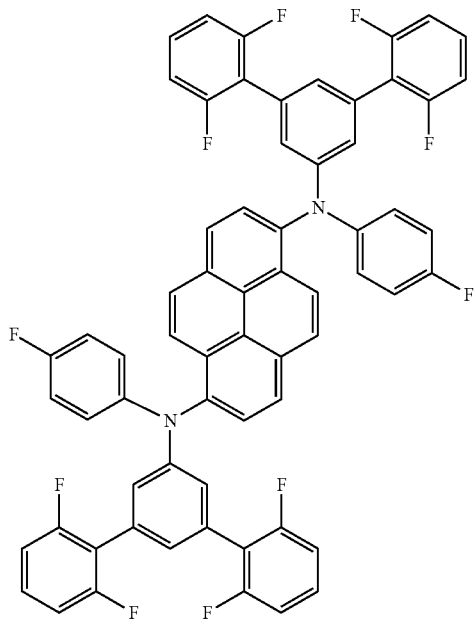
-continued
BD 318
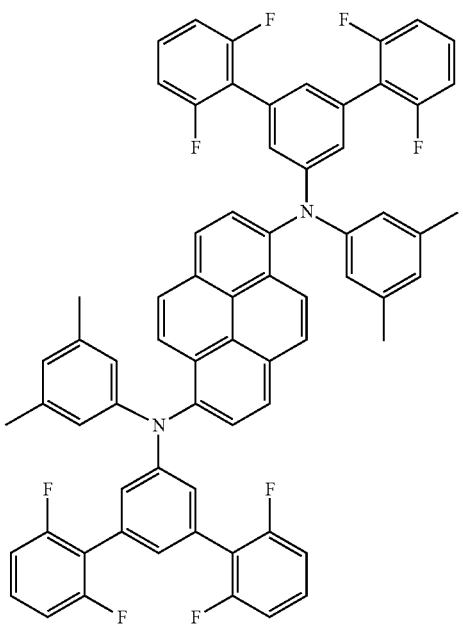
BD 319
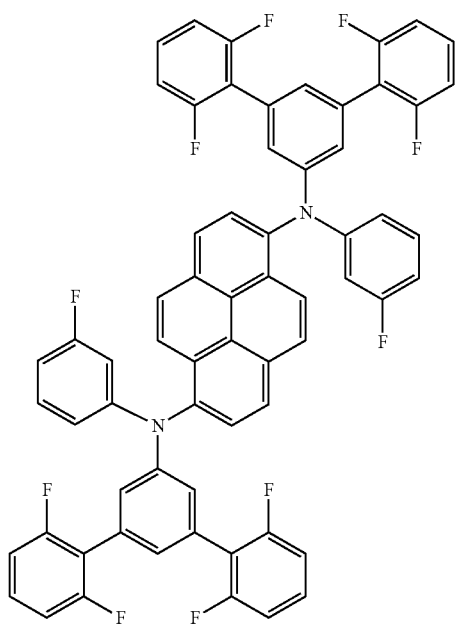

323
-continued
324
-continued
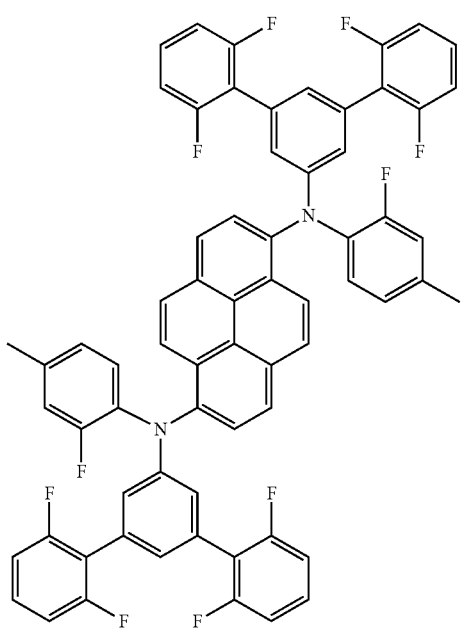
BD 320
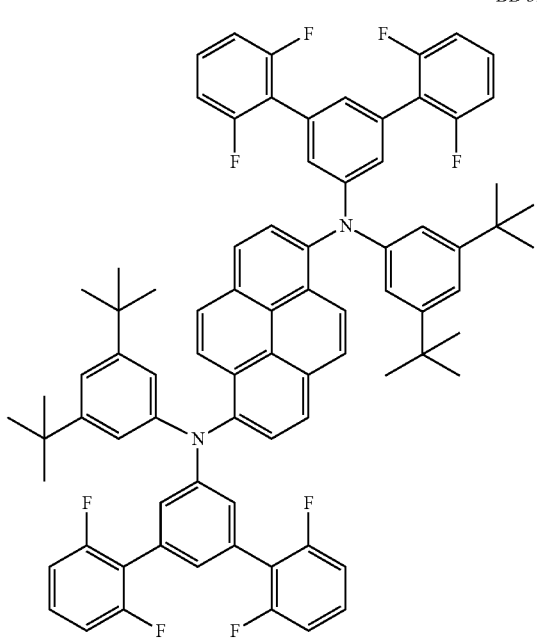
BD 322
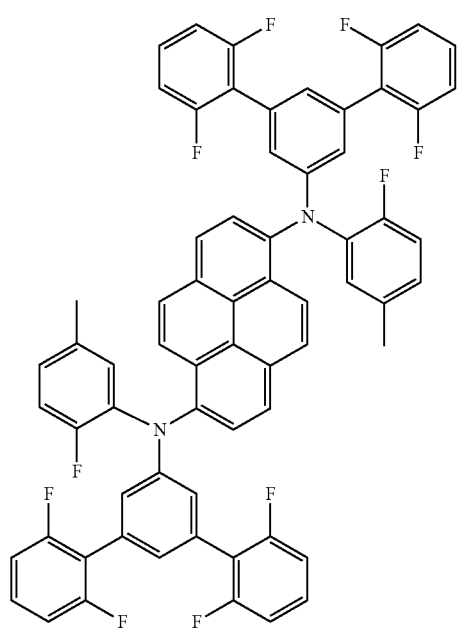
BD 321
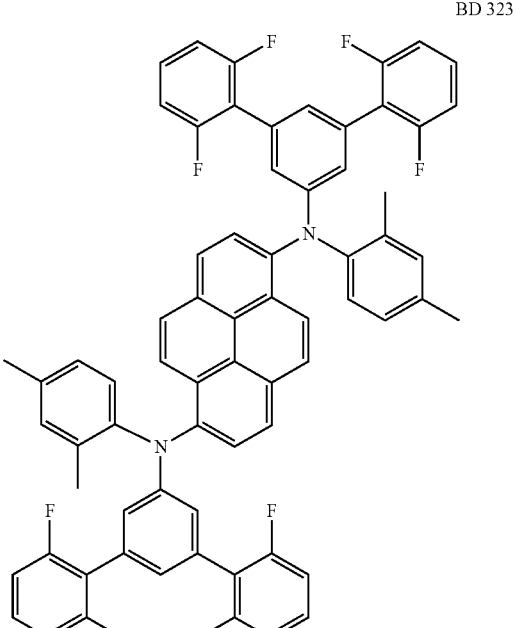
BD 323

325
-continued
BD 324
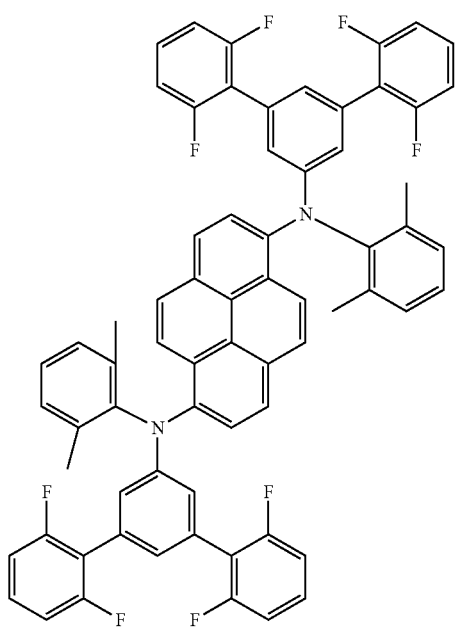
BD 325
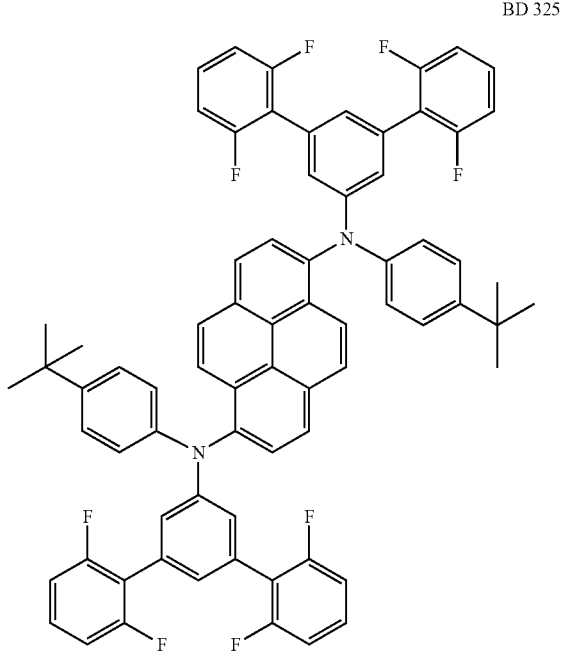
326
-continued
BD 326
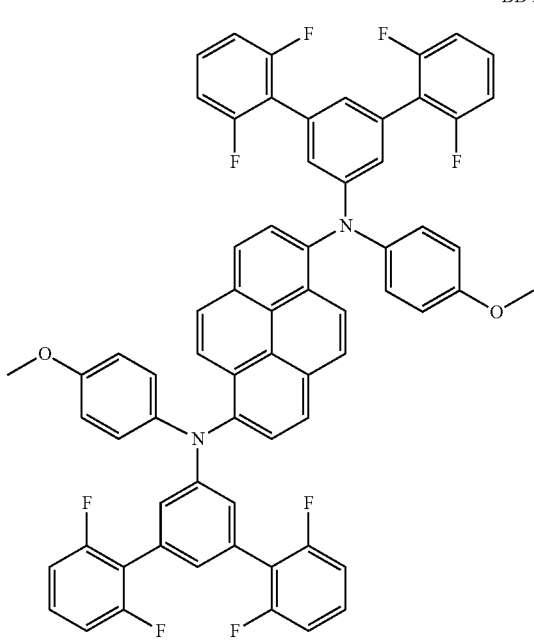
BD 327
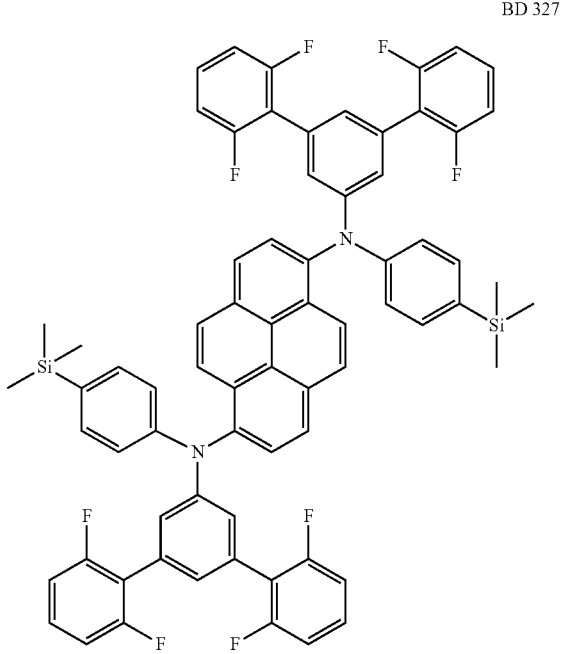

| BD 328 | BD 330 |
|---|---|
| 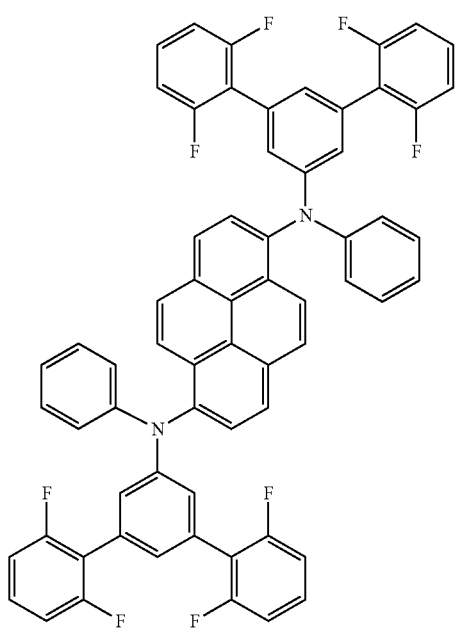 | 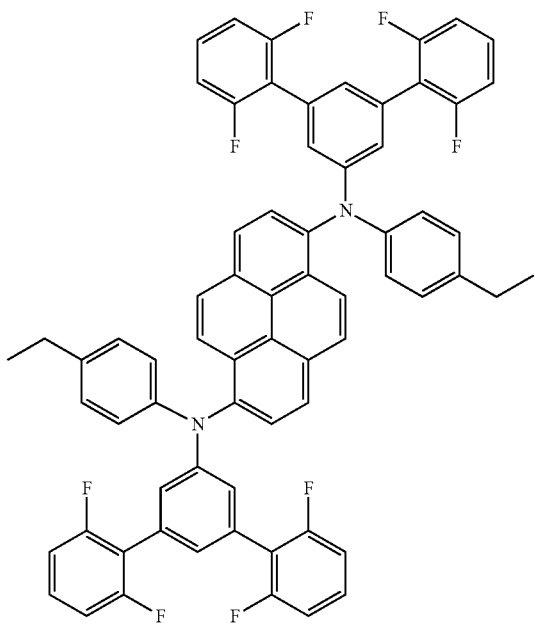 |
| BD 329 | BD 331 |
|---|---|
| 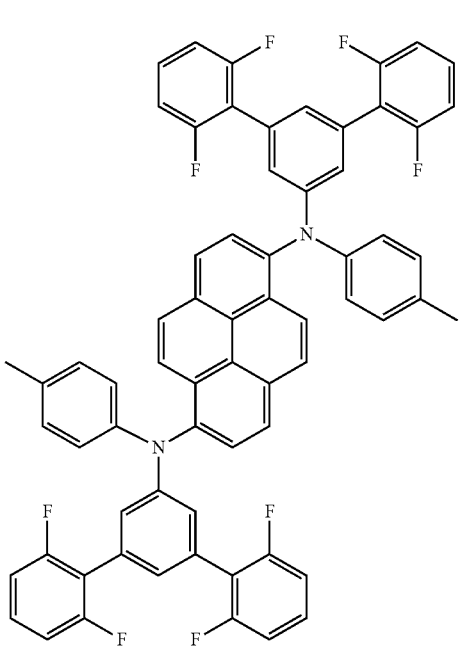 | 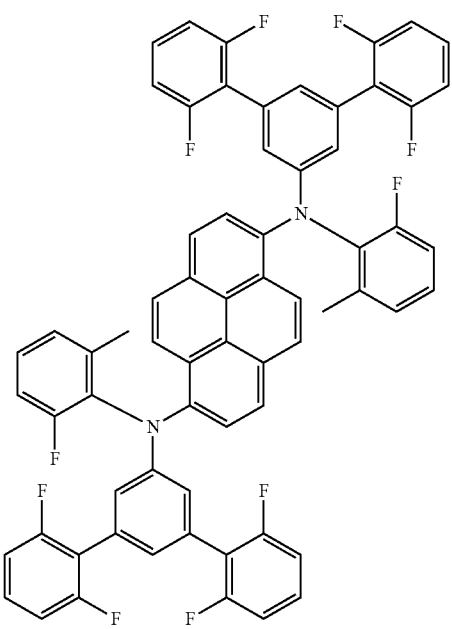 |

329
-continued
BD 332
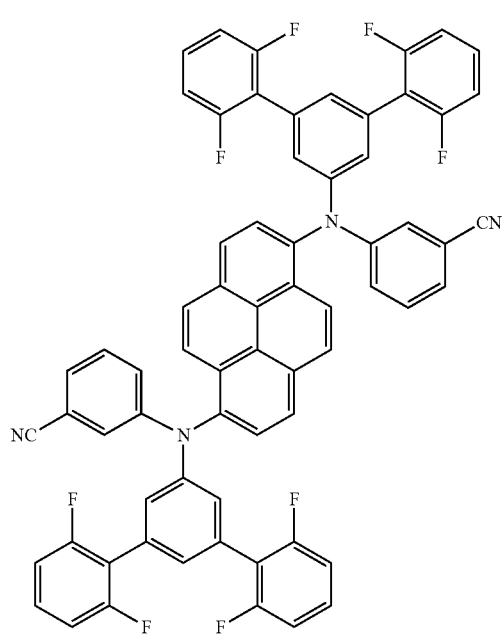
BD 333
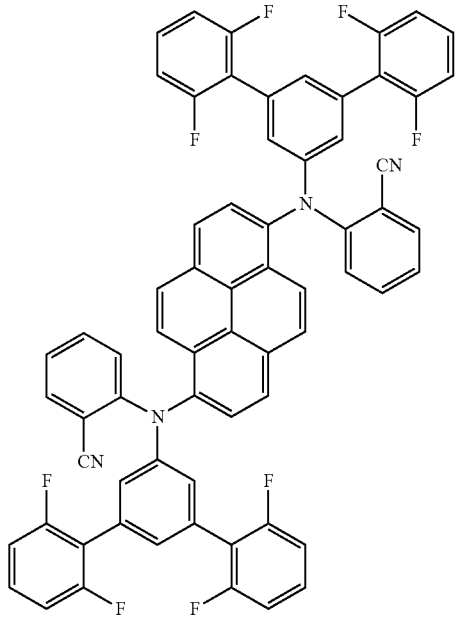
330
-continued
BD 334
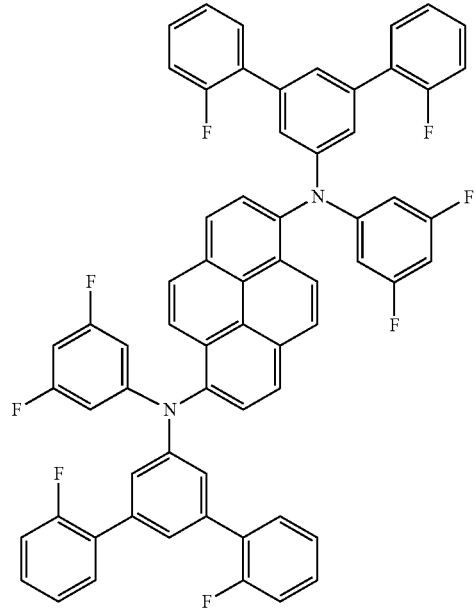
BD 335
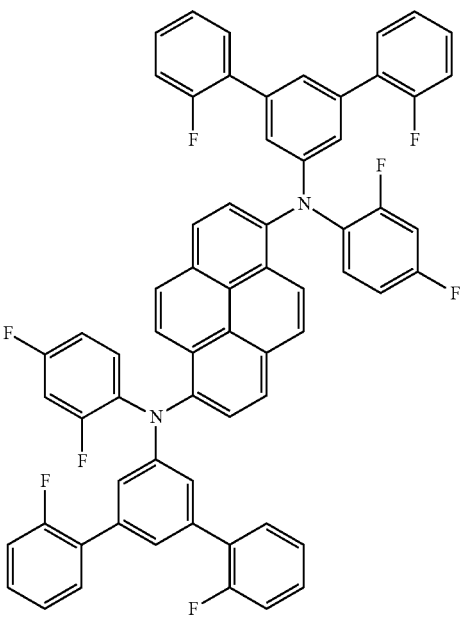

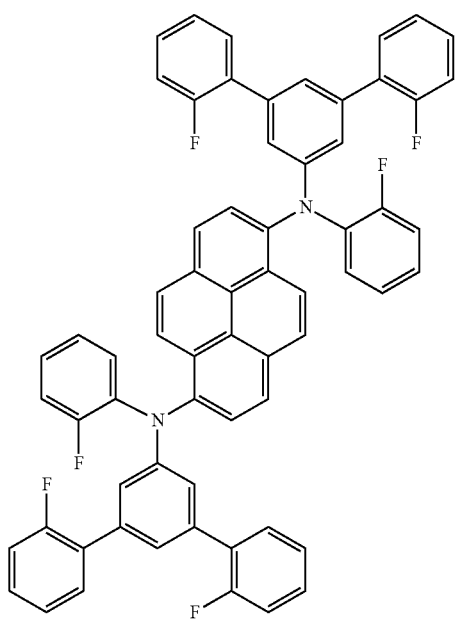
BD 336
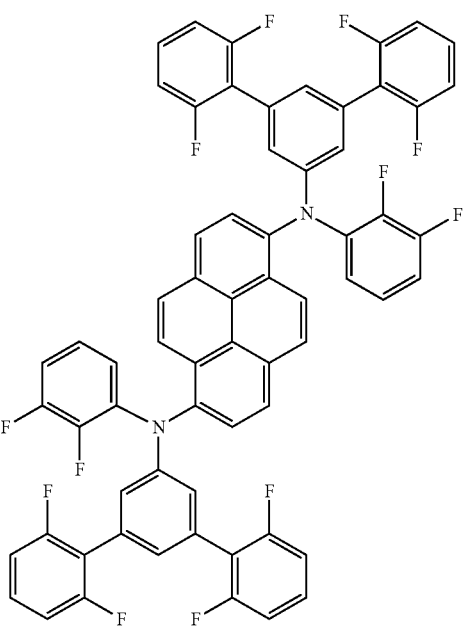
BD 338
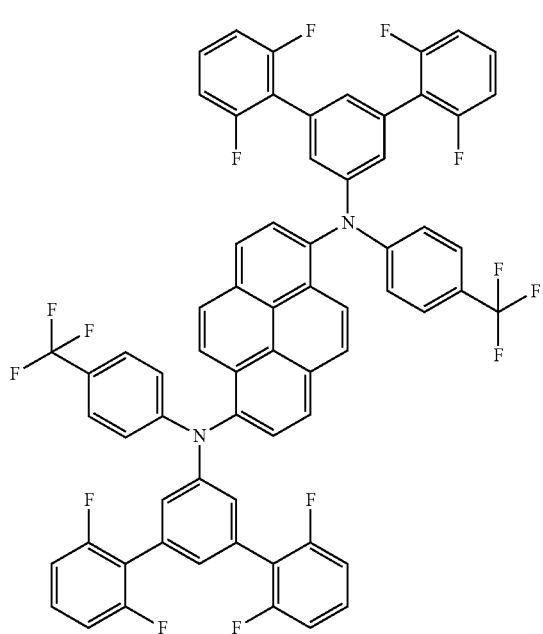
BD 337
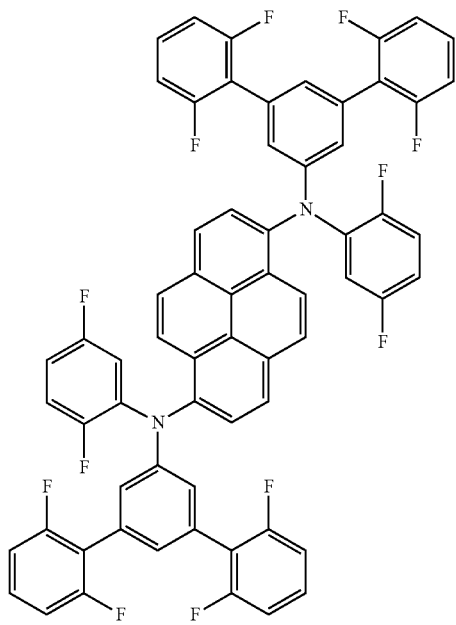
BD 339

333
-continued
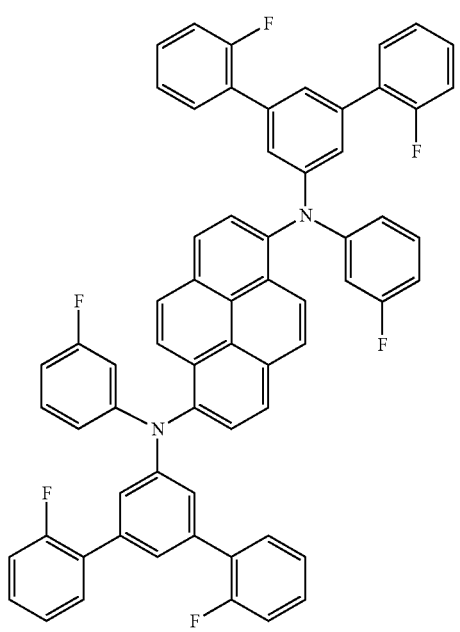
BD 340
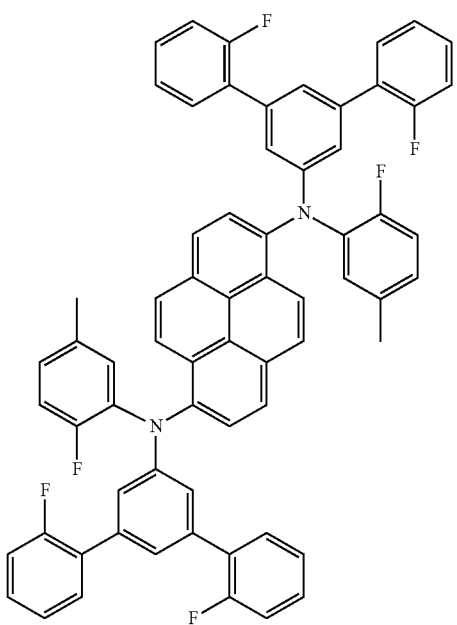
BD 342
334
-continued
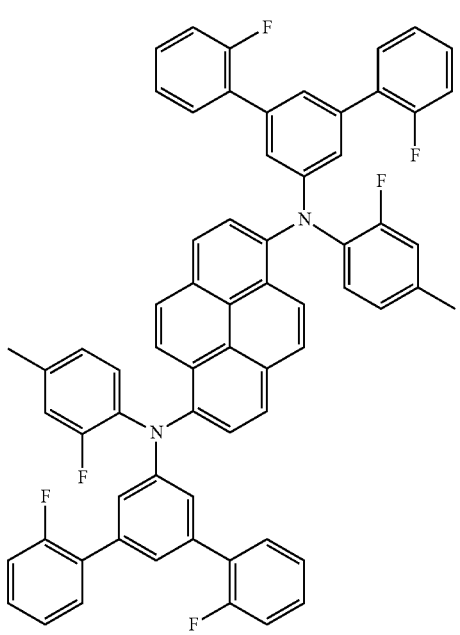
BD 341
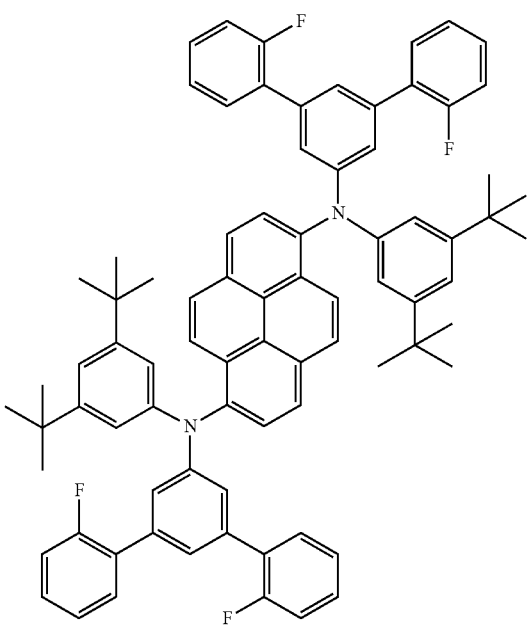
BD 343

BD 344
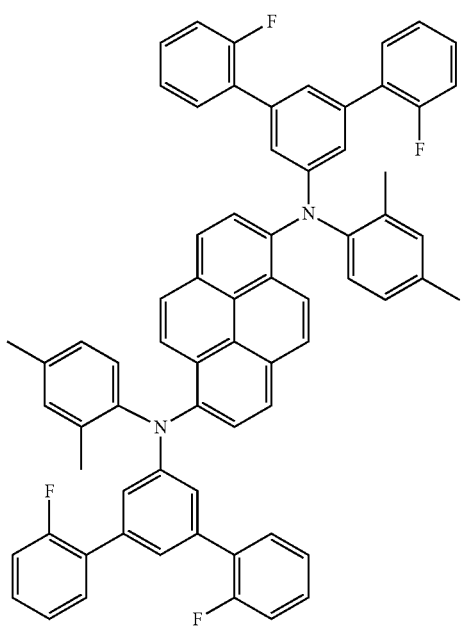
BD 346
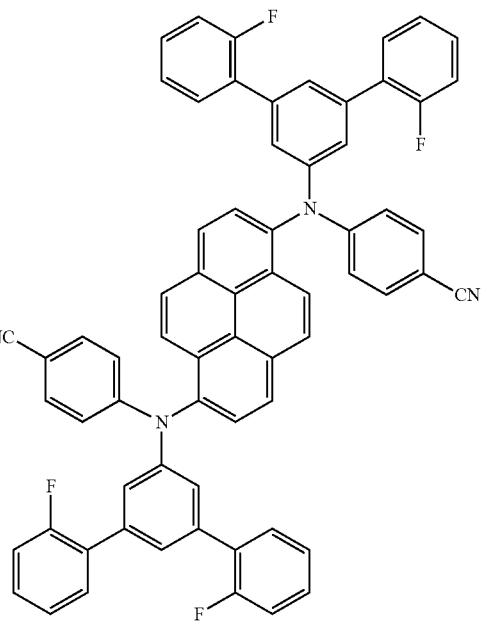
BD 345
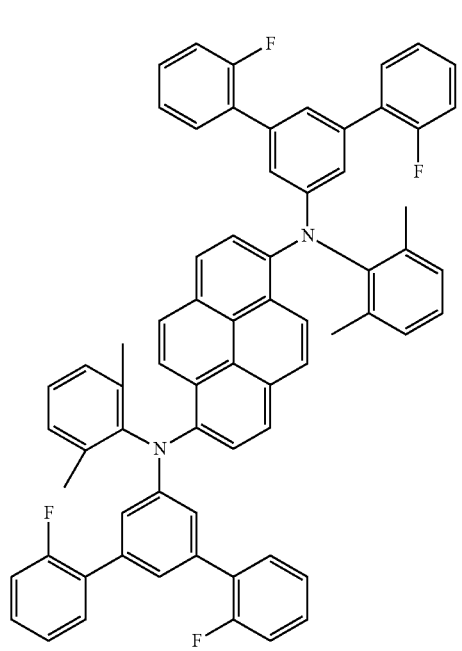
BD 347
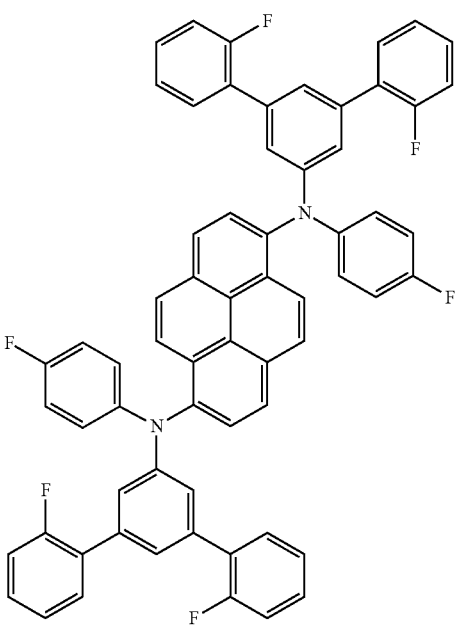

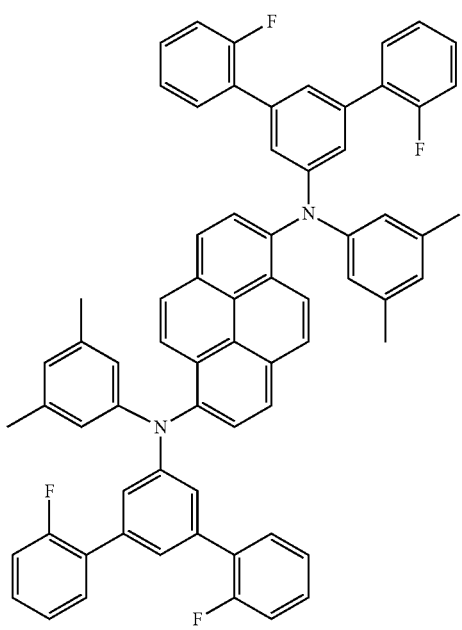
BD 348
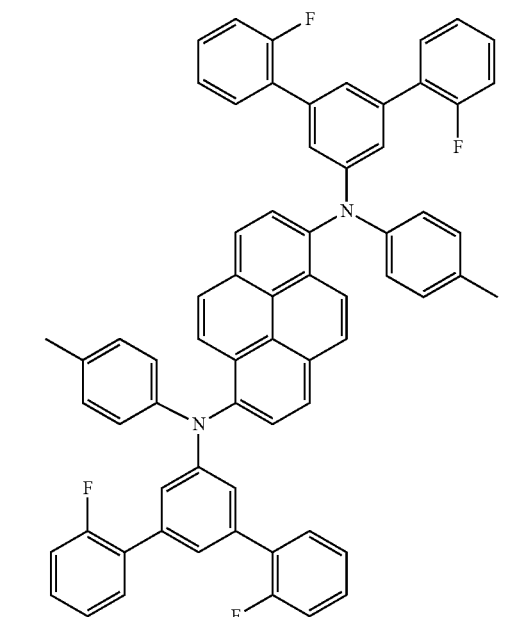
BD 350
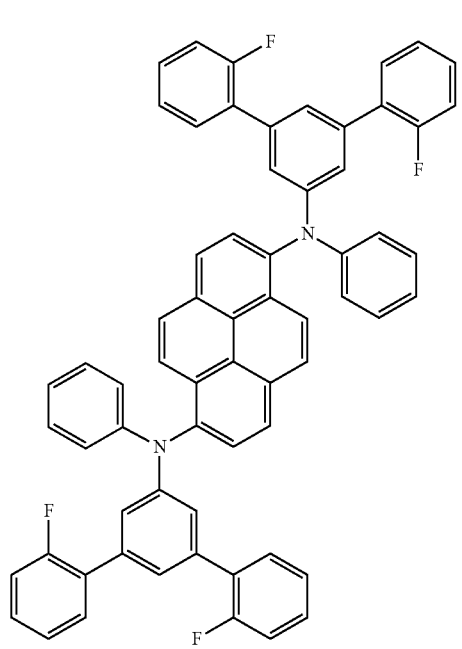
BD 349
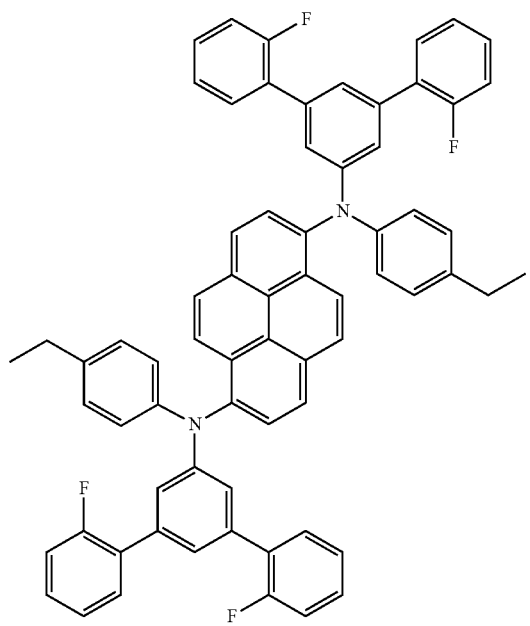
BD 351

-continued
BD 352
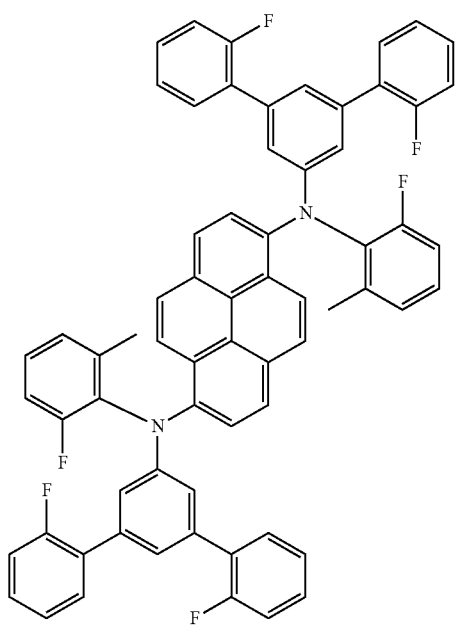
BD 354
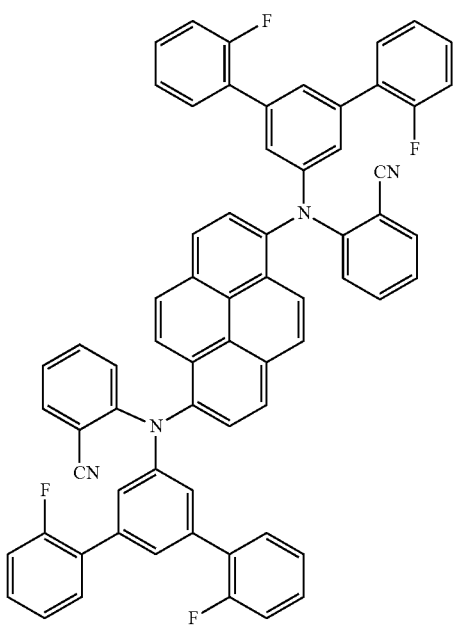
BD 353
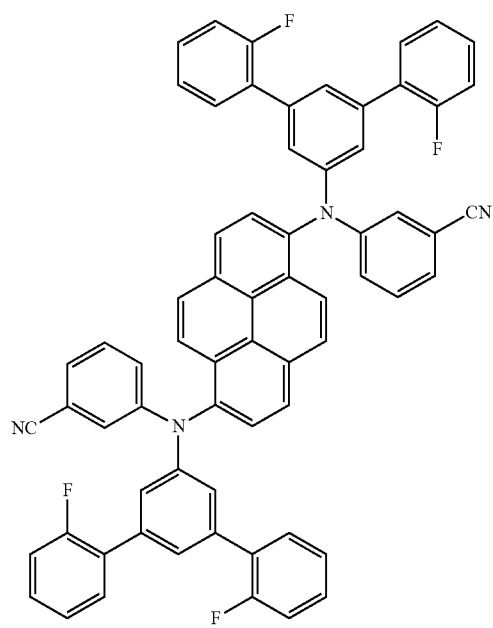
BD 355
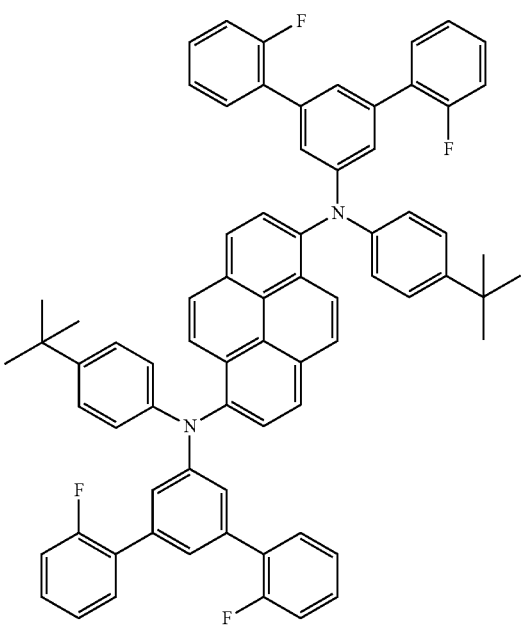

BD 356
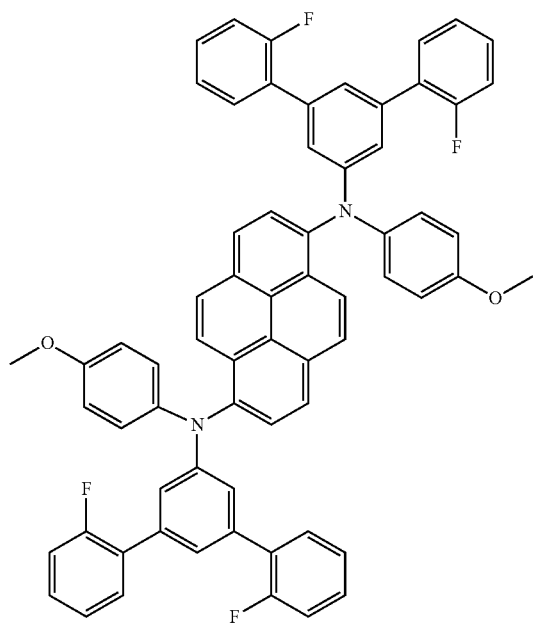
BD 358
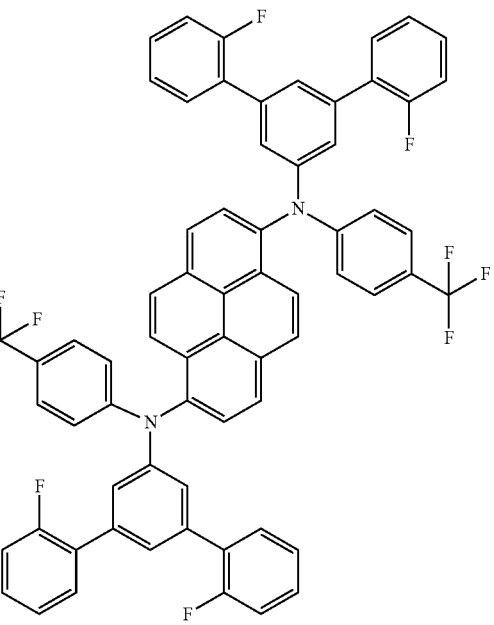
BD 357
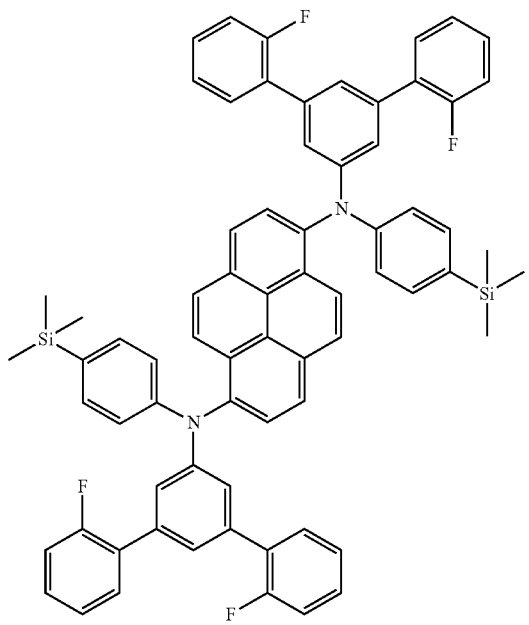
BD 359
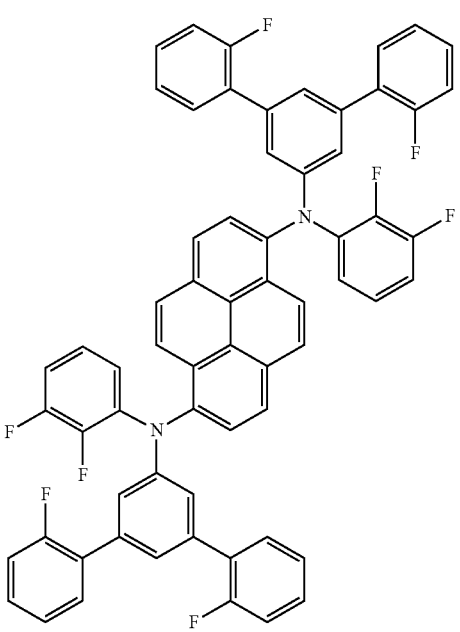

BD 360

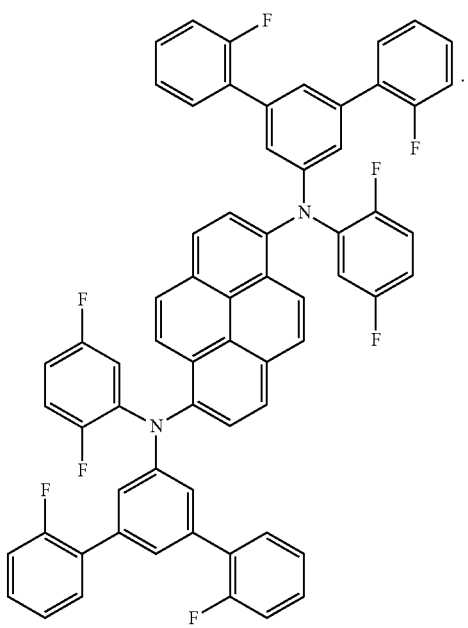

2. An organic electroluminescence device which comprises an electroluminescence layer disposed between a cathode and an anode, said electroluminescence layer comprising a dopant material and a host material, wherein the dopant material is the blue fluorescence compound of claim 1.

3. The device as claimed in claim 2, further comprising a hole injection layer and a hole transport layer formed between the anode and the electroluminescence layer, in succession, and an electron transport layer and an electron injection layer formed between the electroluminescence layer and the cathode, in succession.

4. The organic electroluminescence device of claim 2 which is driven at a voltage of 5.82 to 6.11V.

* * * * *